United States Patent
Cheng et al.

(10) Patent No.: US 12,162,862 B2
(45) Date of Patent: *Dec. 10, 2024

(54) BETA-LACTAM DERIVATIVES FOR THE TREATMENT OF DISEASES

(71) Applicant: Insilico Medicine IP Limited, Hong Kong (HK)

(72) Inventors: Xin Cheng, Shanghai (CN); Yingtao Liu, Shanghai (CN); Luoheng Qin, Shanghai (CN)

(73) Assignee: INSILICO MEDICINE IP LIMITED, Hong Kong (HK)

( * ) Notice: Subject to any disclaimer, the term of this patent is extended or adjusted under 35 U.S.C. 154(b) by 0 days.

This patent is subject to a terminal disclaimer.

(21) Appl. No.: 18/237,140

(22) Filed: Aug. 23, 2023

(65) Prior Publication Data

US 2024/0116899 A1   Apr. 11, 2024

Related U.S. Application Data

(63) Continuation of application No. 18/110,517, filed on Feb. 16, 2023, now Pat. No. 11,834,440, which is a continuation of application No. PCT/CN2022/100889, filed on Jun. 23, 2022.

(30) Foreign Application Priority Data

Jun. 24, 2021 (WO) ............... PCT/CN2021/102061
Jul. 22, 2021 (WO) ............... PCT/CN2021/107806
Dec. 29, 2021 (WO) ............... PCT/CN2021/142624

(51) Int. Cl.
| | | |
|---|---|---|
| *C07D 403/14* | (2006.01) |
| *A61K 39/00* | (2006.01) |
| *A61P 35/00* | (2006.01) |
| *C07D 401/14* | (2006.01) |
| *C07D 403/04* | (2006.01) |
| *C07D 405/14* | (2006.01) |
| *C07D 413/14* | (2006.01) |
| *C07D 417/14* | (2006.01) |

(52) U.S. Cl.
CPC ............ *C07D 403/14* (2013.01); *A61K 39/00* (2013.01); *A61P 35/00* (2018.01); *C07D 401/14* (2013.01); *C07D 403/04* (2013.01); *C07D 405/14* (2013.01); *C07D 413/14* (2013.01); *C07D 417/14* (2013.01)

(58) Field of Classification Search
None
See application file for complete search history.

(56) References Cited

U.S. PATENT DOCUMENTS 5,846,514 A    12/1998 Foster et al.
6,334,997 B1   1/2002 Foster et al.
10,329,282 B2  6/2019 Zhao et al.
11,834,440 B2* 12/2023 Cheng .................. A61P 25/28
2023/0192667 A1 6/2023 Cheng et al.

FOREIGN PATENT DOCUMENTS

| WO | WO-2004098591 A2 | 11/2004 |
| WO | WO-2004098625 A2 | 11/2004 |
| WO | WO-2004099134 A2 | 11/2004 |
| WO | WO-2005039548 A2 | 5/2005 |
| WO | WO-2005075436 A2 | 8/2005 |
| WO | WO-2008055947 A1 | 5/2008 |
| WO | WO-2008104580 A1 | 9/2008 |
| WO | WO-2010026212 A1 | 3/2010 |
| WO | WO-2011029920 A1 | 3/2011 |
| WO | WO-2019000682 A1 | 1/2019 |
| WO | WO-2019001572 A1 | 1/2019 |
| WO | WO-2019018441 A1 | 1/2019 |
| WO | WO-2019022600 A1 | 1/2019 |
| WO | WO-2019063414 A1 | 4/2019 |
| WO | WO-2020033413 A2 | 2/2020 |
| WO | WO-2022076446 A1 | 4/2022 |
| WO | WO-2022268179 A1 | 12/2022 |

OTHER PUBLICATIONS

Evans. Synthesis of radiolabeled compounds. J Radioanal Chem 64(1-2):9-32 (1981).
Fedorak et al. A novel colon-specific steroid prodrug enhances sodium chloride absorption in rat colitis. Am J Physiol. 269(2 Pt 1):G210-8 (1995).
Hochhaus et al. A selective HPLC/RIA for dexamethasone and its prodrug dexamethasone-21-sulphobenzoate sodium in biological fluids. Biomed. Chrom. 6:283-286 (1992).
International search report with written opinion dated Sep. 21, 2022 for PCT/CN2022/100889.
Kabalka et al. The Synthesis of Radiolabeled Compounds via Organometallic Intermediates. Tetrahedron 45(21):6601-6621 (1989).
Larsen et al. Prodrug forms for the sulfonamide group. I. Evaluation of N-acyl derivatives, N-sulfonylamindes, N-sulfonylsulfilimines and sulfonylureas as possible prodrug derivatives. Int. J. Pharmaceutics 37:87-95 (1987).
Larsen et al. Prodrug forms for the sulfonamide group. II. water-soluble amino acid derivatives of N-methylsulfonylaminodes as possible prodrug derivatives. Int'l J of Pharmaceutics 47:103-110 (1988).

(Continued)

*Primary Examiner* — Brian J Davis
(74) *Attorney, Agent, or Firm* — WILSON SONSINI GOODRICH & ROSATI

(57) ABSTRACT

The disclosure provides for compounds and methods for modulating or inhibiting glutaminyl-peptide cyclotransferase-like protein (QPCTL). In one aspect, described herein are compounds of Formulas (I), (Ia), (Ib), (Iaa), (Iab), (Iba), (Ibb), (II), (IIa), (IIb), (IIaa) (IIab), (IIba), and (IIbb), stereoisomer thereof, or salts or solvates thereof. Further provided herein are methods of treating a disease or a condition comprising administering a compound of Formula (I), (Ia), (Ib), (Iaa), (Iab), (Iba), (Ibb), (II), (IIa), (IIb), (IIaa) (IIab), (IIba), or (IIbb), a stereoisomer thereof, or a salt or solvate thereof.

25 Claims, No Drawings

(56) References Cited

OTHER PUBLICATIONS

McLeod et al. A glucocorticoid prodrug facilitates normal mucosal function in rat colitis without adrenal suppression. Gastroenterol 106:405-413 (1994).
Niwa et al. Studies on Ketene and Its Derivatives. CXXII. Reaction of Haloketenes with 1, 3-Diaza-1, 3-diene Compounds. Chemical and Pharmaceutical Bulletin. 32(10):4149-4153 (1984).
Sinkula et al. Rationale for design of biologically reversible drug derivatives: prodrugs. J. Pharm. Sci. 64:181-210 (1975).

* cited by examiner

BETA-LACTAM DERIVATIVES FOR THE TREATMENT OF DISEASES

CROSS-REFERENCE

This patent application is a continuation of U.S. patent application Ser. No. 18/110,517, filed Feb. 16, 2023, which is a continuation of International Application No. PCT/CN2022/100889, filed Jun. 23, 2022, which claims the benefit of PCT/CN2021/102061, filed Jun. 24, 2021, PCT/CN2021/107806, filed Jul. 22, 2021, and PCT/CN2021/142624, filed Dec. 29, 2021, each of which is hereby incorporated by reference in its entirety.

FIELD OF THE INVENTION

The disclosure relates to beta-lactam derivates which function as inhibitors of glutaminyl-peptide cyclotransferase-like protein (QPCTL).

BACKGROUND OF THE INVENTION

Glutaminyl-peptide cyclotransferase, also known as glutaminyl cyclase (GC), catalyzes the conversion of N-terminal L-glutaminyl residues of peptides to pyroglutamyl groups. This enzyme belongs to the family of transferases, specifically the aminoacyltransferases and is present in the pituitary and adrenal glands, where it is important for the generation of the N-terminal pyroglutamyl groups of peptide hormones such as neurotensin and thyrotropin-releasing hormone. Glutaminyl cyclase also catalyzes the conversion of N-terminal residues L-glutamyl residues to pyroglutamyl residues. This activity may contribute to the formation of several amyloid-related plaque forming peptides, contributing to Alzheimer's disease pathology. Glutaminyl cyclase is also considered to be a diagnostic marker of thyroid tumors.

SUMMARY OF THE INVENTION

The present disclosure addresses the above need and provides additional advantages as well.

In some aspects, the present disclosure provides a compound represented by Formula (I) or a pharmaceutically acceptable salt or solvate thereof:

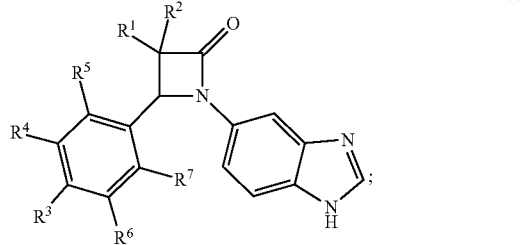

Formula (I)

$R^1$ is halogen, —OH, —OR$^{10a}$, —SR$^{10a}$, —CN, amino, —NR$^{22}$R$^{23}$, substituted or unsubstituted C$_1$-C$_6$ alkyl, substituted or unsubstituted C$_2$-C$_6$ alkenyl, substituted or unsubstituted C$_2$-C$_6$ alkynyl, substituted or unsubstituted C$_1$-C$_6$ heteroalkyl, substituted or unsubstituted C$_3$-C$_8$ cycloalkyl, or substituted or unsubstituted C$_2$-C$_7$ heterocycloalkyl, and $R^2$ is H, halogen, —OH, —OR$^{10b}$, substituted or unsubstituted C$_1$-C$_6$ alkyl, or substituted or unsubstituted C$_1$-C$_6$ heteroalkyl; or $R^1$ and $R^2$ taken together with the carbon atom to which they are attached form a 3-7 membered cyclic or heterocyclic ring; or $R^1$ and $R^2$ taken together form an oxo or a double bond to CR$^{12a}$R$^{12b}$, wherein R$^{12a}$ and R$^{12b}$ are each independently hydrogen, halogen, —OH, amino, substituted or unsubstituted C$_1$-C$_6$ alkyl, substituted or unsubstituted C$_2$-C$_6$ alkenyl, substituted or unsubstituted C$_2$-C$_6$ alkynyl, substituted or unsubstituted C$_1$-C$_6$ heteroalkyl, substituted or unsubstituted C$_3$-C$_8$ cycloalkyl, substituted or unsubstituted C$_2$-C$_7$ heterocycloalkyl, substituted or unsubstituted aryl, or substituted or unsubstituted heteroaryl;

each of $R^4$, $R^5$, $R^6$, and $R^7$ is independently selected from H and halogen; $R^3$ is —OR$^{11}$, halogen, —SR$^{11}$, —S(=O)R$^{21}$, —S(=O)$_2$R$^{21}$, —NHS(=O)$_2$R$^{21}$, —S(=O)$_2$NR$^{22}$R$^{23}$, —C(=O)R$^{21}$, —OC(=O)R$^{21}$, —C(=O)OR$^{22}$, —OC(=O)OR$^{22}$, —C(=O)NR$^{22}$R$^{23}$, —OC(=O)NR$^{22}$R$^{23}$, —NR$^{22}$R$^{23}$, —NO$_2$, —NHS(=O)$_2$R$^{21}$, —NR$^{22}$C(=O)NR$^{22}$R$^{23}$, —NR$^{22}$C(=O)R$^{21}$, —NR$^{22}$C(=O)OR$^{21}$, substituted or unsubstituted C$_1$-C$_8$ alkyl, substituted or unsubstituted C$_2$-C$_8$ alkenyl, substituted or unsubstituted C$_2$-C$_8$ alkynyl, substituted or unsubstituted C$_1$-C$_8$ heteroalkyl, substituted or unsubstituted C$_3$-C$_8$ cycloalkyl, substituted or unsubstituted C$_2$-C$_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl;

$R^{10a}$ and $R^{10b}$ are each independently substituted or unsubstituted C$_1$-C$_6$ alkyl, substituted or unsubstituted C$_2$-C$_6$ alkenyl, substituted or unsubstituted C$_2$-C$_6$ alkynyl, or substituted or unsubstituted C$_1$-C$_6$ heteroalkyl; and $R^{11}$ is substituted or unsubstituted C$_1$-C$_6$ alkyl, substituted or unsubstituted C$_2$-C$_6$ alkenyl, substituted or unsubstituted C$_2$-C$_6$ alkynyl, substituted or unsubstituted C$_1$-C$_6$ heteroalkyl, substituted or unsubstituted C$_3$-C$_8$ cycloalkyl, substituted or unsubstituted C$_2$-C$_7$ heterocycloalkyl, substituted or unsubstituted phenyl, substituted or unsubstituted naphthyl, substituted or unsubstituted monocyclic heteroaryl, or substituted or unsubstituted bicyclic or $R^{21}$, $R^{22}$, and $R^{23}$ are each independently hydrogen, C$_1$-C$_6$ alkyl, C$_1$-C$_6$ heteroalkyl, C$_3$-C$_8$ cycloalkyl, or C$_2$-C$_7$ heterocycloalkyl, wherein each of the alkyl, heteroalkyl, cycloalkyl, or heterocycloalkyl is optionally substituted.

In some aspects, the present disclosure provides a compound represented by Formula (I), or a pharmaceutically acceptable salt or solvate thereof:

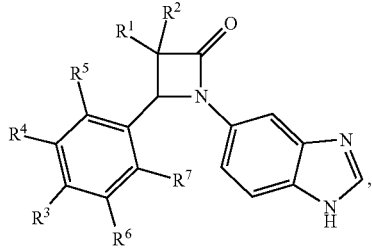

Formula (I)

wherein,
R¹ is H, halogen, —OH, —OR¹⁰ᵃ, —SR¹⁰ᵃ, —CN, amino, —NR²²R²³, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, or substituted or unsubstituted $C_2$-$C_7$ heterocycloalkyl, and R² is H, halogen, —OH, —OR¹⁰ᵇ, substituted or unsubstituted $C_1$-$C_6$ alkyl, or substituted or unsubstituted $C_1$-$C_6$ heteroalkyl; or R¹ and R² taken together with the carbon atom to which they are attached form a 3-7 membered cyclic or heterocyclic ring; or R¹ and R² taken together form an oxo or a double bond to $CR^{12a}R^{12b}$, wherein $R^{12a}$ and $R^{12b}$ are each independently hydrogen, halogen, —OH, amino, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

each of R⁴, R⁵, R⁶, and R⁷ is independently selected from H and halogen;

R³ is —OR¹¹, —SR¹¹, —S(=O)R²¹, —S(=O)₂R²¹, —NHS(=O)₂R²¹, —S(=O)₂NR²²R²³, —C(=O)R²¹, —OC(=O)R²¹, —C(=O)OR²², —OC(=O)OR²², —C(=O)NR²²R²³, —OC(=O)NR²²R²³, —NR²²R²³, —NO₂, —NHS(=O)₂R²¹, —NR²²C(=O)NR²²R²³, —NR²²C(=O)R²¹, —NR²²C(=O)OR²¹, substituted $C_1$-$C_8$ alkyl, substituted $C_2$-$C_8$ alkenyl, substituted $C_2$-$C_8$ alkynyl, substituted $C_1$-$C_8$ heteroalkyl, substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl, wherein the alkyl, alkenyl, alkynyl or heteroalkyl is substituted with at least one substituent selected from substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, and substituted or unsubstituted bicyclic or polycyclic heteroaryl;

R¹⁰ᵃ and R¹⁰ᵇ are each independently substituted or unsubstituted $C_1$-$C_6$ alkyl, substituted or unsubstituted $C_2$-$C_6$ alkenyl, substituted or unsubstituted $C_2$-$C_6$ alkynyl, or substituted or unsubstituted $C_1$-$C_6$ heteroalkyl;

R¹¹ is substituted $C_1$-$C_6$ alkyl, substituted $C_2$-$C_6$ alkenyl, substituted $C_2$-$C_6$ alkynyl, substituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl, wherein the alkyl, alkenyl, alkynyl or heteroalkyl is substituted with at least one substituent selected from substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, and substituted or unsubstituted bicyclic or polycyclic heteroaryl; and R²¹, R²², and R²³ are each independently hydrogen, $C_1$-$C_6$ alkyl, $C_1$-$C_6$ heteroalkyl, $C_3$-$C_8$ cycloalkyl, or $C_2$-$C_7$ heterocycloalkyl, wherein each of the alkyl, heteroalkyl, cycloalkyl, or heterocycloalkyl is optionally substituted.

In some embodiments, the disclosure provides a compound represented by Formula (Ia), or a pharmaceutically acceptable salt or solvate thereof:

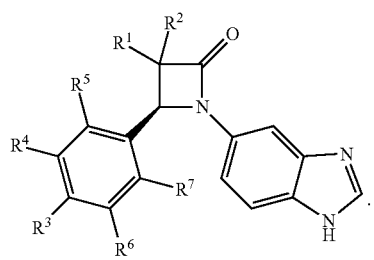

Formula (Ia)

In some embodiments, the disclosure provides a compound represented by Formula (Ib), or a pharmaceutically acceptable salt or solvate thereof:

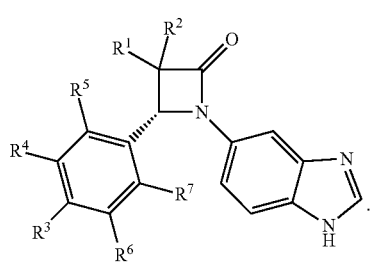

Formula (Ib)

In some embodiments, the disclosure provides a compound represented by Formula (Iaa), or a pharmaceutically acceptable salt or solvate thereof:

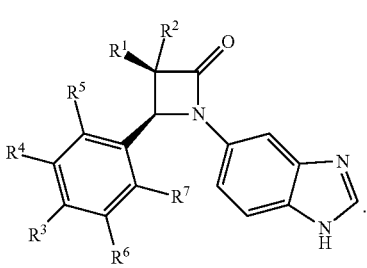

Formula (Iaa)

In some embodiments, the disclosure provides a compound represented by Formula (Iab), or a pharmaceutically acceptable salt or solvate thereof:

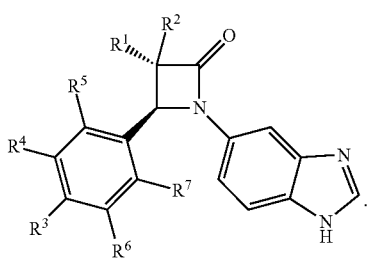

Formula (Iab)

In some embodiments, the disclosure provides a compound represented by Formula (Iba), or a pharmaceutically acceptable salt or solvate thereof:

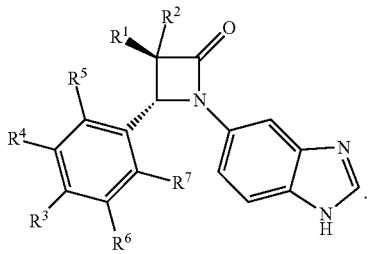

Formula (Iba)

In some embodiments, the disclosure provides a compound represented by Formula (Ibb), or a pharmaceutically acceptable salt or solvate thereof:

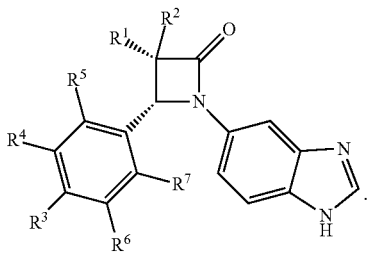

Formula (Ibb)

In another aspect, the disclosure provides for a compound of Formula (II), or a pharmaceutically acceptable salt or solvate thereof:

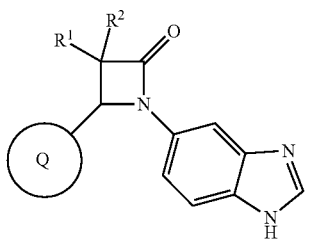

Formula (II)

wherein,
$R^1$ is H, halogen, —OH, —OR$^{10a}$, —SR$^{10a}$, —CN, amino, —NR$^{22}$R$^{23}$, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, or substituted or unsubstituted $C_2$-$C_7$ heterocycloalkyl, and $R^2$ is H, halogen, —OH, —OR$^{10b}$, substituted or unsubstituted $C_1$-$C_6$ alkyl, or substituted or unsubstituted $C_1$-$C_6$ heteroalkyl; or $R^1$ and $R^2$ taken together with the carbon atom to which they are attached form a 3-7 membered cyclic or heterocyclic ring; or $R^1$ and $R^2$ taken together form an oxo or a double bond to CR$^{12a}$R$^{12b}$, wherein R$^{12a}$ and R$^{12b}$ are each independently hydrogen, halogen, —OH, amino, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

ring Q is a substituted or unsubstituted 5 or 6 membered heteroaryl;

R$^{10a}$ and R$^{10b}$ are each independently substituted or unsubstituted $C_1$-$C_6$ alkyl, substituted or unsubstituted $C_2$-$C_6$ alkenyl, substituted or unsubstituted $C_2$-$C_6$ alkynyl, or substituted or unsubstituted $C_1$-$C_6$ heteroalkyl; and R$^{22}$ and R$^{23}$ are each independently hydrogen, $C_1$-$C_6$ alkyl, $C_1$-$C_6$ heteroalkyl, $C_3$-$C_8$ cycloalkyl, or $C_2$-$C_7$ heterocycloalkyl, wherein each of the alkyl, heteroalkyl, cycloalkyl, or heterocycloalkyl is optionally substituted.

In some embodiments, the compound of Formula (II) has a structure of Formula (IIa), pharmaceutically acceptable salt or solvate thereof:

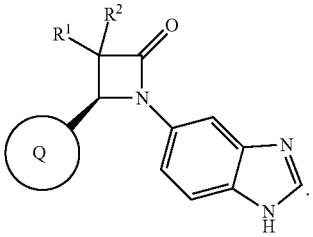

Formula (IIa)

In some embodiments, the compound of Formula (II) has a structure of Formula (IIb), pharmaceutically acceptable salt or solvate thereof:

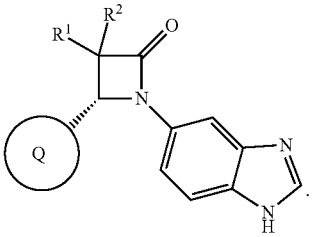

Formula (IIb)

In some embodiments, the compound of Formula (II) has a structure of Formula (IIaa), pharmaceutically acceptable salt or solvate thereof:

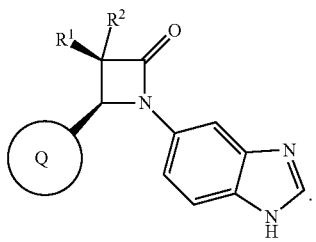

Formula (IIaa)

In some embodiments, the compound of Formula (II) has a structure of Formula (IIab), pharmaceutically acceptable salt or solvate thereof:

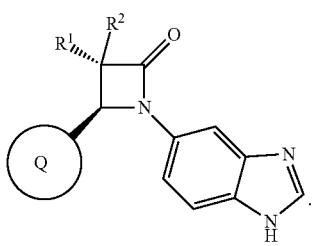

Formula (IIab)

In some embodiments, the compound of Formula (II) has a structure of Formula (IIba), pharmaceutically acceptable salt or solvate thereof:

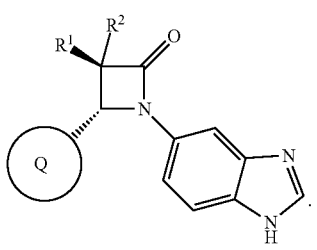

Formula (IIba)

In some embodiments, the compound of Formula (II) has a structure of Formula (IIbb), pharmaceutically acceptable salt or solvate thereof:

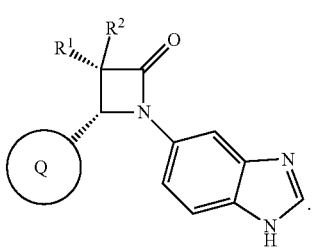

Formula (IIbb)

In some embodiments of Formula (I), (Ia), (Ib), (Iaa), (Iab), (Iba), (Ibb), (II), (IIa), (IIb), (IIaa) (IIab), (IIba), or (IIbb), $R^1$ is halogen, —OH, —$SR^{10a}$, —CN, amino, —$NR^{22}R^{23}$, —$OR^{10a}$, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, or substituted or unsubstituted $C_2$-$C_7$ heterocycloalkyl. In some embodiments of Formula (I), (Ia), (Ib), (Iaa), (Iab), (Iba), (Ibb), (II), (IIa), (IIb), (IIaa) (IIab), (IIba), or (IIbb), $R^1$ is —OH, —$OR^{10a}$, substituted or unsubstituted $C_1$-$C_6$ alkyl, or substituted or unsubstituted $C_3$-$C_6$ cycloalkyl. In some embodiments of Formula (I), (Ia), (Ib), (Iaa), (Iab), (Iba), (Ibb), (II), (IIa), (IIb), (IIaa) (IIab), (IIba), or (IIbb), $R^1$ is —OH. In some embodiments of Formula (I), (Ia), (Ib), (Iaa), (Iab), (Iba), (Ibb), (II), (IIa), (IIb), (IIaa) (IIab), (IIba), or (IIbb), $R^1$ is —$OR^{10a}$, and $R^{10a}$ is substituted or unsubstituted $C_1$-$C_6$ alkyl. In some embodiments, $R^1$ is —$OCH_3$. In some embodiments of Formula (I), (Ia), (Ib), (Iaa), (Iab), (Iba), (Ibb), (II), (IIa), (IIb), (IIaa) (IIab), (IIba), or (IIbb), $R^1$ is substituted or unsubstituted $C_1$-$C_6$ alkyl. In some embodiments of Formula (I), (Ia), (Ib), (Iaa), (Iab), (Iba), (Ibb), (II), (IIa), (IIb), (IIaa) (IIab), (IIba), or (IIbb), $R^1$ is $C_1$-$C_6$ alkyl that is optionally substituted with one to five substituents selected from halogen, —OH, amino, cyano, oxime, oxo, mono-$C_{1-6}$ alkylamino, di-$C_{1-6}$ alkylamino, substituted or unsubstituted $C_{1-6}$ alkoxy, substituted or unsubstituted $C_{3-7}$ cycloalkyl, substituted or unsubstituted $C_{2-8}$ heterocycloalkyl, substituted or unsubstituted aryl, and substituted or unsubstituted heteroaryl. In some embodiments of Formula (I), (Ia), (Ib), (Iaa), (Iab), (Iba), (Ibb), (II), (IIa), (IIb), (IIaa) (IIab), (IIba), or (IIbb), $R^1$ is —$CH_3$, —$CHF_2$, —$CF_3$,

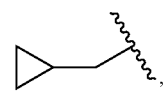

—$CH_2OH$, —$CH_2CH_3$, —$CH_2CH_2CH_3$, —$CH_2CH_2CH_2CH_3$, or benzyl. In some embodiments of Formula (I), (Ia), (Ib), (Iaa), (Iab), (Iba), (Ibb), (II), (IIa), (IIb), (IIaa) (IIab), (IIba), or (IIbb), $R^1$ is substituted or unsubstituted $C_2$-$C_7$ heterocycloalkyl. In some embodiments of Formula (I), (Ia), (Ib), (Iaa), (Iab), (Iba), (Ibb), (II), (IIa), (IIb), (IIaa) (IIab), (IIba), or (IIbb), $R^1$ is

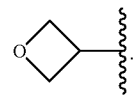

In some embodiments, $R^1$ is H.

In some embodiments of Formula (I), (Ia), (Ib), (Iaa), (Iab), (Iba), (Ibb), (II), (IIa), (IIb), (IIaa) (IIab), (IIba), or (IIbb), $R^2$ is H, halogen, —OH, or substituted or unsubstituted $C_1$-$C_6$ alkyl. In some embodiments of Formula (I), (Ia), (Ib), (Iaa), (Iab), (Iba), (Ibb), (II), (IIa), (IIb), (IIaa) (IIab), (IIba), or (IIbb), $R^2$ is H. In some embodiments of Formula (I), (Ia), (Ib), (Iaa), (Iab), (Iba), (Ibb), (II), (IIa), (IIb), (IIaa) (IIab), (IIba), or (IIbb), $R^2$ is —$CH_3$.

In some embodiments of Formula (I), (Ia), (Ib), (Iaa), (Iab), (Iba), (Ibb), (II), (IIa), (IIb), (IIaa) (IIab), (IIba), or (IIbb), $R^1$ and $R^2$ taken together with the carbon atom to which they are attached form a 3-7 membered cyclic or heterocyclic ring. In some embodiments of Formula (I), (Ia), (Ib), (Iaa), (Iab), (Iba), (Ibb), (II), (IIa), (IIb), (IIaa) (IIab), (IIba), or (IIbb), $R^1$ and $R^2$ taken together with the carbon atom to which they are attached form a cyclopropyl or a cyclobutyl. In some embodiments of Formula (I), (Ia), (Ib), (Iaa), (Iab), (Iba), (Ibb), (II), (IIa), (IIb), (IIaa) (IIab), (IIba), or (IIbb), $R^1$ and $R^2$ taken together form an oxo. In some embodiments of Formula (I), (Ia), (Ib), (Iaa), (Iab), (Iba), (Ibb), (II), (IIa), (IIb), (IIaa) (IIab), (IIba), or (IIbb), $R^1$ and $R^2$ taken together form a double bond to $CR^{12a}R^{12b}$, wherein $R^{12a}$ and $R^{12b}$ are each independently hydrogen, halogen, —OH, amino, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl. In some embodiments of Formula (I), (Ia), (Ib), (Iaa), (Iab), (Iba), (Ibb), (II), (IIa), (IIb), (IIaa) (IIab), (IIba), or (IIbb), $R^{12a}$ is hydrogen and $R^{12b}$ is hydrogen, substituted or unsubstituted $C_1$-$C_6$ alkyl, substituted or unsubstituted phenyl, or substituted or unsubstituted monocyclic heteroaryl. In some embodiments of Formula (I), (Ia), (Ib), (Iaa), (Iab), (Iba), (Ibb), (II), (IIa), (IIb), (IIaa) (IIab), (IIba), or (IIbb), $R^{12a}$ is hydrogen and $R^{12b}$ is hydrogen or phenyl. In some embodiments of Formula (I), (Ia), (Ib), (Iaa), (Iab), (Iba), (Ibb), (II), (IIa), (IIb), (IIaa) (IIab), (IIba), or (IIbb), $R^{12a}$ is hydrogen and $R^{12b}$ is hydrogen.

In some embodiments of Formula (I), (Ia), (Ib), (Iaa), (Iab), (Iba), (Ibb), (II), (IIa), (IIb), (IIaa) (IIab), (IIba), or (IIbb), $R^5$ is H, F, Cl, or Br. In some embodiments, $R^5$ is F. In some embodiments of Formula (I), (Ia), (Ib), (Iaa), (Iab), (Iba), (Ibb), (II), (IIa), (IIb), (IIaa) (IIab), (IIba), or (IIbb), $R^7$ is H, F, Cl, or Br. In some embodiments, $R^7$ is F. In some embodiments of Formula (I), (Ia), (Ib), (Iaa), (Iab), (Iba), (Ibb), (II), (IIa), (IIb), (IIaa) (IIab), (IIba), or (IIbb), $R^4$ is H, F, Cl, or Br. In some embodiments, $R^4$ is H. In some embodiments of Formula (I), (Ia), (Ib), (Iaa), (Iab), (Iba), (Ibb), (II), (IIa), (IIb), (IIaa) (IIab), (IIba), or (IIbb), $R^6$ is H, F, Cl, or Br. In some embodiments, $R^6$ is H.

In some embodiments of Formula (I), (Ia), (Ib), (Iaa), (Iab), (Iba), (Ibb), (II), (IIa), (IIb), (IIaa) (IIab), (IIba), or (IIbb), $R^3$ is substituted or unsubstituted monocyclic heteroaryl. In some embodiments of Formula (I), (Ia), (Ib), (Iaa), (Iab), (Iba), (Ibb), (II), (IIa), (IIb), (IIaa) (IIab), (IIba), or (IIbb), $R^3$ is substituted or unsubstituted 5 or 6 membered monocyclic heteroaryl having 1-4 ring heteroatoms independently selected from N, O and S. In some embodiments of Formula (I), (Ia), (Ib), (Iaa), (Iab), (Iba), (Ibb), (II), (IIa), (IIb), (IIaa) (IIab), (IIba), or (IIbb), $R^3$ is substituted or unsubstituted 5-membered monocyclic heteroaryl. In some embodiments of Formula (I), (Ia), (Ib), (Iaa), (Iab), (Iba), (Ibb), (II), (IIa), (IIb), (IIaa) (IIab), (IIba), or (IIbb), $R^3$ is substituted or unsubstituted bicyclic heteroaryl. In some embodiments of Formula (I), (Ia), (Ib), (Iaa), (Iab), (Iba), (Ibb), (II), (IIa), (IIb), (IIaa) (IIab), (IIba), or (IIbb), $R^3$ is a fused bicyclic heteroaryl having 8 to 10 ring atoms, 1, 2, 3, 4 or 5 ring heteroatoms independently selected from N, O and S. In some embodiments of Formula (I), (Ia), (Ib), (Iaa), (Iab), (Iba), (Ibb), (II), (IIa), (IIb), (IIaa) (IIab), (IIba), or (IIbb), $R^3$ is substituted or unsubstituted $C_2$-$C_7$ heterocycloalkyl. In some embodiments of Formula (I), (Ia), (Ib), (Iaa), (Iab), (Iba), (Ibb), (II), (IIa), (IIb), (IIaa) (IIab), (IIba), or (IIbb), $R^3$ is a monocyclic 5 or 6 membered heterocycloalkyl having 1 to 3 ring heteroatoms independently selected from N, O and S. In some embodiments of Formula (I), (Ia), (Ib), (Iaa), (Iab), (Iba), (Ibb), (II), (IIa), (IIb), (IIaa) (IIab), (IIba), or (IIbb), $R^3$ is substituted or unsubstituted $C_3$-$C_8$ cycloalkyl. In some embodiments of Formula (I), (Ia), (Ib), (Iaa), (Iab), (Iba), (Ibb), (II), (IIa), (IIb), (IIaa) (IIab), (IIba), or (IIbb), $R^3$ is cyclopropyl, cyclobutyl, cyclopentyl, or cyclohexyl, each of which is optionally substituted. In some embodiments of Formula (I), (Ia), (Ib), (Iaa), (Iab), (Iba), (Ibb), (II), (IIa), (IIb), (IIaa) (IIab), (IIba), or (IIbb), $R^3$ is phenyl or naphthyl, each of which is optionally substituted. In some embodiments of Formula (I), (Ia), (Ib), (Iaa), (Iab), (Iba), (Ibb), (II), (IIa), (IIb), (IIaa) (IIab), (IIba), or (IIbb), $R^3$ is substituted with one or more $R^{31}$, and each $R^{31}$ is independently selected from cyano, oxime, oxo, halogen, hydroxy, amino, mono-$C_{1-6}$ alkylamino, di-$C_{1-6}$ alkylamino, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{1-6}$ alkoxy, substituted or unsubstituted $C_{3-7}$ cycloalkyl, substituted or unsubstituted $C_{2-8}$ heterocycloalkyl, heteroaryl, substituted or unsubstituted heterocycloalkyl-$C_{1-6}$ alkyl, substituted or unsubstituted $C_{1-6}$ alkyl-heterocycloalkyl, substituted or unsubstituted $C_{1-6}$ alkyl-aryl, substituted or unsubstituted $C_{1-6}$ alkyl-heteroaryl, substituted or unsubstituted $C_{1-6}$ alkoxy-aryl, substituted or unsubstituted $C_{1-6}$ alkoxy-heterocycloalkyl, and substituted or unsubstituted $C_{1-6}$ alkoxy-heteroaryl. In some embodiments of Formula (I), (Ia), (Ib), (Iaa), (Iab), (Iba), (Ibb), (II), (IIa), (IIb), (IIaa) (IIab), (IIba), or (IIbb), $R^3$ is —$OR^{11}$, —$SR^{11}$, —$S(=O)R^{21}$, —$S(=O)_2R^{21}$, —$NHS(=O)_2R^{21}$, —$S(=O)_2NR^{22}R^{23}$, —$C(=O)R^{21}$, —$OC(=O)R^{21}$, —$C(=O)OR^{22}$, —$OC(=O)OR^{22}$, —$C(=O)NR^{22}R^{23}$, —$OC(=O)NR^{22}R^{23}$, —$NR^{22}R^{23}$, —$NO_2$, —$NHS(=O)_2R^{21}$, —$NR^{22}C(=O)NR^{22}R^{23}$, —$NR^{22}C(=O)R^{21}$, —$NR^{22}C(=O)OR^{21}$, halogen, substituted or unsubstituted $C_1$-$C_8$ alkyl, substituted or unsubstituted $C_2$-$C_8$ alkenyl, substituted or unsubstituted $C_2$-$C_8$ alkynyl, or substituted or unsubstituted $C_1$-$C_8$ heteroalkyl. In some embodiments of Formula (I), (Ia), (Ib), (Iaa), (Iab), (Iba), (Ibb), (II), (IIa), (IIb), (IIaa) (IIab), (IIba), or (IIbb), $R^3$ is —$OR^{11}$, —$SR^{11}$, substituted or unsubstituted $C_1$-$C_8$ alkyl, substituted or unsubstituted $C_2$-$C_8$ alkenyl, substituted or unsubstituted $C_2$-$C_8$ alkynyl, or substituted or unsubstituted $C_1$-$C_8$ heteroalkyl. In some embodiments of Formula (I), (Ia), (Ib), (Iaa), (Iab), (Iba), (Ibb), (II), (IIa), (IIb), (IIaa) (IIab), (IIba), or (IIbb), $R^3$ is —$OR^{11}$.

In some embodiments of Formula (I), (Ia), (Ib), (Iaa), (Iab), (Iba), (Ibb), (II), (IIa), (IIb), (IIaa) (IIab), (IIba), or (IIbb), $R^{11}$ is substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, or substituted or unsubstituted bicyclic heteroaryl. In some embodiments of Formula (I), (Ia), (Ib), (Iaa), (Iab), (Iba), (Ibb), (II), (IIa), (IIb), (IIaa) (IIab), (IIba), or (IIbb), $R^{11}$ is substituted or unsubstituted $C_1$-$C_6$ alkyl or substituted or unsubstituted $C_3$-$C_6$ cycloalkyl. In some embodiments of Formula (I), (Ia), (Ib), (Iaa), (Iab), (Iba), (Ibb), (II), (IIa), (IIb), (IIaa) (IIab), (IIba), or (IIbb), $R^{11}$ is substituted $C_1$-$C_4$ alkyl. In some embodiments of Formula (I), (Ia), (Ib), (Iaa), (Iab), (Iba), (Ibb), (II), (IIa), (IIb), (IIaa) (IIab), (IIba), or (IIbb), $R^{11}$ is substituted with one or more substituents selected from cyano, oxime, oxo, halogen, —CN, —$NH_2$, —$NH(CH_3)$, —$N(CH_3)_2$, —OH, —$CO_2H$, —$CO_2(C_1$-$C_4$ alkyl), —$C(=O)NH_2$, —$C(=O)NH(C_1$-$C_4$ alkyl), —$C(=O)N(C_1$-$C_4$ alkyl)$_2$, —$S(=O)_2NH_2$, —$S(=O)_2NH(C_1$-$C_4$ alkyl), —$S(=O)_2N(C_1$-$C_4$ alkyl)$_2$, —$SC_1$-$C_4$ alkyl, —$S(=O)C_1$-$C_4$ alkyl, —$S(=O)_2(C_1$-$C_4$ alkyl), mono-$C_{1-6}$ alkylamino, di-$C_{1-6}$ alkylamino, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{1-6}$ alkoxy, substituted or unsubstituted $C_{3-7}$ cycloalkyl, substituted or unsubstituted $C_{2-8}$ heterocycloalkyl, heteroaryl, substituted or unsubstituted heterocycloalkyl-$C_{1-6}$ alkyl, substituted or unsubstituted $C_{1-6}$ alkyl-heterocycloalkyl, substituted or unsubstituted $C_{1-6}$ alkyl-aryl, substituted or unsubstituted $C_{1-6}$ alkyl-heteroaryl, substituted or unsubstituted $C_{1-6}$ alkoxy-aryl, substituted or unsubstituted $C_{1-6}$ alkoxy-heterocycloalkyl, and substituted or unsubstituted $C_{1-6}$ alkoxy-heteroaryl. In some embodiments, $R^{11}$ is substituted with one or more substituents selected from halogen, —OH, $C_1$-$C_4$ alkyl, $C_3$-$C_6$ cycloalkyl, $C_1$-$C_4$ fluoroalkyl, $C_1$-$C_4$ heteroalkyl, $C_1$-$C_4$ alkoxy, or $C_1$-$C_4$ fluoroalkoxy. In some embodiments of Formula (I), (Ia), (Ib), (Iaa), (Iab), (Iba), (Ibb), (II), (IIa), (IIb), (IIaa) (IIab), (IIba), or (IIbb), $R^{11}$ is substituted with one or more substituents selected from halogen, —OH, and $C_3$-$C_6$ cycloalkyl. In some embodiments of Formula (I), (Ia), (Ib), (Iaa), (Iab), (Iba), (Ibb), (II), (IIa), (IIb), (IIaa) (IIab), (IIba), or (IIbb), $R^{11}$ is substituted with one or more F.

In some embodiments of Formula (I), (Ia), (Ib), (Iaa), (Iab), (Iba), (Ibb), (II), (IIa), (IIb), (IIaa) (IIab), (IIba), or (IIbb), $R^3$ is —S(=O)$R^{21}$, —S(=O)$_2R^{21}$, —NHS(=O)$_2R^{21}$, —S(=O)$_2NR^{22}R^{23}$, —C(=O)$R^{21}$, —OC(=O)$R^{21}$, —C(=O)O$R^{22}$, —OC(=O)O$R^{22}$, —C(=O)N$R^{22}R^{23}$, —OC(=O)N$R^{22}R^{23}$, —N$R^{22}R^{23}$, —NO$_2$, —NHS(=O)$_2R^{21}$, —N$R^{22}$C(=O)N$R^{22}R^{23}$, —N$R^{22}$C(=O)$R^{21}$, or —N$R^{22}$C(=O)O$R^{21}$. In some embodiments of Formula (I), (Ia), (Ib), (Iaa), (Iab), (Iba), (Ibb), (II), (IIa), (IIb), (IIaa) (IIab), (IIba), or (IIbb), $R^{21}$, $R^{22}$, and $R^{23}$ are each independently selected from hydrogen and $C_1$-$C_4$ alkyl. In some embodiments of Formula (I), (Ia), (Ib), (Iaa), (Iab), (Iba), (Ibb), (II), (IIa), (IIb), (IIaa) (IIab), (IIba), or (IIbb), $R^3$ is substituted $C_1$-$C_8$ alkyl, substituted $C_2$-$C_8$ alkenyl, substituted $C_2$-$C_8$ alkynyl, substituted $C_1$-$C_8$ heteroalkyl, wherein the alkyl, alkenyl, alkynyl or heteroalkyl is substituted with at least one substituent selected from substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, and substituted or unsubstituted bicyclic or polycyclic heteroaryl. In some embodiments of Formula (I), (Ia), (Ib), (Iaa), (Iab), (Iba), (Ibb), (II), (IIa), (IIb), (IIaa) (IIab), (IIba), or (IIbb), $R^3$ is —O$R^{11}$ or —S$R^{11}$, wherein $R^{11}$ is substituted $C_1$-$C_6$ alkyl, substituted $C_2$-$C_6$ alkenyl, substituted $C_2$-$C_6$ alkynyl, substituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl, wherein the alkyl, alkenyl, alkynyl or heteroalkyl is substituted with at least one substituent selected from substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, and substituted or unsubstituted bicyclic or polycyclic heteroaryl.

In some embodiments, provided herein is a stereoisomer of a compound of Formula (I), (Ia), (Ib), (Iaa), (Iab), (Iba), (Ibb), (II), (IIa), (IIb), (IIaa) (IIab), (IIba), or (IIbb).

In some embodiments, the compound is a compound of Table 1, or a pharmaceutically acceptable salt or solvate thereof. In some embodiments, the compound is a compound of Table 3, or a pharmaceutically acceptable salt or solvate thereof. In some embodiments, the compound is a compound of Formula (Iaa). In some embodiments, the compound is a compound of Formula (IIaa).

In some embodiments, the compound has a brain/blood AUC of at most about 0.0001, 0.001, 0.01, 0.1, 0.2, 0.3, 0.4, 0.5, 0.6, 0.7, 0.8, 0.9, 1, 2, 5, or 10.

In another aspect, the disclosure provides a pharmaceutical composition comprising a compound described herein and at least one pharmaceutically acceptable excipient. In some embodiments, the pharmaceutical composition is formulated for administration to a mammal by oral administration, intravenous administration, or subcutaneous administration. In some embodiments, the pharmaceutical composition is in the form of a tablet, a pill, a capsule, a liquid, a suspension, a dispersion, a solution, or an emulsion.

In another aspect, the disclosure provides a method a method of modulating glutaminyl-peptide cyclotransferase-like protein (QPCTL) activity in a subject, comprising administering to the subject a compound described herein, or a pharmaceutically acceptable salt or solvate thereof, or a pharmaceutical composition of described herein. In another aspect, the disclosure provides a method of inhibiting glutaminyl-peptide cyclotransferase-like protein (QPCTL) activity in a subject, comprising administering to the subject a compound described herein, or a pharmaceutically acceptable salt or solvate thereof, or a pharmaceutical composition described herein. In another aspect, the disclosure provides a method of treating a disease or condition in a subject in need thereof, comprising administering to the subject a therapeutically effective amount of a compound described herein, or a pharmaceutically acceptable salt or solvate thereof, or a pharmaceutical composition of described herein. In some embodiments, the disease or condition is associated with an aberrant glutaminyl-peptide cyclotransferase-like protein (QPCTL) activity. In some embodiments, the disease or condition that is associated with an aberrant QPCTL activity is a cancer. In another aspect, the disclosure provides a method of treating cancer in a subject in need thereof, the method comprising administering to the subject a therapeutically effective amount of a compound described herein, or a pharmaceutically acceptable salt or solvate thereof, or a pharmaceutical composition described herein.

In some embodiments, the cancer is leukemia, acute myeloid leukemia (AML), chronic myeloid leukemia, acute lymphoblastic leukemia (ALL), non-Hodgkin lymphoma (NHL), Hodgkin lymphoma (HL), multiple myeloma (MM) or myelodysplastic syndrome (MDS). In some embodiments, the cancer is AML. In some embodiments, the cancer is a solid cancer or a metastatic cancer. In some embodiments, the cancer is a skin cancer, ocular cancer, gastrointestinal cancer, thyroid cancer, breast cancer, ovarian cancer, central nervous system cancer, laryngeal cancer, cervical cancer, lymphatic system cancer, genitourinary tract cancer, bone cancer, biliary tract cancer, endometrial cancer, liver cancer, lung cancer, prostate cancer, or colon cancer.

In one aspect, described herein is a method of treating a disease or condition in a subject in need thereof, the method comprising administering a therapeutically effective amount of a herein described compound, or a pharmaceutically acceptable salt or solvate thereof, or a herein described pharmaceutical composition to the subject, wherein the disease or condition is a disease that engages innate immune system. In some embodiments, the disease is atherosclerosis, a fibrotic disease, ischemia-reperfusion injury, or an infectious disease caused by pathogens. In some embodiments, the disease is a fibrotic disease selected from liver fibrosis, pulmonary fibrosis, renal fibrosis and scleroderma. In some embodiments, the diseases are chronic kidney diseases including diabetic nephropathy and Focal Segmental Glomerulosclerosis (FSGS).

In one aspect, described herein is a method of treating a disease or condition in a subject in need thereof, the method comprising administering a therapeutically effective amount of a herein described compound, or a pharmaceutically acceptable salt or solvate thereof, or a herein described pharmaceutical composition to the subject, wherein the disease or condition is Kennedy's disease, duodenal cancer with or without *Helicobacter pylori* infections, Zolliger-Ellison syndrome, gastric cancer with or without *Helicobacter pylori* infections, pathogenic psychotic conditions, schizophrenia, infertility, neoplasia, inflammatory host responses, cancer, psoriasis, impaired humoral and cell-mediated immune responses, leukocyte adhesion and migration processes in the endothelium, impaired food intake, impaired sleep-wakefulness, impaired homeostatic regulation of energy metabolism, impaired autonomic function, impaired hormonal balance or impaired regulation of body fluids, multiple sclerosis, the Guillain-Barre syndrome, chronic inflammatory demyelinizing polyradiculoneuropathy, mild cognitive impairment, Alzheimer's disease, Familial British Dementia, Familial Danish Dementia, neurodegeneration in Down Syndrome, Huntington's disease, rheumatoid arthritis, pancreatitis and restenosis. In some embodiments, the method comprises administering a second therapeutic agent. In some embodiments, the second therapeutic agent is a monoclonal antibody. In some embodiments, the monoclonal antibody is selected from edrecolomab, rituximab, gemtuzumab ozogamicin, alemtuzumab, ibritumomab tiuxetan, tositumomab, cetuximab, bevacizumab, and trastuzumab. In some embodiments, the second therapeutic agent is an immune checkpoint inhibitor. In some embodiments, the immune checkpoint inhibitor is a CTLA-4 inhibitor, a PD-1 inhibitor, or a PD-L1 inhibitor. In some embodiments, the immune checkpoint inhibitor is Ipilimumab, Nivolumab, Pembrolizumab, Atezolizumab, Avelumab, Durvalumab or Cemiplimab.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

DETAILED DESCRIPTION OF THE INVENTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

A. Definitions

Unless defined otherwise, all technical and scientific terms used herein have the same meaning as is commonly understood by one of skill in the art to which this invention belongs. All patents and publications referred to herein are incorporated by reference.

"Alkyl" refers to a straight or branched hydrocarbon chain radical consisting solely of carbon and hydrogen atoms, containing no unsaturation, and preferably having from one to fifteen carbon atoms (i.e., $C_1$-$C_{15}$ alkyl). In certain embodiments, an alkyl comprises one to thirteen carbon atoms (i.e., $C_1$-$C_{13}$ alkyl). In certain embodiments, an alkyl comprises one to eight carbon atoms (i.e., $C_1$-$C_8$ alkyl). In other embodiments, an alkyl comprises one to five carbon atoms (i.e., $C_1$-$C_5$ alkyl). In other embodiments, an alkyl comprises one to four carbon atoms (i.e., $C_1$-$C_4$ alkyl). In other embodiments, an alkyl comprises one to three carbon atoms (i.e., $C_1$-$C_3$ alkyl). In other embodiments, an alkyl comprises one to two carbon atoms (i.e., $C_1$-$C_2$ alkyl). In other embodiments, an alkyl comprises one carbon atom (i.e., $C_1$ alkyl). In other embodiments, an alkyl comprises five to fifteen carbon atoms (i.e., $C_5$-$C_{15}$ alkyl). In other embodiments, an alkyl comprises five to eight carbon atoms (i.e., $C_5$-$C_8$ alkyl). In other embodiments, an alkyl comprises two to five carbon atoms (i.e., $C_2$-$C_8$ alkyl). In other embodiments, an alkyl comprises three to five carbon atoms (i.e., $C_3$-$C_8$ alkyl). In certain embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkyl is optionally substituted with oxo, halogen, —CN, —COOH, —COOMe, —OH, —OMe, —NH$_2$, or —NO$_2$. In some embodiments, the alkyl is optionally substituted with halogen, —CN, —OH, or —OMe. In some embodiments, the alkyl is optionally substituted with halogen.

The term "$C_{x-y}$" when used in conjunction with a chemical moiety, such as alkyl, alkenyl, or alkynyl is meant to include groups that contain from x to y carbons in the chain. For example, the term "$C_{1-6}$alkyl" refers to substituted or unsubstituted saturated hydrocarbon groups, including straight-chain alkyl and branched-chain alkyl groups that contain from 1 to 6 carbons. The term —$C_{x-y}$ alkylene-refers to a substituted or unsubstituted alkylene chain with from x to y carbons in the alkylene chain. For example —$C_{1-6}$ alkylene- may be selected from methylene, ethylene, propylene, butylene, pentylene, and hexylene, any one of which is optionally substituted. An alkenylene chain may have one double bond or more than one double bond in the alkenylene chain. The term —$C_{x-y}$ alkynylene- refers to a substituted or unsubstituted alkynylene chain with from x to y carbons in the alkenylene chain. For example, —$C_{2-6}$alkenylene- may be selected from ethynylene, propynylene, butynylene, pentynylene, and hexynylene, any one of which is optionally substituted. An alkynylene chain may have one triple bond or more than one triple bond in the alkynylene chain.

"Alkoxy" refers to a radical bonded through an oxygen atom of the formula —O-alkyl, where alkyl is an alkyl chain as defined above. Unless stated otherwise specifically in the specification, an alkoxy group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkoxy is optionally substituted with halogen, —CN, —COOH, COOMe, —OH, —OMe, —NH$_2$, or —NO$_2$. In some embodiments, the alkoxy is optionally substituted with halogen, —CN, —OH, or —OMe. In some embodiments, the alkoxy is optionally substituted with halogen.

"Alkenyl" refers to a straight or branched hydrocarbon chain radical group consisting solely of carbon and hydrogen atoms, containing at least one carbon-carbon double bond, and preferably having from two to twelve carbon atoms (i.e., $C_2$-$C_{12}$ alkenyl). In certain embodiments, an alkenyl comprises two to eight carbon atoms (i.e., $C_2$-$C_8$ alkenyl). In certain embodiments, an alkenyl comprises two to six carbon atoms (i.e., $C_2$-$C_6$ alkenyl). In other embodiments, an alkenyl comprises two to four carbon atoms (i.e., $C_2$-$C_4$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkenyl is optionally substituted with oxo, halogen, —CN, —COOH, —COOMe, —OH, —OMe, —NH$_2$, or —NO$_2$. In some embodiments, the alkenyl is optionally substituted with halogen, —CN, —OH, or —OMe. In some embodiments, the alkenyl is optionally substituted with halogen.

"Alkynyl" refers to a straight or branched hydrocarbon chain radical group consisting solely of carbon and hydrogen atoms, containing at least one carbon-carbon triple bond, and preferably having from two to twelve carbon atoms (i.e., $C_2$-$C_{12}$ alkynyl). In certain embodiments, an alkynyl comprises two to eight carbon atoms (i.e., $C_2$-$C_8$ alkynyl). In other embodiments, an alkynyl comprises two to six carbon atoms (i.e., $C_2$-$C_6$ alkynyl). In other embodiments, an alkynyl comprises two to four carbon atoms (i.e., $C_2$-$C_4$ alkynyl). The alkynyl is attached to the rest of the molecule by a single bond, for example, ethynyl, propynyl, butynyl, pentynyl, hexynyl, and the like. Unless stated otherwise specifically in the specification, an alkynyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkynyl is optionally substituted with oxo, halogen, —CN, —COOH, COOMe, —OH, —OMe, —NH$_2$, or —NO$_2$. In some embodiments, the alkynyl is optionally substituted with halogen, —CN, —OH, or —OMe. In some embodiments, the alkynyl is optionally substituted with halogen.

"Alkylene" or "alkylene chain" refers to a straight or branched divalent hydrocarbon chain linking the rest of the molecule to a radical group, consisting solely of carbon and hydrogen, containing no unsaturation, and preferably having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group may be through any two carbons within the chain. In certain embodiments, an alkylene comprises one to ten carbon atoms (i.e., $C_1$-$C_8$ alkylene). In certain embodiments, an alkylene comprises one to eight carbon atoms (i.e., $C_1$-$C_8$ alkylene). In other embodiments, an alkylene comprises one to five carbon atoms (i.e., $C_1$-$C_5$ alkylene). In other embodiments, an alkylene comprises one to four carbon atoms (i.e., $C_1$-$C_4$ alkylene). In other embodiments, an alkylene comprises one to three carbon atoms (i.e., $C_1$-$C_3$ alkylene). In other embodiments, an alkylene comprises one to two carbon atoms (i.e., $C_1$-$C_2$ alkylene). In other embodiments, an alkylene comprises one carbon atom (i.e., $C_1$ alkylene). In other embodiments, an alkylene comprises five to eight carbon atoms (i.e., $C_5$-$C_8$ alkylene). In other embodiments, an alkylene comprises two to five carbon atoms (i.e., $C_2$-$C_5$ alkylene). In other embodiments, an alkylene comprises three to five carbon atoms (i.e., $C_3$-$C_5$ alkylene). Unless stated otherwise specifically in the specification, an alkylene group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkylene is optionally substituted with oxo, halogen, —CN, —COOH, COOMe, —OH, —OMe, —NH$_2$, or —NO$_2$. In some embodiments, the alkylene is optionally substituted with halogen, —CN, —OH, or —OMe. In some embodiments, the alkylene is optionally substituted with halogen.

"Alkenylene" or "alkenylene chain" refers to a straight or branched divalent hydrocarbon chain linking the rest of the molecule to a radical group, consisting solely of carbon and hydrogen, containing at least one carbon-carbon double bond, and preferably having from two to twelve carbon atoms. The alkenylene chain is attached to the rest of the molecule through a single bond and to the radical group through a single bond. The points of attachment of the alkenylene chain to the rest of the molecule and to the radical group may be through any two carbons within the chain. In certain embodiments, an alkenylene comprises two to ten carbon atoms (i.e., $C_2$-$C_{10}$ alkenylene). In certain embodiments, an alkenylene comprises two to eight carbon atoms (i.e., $C_2$-$C_8$ alkenylene). In other embodiments, an alkenylene comprises two to five carbon atoms (i.e., $C_2$-$C_8$ alkenylene). In other embodiments, an alkenylene comprises two to four carbon atoms (i.e., $C_2$-$C_4$ alkenylene). In other embodiments, an alkenylene comprises two to three carbon atoms (i.e., $C_2$-$C_3$ alkenylene). In other embodiments, an alkenylene comprises two carbon atom (i.e., $C_2$ alkenylene). In other embodiments, an alkenylene comprises five to eight carbon atoms (i.e., $C_5$-$C_8$ alkenylene). In other embodiments, an alkenylene comprises three to five carbon atoms (i.e., $C_3$-$C_8$ alkenylene). Unless stated otherwise specifically in the specification, an alkenylene group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkenylene is optionally substituted with oxo, halogen, —CN, —COOH, COOMe, —OH, —OMe, —NH$_2$, or —NO$_2$. In some embodiments, the alkenylene is optionally substituted with halogen, —CN, —OH, or —OMe. In some embodiments, the alkenylene is optionally substituted with halogen.

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and preferably having from two to twelve carbon atoms. The alkynylene chain is attached to the rest of the molecule through a single bond and to the radical group through a single bond. The points of attachment of the alkynylene chain to the rest of the molecule and to the radical group may be through any two carbons within the chain. In certain embodiments, an alkynylene comprises two to ten carbon atoms (i.e., $C_2$-$C_{10}$ alkynylene). In certain embodiments, an alkynylene comprises two to eight carbon atoms (i.e., $C_2$-$C_8$ alkynylene). In other embodiments, an alkynylene comprises two to five carbon atoms (i.e., $C_2$-$C_8$ alkynylene). In other embodiments, an alkynylene comprises two to four carbon atoms (i.e., $C_2$-$C_4$ alkynylene). In other embodiments, an alkynylene comprises two to three carbon atoms (i.e., $C_2$-$C_3$ alkynylene). In other embodiments, an alkynylene comprises two carbon atom (i.e., $C_2$ alkynylene). In other embodiments, an alkynylene comprises five to eight carbon atoms (i.e., $C_5$-$C_8$ alkynylene). In other embodiments, an alkynylene comprises three to five carbon atoms (i.e., $C_3$-$C_8$ alkynylene). Unless stated otherwise specifically in the specification, an alkynylene group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkynylene is optionally substituted with oxo, halogen, —CN, —COOH, COOMe, —OH, —OMe, —NH$_2$, or —NO$_2$. In some embodiments, the alkynylene is optionally substituted with halogen, —CN, —OH, or —OMe. In some embodiments, the alkynylene is optionally substituted with halogen.

"Aryl" refers to a radical derived from an aromatic monocyclic or aromatic multicyclic hydrocarbon ring system by removing a hydrogen atom from a ring carbon atom. The aromatic monocyclic or aromatic multicyclic hydrocarbon ring system can contain only hydrogen and carbon and from five to eighteen carbon atoms, where at least one of the rings in the ring system is aromatic, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. The aryl radical may be a monocyclic, bicyclic, tricyclic or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl (phenyl). Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the aryl is optionally substituted with halogen, methyl, ethyl, —CN, —COOH, COOMe, —CF$_3$, —OH, —OMe, —NH$_2$, or —NO$_2$. In some embodiments, the aryl is optionally substituted with halogen, methyl, ethyl, —CN, —CF$_3$, —OH, or —OMe. In some embodiments, the aryl is optionally substituted with halogen.

"Aralkyl" refers to a radical of the formula —R$^c$-aryl where R$^c$ is an alkylene chain as defined above, for example, methylene, ethylene, and the like.

"Aralkenyl" refers to a radical of the formula —R$^6$-aryl where R$^d$ is an alkenylene chain as defined above. "Aralkynyl" refers to a radical of the formula —R$^e$-aryl, where R$^e$ is an alkynylene chain as defined above.

"Carbocycle" refers to a saturated, unsaturated or aromatic rings in which each atom of the ring is carbon. Carbocycle may include 3- to 10-membered monocyclic rings, 6- to 12-membered bicyclic rings, and 6- to 12-membered bridged rings. Each ring of a bicyclic carbocycle may be selected from saturated, unsaturated, and aromatic rings. An aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, are included in the definition of carbocyclic. Exemplary carbocycles include cyclopentyl, cyclohexyl, cyclohexenyl, adamantyl, phenyl, indanyl, and naphthyl. Unless stated otherwise specifically in the specification, a carbocycle may be optionally substituted.

"Cycloalkyl" refers to a fully saturated monocyclic or polycyclic hydrocarbon radical consisting solely of carbon and hydrogen atoms, which includes fused or bridged ring systems, and preferably having from three to twelve carbon atoms. In certain embodiments, a cycloalkyl comprises three to ten carbon atoms. In other embodiments, a cycloalkyl comprises five to seven carbon atoms. The cycloalkyl may be attached to the rest of the molecule by a single bond. Examples of monocyclic cycloalkyls include, e.g., cyclopropyl, cyclobutyl, cyclopentyl, cyclohexyl, cycloheptyl, and cyclooctyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1] heptanyl, and the like. Cycloalkyl may also refer to a partially saturated, monocyclic or polycyclic carbocyclic ring such as a cycloalkenyl. A cycloalkyl includes fused (when fused with an aryl or a heteroaryl ring, the cycloalkyl is bonded through a non-aromatic ring atom), spiro, or bridged ring systems. Representative cycloalkyls include, but are not limited to, cycloalkyls having from three to fifteen carbon atoms ($C_3$-$C_{15}$ cycloalkyl, including $C_3$-$C_{15}$ cycloalkenyl), from three to ten carbon atoms ($C_3$-$C_{10}$ cycloalkyl), from three to eight carbon atoms ($C_3$-$C_8$ cycloalkyl), from three to six carbon atoms ($C_3$-$C_6$ cycloalkyl), from three to five carbon atoms ($C_3$-$C_8$ cycloalkyl), or three to four carbon atoms ($C_3$-$C_4$ cycloalkyl). In some embodiments, the cycloalkyl is a 3- to 10-membered cycloalkyl, e.g., a 3- to 10-membered cycloalkenyl. In some embodiments, the cycloalkyl is a 3- to 6-membered cycloalkyl, e.g., a 3- to 6-membered cycloalkenyl. In some embodiments, the cycloalkyl is a 5- to 6-membered cycloalkyl, e.g., a 5- to 6-membered cycloalkenyl. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo [3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, a cycloalkyl is optionally substituted with oxo, halogen, methyl, ethyl, —CN, —COOH, COOMe, —CF$_3$, —OH, —OMe, —NH$_2$, or —NO$_2$. In some embodiments, a cycloalkyl is optionally substituted with oxo, halogen, methyl, ethyl, —CN, —CF$_3$, —OH, or —OMe. In some embodiments, the cycloalkyl is optionally substituted with halogen.

"Cycloalkenyl" refers to an unsaturated non-aromatic monocyclic or polycyclic hydrocarbon radical consisting solely of carbon and hydrogen atoms, which includes fused or bridged ring systems, preferably having from three to twelve carbon atoms and comprising at least one double bond. In certain embodiments, a cycloalkenyl comprises three to ten carbon atoms. In other embodiments, a cycloalkenyl comprises five to seven carbon atoms. The cycloalkenyl may be attached to the rest of the molecule by a single bond. Examples of monocyclic cycloalkenyls includes, e.g., cyclopentenyl, cyclohexenyl, cycloheptenyl, and cyclooctenyl.

"Cycloalkylalkyl" refers to a radical of the formula —R$^c$-cycloalkyl where R$^c$ is an alkylene chain as described above.

"Cycloalkylalkoxy" refers to a radical bonded through an oxygen atom of the formula —O—R$^c$-cycloalkyl where R$^c$ is an alkylene chain as described above.

"Halo" or "halogen" refers to halogen substituents such as bromo, chloro, fluoro and iodo substituents. In some embodiments, halogen is fluoro or chloro. In some embodiments, halogen is fluoro.

As used herein, the term "haloalkyl" or "haloalkane" refers to an alkyl radical, as defined above, that is substituted by one or more halogen radicals, for example, trifluoromethyl, dichloromethyl, bromomethyl, 2,2,2-trifluoroethyl, 1-fluoromethyl-2-fluoroethyl, and the like. In some embodiments, the alkyl part of the fluoroalkyl radical is optionally further substituted. Examples of halogen substituted alkanes ("haloalkanes") include halomethane (e.g., chloromethane, bromomethane, fluoromethane, iodomethane), di- and trihalomethane (e.g., trichloromethane, tribromomethane, trifluoromethane, triiodomethane), 1-haloethane, 2-haloethane, 1,2-dihaloethane, 1-halopropane, 2-halopropane, 3-halopropane, 1,2-dihalopropane, 1,3-dihalopropane, 2,3-dihalopropane, 1,2,3-trihalopropane, and any other suitable combinations of alkanes (or substituted alkanes) and halogens (e.g., Cl, Br, F, I, etc.). When an alkyl group is substituted with more than one halogen radicals, each halogen may be independently selected e.g., 1-chloro,2-fluoroethane.

"Fluoroalkyl" refers to an alkyl radical, as defined above, that is substituted by one or more fluoro radicals, for example, trifluoromethyl, difluoromethyl, fluoromethyl, 2,2, 2-trifluoroethyl, 1-fluoromethyl-2-fluoroethyl, and the like.

"Hydroxyalkyl" refers to an alkyl radical, as defined above, that is substituted by one or more hydroxyls. In some embodiments, the alkyl is substituted with one hydroxyl. In some embodiments, the alkyl is substituted with one, two, or three hydroxyls. Hydroxyalkyl include, for example, hydroxymethyl, hydroxyethyl, hydroxypropyl, hydroxybutyl, or hydroxypentyl. In some embodiments, the hydroxyalkyl is hydroxymethyl.

"Aminoalkyl" refers to an alkyl radical, as defined above, that is substituted by one or more amines. In some embodiments, the alkyl is substituted with one amine. In some embodiments, the alkyl is substituted with one, two, or three amines. Aminoalkyl include, for example, aminomethyl, aminoethyl, aminopropyl, aminobutyl, or aminopentyl. In some embodiments, the aminoalkyl is aminomethyl.

"Heteroalkyl" refers to an alkyl group in which one or more skeletal atoms of the alkyl are selected from an atom other than carbon, e.g., oxygen, nitrogen (e.g., —NH—, —N(alkyl)-), sulfur, phosphorus, or combinations thereof. A heteroalkyl is attached to the rest of the molecule at a carbon atom of the heteroalkyl. In one aspect, a heteroalkyl is a C$_1$-C$_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, phosphorus, or combinations thereof wherein the heteroalkyl is attached to the rest of the molecule at a carbon atom of the heteroalkyl. Examples of such heteroalkyl are, for example, —CH$_2$OCH$_3$, —CH$_2$CH$_2$OCH$_3$, —CH$_2$CH$_2$OCH$_2$CH$_2$OCH$_3$, —CH(CH$_3$)OCH$_3$, —CH$_2$NHCH$_3$, —CH$_2$N(CH$_3$)$_2$, —CH$_2$CH$_2$NHCH$_3$, or —CH$_2$CH$_2$N(CH$_3$)$_2$. Unless stated otherwise specifically in the specification, a heteroalkyl is optionally substituted for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —CF$_3$, —OH, —OMe, —NH$_2$, or —NO$_2$. In some embodiments, a heteroalkyl is optionally substituted with oxo, halogen, methyl, ethyl, —CN, —CF$_3$, —OH, or —OMe. In some embodiments, the heteroalkyl is optionally substituted with halogen.

"Heterocycloalkyl" refers to a 3- to 24-membered partially or fully saturated ring radical comprising 2 to 23 carbon atoms and from one to 8 heteroatoms selected from the group consisting of nitrogen, oxygen, phosphorous, silicon, and sulfur. In some embodiments, the heterocycloalkyl is fully saturated. In some embodiments, the heterocycloalkyl comprises one to three heteroatoms selected from the group consisting of nitrogen, oxygen, and sulfur. In some embodiments, the heterocycloalkyl comprises one to three heteroatoms selected from the group consisting of nitrogen and oxygen. In some embodiments, the heterocycloalkyl comprises one to three nitrogens. In some embodiments, the heterocycloalkyl comprises one or two nitrogens. In some embodiments, the heterocycloalkyl comprises one nitrogen. In some embodiments, the heterocycloalkyl comprises one nitrogen and one oxygen. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom), spiro, or bridged ring systems; and the nitrogen, carbon, or sulfur atoms in the heterocycloalkyl radical may be optionally oxidized; the nitrogen atom may be optionally quaternized. Representative heterocycloalkyls include, but are not limited to, heterocycloalkyls having from two to fifteen carbon atoms (C$_2$-C$_{15}$ heterocycloalkyl or C$_2$-C$_{15}$ heterocycloalkenyl), from two to ten carbon atoms (C$_2$-C$_{10}$ heterocycloalkyl or C$_2$-C$_{10}$ heterocycloalkenyl), from two to eight carbon atoms (C$_2$-C$_8$ heterocycloalkyl or C$_2$-C$_8$ heterocycloalkenyl), from two to seven carbon atoms (C$_2$-C$_7$ heterocycloalkyl or C$_2$-C$_7$ heterocycloalkenyl), from two to six carbon atoms (C$_2$-C$_6$ heterocycloalkyl or C$_2$-C$_7$ heterocycloalkenyl), from two to five carbon atoms (C$_2$-C$_8$ heterocycloalkyl or C$_2$-C$_8$ heterocycloalkenyl), or two to four carbon atoms (C$_2$-C$_4$ heterocycloalkyl or C$_2$-C$_4$ heterocycloalkenyl). Examples of such heterocycloalkyl radicals include, but are not limited to, aziridinyl, azetidinyl, oxetanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides and the oligosaccharides. In some embodiments, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). In some embodiments, the heterocycloalkyl is a 3- to 8-membered heterocycloalkyl. In some embodiments, the heterocycloalkyl is a 3- to 7-membered heterocycloalkyl. In some embodiments, the heterocycloalkyl is a 3- to 6-membered heterocycloalkyl. In some embodiments, the heterocycloalkyl is a 4- to 6-membered heterocycloalkyl. In some embodiments, the heterocycloalkyl is a 5- to 6-membered heterocycloalkyl. In some embodiments, the heterocycloalkyl is a 3- to 8-membered heterocycloalkenyl. In some embodiments, the heterocycloalkyl is a 3- to 7-membered heterocycloalkenyl. In some embodiments, the heterocycloalkyl is a 3- to 6-membered heterocycloalkenyl. In some embodiments, the heterocycloalkyl is a 4- to 6-membered heterocycloalkenyl. In some embodiments, the heterocycloalkyl is a 5- to 6-membered heterocycloalkenyl. Unless stated otherwise specifically in the specification, a heterocycloalkyl may be optionally substituted as described below, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heterocycloalkyl is optionally substituted with oxo, halogen, methyl, ethyl, —CN, —COOH, COOMe, —CF$_3$, —OH, —OMe, —NH$_2$, or —NO$_2$. In some embodiments, the heterocycloalkyl is optionally substituted with halogen, methyl, ethyl, —CN, —CF$_3$, —OH, or —OMe. In some embodiments, the heterocycloalkyl is optionally substituted with halogen.

"Heterocycle" refers to a saturated, unsaturated or aromatic ring comprising one or more heteroatoms. Exemplary heteroatoms include N, O, Si, P, B, and S atoms. Heterocycles include 3- to 10-membered monocyclic rings, 6- to 12-membered bicyclic rings, and 6- to 12-membered bridged rings. Each ring of a bicyclic heterocycle may be selected from saturated, unsaturated, and aromatic rings. "Heterocyclene" refers to a divalent heterocycle linking the rest of the molecule to a radical group.

"Heteroaryl" or "aromatic heterocycle" refers to a radical derived from a heteroaromatic ring radical that comprises one to eleven carbon atoms and at least one heteroatom wherein each heteroatom may be selected from N, O, and S. As used herein, the heteroaryl ring may be selected from monocyclic or bicyclic and fused or bridged ring systems rings wherein at least one of the rings in the ring system is aromatic, i.e., it contains a cyclic, delocalized (4n+2) π-electron system in accordance with the Hückel theory. The heteroatom(s) in the heteroaryl radical may be optionally oxidized. One or more nitrogen atoms, if present, are optionally quaternized. The heteroaryl may be attached to the rest of the molecule through any atom of the heteroaryl, valence permitting, such as a carbon or nitrogen atom of the heteroaryl. Examples of heteroaryls include, but are not limited to, pyridine, pyrimidine, oxazole, furan, thiophene, benzthiazole, and imdazopyridine. An "X-membered heteroaryl" refers to the number of endocylic atoms, i.e., X, in the ring. For example, a 5-membered heteroaryl ring or 5-membered aromatic heterocycle has 5 endocyclic atoms, e.g., triazole, oxazole, thiophene, etc. In some embodiments, the heteroaryl comprises one to three heteroatoms selected from the group consisting of nitrogen, oxygen, and sulfur. In some embodiments, the heteroaryl comprises one to three heteroatoms selected from the group consisting of nitrogen and oxygen. In some embodiments, the heteroaryl comprises one to three nitrogens. In some embodiments, the heteroaryl comprises one or two nitrogens. In some embodiments, the heteroaryl comprises one nitrogen. The heteroaryl radical may be a monocyclic, bicyclic, tricyclic or tetracyclic ring system, which may include fused (when fused with a cycloalkyl or heterocycloalkyl ring, the heteroaryl is bonded through an aromatic ring atom) or bridged ring systems; and the nitrogen, carbon or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. In some embodiments, the heteroaryl is a 6-membered heteroaryl. In some embodiments, the heteroaryl is a 5-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heteroaryl is optionally substituted with halogen, methyl, ethyl, —CN, —COOH, COOMe, —CF$_3$, —OH, —OMe, —NH$_2$, or —NO$_2$. In some embodiments, the heteroaryl is optionally substituted with halogen, methyl, ethyl, —CN, —CF$_3$, —OH, or —OMe. In some embodiments, the heteroaryl is optionally substituted with halogen.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc.).

The term "substituted" refers to moieties having substituents replacing a hydrogen on one or more carbons or substitutable heteroatoms, e.g., NH, of the structure. It will be understood that "substitution" or "substituted with" includes the implicit proviso that such substitution is in accordance with permitted valence of the substituted atom and the substituent, and that the substitution results in a stable compound, i.e., a compound which does not spontaneously undergo transformation such as by rearrangement, cyclization, elimination, etc. In certain embodiments, substituted refers to moieties having substituents replacing two hydrogen atoms on the same carbon atom, such as substituting the two hydrogen atoms on a single carbon with an oxo, imino or thioxo group. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms.

In some embodiments, substituents may include any substituents described herein, for example: halogen, hydroxy, oxo (=O), thioxo (=S), cyano (—CN), nitro (—NO$_2$), imino (=N—H), oximo (=N—OH), hydrazino (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$) C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2), and —R$^b$—S(O)$_t$N(R$^a$)$_2$ (where t is 1 or 2); and alkyl, alkenyl, alkynyl, aryl, aralkyl, aralkenyl, aralkynyl, cycloalkyl, cycloalkylalkyl, and heterocycle, any of which may be optionally substituted by alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$) C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); wherein each R$^a$ is independently selected from hydrogen, alkyl, cycloalkyl, cycloalkylalkyl, aryl, aralkyl, and heterocycle, wherein each R$^a$, valence permitting, may be optionally substituted with alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2) and —R$^b$—S(O)$_t$N(R$^a$)$_2$ (where t is 1 or 2); and wherein each R$^b$ is independently selected from a direct bond or a straight or branched alkylene, alkenylene, or alkynylene chain, and each R$^c$ is a straight or branched alkylene, alkenylene or alkynylene chain.

As used in the specification and claims, the singular form "a", "an" and "the" includes plural references unless the context clearly dictates otherwise.

The term "salt" or "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In certain embodiments, the term "prevent" or "preventing" as related to a disease or disorder may refer to a compound that, in a statistical sample, reduces the occurrence of the disorder or condition in the treated sample relative to an untreated control sample, or delays the onset or reduces the severity of one or more symptoms of the disorder or condition relative to the untreated control sample.

The terms "treat," "treating" or "treatment," as used herein, may include alleviating, abating or ameliorating a disease or condition symptoms, preventing additional symptoms, ameliorating or preventing the underlying causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

B. Compounds of the Disclosure

In one aspect, the disclosure provides a compound represented by Formula (I), or a pharmaceutically acceptable salt or solvate thereof.

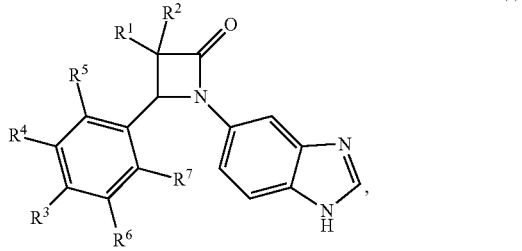

Formula (I)

$R^1$ is halogen, —OH, —OR$^{10a}$, —SR$^{10a}$, —CN, amino, —NR$^{22}$R$^{23}$, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, or substituted or unsubstituted $C_2$-$C_7$ heterocycloalkyl, and $R^2$ is H, halogen, —OH, —OR$^{10b}$, substituted or unsubstituted $C_1$-$C_6$ alkyl, or substituted or unsubstituted $C_1$-$C_6$ heteroalkyl; or $R^1$ and $R^2$ taken together with the carbon atom to which they are attached form a 3-7 membered cyclic or heterocyclic ring; or $R^1$ and $R^2$ taken together form an oxo or a double bond to CR$^{12a}$R$^{12b}$, wherein R$^{12a}$ and R$^{12b}$ are each independently hydrogen, halogen, —OH, amino, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

each of $R^4$, $R^5$, $R^6$, and $R^7$ is independently selected from H and halogen;

$R^3$ is —OR$^{11}$, halogen, —SR$^{11}$, —S(=O)R$^{21}$, —S(=O)$_2$R$^{21}$, —NHS(=O)$_2$R$^{21}$, —S(=O)$_2$NR$^{22}$R$^{23}$, —C(=O)R$^{21}$, —OC(=O)R$^{21}$, —C(=O)OR$^{22}$, —OC(=O)OR$^{22}$, —C(=O)NR$^{22}$R$^{23}$, —OC(=O)NR$^{22}$R$^{23}$, —NR$^{22}$R$^{23}$, —NO$_2$, —NHS(=O)$_2$R$^{21}$, —NR$^{22}$C(=O)NR$^{22}$R$^{23}$, —NR$^{22}$C(=O)R$^{21}$, —NR$^{22}$C(=O)OR$^{21}$, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted $C_1$-$C_8$ heteroalkyl, substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl;

R$^{10a}$ and R$^{10b}$ are each independently substituted or unsubstituted $C_1$-$C_6$ alkyl, substituted or unsubstituted $C_2$-$C_6$ alkenyl, substituted or unsubstituted $C_2$-$C_6$ alkynyl, or substituted or unsubstituted $C_1$-$C_6$ heteroalkyl; and R$^{11}$ is substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl; and R$^{21}$, R$^{22}$, and R$^{23}$ are each independently hydrogen, $C_1$-$C_6$ alkyl, $C_1$-$C_6$ heteroalkyl, $C_3$-$C_8$ cycloalkyl, or $C_2$-$C_7$ heterocycloalkyl, wherein each of the alkyl, heteroalkyl, cycloalkyl, or heterocycloalkyl is optionally substituted.

In another aspect, the disclosure provides for a compound represented by Formula (I), or a pharmaceutically acceptable salt or solvate thereof:

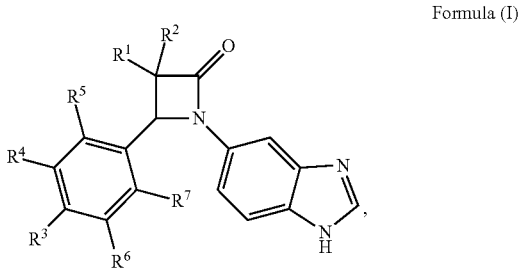

Formula (I)

wherein, $R^1$ is H, halogen, —OH, —OR$^{10a}$, —SR$^{10a}$, —CN, amino, —NR$^{22}$R$^{23}$, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, or substituted or unsubstituted $C_2$-$C_7$ heterocycloalkyl, and $R^2$ is H, halogen, —OH, —OR$^{10b}$, substituted or unsubstituted $C_1$-$C_6$ alkyl, or substituted or unsubstituted $C_1$-$C_6$ heteroalkyl; or $R^1$ and $R^2$ taken together with the carbon atom to which they are attached form a 3-7 membered cyclic or heterocyclic ring; or $R^1$ and $R^2$ taken together form an oxo or a double bond to CR$^{12a}$R$^{12b}$, wherein R$^{12a}$ and R$^{12b}$ are each independently hydrogen, halogen, —OH, amino, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

each of $R^4$, $R^5$, $R^6$, and $R^7$ is independently selected from H and halogen;

$R^3$ is —$OR^{11}$, —$SR^{11}$, —$S(=O)R^{21}$, —$S(=O)_2R^{21}$, —$NHS(=O)_2R^{21}$, —$S(=O)_2NR^{22}R^{23}$, —$C(=O)R^{21}$, —$OC(=O)R^{21}$, —$C(=O)OR^{22}$, —$OC(=O)OR^{22}$, —$C(=O)NR^{22}R^{23}$, —$OC(=O)NR^{22}R^{23}$, —$NR^{22}R^{23}$, —$NO_2$, —$NHS(=O)_2R^{21}$, —$NR^{22}C(=O)NR^{22}R^{23}$, —$NR^{22}C(=O)R^{21}$, —$NR^{22}C(=O)OR^{21}$, substituted $C_1$-$C_8$ alkyl, substituted $C_2$-$C_8$ alkenyl, substituted $C_2$-$C_8$ alkynyl, substituted $C_1$-$C_8$ heteroalkyl, substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl, wherein the alkyl, alkenyl, alkynyl or heteroalkyl is substituted with at least one substituent selected from substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, and substituted or unsubstituted bicyclic or polycyclic heteroaryl;

$R^{10a}$ and $R^{10b}$ are each independently substituted or unsubstituted $C_1$-$C_6$ alkyl, substituted or unsubstituted $C_2$-$C_6$ alkenyl, substituted or unsubstituted $C_2$-$C_6$ alkynyl, or substituted or unsubstituted $C_1$-$C_6$ heteroalkyl;

$R^{11}$ is substituted $C_1$-$C_6$ alkyl, substituted $C_2$-$C_6$ alkenyl, substituted $C_2$-$C_6$ alkynyl, substituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl, wherein the alkyl, alkenyl, alkynyl or heteroalkyl is substituted with at least one substituent selected from substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, and substituted or unsubstituted bicyclic or polycyclic heteroaryl; and $R^{21}$, $R^{22}$, and $R^{23}$ are each independently hydrogen, $C_1$-$C_6$ alkyl, $C_1$-$C_6$ heteroalkyl, $C_3$-$C_8$ cycloalkyl, or $C_2$-$C_7$ heterocycloalkyl, wherein each of the alkyl, heteroalkyl, cycloalkyl, or heterocycloalkyl is optionally substituted.

In another aspect, the disclosure provides for a compound represented by Formula (I), or a pharmaceutically acceptable salt or solvate thereof:

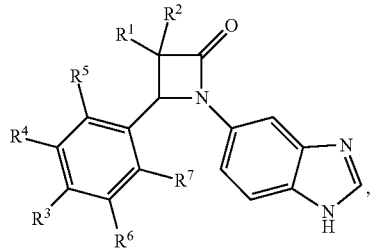

Formula (I)

wherein, $R^1$ is H, halogen, —OH, —$OR^{10a}$, —$SR^{10a}$, —CN, amino, —$NR^{22}R^{23}$, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, or unsubstituted $C_3$-$C_8$ cycloalkyl, or substituted or unsubstituted $C_2$-$C_7$ heterocycloalkyl, and $R^2$ is H, halogen, —OH, —$OR^{10b}$, substituted or unsubstituted $C_1$-$C_6$ alkyl, or substituted or unsubstituted $C_1$-$C_6$ heteroalkyl; or $R^1$ and $R^2$ taken together with the carbon atom to which they are attached form a 3-7 membered cyclic or heterocyclic ring; or $R^1$ and $R^2$ taken together form an oxo or a double bond to $CR^{12a}R^{12b}$, wherein $R^{12a}$ and $R^{12b}$ are each independently hydrogen, halogen, —OH, amino, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

each of $R^4$, $R^5$, $R^6$, and $R^7$ is independently selected from H and halogen;

$R^3$ is —$OR^{11}$, —$SR^{11}$, —$S(=O)R^{21}$, —$S(=O)_2R^{21}$, —$NHS(=O)_2R^{21}$, —$S(=O)_2NR^{22}R^{23}$, —$C(=O)R^{21}$, —$OC(=O)R^{21}$, —$C(=O)OR^{22}$, —$OC(=O)OR^{22}$, —$C(=O)NR^{22}R^{23}$, —$OC(=O)NR^{22}R^{23}$, —$NR^{22}R^{23}$, —$NO_2$, —$NHS(=O)_2R^{21}$, —$NR^{22}C(=O)NR^{22}R^{23}$, —$NR^{22}C(=O)R^{21}$, —$NR^{22}C(=O)OR^{21}$, substituted $C_1$-$C_8$ alkyl, substituted $C_2$-$C_8$ alkenyl, substituted $C_2$-$C_8$ alkynyl, substituted $C_1$-$C_8$ heteroalkyl, substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl;

$R^{10a}$ and $R^{10b}$ are each independently substituted or unsubstituted $C_1$-$C_6$ alkyl, substituted or unsubstituted $C_2$-$C_6$ alkenyl, substituted or unsubstituted $C_2$-$C_6$ alkynyl, or substituted or unsubstituted $C_1$-$C_6$ heteroalkyl;

$R^{11}$ is substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl; and $R^{21}$, $R^{22}$, and $R^{23}$ are each independently hydrogen, $C_1$-$C_6$ alkyl, $C_1$-$C_6$ heteroalkyl, $C_3$-$C_8$ cycloalkyl, or $C_2$-$C_7$ heterocycloalkyl, wherein each of the alkyl, heteroalkyl, cycloalkyl, or heterocycloalkyl is optionally substituted.

In some embodiments of Formula (I), wherein:
$R^1$ is H, halogen, —OH, —OR$^{10a}$, —SR$^{10a}$, —CN, amino, —NR$^{22}$R$^{23}$, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, or substituted or unsubstituted $C_2$-$C_7$ heterocycloalkyl, and $R^3$ is —SR$^{11}$, SF$_5$, —S(=O)R$^{21}$, —S(=O)$_2$R$^{21}$, —NHS(=O)$_2$R$^{21}$, —N=S(=O)R$^{22}$R$^{23}$, —S(=O)$_2$NR$^{22}$R$^{23}$, —S(=O)(NR$^{21}$)R$^{21}$, —C(=O)R$^{21}$, —OC(=O)R$^{21}$, —C(=O)OR$^{22}$, —OC(=O)OR$^{22}$, —C(=O)NR$^{22}$R$^{23}$, —OC(=O)NR$^{22}$R$^{23}$, —NR$^{22}$R$^{23}$, —NO$_2$, —NHS(=O)$_2$R$^{21}$, —NR$^{22}$C(=O)NR$^{22}$R$^{23}$, —NR$^{22}$C(=O)R$^{21}$, —NR$^{22}$C(=O)OR$^{21}$, —P(=O)R$^{22}$R$^{23}$, substituted $C_1$-$C_8$ alkyl, substituted $C_2$-$C_8$ alkenyl, substituted $C_2$-$C_8$ alkynyl, substituted $C_1$-$C_8$ heteroalkyl, substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl, wherein the alkyl, alkenyl, alkynyl or heteroalkyl is substituted with at least one substituent selected from substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, and substituted or unsubstituted bicyclic or polycyclic heteroaryl; and $R^{11}$ is substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl.

In some embodiments of Formula (I), wherein:
$R^1$ is H, halogen, —OH, —OR$^{10a}$, —SR$^{10a}$, —CN, amino, —NR$^{22}$R$^{23}$, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, or substituted or unsubstituted $C_2$-$C_7$ heterocycloalkyl, and $R^3$ is —OR$^{11}$, —SR$^{11}$, SF$_5$, —S(=O)R$^{21}$, —S(=O)$_2$R$^{21}$, —NHS(=O)$_2$R$^{21}$, —N=S(=O)R$^{22}$R$^{23}$, —S(=O)$_2$NR$^{22}$R$^{23}$, —S(=O)(NR$^{21}$)R$^{21}$, —C(=O)R$^{21}$, —OC(=O)R$^{21}$, —C(=O)OR$^{22}$, —OC(=O)OR$^{22}$, —C(=O)NR$^{22}$R$^{23}$, —OC(=O)NR$^{22}$R$^{23}$, —NR$^{22}$R$^{23}$, —NO$_2$, —NHS(=O)$_2$R$^{21}$, —NR$^{22}$C(=O)NR$^{22}$R$^{23}$, —NR$^{22}$C(=O)R$^{21}$, —NR$^{22}$C(=O)OR$^{21}$, —P(=O)R$^{22}$R$^{23}$, substituted $C_1$-$C_8$ alkyl, substituted $C_2$-$C_8$ alkenyl, substituted $C_2$-$C_8$ alkynyl, substituted $C_1$-$C_8$ heteroalkyl, substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl, wherein the alkyl, alkenyl, alkynyl or heteroalkyl is substituted with at least one substituent selected from substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, and substituted or unsubstituted bicyclic or polycyclic heteroaryl, and wherein when $R^3$ is —OR$^{11}$, $R^{11}$ is substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl.

In another aspect, the disclosure provides for a compound represented by Formula (I), a stereoisomer, or a pharmaceutically acceptable salt or solvate thereof:

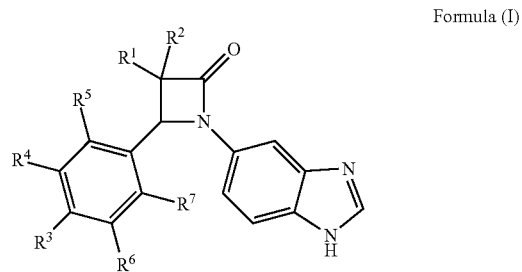

Formula (I)

wherein,
$R^1$ is halogen, —OH, —OR$^{10a}$, —SR$^{10a}$, —CN, amino, —NR$^{22}$R$^{23}$, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, or substituted or unsubstituted $C_2$-$C_7$ heterocycloalkyl, and $R^2$ is H, halogen, —OH, —OR$^{10b}$, substituted or unsubstituted $C_1$-$C_6$ alkyl, or substituted or unsubstituted $C_1$-$C_6$ heteroalkyl; or $R^1$ and $R^2$ taken together with the carbon atom to which they are attached form a 3-7 membered cyclic or heterocyclic ring; or $R^1$ and $R^2$ taken together form an oxo or a double bond to CR$^{12a}$R$^{12b}$, wherein R$^{12a}$ and R$^{12b}$ are each independently hydrogen, halogen, —OH, amino, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

each of $R^4$, $R^5$, $R^6$, and $R^7$ is independently selected from H, halogen and substituted or unsubstituted $C_1$-$C_6$ alky;

$R^3$ is —OR$^{11}$, halogen, —SR$^{11}$, SF$_5$, —S(=O)R$^{21}$, —S(=O)$_2$R$^{21}$, —NHS(=O)$_2$R$^{21}$, —N=S(=O)R$^{22}$R$^{23}$, —S(=O)$_2$NR$^{22}$R$^{23}$, —S(=O)(NR$^{21}$)R$^{21}$, —C(=O)R$^{21}$, —OC(=O)R$^{21}$, —C(=O)OR$^{22}$, —OC(=O)OR$^{22}$, —C(=O)NR$^{22}$R$^{23}$, —OC(=O)NR$^{22}$R$^{23}$, —NR$^{22}$R$^{23}$, —NO$_2$, —NHS(=O)$_2$R$^{21}$, —NR$^{22}$C (=O)NR$^{22}$R$^{23}$, —NR$^{22}$C(=O)R$^{21}$, —NR$^{22}$C(=O)OR$^{21}$, —P(=O)R$^{22}$R$^{23}$, substituted or unsubstituted C$_1$-C$_8$ alkyl, substituted or unsubstituted C$_2$-C$_8$ alkenyl, substituted or unsubstituted C$_2$-C$_8$ alkynyl, substituted or unsubstituted C$_1$-C$_8$ heteroalkyl, substituted or unsubstituted C$_3$-C$_8$ cycloalkyl, substituted or unsubstituted C$_2$-C$_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl;

R$^{10a}$ and R$^{10b}$ are each independently substituted or unsubstituted C$_1$-C$_6$ alkyl, substituted or unsubstituted C$_2$-C$_6$ alkenyl, substituted or unsubstituted C$_2$-C$_6$ alkynyl, or substituted or unsubstituted C$_1$-C$_6$ heteroalkyl; and R$^{11}$ is substituted or unsubstituted C$_1$-C$_6$ alkyl, substituted or unsubstituted C$_2$-C$_6$ alkenyl, substituted or unsubstituted C$_2$-C$_6$ alkynyl, substituted or unsubstituted C$_1$-C$_6$ heteroalkyl, substituted or unsubstituted C$_3$-C$_8$ cycloalkyl, substituted or unsubstituted C$_2$-C$_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl; and R$^{21}$, R$^{22}$, and R$^{23}$ are each independently hydrogen, C$_1$-C$_6$ alkyl, C$_1$-C$_6$ heteroalkyl, C$_3$-C$_8$ cycloalkyl, or C$_2$-C$_7$ heterocycloalkyl, wherein each of the alkyl, heteroalkyl, cycloalkyl, or heterocycloalkyl is optionally substituted.

In another aspect, the disclosure provides for a compound represented by Formula (I), a stereoisomer, or a pharmaceutically acceptable salt or solvate thereof:

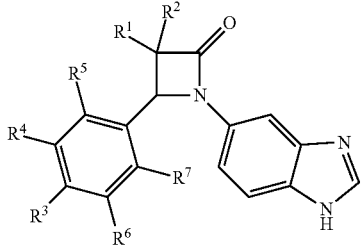

Formula (I)

R$^1$ is H, halogen, —OH, —OR$^{10a}$, —SR$^{10a}$, —CN, amino, —NR$^{22}$R$^{23}$, substituted or unsubstituted C$_1$-C$_6$ alkyl, substituted or unsubstituted C$_2$-C$_6$ alkenyl, substituted or unsubstituted C$_2$-C$_6$ alkynyl, substituted or unsubstituted C$_1$-C$_6$ heteroalkyl, substituted or unsubstituted C$_3$-C$_6$ cycloalkyl, or substituted or unsubstituted C$_2$-C$_7$ heterocycloalkyl, and R$^2$ is H, halogen, —OH, —OR$^{10b}$, substituted or unsubstituted C$_1$-C$_6$ alkyl, or substituted or unsubstituted C$_1$-C$_6$ heteroalkyl; or R$^1$ and R$^2$ taken together with the carbon atom to which they are attached form a 3-7 membered cyclic or heterocyclic ring; or R$^1$ and R$^2$ taken together form an oxo or a double bond to CR$^{12a}$R$^{12b}$, wherein R$^{12a}$ and R$^{12b}$ are each independently hydrogen, halogen, —OH, amino, substituted or unsubstituted C$_1$-C$_6$ alkyl, substituted or unsubstituted C$_2$-C$_6$ alkenyl, substituted or unsubstituted C$_2$-C$_6$ alkynyl, substituted or unsubstituted C$_1$-C$_6$ heteroalkyl, substituted or unsubstituted C$_3$-C$_8$ cycloalkyl, substituted or unsubstituted C$_2$-C$_7$ heterocycloalkyl, substituted or unsubstituted aryl, or substituted or unsubstituted heteroaryl;

each of R$^4$, R$^5$, R$^6$, and R$^7$ is independently selected from H, —OR$^{11}$, —NR$^{22}$R$^{23}$, halogen, and substituted or unsubstituted C$_1$-C$_6$ alky;

R$^3$ is —OR$^{11}$, —SR$^{11}$, SF$_5$, —S(=O)R$^{21}$, —S(=O)$_2$R$^{21}$, —NHS(=O)$_2$R$^{21}$, —N=S(=O)R$^{22}$R$^{23}$, —S(=O)$_2$NR$^{22}$R$^{23}$, —S(=O)(NR$^{21}$)R$^{21}$, —C(=O)R$^{21}$, —OC(=O)R$^{21}$, —C(=O)OR$^{22}$, —OC(=O)OR$^{22}$, —C(=O)NR$^{22}$R$^{23}$, —OC(=O)NR$^{22}$R$^{23}$, —NR$^{22}$R$^{23}$, —NO$_2$, —NHS(=O)$_2$R$^{21}$, —NR$^{22}$C(=O)NR$^{22}$R$^{23}$, —NR$^{22}$C(=O)R$^{21}$, —NR$^{22}$C(=O)OR$^{21}$, —P(=O)R$^{22}$R$^{23}$, substituted C$_1$-C$_8$ alkyl, substituted C$_2$-C$_8$ alkenyl, substituted C$_2$-C$_8$ alkynyl, substituted C$_1$-C$_8$ heteroalkyl, substituted or unsubstituted C$_3$-C$_8$ cycloalkyl, substituted or unsubstituted C$_2$-C$_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl, wherein the alkyl, alkenyl, alkynyl or heteroalkyl is substituted with at least one substituent selected from substituted or unsubstituted C$_3$-C$_8$ cycloalkyl, substituted or unsubstituted C$_2$-C$_7$ heterocycloalkyl, substituted or unsubstituted phenyl, substituted or unsubstituted naphthyl, substituted or unsubstituted monocyclic heteroaryl, and substituted or unsubstituted bicyclic or polycyclic heteroaryl;

R$^{10a}$ and R$^{10b}$ are each independently substituted or unsubstituted C$_1$-C$_6$ alkyl, substituted or unsubstituted C$_2$-C$_6$ alkenyl, substituted or unsubstituted C$_2$-C$_6$ alkynyl, or substituted or unsubstituted C$_1$-C$_6$ heteroalkyl;

R$^{11}$ is substituted C$_1$-C$_6$ alkyl, substituted C$_2$-C$_6$ alkenyl, substituted C$_2$-C$_6$ alkynyl, substituted C$_1$-C$_6$ heteroalkyl, substituted or unsubstituted C$_3$-C$_8$ cycloalkyl, substituted or unsubstituted C$_2$-C$_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl, wherein the alkyl, alkenyl, alkynyl or heteroalkyl is substituted with at least one substituent selected from substituted or unsubstituted C$_3$-C$_8$ cycloalkyl, substituted or unsubstituted C$_2$-C$_7$ heterocycloalkyl, substituted or unsubstituted phenyl, substituted or unsubstituted naphthyl, substituted or unsubstituted monocyclic heteroaryl, and substituted or unsubstituted bicyclic or polycyclic heteroaryl; and R$^{21}$, R$^{22}$, and R$^{23}$ are each independently hydrogen, C$_1$-C$_6$ alkyl, C$_1$-C$_6$ heteroalkyl, C$_3$-C$_8$ cycloalkyl, or C$_2$-C$_7$ heterocycloalkyl, wherein each of the alkyl, heteroalkyl, cycloalkyl, or heterocycloalkyl is optionally substituted.

In some embodiments, the compound of Formula (I) is represented by Formula (Ia), or a pharmaceutically acceptable salt or solvate thereof:

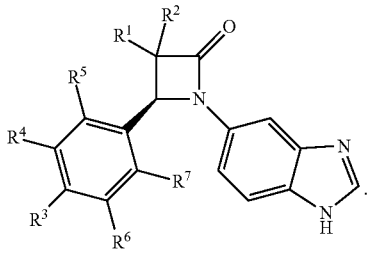

Formula (Ia)

In some embodiments, the compound of Formula (I) is represented by Formula (Ib), or a pharmaceutically acceptable salt or solvate thereof:

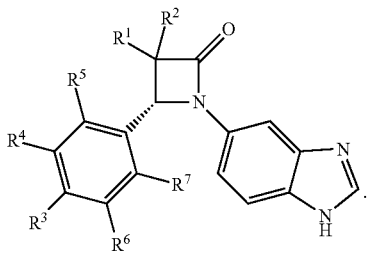

Formula (Ib)

In some embodiments, the compound of Formula (I) is represented by Formula (Iaa), or a pharmaceutically acceptable salt or solvate thereof:

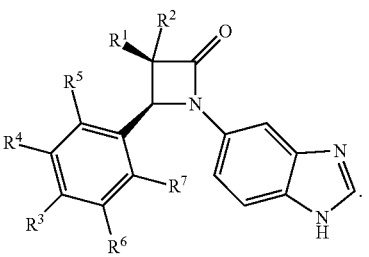

Formula (Iaa)

In some embodiments, the compound of Formula (I) is represented by Formula (Iab), or a pharmaceutically acceptable salt or solvate thereof:

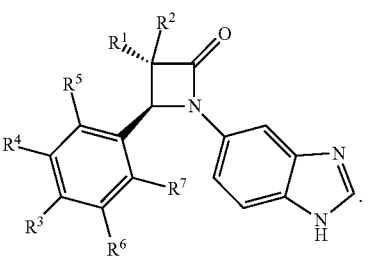

Formula (Iab)

In some aspects, the compound of Formula (I) is represented by Formula (Iba), or a pharmaceutically acceptable salt or solvate thereof:

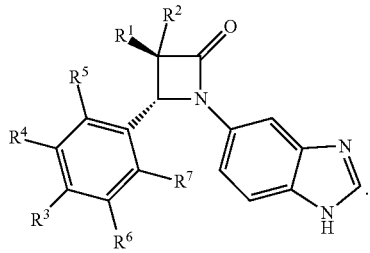

Formula (Iba)

In some embodiments, the compound of Formula (I) is represented by Formula (Ibb), or a pharmaceutically acceptable salt or solvate thereof:

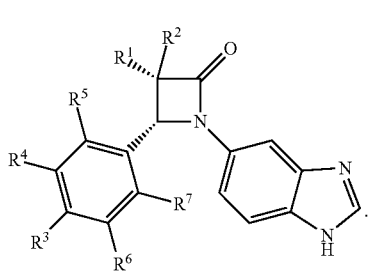

Formula (Ibb)

In another aspect, the disclosure provides for a stereoisomer compound represented by Formula (Ia), or a pharmaceutically acceptable salt or solvate thereof:

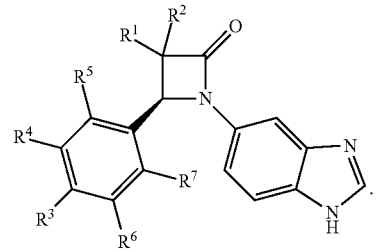

Formula (Ia)

wherein, $R^1$ is halogen, —OH, —$OR^{10a}$, —$SR^{10a}$, —CN, amino, —$NR^{22}R^{23}$, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, or substituted or unsubstituted $C_2$-$C_7$ heterocycloalkyl, and $R^2$ is H, halogen, —OH, —$OR^{10b}$, substituted or unsubstituted $C_1$-$C_6$ alkyl, or substituted or unsubstituted $C_1$-$C_6$ heteroalkyl; or $R^1$ and $R^2$ taken together with the carbon atom to which they are attached form a 3-7 membered cyclic or heterocyclic ring; or $R^1$ and $R^2$ taken together form an oxo or a double bond to $CR^{12a}R^{12b}$, wherein $R^{12a}$ and $R^{12b}$ are each independently hydrogen, halogen, —OH, amino, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

each of $R^4$, $R^5$, $R^6$, and $R^7$ is independently selected from H, halogen and substituted or unsubstituted $C_1$-$C_6$ alky;

$R^3$ is —$OR^{11}$, halogen, —$SR^{11}$, $SF_5$, —$S(=O)R^{21}$, —$S(=O)_2R^{21}$, —$NHS(=O)_2R^{21}$, —$N=S(=O)R^{22}R^{23}$, —$S(=O)_2NR^{22}R^{23}$, —$S(=O)(NR^{21})R^{21}$, —$C(=O)R^{21}$, —$OC(=O)R^{21}$, —$C(=O)OR^{22}$, —$OC(=O)OR^{22}$, —$C(=O)NR^{22}R^{23}$, —$OC(=O)NR^{22}R^{23}$, —$NR^{22}R^{23}$, —$NO_2$, —$NHS(=O)_2R^{21}$, —$NR^{22}C(=O)NR^{22}R^{23}$, —$NR^{22}C(=O)R^{21}$, —$NR^{22}C(=O)OR^{21}$, —$P(=O)R^{22}R^{23}$, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted $C_1$-$C_8$ heteroalkyl, substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl;

$R^{11a}$ and $R^{11b}$ are each independently substituted or unsubstituted $C_1$-$C_6$ alkyl, substituted or unsubstituted $C_2$-$C_6$ alkenyl, substituted or unsubstituted $C_2$-$C_6$ alkynyl, or substituted or unsubstituted $C_1$-$C_6$ heteroalkyl; and $R^{11}$ is substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl; and $R^{21}$, $R^{22}$, and $R^{23}$ are each independently hydrogen, $C_1$-$C_6$ alkyl, $C_1$-$C_6$ heteroalkyl, $C_3$-$C_8$ cycloalkyl, or $C_2$-$C_7$ heterocycloalkyl, wherein each of the alkyl, heteroalkyl, cycloalkyl, or heterocycloalkyl is optionally substituted.

In another aspect, the disclosure provides for a stereoisomer compound represented by Formula (Iaa), or a pharmaceutically acceptable salt or solvate thereof:

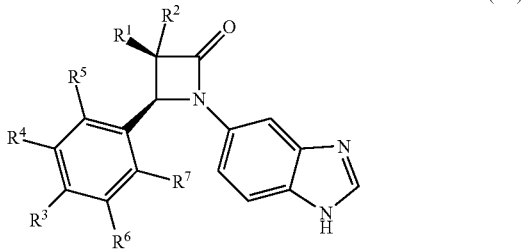

Formula (Iaa)

wherein, $R^1$ is halogen, —OH, —$OR^{10a}$, —$SR^{10a}$, —CN, amino, —$NR^{22}R^{23}$, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, or substituted or unsubstituted $C_2$-$C_7$ heterocycloalkyl, and $R^2$ is H, halogen, —OH, —$OR^{10b}$, substituted or unsubstituted $C_1$-$C_6$ alkyl, or substituted or unsubstituted $C_1$-$C_6$ heteroalkyl; or $R^1$ and $R^2$ taken together form an oxo or a double bond to $CR^{12a}R^{12b}$, wherein $R^{12a}$ and $R^{12b}$ are each independently hydrogen, halogen, —OH, amino, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

each of $R^4$, $R^5$, $R^6$, and $R^7$ is independently selected from H, —$OR^{11}$, —$NR^{22}R^{23}$, halogen, and substituted or unsubstituted $C_1$-$C_6$ alky;

$R^3$ is —$OR^{11}$, halogen, —$SR^{11}$, $SF_5$, —$S(=O)R^{21}$, —$S(=O)_2R^{21}$, —$NHS(=O)_2R^{21}$, —$N=S(=O)R^{22}R^{23}$, —$S(=O)_2NR^{22}R^{23}$, —$S(=O)(NR^{21})R^{21}$, —$C(=O)R^{21}$, —$OC(=O)R^{21}$, —$C(=O)OR^{22}$, —$OC(=O)OR^{22}$, —$C(=O)NR^{22}R^{23}$, —$OC(=O)NR^{22}R^{23}$, —$NR^{22}R^{23}$, —$NO_2$, —$NHS(=O)_2R^{21}$, —$NR^{22}C(=O)NR^{22}R^{23}$, —$NR^{22}C(=O)R^{21}$, —$NR^{22}C(=O)OR^{21}$, —$P(=O)R^{22}R^{23}$, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted $C_1$-$C_8$ heteroalkyl, substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl;

$R^{10a}$ and $R^{10b}$ are each independently substituted or unsubstituted $C_1$-$C_6$ alkyl, substituted or unsubstituted $C_2$-$C_6$ alkenyl, substituted or unsubstituted $C_2$-$C_6$ alkynyl, or substituted or unsubstituted $C_1$-$C_6$ heteroalkyl; and $R^{11}$ is substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl; and $R^{21}$, $R^{22}$, and $R^{23}$ are each independently hydrogen, $C_1$-$C_6$ alkyl, $C_1$-$C_6$ heteroalkyl, $C_3$-$C_8$ cycloalkyl, or $C_2$-$C_7$ heterocycloalkyl, wherein each of the alkyl, heteroalkyl, cycloalkyl, or heterocycloalkyl is optionally substituted.

In another aspect, the disclosure provides for a stereoisomer compound represented by Formula (Iab), or a pharmaceutically acceptable salt or solvate thereof:

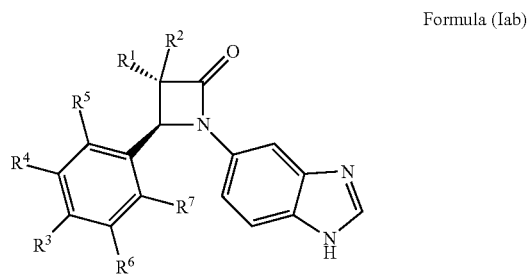

Formula (Iab)

wherein,

R$^1$ is halogen, —OH, —OR$^{10a}$, —SR$^{10a}$, —CN, amino, —NR$^{22}$R$^{23}$, substituted or unsubstituted C$_1$-C$_6$ alkyl, substituted or unsubstituted C$_2$-C$_6$ alkenyl, substituted or unsubstituted C$_2$-C$_6$ alkynyl, substituted or unsubstituted C$_1$-C$_6$ heteroalkyl, substituted or unsubstituted C$_3$-C$_8$ cycloalkyl, or substituted or unsubstituted C$_2$-C$_7$ heterocycloalkyl, and R$^2$ is H, halogen, —OH, —OR$^{10b}$, substituted or unsubstituted C$_1$-C$_6$ alkyl, or substituted or unsubstituted C$_1$-C$_6$ heteroalkyl; or R$^1$ and R$^2$ taken together form an oxo or a double bond to CR$^{12a}$R$^{12b}$, wherein R$^{12a}$ and R$^{12b}$ are each independently hydrogen, halogen, —OH, amino, substituted or unsubstituted C$_1$-C$_6$ alkyl, substituted or unsubstituted C$_2$-C$_6$ alkenyl, substituted or unsubstituted C$_2$-C$_6$ alkynyl, substituted or unsubstituted C$_1$-C$_6$ heteroalkyl, substituted or unsubstituted C$_3$-C$_8$ cycloalkyl, substituted or unsubstituted C$_2$-C$_7$ heterocycloalkyl, substituted or unsubstituted aryl, or substituted or unsubstituted heteroaryl;

each of R$^4$, R$^5$, R$^6$, and R$^7$ is independently selected from H, —OR$^{11}$, —NR$^{22}$R$^{23}$, halogen, and substituted or unsubstituted C$_1$-C$_6$ alky;

R$^3$ is —OR$^{11}$, halogen, —SR$^{11}$, SF$_5$, —S(=O)R$^{21}$, —S(=O)$_2$R$^{21}$, —NHS(=O)$_2$R$^{21}$, —N=S(=O)R$^{22}$R$^{23}$, —S(=O)$_2$NR$^{22}$R$^{23}$, —S(=O)(NR$^{21}$)R$^{21}$, —C(=O)R$^{21}$, —OC(=O)R$^{21}$, —C(=O)OR$^{22}$, —OC(=O)OR$^{22}$, —C(=O)NR$^{22}$R$^{23}$, —OC(=O)NR$^{22}$R$^{23}$, —NR$^{22}$R$^{23}$, —NO$_2$, —NHS(=O)$_2$R$^{21}$, —NR$^{22}$C(=O)NR$^{22}$R$^{23}$, —NR$^{22}$C(=O)R$^{21}$, —NR$^{22}$C(=O)OR$^{21}$, —P(=O)R$^{22}$R$^{23}$, substituted or unsubstituted C$_1$-C$_8$ alkyl, substituted or unsubstituted C$_2$-C$_8$ alkenyl, substituted or unsubstituted C$_2$-C$_8$ alkynyl, substituted or unsubstituted C$_1$-C$_8$ heteroalkyl, substituted or unsubstituted C$_3$-C$_8$ cycloalkyl, substituted or unsubstituted C$_2$-C$_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl;

R$^{10a}$ and R$^{10b}$ are each independently substituted or unsubstituted C$_1$-C$_6$ alkyl, substituted or unsubstituted C$_2$-C$_6$ alkenyl, or substituted or unsubstituted C$_1$-C$_6$ heteroalkyl; and R$^{11}$ is substituted or unsubstituted C$_1$-C$_6$ alkyl, substituted or unsubstituted C$_2$-C$_6$ alkenyl, or unsubstituted C$_2$-C$_6$ alkynyl, substituted or unsubstituted C$_1$-C$_6$ heteroalkyl, substituted or unsubstituted C$_3$-C$_8$ cycloalkyl, substituted or unsubstituted C$_2$-C$_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl; and R$^{21}$, R$^{22}$, and R$^{23}$ are each independently hydrogen, C$_1$-C$_6$ alkyl, C$_1$-C$_6$ heteroalkyl, C$_3$-C$_8$ cycloalkyl, or C$_2$-C$_7$ heterocycloalkyl, wherein each of the alkyl, heteroalkyl, cycloalkyl, or heterocycloalkyl is optionally substituted.

In some embodiments of Formula (I), (Ia), (Ib), (Iaa) (Iab), (Iba), or (Ibb), wherein, R$^1$ is halogen, —OH, —OR$^{10a}$, —SH, —SR$^{10a}$, —CN, amino, —NR$^{22}$R$^{23}$, substituted or unsubstituted C$_1$-C$_6$ alkyl, substituted or unsubstituted C$_2$-C$_6$ alkenyl, substituted or unsubstituted C$_2$-C$_6$ alkynyl, or substituted or unsubstituted C$_3$-C$_8$ cycloalkyl, and R$^2$ is H or halogen; or R$^1$ and R$^2$ taken together form a double bond to CR$^{12a}$R$^{12b}$, wherein R$^{12a}$ is hydrogen and R$^{12b}$ is hydrogen, halogen, —OH, amino, substituted or unsubstituted C$_1$-C$_6$ alkyl, substituted or unsubstituted C$_3$-C$_8$ cycloalkyl, substituted or unsubstituted C$_2$-C$_7$ heterocycloalkyl, substituted or unsubstituted aryl, or substituted or unsubstituted heteroaryl;

each of R$^4$, R$^5$, R$^6$, and R$^7$ is independently selected from H, halogen, substituted or unsubstituted C$_1$-C$_6$ alkyl;

R$^3$ is —OR$^{11}$, halogen, —SR$^{11}$, SF$_5$, —S(=O)R$^{21}$, —S(=O)$_2$R$^{21}$, —NHS(=O)$_2$R$^{21}$, —N=S(=O)R$^{22}$R$^{23}$, —S(=O)$_2$NR$^{22}$R$^{23}$, —S(=O)(NR$^{21}$)R$^{21}$, —C(=O)R$^{21}$, —OC(=O)R$^{21}$, —C(=O)OR$^{22}$, —OC(=O)OR$^{22}$, —C(=O)NR$^{22}$R$^{23}$, —OC(=O)NR$^{22}$R$^{23}$, —NR$^{22}$R$^{23}$, —NO$_2$, —NHS(=O)$_2$R$^{21}$, —NR$^{22}$C(=O)NR$^{22}$R$^{23}$, —NR$^{22}$C(=O)R$^{21}$, —NR$^{22}$C(=O)OR$^{21}$, —P(=O)R$^{22}$R$^{23}$, substituted or unsubstituted C$_1$-C$_8$ alkyl, substituted or unsubstituted C$_2$-C$_8$ alkenyl, substituted or unsubstituted C$_2$-C$_8$ alkynyl, substituted or unsubstituted C$_3$-C$_8$ cycloalkyl, substituted or unsubstituted C$_2$-C$_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl;

R$^{10a}$ and R$^{10b}$ are each independently substituted or unsubstituted C$_1$-C$_6$ alkyl, substituted or unsubstituted C$_2$-C$_6$ alkenyl, or substituted or unsubstituted C$_2$-C$_6$ alkynyl; and R$^{11}$ is substituted or unsubstituted C$_1$-C$_6$ alkyl, substituted or unsubstituted C$_2$-C$_6$ alkenyl, substituted or unsubstituted C$_2$-C$_6$ alkynyl, substituted or unsubstituted C$_3$-C$_8$ cycloalkyl, substituted or unsubstituted C$_2$-C$_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl; and R$^{21}$, R$^{22}$, and R$^{23}$ are each independently hydrogen, C$_1$-C$_6$ alkyl, C$_3$-C$_8$ cycloalkyl, or C$_2$-C$_7$ heterocycloalkyl, wherein each of the alkyl, cycloalkyl, or heterocycloalkyl is optionally substituted.

In some embodiments of Formula (I), (Ia), (Ib), (Iaa) (Iab), (Iba), or (Ibb), each of R$^4$, R$^5$, R$^6$, and R$^7$ is independently selected from H, halogen, —OH, oxo, —NO$_2$, CN, SH, —OR$^{11}$, —SR$^{11}$, —S(=O)R$^{21}$, —S(=O)$_2$R$^{21}$, —NHS(=O)$_2$R$^{21}$, —S(=O)$_2$NR$^{22}$R$^{23}$, —C(=O)R$^{21}$, —OC(=O)R$^{21}$, —C(=O)OR$^{22}$, —OC(=O)OR$^{22}$, —C(=O)NR$^{22}$R$^{23}$, —OC(=O)NR$^{22}$R$^{23}$, —NR$^{22}$R$^{23}$, —NO$_2$, —NHS(=O)$_2$R$^{21}$, —NR$^{22}$C(=O)NR$^{22}$R$^{23}$, —NR$^{22}$C(=O)R$^{21}$, —NR$^{22}$C(=O)OR$^{21}$, substituted or unsubstituted C$_1$-C$_6$ alkyl, substituted or unsubstituted C$_2$-C$_6$ alkenyl, substituted or unsubstituted C$_2$-C$_6$ alkynyl, substituted or unsubstituted C$_1$-C$_8$ heteroalkyl, substituted or unsubstituted C$_3$-C$_8$ cycloalkyl, substituted or unsubstituted C$_2$-C$_7$ heterocycloalkyl, substituted or unsubstituted aryl, and substituted or unsubstituted heteroaryl. In some embodiments of Formula (I), (Ia), (Ib), (Iaa) (Iab), (Iba), (Ibb), (II), (IIa), (IIb), (IIaa) (IIab), (IIba), or (IIbb), each of R$^4$, R$^5$, R$^6$, and R$^7$ is independently selected from H, —OR$^{11}$, —NR$^{22}$R$^{23}$, halogen, and substituted or unsubstituted C$_1$-C$_6$ alky.

In another aspect, the disclosure provides for a compound of Formula (II), or a pharmaceutically acceptable salt or solvate thereof:

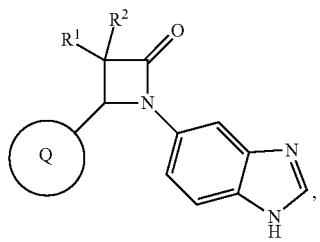

Formula (II)

wherein, $R^1$ is H, halogen, —OH, —OR$^{10a}$, —SR$^{10a}$, —CN, amino, —NR$^{22}$R$^{23}$, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, or substituted or unsubstituted $C_2$-$C_7$ heterocycloalkyl, and $R^2$ is H, halogen, —OH, —OR$^{10b}$, substituted or unsubstituted $C_1$-$C_6$ alkyl, or substituted or unsubstituted $C_1$-$C_6$ heteroalkyl; or $R^1$ and $R^2$ taken together with the carbon atom to which they are attached form a 3-7 membered cyclic or heterocyclic ring; or $R^1$ and $R^2$ taken together form an oxo or a double bond to CR$^{12a}$R$^{12b}$, wherein R$^{12a}$ and R$^{12b}$ are each independently hydrogen, halogen, —OH, amino, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

ring Q is a substituted or unsubstituted 5 or 6 membered heteroaryl;

$R^{10a}$ and $R^{10b}$ are each independently substituted or unsubstituted $C_1$-$C_6$ alkyl, substituted or unsubstituted $C_2$-$C_6$ alkenyl, substituted or unsubstituted $C_2$-$C_6$ alkynyl, or substituted or unsubstituted $C_1$-$C_6$ heteroalkyl; and $R^{22}$ and $R^{23}$ are each independently hydrogen, $C_1$-$C_6$ alkyl, $C_1$-$C_6$ heteroalkyl, $C_3$-$C_8$ cycloalkyl, or $C_2$-$C_7$ heterocycloalkyl, wherein each of the alkyl, heteroalkyl, cycloalkyl, or heterocycloalkyl is optionally substituted.

In another aspect, the disclosure provides for a stereoisomer compound represented by Formula (II), or a pharmaceutically acceptable salt or solvate thereof:

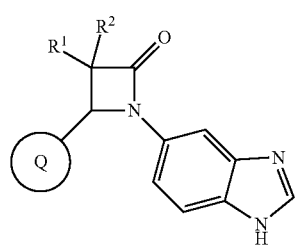

Formula (II)

wherein ring Q is a substituted or unsubstituted aryl (such as phenyl); and the remaining groups have the same definitions described above.

In some embodiments, the compound of Formula (II) has a structure of Formula (IIa), pharmaceutically acceptable salt or solvate thereof:

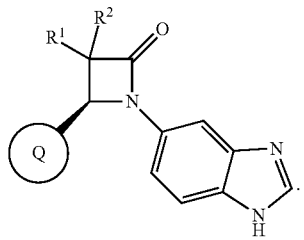

Formula (IIa)

In some embodiments, the compound of Formula (II) has a structure of Formula (IIb), pharmaceutically acceptable salt or solvate thereof:

Formula (IIb)

In some embodiments, the compound of Formula (II) has a structure of Formula (IIaa), pharmaceutically acceptable salt or solvate thereof:

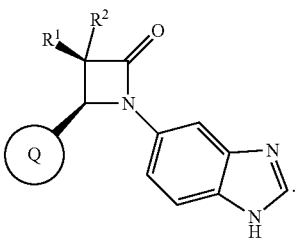

Formula (IIaa)

In some embodiments, the compound of Formula (II) has a structure of Formula (IIab), pharmaceutically acceptable salt or solvate thereof:

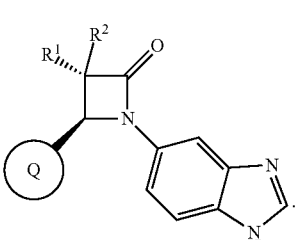

Formula (IIab)

In some embodiments, the compound of Formula (II) has a structure of Formula (IIba), pharmaceutically acceptable salt or solvate thereof:

Formula (IIba)

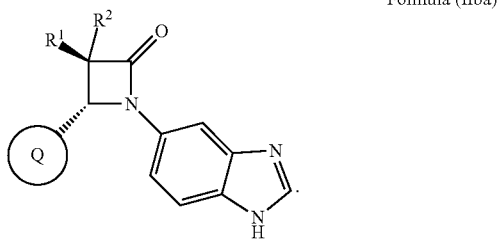

In some embodiments, the compound of Formula (II) has a structure of Formula (IIbb), pharmaceutically acceptable salt or solvate thereof:

Formula (IIbb)

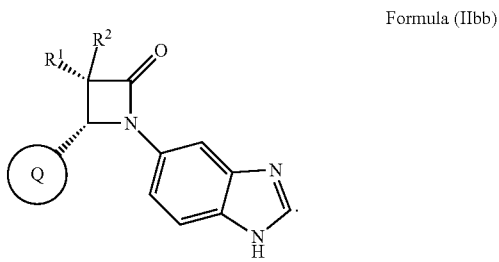

In another aspect, the disclosure provides for a stereoisomer compound represented by Formula (IIa), or a pharmaceutically acceptable salt or solvate thereof:

Formula (IIa)

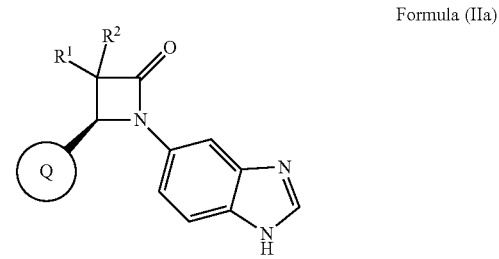

wherein,
$R^1$ is H, halogen, —OH, —OR$^{10a}$, —SR$^{10a}$, —CN, amino, —NR$^{22}$R$^{23}$, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, or substituted or unsubstituted $C_2$-$C_7$ heterocycloalkyl, and $R^2$ is H, halogen, —OH, —OR$^{10b}$, substituted or unsubstituted $C_1$-$C_6$ alkyl, or substituted or unsubstituted $C_1$-$C_6$ heteroalkyl; or $R^1$ and $R^2$ taken together with the carbon atom to which they are attached form a 3-7 membered cyclic or heterocyclic ring; or $R^1$ and $R^2$ taken together form an oxo or a double bond to CR$^{12a}$R$^{12b}$, wherein R$^{12a}$ and R$^{12b}$ are each independently hydrogen, halogen, —OH, amino, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

ring Q is a substituted or unsubstituted 5 or 6 membered heteroaryl;

R$^{10a}$ and R$^{10b}$ are each independently substituted or unsubstituted $C_1$-$C_6$ alkyl, substituted or unsubstituted $C_2$-$C_6$ alkenyl, substituted or unsubstituted $C_2$-$C_6$ alkynyl, or substituted or unsubstituted $C_1$-$C_6$ heteroalkyl; and R$^{22}$ and R$^{23}$ are each independently hydrogen, $C_1$-$C_6$ alkyl, $C_1$-$C_6$ heteroalkyl, $C_3$-$C_8$ cycloalkyl, or $C_2$-$C_7$ heterocycloalkyl, wherein each of the alkyl, heteroalkyl, cycloalkyl, or heterocycloalkyl is optionally substituted.

In another aspect, the disclosure provides for a stereoisomer compound represented by Formula (IIaa), or a pharmaceutically acceptable salt or solvate thereof:

Formula (IIaa)

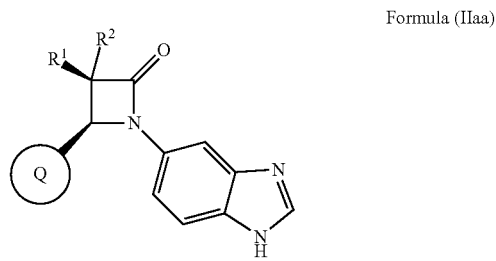

wherein,
$R^1$ is H, halogen, —OH, —OR$^{10a}$, —SR$^{10a}$, —CN, amino, —NR$^{22}$R$^{23}$, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, or substituted or unsubstituted $C_2$-$C_7$ heterocycloalkyl, and $R^2$ is H, halogen, —OH, —OR$^{10b}$, substituted or unsubstituted $C_1$-$C_6$ alkyl, or substituted or unsubstituted $C_1$-$C_6$ heteroalkyl; or $R^1$ and $R^2$ taken together form an oxo or a double bond to CR$^{12a}$R$^{12b}$, wherein R$^{12a}$ and R$^{12b}$ are each independently hydrogen, halogen, —OH, amino, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

ring Q is a substituted or unsubstituted 5 or 6 membered heteroaryl;

R$^{10a}$ and R$^{10b}$ are each independently substituted or unsubstituted $C_1$-$C_6$ alkyl, substituted or unsubstituted $C_2$-$C_6$ alkenyl, substituted or unsubstituted $C_2$-$C_6$ alkynyl, or substituted or unsubstituted $C_1$-$C_6$ heteroalkyl; and R$^{22}$ and R$^{23}$ are each independently hydrogen, $C_1$-$C_6$ alkyl, $C_1$-$C_6$ heteroalkyl, $C_3$-$C_8$ cycloalkyl, or $C_2$-$C_7$ heterocycloalkyl, wherein each of the alkyl, heteroalkyl, cycloalkyl, or heterocycloalkyl is optionally substituted.

In another aspect, the disclosure provides for a stereoisomer compound represented by Formula (IIaa), or a pharmaceutically acceptable salt or solvate thereof:

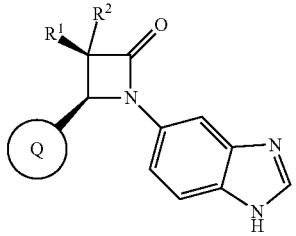

Formula (IIaa)

wherein ring Q is a substituted or unsubstituted aryl (such as phenyl); and
the remaining groups have the same definitions described above.

In another aspect, the disclosure provides for a stereoisomer compound represented by Formula (IIab), or a pharmaceutically acceptable salt or solvate thereof:

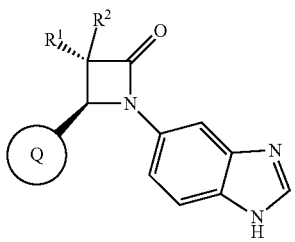

Formula (IIab)

wherein,
$R^1$ is H, halogen, —OH, —OR$^{10a}$, —SR$^{10a}$, —CN, amino, —NR$^{22}$R$^{23}$, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, or substituted or unsubstituted $C_2$-$C_7$ heterocycloalkyl, and
$R^2$ is H, halogen, —OH, —OR$^{10b}$, substituted or unsubstituted $C_1$-$C_6$ alkyl, or substituted or unsubstituted $C_1$-$C_6$ heteroalkyl; or
$R^1$ and $R^2$ taken together form an oxo or a double bond to CR$^{12a}$R$^{12b}$, wherein R$^{12a}$ and R$^{12b}$ are each independently hydrogen, halogen, —OH, amino, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;
ring Q is a substituted or unsubstituted 5 or 6 membered heteroaryl;
$R^{10a}$ and $R^{10b}$ are each independently substituted or unsubstituted $C_1$-$C_6$ alkyl, substituted or unsubstituted $C_2$-$C_6$ alkenyl, or substituted or unsubstituted $C_2$-$C_6$ alkynyl, or substituted or unsubstituted $C_1$-$C_6$ heteroalkyl; and
$R^{22}$ and $R^{23}$ are each independently hydrogen, $C_1$-$C_6$ alkyl, $C_1$-$C_6$ heteroalkyl, $C_3$-$C_8$ cycloalkyl, or $C_2$-$C_7$ heterocycloalkyl, wherein each of the alkyl, heteroalkyl, cycloalkyl, or heterocycloalkyl is optionally substituted.

In another aspect, the disclosure provides for a stereoisomer compound represented by Formula (IIab), or a pharmaceutically acceptable salt or solvate thereof:

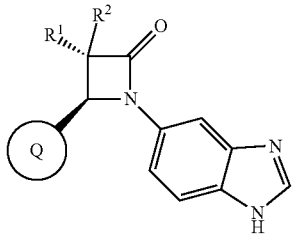

Formula (IIab)

wherein ring Q is a substituted or unsubstituted aryl (such as phenyl); and
the remaining groups have the same definitions described above.

In some embodiments of a compound of Formula (II), (IIa), (IIb), (IIaa) (IIab), (IIba), or (IIbb), wherein
$R^1$ is H, halogen, —OH, —OR$^{10a}$, —SH, —SR$^{10a}$, —CN, amino, —NR$^{22}$R$^{23}$, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_8$ cycloalkyl, or substituted or unsubstituted $C_2$-$C_7$ heterocycloalkyl, and
$R^2$ is H or halogen; or
$R^1$ and $R^2$ taken together form a double bond to CR$^{12a}$R$^{12b}$, wherein R$^{12a}$ is hydrogen, and R$^{12b}$ is hydrogen, halogen, —OH, amino, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;
ring Q is a substituted or unsubstituted 5 or 6 membered heteroaryl or substituted or unsubstituted phenyl;
$R^{10a}$ and $R^{10b}$ are each independently substituted or unsubstituted $C_1$-$C_6$ alkyl, substituted or unsubstituted $C_2$-$C_6$ alkenyl, or substituted or unsubstituted $C_2$-$C_6$ alkynyl; and
$R^{22}$ and $R^{23}$ are each independently hydrogen, $C_1$-$C_6$ alkyl, $C_3$-$C_8$ cycloalkyl, or $C_2$-$C_7$ heterocycloalkyl, wherein each of the alkyl, cycloalkyl, or heterocycloalkyl is optionally substituted.

In some embodiments of Formula (II), (IIa), (IIb), (IIaa) (IIab), (IIba), or (IIbb), ring Q is a substituted or unsubstituted 5 membered heteroaryl having 1 to 4 ring heteroatoms independently selected from N, O and S. In some embodiments of Formula (II), (IIa), (IIb), (IIaa) (IIab), (IIba), or (IIbb), ring Q is pyrrolyl, furyl, thiophenyl, pyrazolyl, imidazolyl, thiazolyl, isothiazolyl, triazolyl, tetrazolyl, thiadiazolyl, or oxadiazolyl, each of which is optionally substituted. In some embodiments of Formula (II), (IIa), (IIb), (IIaa) (IIab), (IIba), or (IIbb), ring Q is a substituted or unsubstituted pyrrolyl. In some embodiments of Formula (II), (IIa), (IIb), (IIaa) (IIab), (IIba), or (IIbb), ring Q is a substituted or unsubstituted furyl. In some embodiments of Formula (II), (IIa), (IIb), (IIaa) (IIab), (IIba), or (IIbb), ring Q is a substituted or unsubstituted thiophenyl. In some embodiments of Formula (II), (IIa), (IIb), (IIaa) (IIab), (IIba), or (IIbb), ring Q is a substituted or unsubstituted pyrazolyl. In some embodiments of Formula (II), (IIa), (IIb), (IIaa) (IIab), (IIba), or (IIbb), ring Q is a substituted or unsubstituted imidazolyl. In some embodiments of Formula (II), (IIa), (IIb), (IIaa) (IIab), (IIba), or (IIbb), ring Q is a substituted or unsubstituted thiazolyl. In some embodiments of Formula (II), (IIa), (IIb), (IIaa) (IIab), (IIba), or (IIbb), ring Q is a substituted or unsubstituted isothiazolyl. In some embodiments of Formula (II), (IIa), (IIb), (IIaa) (IIab), (IIba), or (IIbb), ring Q is a substituted or unsubstituted triazolyl. In some embodiments of Formula (II), (IIa), (IIb), (IIaa) (IIab), (IIba), or (IIbb), ring Q is a substituted or unsubstituted tetrazolyl. In some embodiments of Formula (II), (IIa), (IIb), (IIaa) (IIab), (IIba), or (IIbb), ring Q is a substituted or unsubstituted thiadiazolyl. In some embodiments of Formula (II), (IIa), (IIb), (IIaa) (IIab), (IIba), or (IIbb), ring Q is a substituted or unsubstituted oxadiazolyl. In some embodiments of Formula (II), (IIa), (IIb), (IIaa) (IIab), (IIba), or (IIbb), ring Q is a substituted or unsubstituted phenyl. In some embodiments of Formula (II), (IIa), (IIb), (IIaa) (IIab), (IIba), or (IIbb), ring Q is a substituted or unsubstituted aryl.

In some embodiments of Formula (II), (IIa), (IIb), (IIaa) (IIab), (IIba), or (IIbb), ring Q is a substituted or unsubstituted 6 membered heteroaryl having 1 to 4 ring heteroatoms independently selected from N, O and S. In some embodiments of Formula (II), (IIa), (IIb), (IIaa) (IIab), (IIba), or (IIbb), ring Q is a substituted or unsubstituted 6 membered heteroaryl having 1 to 3 ring nitrogen atoms.

In some embodiments of Formula (II), (IIa), (IIb), (IIaa) (IIab), (IIba), or (IIbb), ring Q is substituted with 0 to 3 halogen groups and 0 to 4 $R^3$ groups, wherein $R^3$ is independently selected from —OH, —SH, oxo, —OR$^{11}$, halogen, —SR$^{11}$, SF$_5$, —S(=O)R$^{21}$, —S(=O)$_2$R$^{21}$, —NHS(=O)$_2$R$^{21}$, —N=S(=O)R$^{22}$R$^{23}$, —S(=O)$_2$NR$^{22}$R$^{23}$, —S(=O)(NR$^{21}$)R$^{21}$, —C(=O)R$^{21}$, —OC(=O)R$^{21}$, —C(=O)OR$^{22}$, —OC(=O)OR$^{22}$, —C(=O)NR$^{22}$R$^{23}$, —OC(=O)NR$^{22}$R$^{23}$, —NR$^{22}$R$^{23}$, —NO$_2$, —NHS(=O)$_2$R$^{21}$, —NR$^{22}$C(=O)NR$^{22}$R$^{23}$, —NR$^{22}$C(=O)R$^{21}$, —NR$^{22}$C(=O)OR$^{21}$, —P(=O)R$^{22}$R$^{23}$, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted $C_1$-$C_8$ heteroalkyl, substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl.

In some embodiments of Formula (II), (IIa), (IIb), (IIaa) (IIab), (IIba), or (IIbb), ring Q is substituted with 0 to 3 halogen groups and 0 to 1 $R^3$ group, wherein $R^3$ is —OR$^{11}$, halogen, —SR$^{11}$, —S(=O)R$^{21}$, —S(=O)$_2$R$^{21}$, —NHS(=O)$_2$R$^{21}$, —S(=O)$_2$NR$^{22}$R$^{23}$, —C(=O)R$^{21}$, —OC(=O)R$^{21}$, —C(=O)OR$^{22}$, —OC(=O)OR$^{22}$, —C(=O)NR$^{22}$R$^{23}$, —OC(=O)NR$^{22}$R$^{23}$, —NR$^{22}$R$^{23}$, —NO$_2$, —NHS(=O)$_2$R$^{21}$, —NR$^{22}$C(=O)NR$^{22}$R$^{23}$, —NR$^{22}$C(=O)R$^{21}$, —NR$^{22}$C(=O)OR$^{21}$, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted $C_1$-$C_8$ heteroalkyl, substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl.

In some embodiments of Formula (I), (Ia), (Ib), (Iaa), (Iab), (Iba), (Ibb), (II), (IIa), (IIb), (IIaa) (IIab), (IIba), or (IIbb), $R^{11}$ is substituted $C_1$-$C_6$ alkyl, substituted $C_2$-$C_6$ alkenyl, substituted $C_2$-$C_6$ alkynyl, substituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl, wherein the alkyl, alkenyl, alkynyl or heteroalkyl is substituted with at least one substituent selected from substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, and substituted or unsubstituted bicyclic or polycyclic heteroaryl. In some embodiments of Formula (I), (Ia), (Ib), (Iaa), (Iab), (Iba), (Ibb), (II), (IIa), (IIb), (IIaa) (IIab), (IIba), or (IIbb), $R^{11}$ is optionally substituted $C_1$-$C_6$ alkyl. In some embodiments of Formula (I), (Ia), (Ib), (Iaa), (Iab), (Iba), (Ibb), (II), (IIa), (IIb), (IIaa) (IIab), (IIba), or (IIbb), $R^{11}$ is substituted or unsubstituted $C_3$-$C_8$ cycloalkyl.

In some embodiments of Formula (I), (Ia), (Ib), (Iaa), (Iab), (Iba), (Ibb), (II), (IIa), (IIb), (IIaa) (IIab), (IIba), or (IIbb), $R^{21}$, $R^{22}$, and $R^{23}$ are each independently hydrogen, $C_1$-$C_6$ alkyl, $C_1$-$C_6$ heteroalkyl, $C_3$-$C_8$ cycloalkyl, or $C_2$-$C_7$ heterocycloalkyl, wherein each of the alkyl, heteroalkyl, cycloalkyl, or heterocycloalkyl is optionally substituted.

In some embodiments of Formula (II), (IIa), (IIb), (IIaa) (IIab), (IIba), or (IIbb), ring Q is

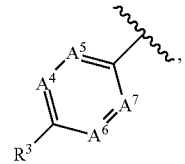

wherein
$A^5$ is N or CR$^5$;
$A^4$ is N or CR$^4$;
$A^6$ is N or CR$^6$;
$A^7$ is N or CR$^7$;
each of $R^4$, $R^5$, $R^6$, and $R^7$ is independently selected from H and halogen;
$R^3$ is —OR$^{11}$, halogen, —SR$^{11}$, —S(=O)R$^{21}$, —S(=O)$_2$R$^{21}$, —NHS(=O)$_2$R$^{21}$, —S(=O)$_2$NR$^{22}$R$^{23}$, —C(=O)R$^{21}$, —OC(=O)R$^{21}$, —C(=O)OR$^{22}$, —OC(=O)OR$^{22}$, —C(=O)NR$^{22}$R$^{23}$, —OC(=O)NR$^{22}$R$^{23}$, —NR$^{22}$R$^{23}$, —NO$_2$, —NHS(=O)$_2$R$^{21}$, —NR$^{22}$C(=O)NR$^{22}$R$^{23}$, —NR$^{22}$C(=O)R$^{21}$, —NR$^{22}$C(=O)OR$^{21}$, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted $C_1$-$C_8$ heteroalkyl, substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl;
$R^{11}$ is substituted $C_1$-$C_6$ alkyl, substituted $C_2$-$C_6$ alkenyl, substituted $C_2$-$C_6$ alkynyl, substituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl, wherein the alkyl, alkenyl, alkynyl or heteroalkyl is substituted with at least one substituent selected from substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, and substituted or unsubstituted bicyclic or polycyclic heteroaryl; and $R^{21}$, $R^{22}$, and $R^{23}$ are each independently hydrogen, $C_1$-$C_6$ alkyl, $C_1$-$C_6$ heteroalkyl, $C_3$-$C_8$ cycloalkyl, or $C_2$-$C_7$ heterocycloalkyl, wherein each of the alkyl, heteroalkyl, cycloalkyl, or heterocycloalkyl is optionally substituted.

In some embodiments of Formula (II), (IIa), (IIb), (IIaa) (IIab), (IIba), or (IIbb), ring Q is

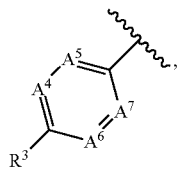

wherein
$A^5$ is N or $CR^5$;
$A^4$ is N or $CR^4$;
$A^6$ is N or $CR^6$;
$A^7$ is N or $CR^7$;
each of $R^4$, $R^5$, $R^6$, and $R^7$ is independently selected from H, halogen, —OH, oxo, —$NO_2$, CN, SH, —$OR^{11}$, —$SR^{11}$, —S(=O)$R^{21}$, —S(=O)$_2R^{21}$, —NHS(=O)$_2$$R^{21}$, —S(=O)$_2NR^{22}R^{23}$, —C(=O)$R^{21}$, —OC(=O)$R^{21}$, —C(=O)$OR^{22}$, —OC(=O)$OR^{22}$, —C(=O)$NR^{22}R^{23}$, —OC(=O)$NR^{22}R^{23}$, —$NR^{22}R^{23}$, —$NO_2$, —NHS(=O)$_2R^{21}$, —$NR^{22}$C(=O)$NR^{22}R^{23}$, —$NR^{22}$C(=O)$R^{21}$, —$NR^{22}$C(=O)$OR^{21}$, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_8$ heteroalkyl, substituted or unsubstituted $C_3$-$C_8$ cycloalkyl, substituted or unsubstituted $C_2$-$C_7$ heterocycloalkyl, substituted or unsubstituted aryl, and substituted or unsubstituted heteroaryl;

$R^3$ is —$OR^{11}$, halogen, —$SR^{11}$, —S(=O)$R^{21}$, —S(=O)$_2$$R^{21}$, —NHS(=O)$_2R^{21}$, —S(=O)$_2NR^{22}R^{23}$, —C(=O)$R^{21}$, —OC(=O)$R^{21}$, —C(=O)$OR^{22}$, —OC(=O)$OR^{22}$, —C(=O)$NR^{22}R^{23}$, —OC(=O)$NR^{22}R^{23}$, —$NR^{22}R^{23}$, —$NO_2$, —NHS(=O)$_2R^{21}$, —$NR^{22}$C(=O)$NR^{22}R^{23}$, —$NR^{22}$C(=O)$R^{21}$, —$NR^{22}$C(=O)$OR^{21}$, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted $C_1$-$C_8$ heteroalkyl, substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl;

$R^{11}$ is substituted $C_1$-$C_6$ alkyl, substituted $C_2$-$C_6$ alkenyl, substituted $C_2$-$C_6$ alkynyl, substituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl, wherein the alkyl, alkenyl, alkynyl or heteroalkyl is substituted with at least one substituent selected from substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, and substituted or unsubstituted bicyclic or polycyclic heteroaryl; and $R^{21}$, $R^{22}$, and $R^{23}$ are each independently hydrogen, $C_1$-$C_6$ alkyl, $C_1$-$C_6$ heteroalkyl, $C_3$-$C_8$ cycloalkyl, or $C_2$-$C_7$ heterocycloalkyl, wherein each of the alkyl, heteroalkyl, cycloalkyl, or heterocycloalkyl is optionally substituted.

In some embodiments of Formula (II), (IIa), (IIb), (IIaa) (IIab), (IIba), or (IIbb),

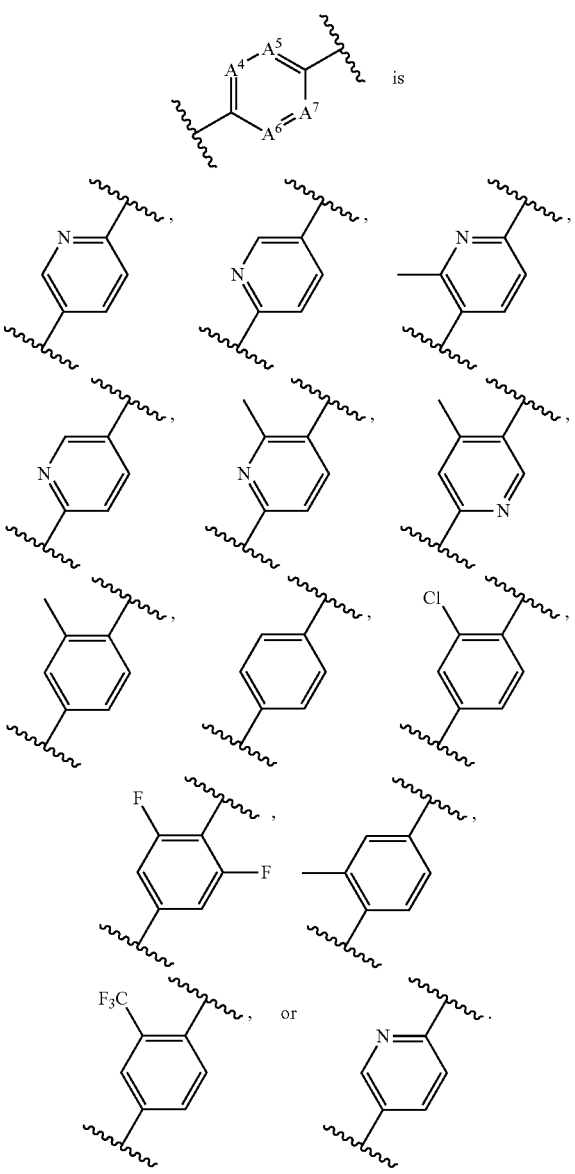

In some embodiments,
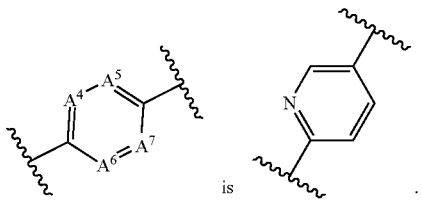
is .
In some embodiments,
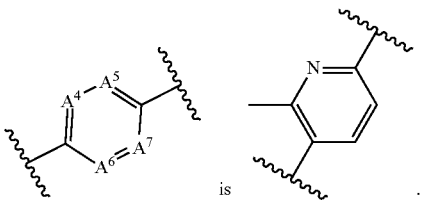
is .
In some embodiments,
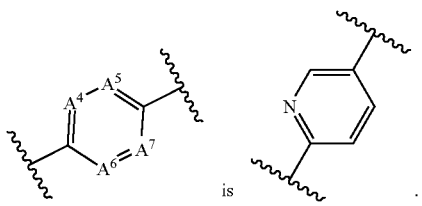
is .
In some embodiments
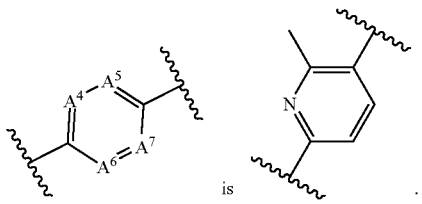
is .
In some embodiments,
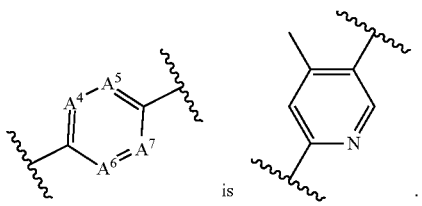
is .
In some embodiments
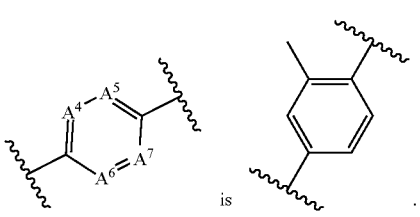
is .
In some embodiments,
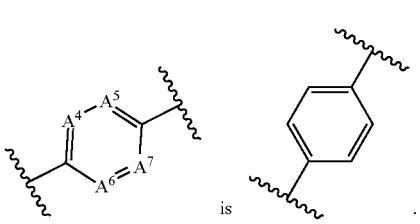
is .
In some embodiments
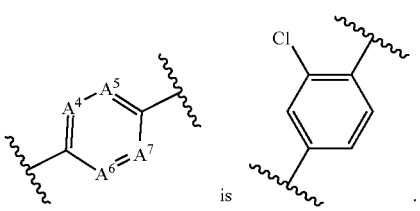
is .
In some embodiments,
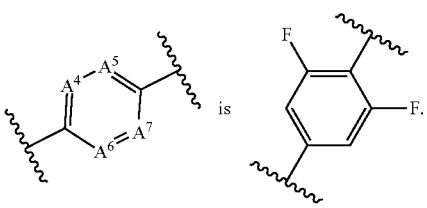
is .
In some embodiments
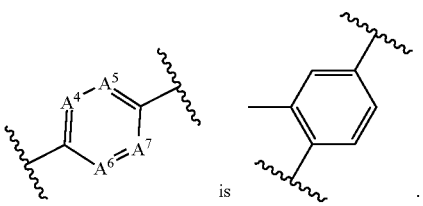
is .

In some embodiments,

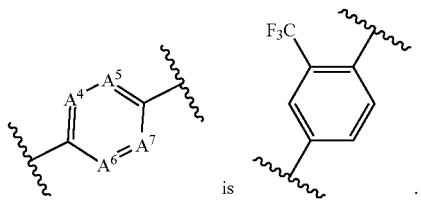

In some embodiments of Formula (I), (Ia), (Ib), (Iaa), (Iab), (Iba), or (Ibb),

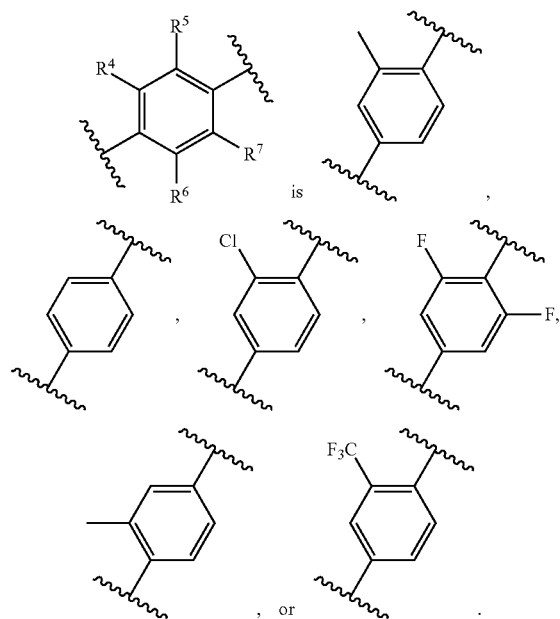

In some embodiments,

In some embodiments,

In some embodiments,

In some embodiments,

In some embodiments,

In some embodiments,

In some embodiments of Formula (II), (IIa), (IIb), (IIaa) (IIab), (IIba), or (IIbb), $A^5$ is N. In some embodiments of Formula (II), (IIa), (IIb), (IIaa) (IIab), (IIba), or (IIbb), $A^5$ is $CR^5$. In some embodiments of Formula (II), (IIa), (IIb), (IIaa) (IIab), (IIba), or (IIbb), $A^4$ is N. In some embodiments of Formula (II), (IIa), (IIb), (IIaa) (IIab), (IIba), or (IIbb), $A^4$ is $CR^4$. In some embodiments of Formula (II), (IIa), (IIb), (IIaa) (IIab), (IIba), or (IIbb), $A^6$ is N. In some embodiments of Formula (II), (IIa), (IIb), (IIaa) (IIab), (IIba), or (IIbb), $A^6$ is $CR^6$. In some embodiments of Formula (II), (IIa), (IIb), (IIaa) (IIab), (IIba), or (IIbb), $A^7$ is N. In some embodiments of Formula (II), (IIa), (IIb), (IIaa) (IIab), (IIba), or (IIbb), $A^7$ is $CR^7$. In some embodiments of Formula (II), (IIa), (IIb), (IIaa) (IIab), (IIba), or (IIbb), $A^5$ is $CR^5$, $A^4$ is N, $A^6$ is $CR^6$, and $A^7$ is $CR^7$. In some embodiments of Formula (II), (IIa), (IIb), (IIaa) (IIab), (IIba), or (IIbb), $A^5$ is $CR^5$, $A^4$ is $CR^4$, $A^6$ is N, and $A^7$ is $CR^7$. In some embodiments of Formula (II), (IIa), (IIb), (IIaa) (IIab), (IIba), or (IIbb), at least one of $A^4$, $A^5$, $A^6$, $A^7$ is N. In some embodiments of Formula (II), (IIa), (IIb), (IIaa) (IIab), (IIba), or (IIbb), one of $A^4$, $A^5$, $A^6$, $A^7$ is N. In some embodiments of Formula (II), (IIa), (IIb), (IIaa)

(IIab), (IIba), or (IIbb), two of $A^4$, $A^5$, $A^6$, $A^7$ are N. In some embodiments of Formula (II), (IIa), (IIb), (IIaa) (IIab), (IIba), or (IIbb), three of $A^4$, $A^5$, $A^6$, $A^7$ are N.

In some embodiments of Formula (I), (Ia), (Ib), (Iaa), (Iab), (Iba), (Ibb), (II), (IIa), (IIb), (IIaa), (IIab), (IIba), or (IIbb), $R^1$ is halogen, —OH, —$SR^{10a}$, —CN, amino, —$NR^{22}R^{23}$, —$OR^{10a}$, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, or substituted or unsubstituted $C_2$-$C_7$ heterocycloalkyl. In some embodiments, $R^1$ is —OH. In some embodiments, $R^1$ is —SH. In some embodiments, $R^1$ is —$SR^{10a}$. In some embodiments, $R^1$ is —CN. In some embodiments, $R^1$ is amino. In some embodiments, $R^1$ is —$NR^{22}R^{23}$. In some embodiments, $R^1$ is —$OR^{10a}$. In some embodiments, $R^1$ is substituted or unsubstituted $C_1$-$C_6$ alkyl. In some embodiments, $R^1$ is substituted or unsubstituted $C_2$-$C_6$ alkenyl. In some embodiments, $R^1$ is substituted or unsubstituted $C_2$-$C_6$ alkynyl. In some embodiments, $R^1$ is substituted or unsubstituted $C_1$-$C_6$ heteroalkyl. In some embodiments, $R^1$ is substituted or unsubstituted $C_3$-$C_8$ cycloalkyl. In some embodiments, $R^1$ is substituted or unsubstituted $C_2$-$C_7$ heterocycloalkyl.

In some embodiments of Formula (I), (Ia), (Ib), (Iaa), (Iab), (Iba), (Ibb), (II), (IIa), (IIb), (IIaa) (IIab), (IIba), or (IIbb), $R^1$ is halogen, substituted or unsubstituted $C_1$-$C_6$ alkyl, substituted or unsubstituted $C_1$-$C_6$ heteroalkyl, or substituted or unsubstituted $C_3$-$C_8$ cycloalkyl. In some embodiments $R^1$ is halogen, substituted or unsubstituted $C_1$-$C_6$ alkyl, substituted or unsubstituted $C_1$-$C_6$ heteroalkyl, substituted or unsubstituted $C_3$-$C_8$ cycloalkyl.

In some embodiments of Formula (I), (Ia), (Ib), (Iaa), (Iab), (Iba), (Ibb), (II), (IIa), (IIb), (IIaa) (IIab), (IIba), or (IIbb), $R^1$ is —OH, —$OR^{10a}$, substituted or unsubstituted $C_1$-$C_6$ alkyl, or substituted or unsubstituted $C_3$-$C_6$ cycloalkyl. In some embodiments of Formula (I), (Ia), (Ib), (Iaa), (Iab), (Iba), (Ibb), (II), (IIa), (IIb), (IIaa) (IIab), (IIba), or (IIbb), $R^1$ is —OH. In some embodiments of Formula (I), (Ia), (Ib), (Iaa), (Iab), (Iba), (Ibb), (II), (IIa), (IIb), (IIaa) (IIab), (IIba), or (IIbb), $R^1$ is —$OR^{10a}$, and $R^{10a}$ is substituted or unsubstituted $C_3$-$C_6$ cycloalkyl. In some embodiments of Formula (I), (Ia), (Ib), (Iaa), (Iab), (Iba), (Ibb), (II), (IIa), (IIb), (IIaa) (IIab), (IIba), or (IIbb), $R^1$ is —OH. In some embodiments of Formula (I), (Ia), (Ib), (Iaa), (Iab), (Iba), (Ibb), (II), (IIa), (IIb), (IIaa) (IIab), (IIba), or (IIbb), $R^1$ is —$OR^{10a}$, and $R^{10a}$ is substituted or unsubstituted $C_1$-$C_6$ alkyl. In some embodiments of Formula (I), (Ia), (Ib), (Iaa), (Iab), (Iba), (Ibb), (II), (IIa), (IIb), (IIaa) (IIab), (IIba), or (IIbb), $R^1$ is —$OCH_3$.

In some embodiments of Formula (I), (Ia), (Ib), (Iaa), (Iab), (Iba), (Ibb), (II), (IIa), (IIb), (IIaa) (IIab), (IIba), or (IIbb), $R^1$ is substituted or unsubstituted $C_1$-$C_6$ alkyl. In some embodiments of Formula (I), (Ia), (Ib), (Iaa), (Iab), (Iba), (Ibb), (II), (IIa), (IIb), (IIaa) (IIab), (IIba), or (IIbb), $R^1$ is $C_1$-$C_6$ alkyl that is optionally substituted with one to five substituents selected from halogen, —OH, amino, cyano, oxime, oxo, mono-$C_{1-6}$ alkylamino, di-$C_{1-6}$ alkylamino, substituted or unsubstituted $C_{1-6}$ alkoxy, substituted or unsubstituted $C_{3-7}$ cycloalkyl, substituted or unsubstituted $C_{2-8}$ heterocycloalkyl, substituted or unsubstituted aryl, and substituted or unsubstituted heteroaryl.

In some embodiments of Formula (I), (Ia), (Ib), (Iaa), (Iab), (Iba), (Ibb), (II), (IIa), (IIb), (IIaa) (IIab), (IIba), or (IIbb), $R^1$ is halogen, —OH, —$OR^{10a}$, —$SR^{10a}$, —CN, amino, —$NR^{22}R^{23}$, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, or substituted or unsubstituted $C_2$-$C_7$ heterocycloalkyl; wherein the alkyl, alkenyl, alkynyl, heteroalkyl, cycloalkyl or heteroalkyl is optionally, independently substituted with one to five substituents selected from halogen, —OH, oxo, —$NO_2$, CN, SH, —$OR^{11}$, —$SR^{11}$, —S(=O)$R^{21}$, —S(=O)$_2R^{21}$, —NHS(=O)$_2R^{21}$, —S(=O)$_2NR^{22}R^{23}$, —C(=O)$R^{21}$, —OC(=O)$R^{21}$, —C(=O)$OR^{22}$, —OC(=O)$OR^{22}$, —C(=O)$NR^{22}R^{23}$, —OC(=O)$NR^{22}R^{23}$, —$NR^{22}R^{23}$, —$NO_2$, —NHS(=O)$_2R^{21}$, —$NR^{22}$C(=O)$NR^{22}R^{23}$, —$NR^{22}$C(=O)$R^{21}$, —$NR^{22}$C(=O)$OR^{21}$, $C_1$-$C_6$ alkyl, $C_1$-$C_6$ aminoalkyl, $C_1$-$C_6$ haloalkyl, $C_1$-$C_6$ hydroxyalkyl, $C_2$-$C_6$ alkenyl, $C_2$-$C_6$ alkynyl, $C_1$-$C_8$ heteroalkyl, optionally substituted $C_3$-$C_8$ cycloalkyl, $C_2$-$C_7$ optionally substituted heterocycloalkyl, optionally substituted aryl, and optionally substituted heteroaryl.

In some embodiments of Formula (I), (Ia), (Ib), (Iaa), (Iab), (Iba), (Ibb), (II), (IIa), (IIb), (IIaa) (IIab), (IIba), or (IIbb), $R^1$ is optionally, independently substituted with one to five substituents selected from halogen, —OH, oxo, —$NO_2$, CN, SH, —$OR^{11}$, —$SR^{11}$, —S(=O)$R^{21}$, —S(=O)$_2$ $R^{21}$, —NHS(=O)$_2R^{21}$, —S(=O)$_2NR^{22}R^{23}$, —C(=O)$R^{21}$, —OC(=O)$R^{21}$, —C(=O)$OR^{22}$, —OC(=O)$OR^{22}$, —C(=O)$NR^{22}R^{23}$, —OC(=O)$NR^{22}R^{23}$, —$NR^{22}R^{23}$, —$NO_2$, —NHS(=O)$_2R^{21}$, —$NR^{22}$C(=O)$NR^{22}R^{23}$, —$NR^{22}$C(=O)$R^{21}$, —$NR^{22}$C(=O)$OR^{21}$, $C_1$-$C_6$ alkyl, $C_1$-$C_6$ aminoalkyl, $C_1$-$C_6$ haloalkyl, $C_1$-$C_6$ hydroxyalkyl, $C_2$-$C_6$ alkenyl, $C_2$-$C_6$ alkynyl, $C_1$-$C_8$ heteroalkyl, optionally substituted $C_3$-$C_8$ cycloalkyl, $C_2$-$C_7$ optionally substituted heterocycloalkyl, optionally substituted aryl, and optionally substituted heteroaryl. In some embodiments of Formula (I), (Ia), (Ib), (Iaa), (Iab), (Iba), (Ibb), (II), (IIa), (IIb), (IIaa) (IIab), (IIba), or (IIbb), $R^1$ is optionally, independently substituted with one to five substituents selected from halogen, —OH, oxo, —$NO_2$, CN, SH, —$OR^{11}$, —$SR^{11}$, —$C_1$-$C_6$ alkyl, $C_1$-$C_6$ aminoalkyl, $C_1$-$C_6$ haloalkyl, $C_1$-$C_6$ hydroxyalkyl, $C_1$-$C_6$ heteroalkyl, optionally substituted $C_3$-$C_8$ cycloalkyl, $C_2$-$C_7$ optionally substituted heterocycloalkyl, optionally substituted aryl, and optionally substituted heteroaryl. In some embodiments of Formula (I), (Ia), (Ib), (Iaa), (Iab), (Iba), (Ibb), (II), (IIa), (IIb), (IIaa) (IIab), (IIba), or (IIbb), $R^1$ is optionally, independently substituted with one to three substituents selected from halogen, —OH, oxo, $NH_2$, —$NO_2$, CN, SH, —O($C_1$-$C_6$ alkyl), —S($C_1$-$C_6$ alkyl), —$C_1$-$C_6$ alkyl, $C_1$-$C_6$ aminoalkyl, $C_1$-$C_6$ haloalkyl, $C_1$-$C_6$ hydroxyalkyl, $C_1$-$C_6$ heteroalkyl, $C_3$-$C_8$ cycloalkyl, $C_2$-$C_7$ heterocycloalkyl, optionally substituted aryl, and optionally substituted heteroaryl. In some embodiments of Formula (I), (Ia), (Ib), (Iaa), (Iab), (Iba), (Ibb), (II), (IIa), (IIb), (IIaa) (IIab), (IIba), or (IIbb), $R^1$ is optionally, independently substituted with one to three substituents selected from halogen, —OH, oxo, —$NO_2$, CN, SH, $NH_2$, —O($C_1$-$C_6$ alkyl), —S($C_1$-$C_6$ alkyl), —$C_1$-$C_6$ alkyl, $C_1$-$C_6$ aminoalkyl, $C_1$-$C_6$ haloalkyl, $C_1$-$C_6$ hydroxyalkyl, $C_3$-$C_8$ cycloalkyl, $C_2$-$C_7$ heterocycloalkyl, aryl, and heteroaryl. In some embodiments of Formula (I), (Ia), (Ib), (Iaa), (Iab), (Iba), (Ibb), (II), (IIa), (IIb), (IIaa) (IIab), (IIba), or (IIbb), $R^1$ is optionally, independently substituted with one to three substituents selected from halogen, —OH, oxo, —$NO_2$, CN, $NH_2$, —O($C_1$-$C_6$ alkyl), and —S($C_1$-$C_6$ alkyl). In some embodiments of Formula (I), (Ia), (Ib), (Iaa), (Iab), (Iba), (Ibb), (II), (IIa), (IIb), (IIaa) (IIab), (IIba), or (IIbb), $R^1$ is optionally, independently substituted with one to three substituents. In some embodiments of Formula (I), (Ia), (Ib), (Iaa), (Iab), (Iba), (Ibb), (II), (IIa), (IIb), (IIaa) (IIab), (IIba), or (IIbb), R¹ is optionally, independently substituted with one or two substituents.

In some embodiments of Formula (I), (Ia), (Ib), (Iaa), (Iab), (Iba), (Ibb), (II), (IIa), (IIb), (IIaa) (IIab), (IIba), or (IIbb), R¹ is halo (such as F or Cl), —CH₃, —CHF₂, —CF₃, —CH₂OH,

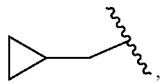

—CH₂CH₃, —CH₂CH₂CH₃, —CH₂CH₂CH₂CH₃, or benzyl. In some embodiments of Formula (I), (Ia), (Ib), (Iaa), (Iab), (Iba), (Ibb), (II), (IIa), (IIb), (IIaa) (IIab), (IIba), or (IIbb), R¹ is —CH₃. In some embodiments of Formula (I), (Ia), (Ib), (Iaa), (Iab), (Iba), (Ibb), (II), (IIa), (IIb), (IIaa) (IIab), (IIba), or (IIbb), R¹ is

In some embodiments, R¹ is ethyl. In some embodiments, R¹ is propyl In some embodiments, R¹ is butyl. In some embodiments, R¹ is —CH₂-phenyl. In some embodiments, R¹ is —CH₂CF₃. In some embodiments, R¹ is —CHF₂. In some embodiments, R¹ is —CH₂OH.

In some embodiments of Formula (I), (Ia), (Ib), (Iaa), (Iab), (Iba), (Ibb), (II), (IIa), (IIb), (IIaa) (IIab), (IIba), or (IIbb), R¹ is substituted or unsubstituted C₃-C₆ cycloalkyl. In some embodiments of Formula (I), (Ia), (Ib), (Iaa), (Iab), (Iba), (Ibb), (II), (IIa), (IIb), (IIaa) (IIab), (IIba), or (IIbb), R¹ is cyclopropyl, cyclobutyl, cyclopentyl or cyclohexyl. In some embodiments of Formula (I), (Ia), (Ib), (Iaa), (Iab), (Iba), (Ibb), (II), (IIa), (IIb), (IIaa) (IIab), (IIba), or (IIbb), R¹ is cyclopropyl. In some embodiments of Formula (I), (Ia), (Ib), (Iaa), (Iab), (Iba), (Ibb), (II), (IIa), (IIb), (IIaa) (IIab), (IIba), or (IIbb), R¹ is

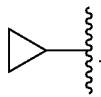 [SMILES: *C1CC1]

In some embodiments of Formula (I), (Ia), (Ib), (Iaa), (Iab), (Iba), (Ibb), (II), (IIa), (IIb), (IIaa) (IIab), (IIba), or (IIbb), R¹ is substituted or unsubstituted C₂-C₇ heterocycloalkyl. In some embodiments of Formula (I), (Ia), (Ib), (Iaa), (Iab), (Iba), (Ibb), (II), (IIa), (IIb), (IIaa) (IIab), (IIba), or (IIbb), R¹ is substituted or unsubstituted C₃-C₈ heterocycloalkyl. In some embodiments of Formula (I), (Ia), (Ib), (Iaa), (Iab), (Iba), (Ibb), (II), (IIa), (IIb), (IIaa) (IIab), (IIba), or (IIbb), R¹ is

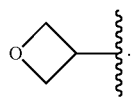

In some embodiments of Formula (I), (Ia), (Ib), (Iaa), (Iab), (Iba), (Ibb), (II), (IIa), (IIb), (IIaa) (IIab), (IIba), or (IIbb), R¹ is H.

In some embodiments of Formula (I), (Ia), (Ib), (Iaa), (Iab), (Iba), (Ibb), (II), (IIa), (IIb), (IIaa) (IIab), (IIba), or (IIbb), R² is H, halogen, —OH, —OR¹⁰b, substituted or unsubstituted C₁-C₆ alkyl, or substituted or unsubstituted C₁-C₆ heteroalkyl. In some embodiments of Formula (I), (Ia), (Ib), (Iaa), (Iab), (Iba), (Ibb), (II), (IIa), (IIb), (IIaa) (IIab), (IIba), or (IIbb), R² is H, halogen, —OH, or substituted or unsubstituted C₁-C₆ alkyl. In some embodiments of Formula (I), (Ia), (Ib), (Iaa), (Iab), (Iba), (Ibb), (II), (IIa), (IIb), (IIaa) (IIab), (IIba), or (IIbb), R² is H or halogen. In some embodiments of Formula (I), (Ia), (Ib), (Iaa), (Iab), (Iba), (Ibb), (II), (IIa), (IIb), (IIaa) (IIab), (IIba), or (IIbb), R² is halogen. In some embodiments of Formula (I), (Ia), (Ib), (Iaa), (Iab), (Iba), (Ibb), (II), (IIa), (IIb), (IIaa) (IIab), (IIba), or (IIbb), R² is H. In some embodiments of Formula (I), (Ia), (Ib), (Iaa), (Iab), (Iba), (Ibb), (II), (IIa), (IIb), (IIaa) (IIab), (IIba), or (IIbb), R² is —CH₃.

In some embodiments of Formula (I), (Ia), (Ib), (Iaa), (Iab), (Iba), (Ibb), (II), (IIa), (IIb), (IIaa) (IIab), (IIba), or (IIbb), R¹ and R² taken together with the carbon atom to which they are attached form a 3-7 membered cyclic or heterocyclic ring. In some embodiments of Formula (I), (Ia), (Ib), (Iaa), (Iab), (Iba), (Ibb), (II), (IIa), (IIb), (IIaa) (IIab), (IIba), or (IIbb), R¹ and R² taken together with the carbon atom to which they are attached form a cyclopropyl or a cyclobutyl. In some embodiments of Formula (I), (Ia), (Ib), (Iaa), (Iab), (Iba), (Ibb), (II), (IIa), (IIb), (IIaa) (IIab), (IIba), or (IIbb), R¹ and R² taken together with the carbon atom to which they are attached form a cyclopropyl. In some embodiments of Formula (I), (Ia), (Ib), (Iaa), (Iab), (Iba), (Ibb), (II), (IIa), (IIb), (IIaa) (IIab), (IIba), or (IIbb), R¹ and R² taken together with the carbon atom to which they are attached form a cyclobutyl.

In some embodiments of Formula (I), (Ia), (Ib), (Iaa), (Iab), (Iba), (Ibb), (II), (IIa), (IIb), (IIaa) (IIab), (IIba), or (IIbb), R¹ and R² taken together form an oxo.

In some embodiments of Formula (I), (Ia), (Ib), (Iaa), (Iab), (Iba), (Ibb), (II), (IIa), (IIb), (IIaa) (IIab), (IIba), or (IIbb), R¹ and R² taken together form a double bond to CR¹²ᵃR¹²ᵇ, wherein R¹²ᵃ and R¹²ᵇ are each independently hydrogen, halogen, —OH, amino, substituted or unsubstituted C₁-C₆ alkyl, substituted or unsubstituted C₂-C₆ alkenyl, substituted or unsubstituted C₂-C₆ alkynyl, substituted or unsubstituted C₁-C₆ heteroalkyl, substituted or unsubstituted C₃-C₈ cycloalkyl, substituted or unsubstituted C₂-C₇ heterocycloalkyl, substituted or unsubstituted aryl, or substituted or unsubstituted heteroaryl.

In some embodiments of Formula (I), (Ia), (Ib), (Iaa), (Iab), (Iba), (Ibb), (II), (IIa), (IIb), (IIaa) (IIab), (IIba), or (IIbb), R¹²ᵃ and R¹²ᵇ are each independently hydrogen, halogen, —OH, amino, substituted or unsubstituted C₁-C₆ alkyl, substituted or unsubstituted C₂-C₆ alkenyl, substituted or unsubstituted C₂-C₆ alkynyl, substituted or unsubstituted C₁-C₆ heteroalkyl, substituted or unsubstituted C₃-C₈ cycloalkyl, substituted or unsubstituted C₂-C₇ heterocycloalkyl, substituted or unsubstituted aryl, or substituted or unsubstituted heteroaryl.

In some embodiments of Formula (I), (Ia), (Ib), (Iaa), (Iab), (Iba), (Ibb), (II), (IIa), (IIb), (IIaa) (IIab), (IIba), or (IIbb), R¹²ᵃ is hydrogen and R¹²ᵇ is hydrogen, substituted or unsubstituted C₁-C₆ alkyl, substituted or unsubstituted phenyl, or substituted or unsubstituted monocyclic heteroaryl.

In some embodiments of Formula (I), (Ia), (Ib), (Iaa), (Iab), (Iba), (Ibb), (II), (IIa), (IIb), (IIaa) (IIab), (IIba), or (IIbb), $R^{12a}$ is hydrogen and $R^{12b}$ is hydrogen or phenyl. In some embodiments of Formula (I), (Ia), (Ib), (Iaa), (Iab), (Iba), (Ibb), (II), (IIa), (IIb), (IIaa) (IIab), (IIba), or (IIbb), $R^{12a}$ is hydrogen and $R^{12b}$ is hydrogen. In some embodiments, R and $R^2$ taken together form

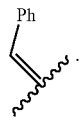

In some embodiments, $R^1$ and $R^2$ taken together form

In some embodiments of Formula (I), (Ia), (Ib), (Iaa), (Iab), (Iba), (Ibb), (II), (IIa), (IIb), (IIaa) (IIab), (IIba), or (IIbb), each of $R^4$, $R^5$, $R^6$, and $R^7$ is independently selected H, $-OR^{11}$, $-NR^{22}R^{23}$, halogen, and substituted or unsubstituted $C_1$-$C_6$ alky.

In some embodiments of Formula (I), (Ia), (Ib), (Iaa), (Iab), (Iba), (Ibb), (II), (IIa), (IIb), (IIaa) (IIab), (IIba), or (IIbb), each of $R^4$, $R^5$, $R^6$, and $R^7$ is independently selected from H, halogen, substituted or unsubstituted $C_1$-$C_6$ alkyl, substituted or unsubstituted $C_1$-$C_6$ heteroalkyl, substituted or unsubstituted $C_3$-$C_8$ cycloalkyl, and substituted or unsubstituted $C_2$-$C_7$ heterocycloalkyl. In some embodiments of Formula (I), (Ia), (Ib), (Iaa), (Iab), (Iba), (Ibb), (II), (IIa), (IIb), (IIaa) (IIab), (IIba), or (IIbb), each of $R^4$, $R^5$, $R^6$, and $R^7$ is independently selected from H and halogen. In some embodiments of Formula (I), (Ia), (Ib), (Iaa), (Iab), (Iba), (Ibb), (II), (IIa), (IIb), (IIaa) (IIab), (IIba), or (IIbb), each of $R^4$, $R^5$, $R^6$, and $R^7$ is independently selected from H, halogen, and substituted or unsubstituted $C_1$-$C_6$ alkyl. In some embodiments of Formula (I), (Ia), (Ib), (Iaa), (Iab), (Iba), (Ibb), (II), (IIa), (IIb), (IIaa) (IIab), (IIba), or (IIbb), each of $R^4$, $R^5$, $R^6$, and $R^7$ is independently selected from H, halogen, $C_1$-$C_6$ alkyl, $C_1$-$C_6$ haloalkyl, $C_1$-$C_6$ hydroxyalkyl, or $C_1$-$C_6$ aminoalkyl.

In some embodiments of Formula (I), (Ia), (Ib), (Iaa), (Iab), (Iba), (Ibb), (II), (IIa), (IIb), (IIaa) (IIab), (IIba), or (IIbb), $R^4$ is selected from H, $-OR^{11}$, $-NR^{22}R^{23}$, halogen, and substituted or unsubstituted $C_1$-$C_6$ alky. In some embodiments, $R^4$ is $-OR^{11}$ (e.g., $C_1$-$C_6$ alkoxy). In some embodiments, $R^4$ is $-NR^{22}R^{23}$ (such as amino, NH($C_1$-$C_6$ alkyl) and N($C_1$-$C_6$ alkyl)$_2$). In some embodiments of Formula (I), (Ia), (Ib), (Iaa), (Iab), (Iba), (Ibb), (II), (IIa), (IIb), (IIaa) (IIab), (IIba), or (IIbb), $R^4$ is H and halogen. In some embodiments of Formula (I), (Ia), (Ib), (Iaa), (Iab), (Iba), (Ibb), (II), (IIa), (IIb), (IIaa) (IIab), (IIba), or (IIbb), $R^4$ is H, F, Cl, or Br. In some embodiments of Formula (I), (Ia), (Ib), (Iaa), (Iab), (Iba), (Ibb), (II), (IIa), (IIb), (IIaa) (IIab), (IIba), or (IIbb), $R^4$ is F. In some embodiments of Formula (I), (Ia), (Ib), (Iaa), (Iab), (Iba), (Ibb), (II), (IIa), (IIb), (IIaa) (IIab), (IIba), or (IIbb), $R^4$ is Cl. In some embodiments of Formula (I), (Ia), (Ib), (Iaa), (Iab), (Iba), (Ibb), (II), (IIa), (IIb), (IIaa) (IIab), (IIba), or (IIbb), $R^4$ is Br. In some embodiments of Formula (I), (Ia), (Ib), (Iaa), (Iab), (Iba), (Ibb), (II), (IIa), (IIb), (IIaa) (IIab), (IIba), or (IIbb), $R^4$ is H. In some embodiments, $R^4$ is H, halogen, substituted or unsubstituted $C_1$-$C_6$ alkyl, or substituted or unsubstituted $C_1$-$C_6$ heteroalkyl. In some embodiments, $R^4$ is H, halogen, $-C_1$-$C_6$ alkyl, $C_1$-$C_6$ aminoalkyl, $C_1$-$C_6$ haloalkyl, $C_1$-$C_6$ hydroxyalkyl, $C_1$-$C_6$ heteroalkyl. In some embodiments, $R^4$ is H, halogen, $-C_1$-$C_6$ alkyl, $C_1$-$C_6$ aminoalkyl, $C_1$-$C_6$ haloalkyl, or $C_1$-$C_6$ hydroxyalkyl. In some embodiments, $R^4$ is $CF_3$. In some embodiments, $R^4$ is methyl.

In some embodiments of Formula (I), (Ia), (Ib), (Iaa), (Iab), (Iba), (Ibb), (II), (IIa), (IIb), (IIaa) (IIab), (IIba), or (IIbb), $R^5$ is selected from H, $-OR^{11}$, $-NR^{22}R^{23}$, halogen, and substituted or unsubstituted $C_1$-$C_6$ alky. In some embodiments, $R^5$ is $-OR^{11}$ (e.g., $C_1$-$C_6$ alkoxy). In some embodiments, $R^5$ is $-NR^{22}R^{23}$ (such as amino, NH($C_1$-$C_6$ alkyl) and N($C_1$-$C_6$ alkyl)$_2$). In some embodiments of Formula (I), (Ia), (Ib), (Iaa), (Iab), (Iba), (Ibb), (II), (IIa), (IIb), (IIaa) (IIab), (IIba), or (IIbb), $R^5$ is H and halogen. In some embodiments of Formula (I), (Ia), (Ib), (Iaa), (Iab), (Iba), (Ibb), (II), (IIa), (IIb), (IIaa) (IIab), (IIba), or (IIbb), $R^5$ is H, F, Cl, or Br. In some embodiments of Formula (I), (Ia), (Ib), (Iaa), (Iab), (Iba), (Ibb), (II), (IIa), (IIb), (IIaa) (IIab), (IIba), or (IIbb), $R^5$ is F. In some embodiments of Formula (I), (Ia), (Ib), (Iaa), (Iab), (Iba), (Ibb), (II), (IIa), (IIb), (IIaa) (IIab), (IIba), or (IIbb), $R^5$ is Cl. In some embodiments of Formula (I), (Ia), (Ib), (Iaa), (Iab), (Iba), (Ibb), (II), (IIa), (IIb), (IIaa) (IIab), (IIba), or (IIbb), $R^5$ is Br. In some embodiments of Formula (I), (Ia), (Ib), (Iaa), (Iab), (Iba), (Ibb), (II), (IIa), (IIb), (IIaa) (IIab), (IIba), or (IIbb), $R^5$ is H. In some embodiments, $R^5$ is H, halogen, substituted or unsubstituted $C_1$-$C_6$ alkyl, or substituted or unsubstituted $C_1$-$C_6$ heteroalkyl. In some embodiments, $R^5$ is H, halogen, $-C_1$-$C_6$ alkyl, $C_1$-$C_6$ aminoalkyl, $C_1$-$C_6$ haloalkyl, $C_1$-$C_6$ hydroxyalkyl, $C_1$-$C_6$ heteroalkyl. In some embodiments, $R^5$ is H, halogen, $-C_1$-$C_6$ alkyl, $C_1$-$C_6$ aminoalkyl, $C_1$-$C_6$ haloalkyl, or $C_1$-$C_6$ hydroxyalkyl. In some embodiments, $R^5$ is $CF_3$. In some embodiments, $R^5$ is methyl.

In some embodiments of Formula (I), (Ia), (Ib), (Iaa), (Iab), (Iba), (Ibb), (II), (IIa), (IIb), (IIaa) (IIab), (IIba), or (IIbb), $R^6$ is selected from H, $-OR^{11}$, $-NR^{22}R^{23}$, halogen, and substituted or unsubstituted $C_1$-$C_6$ alky. In some embodiments, $R^6$ is $-OR^{11}$ (e.g., $C_1$-$C_6$ alkoxy). In some embodiments, $R^6$ is $-NR^{22}R^{23}$ (such as amino, NH($C_1$-$C_6$ alkyl) and N($C_1$-$C_6$ alkyl)$_2$). In some embodiments of Formula (I), (Ia), (Ib), (Iaa), (Iab), (Iba), (Ibb), (II), (IIa), (IIb), (IIaa) (IIab), (IIba), or (IIbb), $R^6$ is H and halogen. In some embodiments of Formula (I), (Ia), (Ib), (Iaa), (Iab), (Iba), (Ibb), (II), (IIa), (IIb), (IIaa) (IIab), (IIba), or (IIbb), $R^6$ is H, F, Cl, or Br. In some embodiments of Formula (I), (Ia), (Ib), (Iaa), (Iab), (Iba), (Ibb), (II), (IIa), (IIb), (IIaa) (IIab), (IIba), or (IIbb), $R^6$ is F. In some embodiments of Formula (I), (Ia), (Ib), (Iaa), (Iab), (Iba), (Ibb), (II), (IIa), (IIb), (IIaa) (IIab), (IIba), or (IIbb), $R^6$ is Cl. In some embodiments of Formula (I), (Ia), (Ib), (Iaa), (Iab), (Iba), (Ibb), (II), (IIa), (IIb), (IIaa) (IIab), (IIba), or (IIbb), $R^6$ is Br. In some embodiments of Formula (I), (Ia), (Ib), (Iaa), (Iab), (Iba), (Ibb), (II), (IIa), (IIb), (IIaa) (IIab), (IIba), or (IIbb), $R^6$ is H. In some embodiments, $R^6$ is H, halogen, substituted or unsubstituted $C_1$-$C_6$ alkyl, or substituted or unsubstituted $C_1$-$C_6$ heteroalkyl. In some embodiments, $R^6$ is H, halogen, $-C_1$-$C_6$ alkyl, $C_1$-$C_6$ aminoalkyl, $C_1$-$C_6$ haloalkyl, $C_1$-$C_6$ hydroxyalkyl, $C_1$-$C_6$ heteroalkyl. In some embodiments, $R^6$ is H, halogen, $-C_1$-$C_6$ alkyl, $C_1$-$C_6$ aminoalkyl, $C_1$-$C_6$ haloalkyl, or $C_1$-$C_6$ hydroxyalkyl. In some embodiments, $R^6$ is $CF_3$. In some embodiments, $R^6$ is methyl.

In some embodiments of Formula (I), (Ia), (Ib), (Iaa), (Iab), (Iba), (Ibb), (II), (IIa), (IIb), (IIaa) (IIab), (IIba), or (IIbb), $R^7$ is selected from H, $-OR^{11}$, $-NR^{22}R^{23}$, halogen, and substituted or unsubstituted $C_1$-$C_6$ alky. In some embodiments, $R^7$ is $-OR^{11}$ (e.g., $C_1$-$C_6$ alkoxy). In some embodiments, $R^7$ is —$NR^{22}R^{23}$ (such as amino, $NH(C_1\text{-}C_6$ alkyl) and $N(C_1\text{-}C_6$ alkyl)$_2$). In some embodiments of Formula (I), (Ia), (Ib), (Iaa), (Iab), (Iba), (Ibb), (II), (IIa), (IIb), (IIaa) (IIab), (IIba), or (IIbb), $R^7$ is H and halogen. In some embodiments of Formula (I), (Ia), (Ib), (Iaa), (Iab), (Iba), (Ibb), (II), (IIa), (IIb), (IIaa) (IIab), (IIba), or (IIbb), $R^7$ is H, F, Cl, or Br. In some embodiments of Formula (I), (Ia), (Ib), (Iaa), (Iab), (Iba), (Ibb), (II), (IIa), (IIb), (IIaa) (IIab), (IIba), or (IIbb), $R^7$ is F. In some embodiments of Formula (I), (Ia), (Ib), (Iaa), (Iab), (Iba), (Ibb), (II), (IIa), (IIb), (IIaa) (IIab), (IIba), or (IIbb), $R^7$ is Cl. In some embodiments of Formula (I), (Ia), (Ib), (Iaa), (Iab), (Iba), (Ibb), (II), (IIa), (IIb), (IIaa) (IIab), (IIba), or (IIbb), $R^7$ is Br. In some embodiments of Formula (I), (Ia), (Ib), (Iaa), (Iab), (Iba), (Ibb), (II), (IIa), (IIb), (IIaa) (IIab), (IIba), or (IIbb), $R^7$ is H. In some embodiments, $R^7$ is H, halogen, substituted or unsubstituted $C_1\text{-}C_6$ alkyl, or substituted or unsubstituted $C_1\text{-}C_6$ heteroalkyl. In some embodiments, $R^7$ is H, halogen, $C_1\text{-}C_6$ alkyl, $C_1\text{-}C_6$ aminoalkyl, $C_1\text{-}C_6$ haloalkyl, $C_1\text{-}C_6$ hydroxyalkyl, $C_1\text{-}C_6$ heteroalkyl. In some embodiments, $R^7$ is H, halogen, —$C_1\text{-}C_6$ alkyl, $C_1\text{-}C_6$ aminoalkyl, $C_1\text{-}C_6$ haloalkyl, or $C_1\text{-}C_6$ hydroxyalkyl. In some embodiments, $R^7$ is $CF_3$. In some embodiments, $R^7$ is methyl.

In some embodiments of Formula (I), (Ia), (Ib), (Iaa), (Iab), (Iba), (Ibb), (II), (IIa), (IIb), (IIaa) (IIab), (IIba), or (IIbb), $R^3$ is —$OR^{11}$, halogen, —$SR^{11}$, —$S(=O)R^{21}$, —$S(=O)_2R^{21}$, —$NHS(=O)_2R^{21}$, —$S(=O)_2NR^{22}R^{23}$, —$C(=O)R^{21}$, —$OC(=O)R^{21}$, —$C(=O)OR^{22}$, —$OC(=O)OR^{22}$, —$C(=O)NR^{22}R^{23}$, —$OC(=O)NR^{22}R^{23}$, —$NR^{22}R^{23}$, —$NO_2$, —$NHS(=O)_2R^{21}$, —$NR^{22}C(=O)NR^{22}R^{23}$, —$NR^{22}C(=O)R^{21}$, —$NR^{22}C(=O)OR^{21}$, substituted or unsubstituted $C_1\text{-}C_8$ alkyl, substituted or unsubstituted $C_2\text{-}C_8$ alkenyl, substituted or unsubstituted $C_2\text{-}C_8$ alkynyl, substituted or unsubstituted $C_1\text{-}C_8$ heteroalkyl, substituted or unsubstituted $C_3\text{-}C_8$ cycloalkyl, substituted or unsubstituted $C_2\text{-}C_7$ heterocycloalkyl, substituted or unsubstituted phenyl, substituted or unsubstituted naphthyl, substituted or unsubstituted monocyclic heteroaryl, or substituted or unsubstituted bicyclic or polycyclic heteroaryl.

In some embodiments of Formula (I), (Ia), (Ib), (Iaa), (Iab), (Iba), (Ibb), (II), (IIa), (IIb), (IIaa) (IIab), (IIba), or (IIbb), $R^3$ is substituted or unsubstituted monocyclic heteroaryl. In some embodiments of Formula (I), (Ia), (Ib), (Iaa), (Iab), (Iba), (Ibb), (II), (IIa), (IIb), (IIaa) (IIab), (IIba), or (IIbb), $R^3$ is substituted or unsubstituted 5 or 6 membered monocyclic heteroaryl having 1-4 ring heteroatoms independently selected from N, O and S. In some embodiments, $R^3$ is substituted or unsubstituted 5 membered monocyclic heteroaryl. In some embodiments, $R^3$ is substituted or unsubstituted 6 membered monocyclic heteroaryl. In some embodiments of Formula (I), (Ia), (Ib), (Iaa), (Iab), (Iba), (Ibb), (II), (IIa), (IIb), (IIaa) (IIab), (IIba), or (IIbb), $R^3$ is substituted or unsubstituted 5-membered monocyclic heteroaryl. In some embodiments of Formula (I), (Ia), (Ib), (Iaa), (Iab), (Iba), (Ibb), (II), (IIa), (IIb), (IIaa) (IIab), (IIba), or (IIbb), $R^3$ is substituted or unsubstituted 6-membered monocyclic heteroaryl.

In some embodiments of Formula (I), (Ia), (Ib), (Iaa), (Iab), (Iba), (Ibb), (II), (IIa), (IIb), (IIaa) (IIab), (IIba), or (IIbb), $R^3$ is

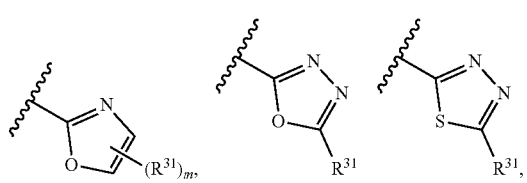

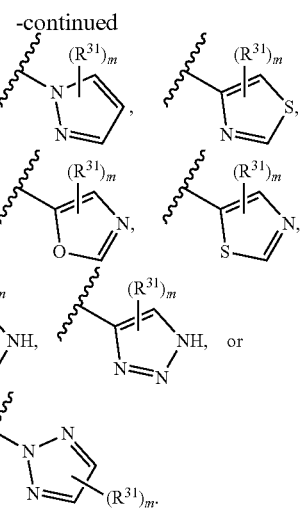

In some embodiments of Formula (I), (Ia), (Ib), (Iaa), (Iab), (Iba), (Ibb), (II), (IIa), (IIb), (IIaa) (IIab), (IIba), or (IIbb), $R^3$ is

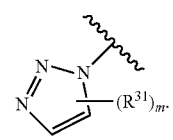

In some embodiments of Formula (I), (Ia), (Ib), (Iaa), (Iab), (Iba), (Ibb), (II), (IIa), (IIb), (IIaa) (IIab), (IIba), or (IIbb), $R^3$ is

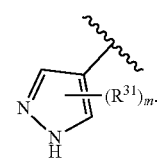

In some embodiments, $R^3$ is

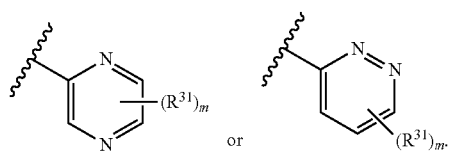

In some embodiments, each $R^{31}$ is independently selected from hydrogen, cyano, halogen, hydroxy, substituted or unsubstituted $C_{1\text{-}6}$ alkyl, —$OCH_3$, —$OCD_3$, substituted or unsubstituted $C_{2\text{-}6}$ alkenyl, substituted or unsubstituted $C_{2\text{-}6}$ alkynyl, substituted or unsubstituted $C_{1\text{-}6}$ alkoxy, substituted or unsubstituted $C_{3\text{-}7}$ cycloalkyl, substituted or unsubstituted $C_{2\text{-}8}$ heterocycloalkyl, heteroaryl, substituted or unsubstituted heterocycloalkyl-$C_{1\text{-}6}$ alkyl, substituted or unsubstituted $C_{1\text{-}6}$ alkyl-aryl, substituted or unsubstituted $C_{1\text{-}6}$ alkyl-heterocycloalkyl, substituted or unsubstituted $C_{1\text{-}6}$ alkyl-heteroaryl, substituted or unsubstituted $C_{1\text{-}6}$ alkoxy-aryl, substituted or unsubstituted $C_{1\text{-}6}$ alkoxy-heterocycloalkyl, substituted or unsubstituted $C_{1-6}$ alkoxy-heteroaryl, and $C_{1-6}$ alkoxy substituted with hydroxy, $C_{1-6}$ alkoxy, amino, mono-$C_{1-6}$ alkylamino and di-$C_{1-6}$ alkylamino; and m is 0, 1, 2, or 3. In some embodiments, each $R^{31}$ is independently selected from hydrogen, cyano, halogen, hydroxy, substituted or unsubstituted $C_{1-6}$ alkyl, —OCH$_3$, —OCD$_3$, CN, NO$_2$, —OR$^{11}$, —SR$^{11}$, —S(=O)R$^{21}$, —S(=O)$_2$R$^{21}$, —NHS(=O)$_2$R$^{21}$, —S(=O)$_2$NR$^{22}$R$^{23}$, —C(=O)R$^{21}$, —OC(=O)R$^{21}$, —C(=O)OR$^{22}$, —OC(=O)OR$^{22}$, —C(=O)NR$^{22}$R$^{23}$, —OC(=O)NR$^{22}$R$^{23}$, —NR$^{22}$R$^{23}$, —NO$_2$, —NHS(=O)$_2$R$^{21}$, —NR$^{22}$C(=O)NR$^{22}$R$^{23}$, —NR$^{22}$C(=O)R$^{21}$, —NR$^{22}$C(=O)OR$^{21}$, substituted or unsubstituted $C_{2-6}$ alkenyl, substituted or unsubstituted $C_{2-6}$ alkynyl, substituted or unsubstituted $C_{1-6}$ alkoxy, substituted or unsubstituted $C_{3-7}$ cycloalkyl, substituted or unsubstituted $C_{2-8}$ heterocycloalkyl, heteroaryl, substituted or unsubstituted heterocycloalkyl-$C_{1-6}$ alkyl, substituted or unsubstituted $C_{1-6}$ alkyl-aryl, substituted or unsubstituted $C_{1-6}$ alkyl-heterocycloalkyl, substituted or unsubstituted $C_{1-6}$ alkyl-heteroaryl, substituted or unsubstituted $C_{1-6}$ alkoxy-aryl, substituted or unsubstituted $C_{1-6}$ alkoxy-heterocycloalkyl, substituted or unsubstituted $C_{1-6}$ alkoxy-heteroaryl, and $C_{1-6}$ alkoxy substituted with hydroxy, $C_{1-6}$ alkoxy, amino, mono-$C_{1-6}$ alkylamino and di-$C_{1-6}$ alkylamino; and m is 0, 1, 2, or 3.

In some embodiments of Formula (I), (Ia), (Ib), (Iaa), (Iab), (Iba), (Ibb), (II), (IIa), (IIb), (IIaa) (IIab), (IIba), or (IIbb), $R^3$ is a 6-membered heteroaryl substituted with 1, 2, 3, or 4 $R^{31}$, wherein each $R^{31}$ is independently selected from cyano, halogen, hydroxy, substituted or unsubstituted $C_{1-6}$ alkyl, —OCH$_3$, —OCD$_3$, substituted or unsubstituted $C_{2-6}$ alkenyl, substituted or unsubstituted $C_{2-6}$ alkynyl, substituted or unsubstituted $C_{1-6}$ alkoxy, substituted or unsubstituted $C_{3-7}$ cycloalkyl, substituted or unsubstituted $C_{2-8}$ heterocycloalkyl, heteroaryl, substituted or unsubstituted heterocycloalkyl-$C_{1-6}$ alkyl, substituted or unsubstituted $C_{1-6}$ alkyl-aryl, substituted or unsubstituted $C_{1-6}$ alkyl-heterocycloalkyl, substituted or unsubstituted $C_{1-6}$ alkyl-heteroaryl, substituted or unsubstituted $C_{1-6}$ alkoxy-aryl, substituted or unsubstituted $C_{1-6}$ alkoxy-heterocycloalkyl, substituted or unsubstituted $C_{1-6}$ alkoxy-heteroaryl, and $C_{1-6}$ alkoxy substituted with hydroxy, $C_{1-6}$ alkoxy, amino, mono-$C_{1-6}$ alkylamino and di-$C_{1-6}$ alkylamino; and m is 0, 1, 2, or 3.

In some embodiments of Formula (I), (Ia), (Ib), (Iaa), (Iab), (Iba), (Ibb), (II), (IIa), (IIb), (IIaa) (IIab), (IIba), or (IIbb), $R^3$ is

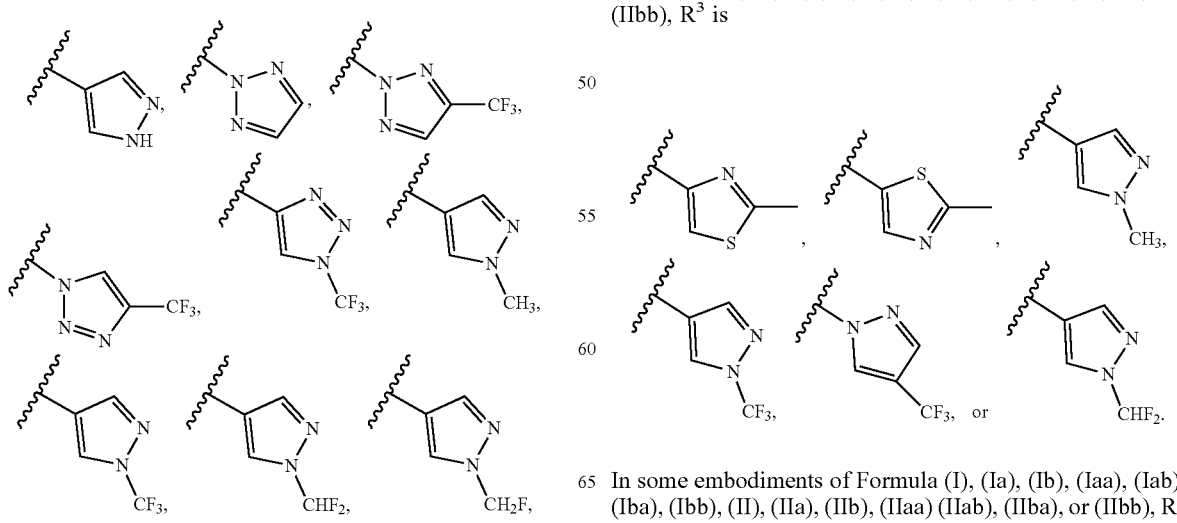

In some embodiments, $R^3$ is

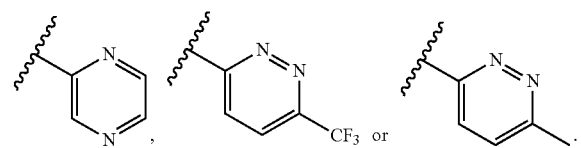

In some embodiments of Formula (I), (Ia), (Ib), (Iaa), (Iab), (Iba), (Ibb), (II), (IIa), (IIb), (IIaa) (IIab), (IIba), or (IIbb), $R^3$ is In some embodiments of Formula (I), (Ia), (Ib), (Iaa), (Iab), (Iba), (Ibb), (II), (IIa), (IIb), (IIaa) (IIab), (IIba), or (IIbb), $R^3$ is

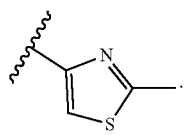

In some embodiments of Formula (I), (Ia), (Ib), (Iaa), (Iab), (Iba), (Ibb), (II), (IIa), (IIb), (IIaa) (IIab), (IIba), or (IIbb), $R^3$ is

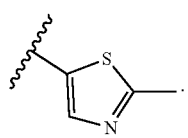 [SMILES: *c1cnc(C)s1]

In some embodiments of Formula (I), (Ia), (Ib), (Iaa), (Iab), (Iba), (Ibb), (II), (IIa), (IIb), (IIaa) (IIab), (IIba), or (IIbb), $R^3$ is

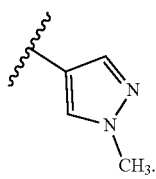

In some embodiments of Formula (I), (Ia), (Ib), (Iaa), (Iab), (Iba), (Ibb), (II), (IIa), (IIb), (IIaa) (IIab), (IIba), or (IIbb), $R^3$ is

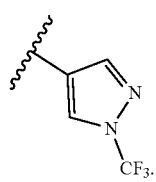

In some embodiments of Formula (I), (Ia), (Ib), (Iaa), (Iab), (Iba), (Ibb), (II), (IIa), (IIb), (IIaa) (IIab), (IIba), or (IIbb), $R^3$ is

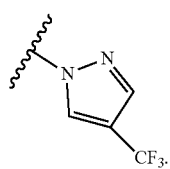 [SMILES: *n1cc(C(F)(F)F)cn1]

In some embodiments of Formula (I), (Ia), (Ib), (Iaa), (Iab), (Iba), (Ibb), (II), (IIa), (IIb), (IIaa) (IIab), (IIba), or (IIbb), $R^3$ is

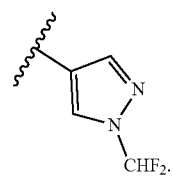 [SMILES: *c1cnn(C(F)F)c1]

In some embodiments of Formula (I), (Ia), (Ib), (Iaa), (Iab), (Iba), (Ibb), (II), (IIa), (IIb), (IIaa) (IIab), (IIba), or (IIbb), $R^3$ is substituted or unsubstituted bicyclic heteroaryl. In some embodiments of Formula (I), (Ia), (Ib), (Iaa), (Iab), (Iba), (Ibb), (II), (IIa), (IIb), (IIaa) (IIab), (IIba), or (IIbb), $R^3$ is a fused bicyclic heteroaryl having 8 to 10 ring atoms, 1, 2, 3, 4 or 5 ring heteroatoms independently selected from N, O and S.

In some embodiments of Formula (I), (Ia), (Ib), (Iaa), (Iab), (Iba), (Ibb), (II), (IIa), (IIb), (IIaa) (IIab), (IIba), or (IIbb), $R^3$ is substituted or unsubstituted $C_2$-$C_7$ heterocycloalkyl. In some embodiments of Formula (I), (Ia), (Ib), (Iaa), (Iab), (Iba), (Ibb), (II), (IIa), (IIb), (IIaa) (IIab), (IIba), or (IIbb), $R^3$ is a monocyclic 5 or 6 membered heterocycloalkyl having 1 to 3 ring heteroatoms independently selected from N, O and S.

In some embodiments of Formula (I), (Ia), (Ib), (Iaa), (Iab), (Iba), (Ibb), (II), (IIa), (IIb), (IIaa) (IIab), (IIba), or (IIbb), $R^3$ is

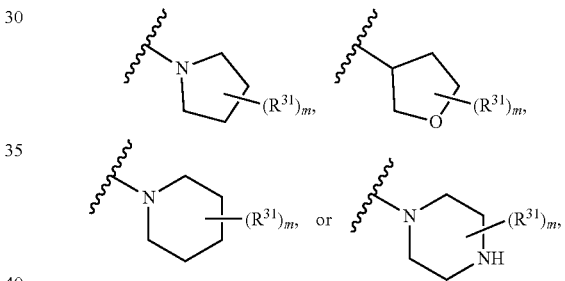

wherein each $R^{31}$ is independently selected from cyano, halogen, hydroxy, substituted or unsubstituted $C_{1-6}$ alkyl, —OCH$_3$, —OCD$_3$, substituted or unsubstituted $C_{2-6}$ alkenyl, substituted or unsubstituted $C_{2-6}$ alkynyl, substituted or unsubstituted $C_{1-6}$ alkoxy, substituted or unsubstituted $C_{3-7}$ cycloalkyl, substituted or unsubstituted $C_{2-8}$ heterocycloalkyl, heteroaryl, substituted or unsubstituted heterocycloalkyl-$C_{1-6}$ alkyl, substituted or unsubstituted $C_{1-6}$ alkyl-aryl, substituted or unsubstituted $C_{1-6}$ alkyl-heterocycloalkyl, substituted or unsubstituted $C_{1-6}$ alkyl-heteroaryl, substituted or unsubstituted $C_{1-6}$ alkoxy-aryl, substituted or unsubstituted $C_{1-6}$ alkoxy-heterocycloalkyl, substituted or unsubstituted $C_{1-6}$ alkoxy-heteroaryl, and $C_{1-6}$ alkoxy substituted with hydroxy, $C_{1-6}$ alkoxy, amino, mono-$C_{1-6}$ alkylamino and di-$C_{1-6}$ alkylamino; and m is 0, 1, 2, 3, 4 or 5.

In some embodiments of Formula (I), (Ia), (Ib), (Iaa), (Iab), (Iba), (Ibb), (II), (IIa), (IIb), (IIaa) (IIab), (IIba), or (IIbb), $R^3$ is

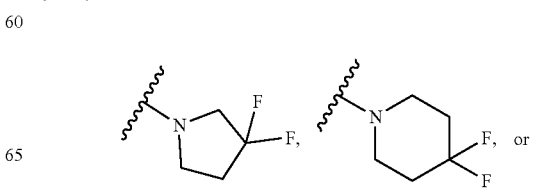

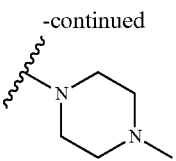

In some embodiments of Formula (I), (Ia), (Ib), (Iaa), (Iab), (Iba), (Ibb), (II), (IIa), (IIb), (IIaa) (IIab), (IIba), or (IIbb), R³ is

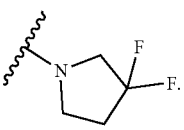 [SMILES: *N1CCC(F)(F)C1]

In some embodiments of Formula (I), (Ia), (Ib), (Iaa), (Iab), (Iba), (Ibb), (II), (IIa), (IIb), (IIaa) (IIab), (IIba), or (IIbb), R³ is

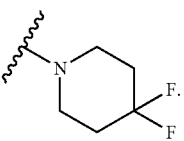 [SMILES: *N1CCC(F)(F)CC1]

In some embodiments of Formula (I), (Ia), (Ib), (Iaa), (Iab), (Iba), (Ibb), (II), (IIa), (IIb), (IIaa) (IIab), (IIba), or (IIbb), R³ is

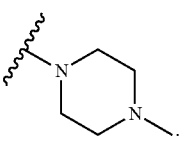 [SMILES: *N1CCN(C)CC1]

In some embodiments of Formula (I), (Ia), (Ib), (Iaa), (Iab), (Iba), (Ibb), (II), (IIa), (IIb), (IIaa) (IIab), (IIba), or (IIbb), R³ is substituted or unsubstituted $C_3$-$C_8$ cycloalkyl. In some embodiments of Formula (I), (Ia), (Ib), (Iaa), (Iab), (Iba), (Ibb), (II), (IIa), (IIb), (IIaa) (IIab), (IIba), or (IIbb), R³ is cyclopropyl, cyclobutyl, cyclopentyl, or cyclohexyl, each of which is optionally substituted. In some embodiments of Formula (I), (Ia), (Ib), (Iaa), (Iab), (Iba), (Ibb), (II), (IIa), (IIb), (IIaa) (IIab), (IIba), or (IIbb), R³ is cyclopropyl. In some embodiments of Formula (I), (Ia), (Ib), (Iaa), (Iab), (Iba), (Ibb), (II), (IIa), (IIb), (IIaa) (IIab), (IIba), or (IIbb), R³ is cyclobutyl. In some embodiments of Formula (I), (Ia), (Ib), (Iaa), (Iab), (Iba), (Ibb), (II), (IIa), (IIb), (IIaa) (IIab), (IIba), or (IIbb), R³ is cyclopentyl. In some embodiments of Formula (I), (Ia), (Ib), (Iaa), (Iab), (Iba), (Ibb), (II), (IIa), (IIb), (IIaa) (IIab), (IIba), or (IIbb), R³ is cyclohexyl. In some embodiments of Formula (I), (Ia), (Ib), (Iaa), (Iab), (Iba), (Ibb), (II), (IIa), (IIb), (IIaa) (IIab), (IIba), or (IIbb), R³ is

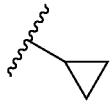

In some embodiments of Formula (I), (Ia), (Ib), (Iaa), (Iab), (Iba), (Ibb), (II), (IIa), (IIb), (IIaa) (IIab), (IIba), or (IIbb), R³ is phenyl or naphthyl, each of which is optionally substituted. In some embodiments of Formula (I), (Ia), (Ib), (Iaa), (Iab), (Iba), (Ibb), (II), (IIa), (IIb), (IIaa) (IIab), (IIba), or (IIbb), R³ is phenyl. In some embodiments of Formula (I), (Ia), (Ib), (Iaa), (Iab), (Iba), (Ibb), (II), (IIa), (IIb), (IIaa) (IIab), (IIba), or (IIbb), R³ is naphthyl.

In some embodiments of Formula (I), (Ia), (Ib), (Iaa), (Iab), (Iba), (Ibb), (II), (IIa), (IIb), (IIaa) (IIab), (IIba), or (IIbb), R³ is substituted with one or more $R^{31}$, and each $R^{31}$ is independently selected from cyano, oxime, oxo, halogen, hydroxy, $NO_2$, amino, —$OR^{11}$, —$SR^{11}$, —$S(=O)R^{21}$, —$S(=O)_2R^{21}$, —$NHS(=O)_2R^{21}$, —$S(=O)_2NR^{22}R^{23}$, —$C(=O)R^{21}$, —$OC(=O)R^{21}$, —$C(=O)OR^{22}$, —$OC(=O)OR^{22}$, —$C(=O)NR^{22}R^{23}$, —$OC(=O)NR^{22}R^{23}$, —$NR^{22}R^{23}$, —$NO_2$, —$NHS(=O)_2R^{21}$, —$NR^{22}C(=O)NR^{22}R^{23}$, —$NR^{22}C(=O)R^{21}$, —$NR^{22}C(=O)OR^{21}$, mono-$C_{1-6}$ alkylamino, di-$C_{1-6}$ alkylamino, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{1-6}$ alkoxy, substituted or unsubstituted $C_{3-7}$ cycloalkyl, substituted or unsubstituted $C_{2-8}$ heterocycloalkyl, heteroaryl, substituted or unsubstituted heterocycloalkyl-$C_{1-6}$ alkyl, substituted or unsubstituted $C_{1-6}$ alkyl-heterocycloalkyl, substituted or unsubstituted $C_{1-6}$ alkyl-aryl, substituted or unsubstituted $C_{1-6}$ alkyl-heteroaryl, substituted or unsubstituted $C_{1-6}$ alkoxy-aryl, substituted or unsubstituted $C_{1-6}$ alkoxy-heterocycloalkyl, and substituted or unsubstituted $C_{1-6}$ alkoxy-heteroaryl. In some embodiments of Formula (I), (Ia), (Ib), (Iaa), (Iab), (Iba), (Ibb), (II), (IIa), (IIb), (IIaa) (IIab), (IIba), or (IIbb), R³ is substituted with one or more $R^{31}$, and each $R^{31}$ is independently selected from cyano, oxo, halogen, hydroxy, —SH, $NO_2$, amino, $C_{1-6}$ alkyl, $C_{1-6}$ haloalkyl, $C_{1-6}$ hydroxyalkyl, $C_{1-6}$ aminoalkyl, and $C_{1-6}$ heteroalkyl.

In some embodiments of Formula (I), (Ia), (Ib), (Iaa), (Iab), (Iba), (Ibb), (II), (IIa), (IIb), (IIaa) (IIab), (IIba), or (IIbb), R³ is —$OR^{11}$, —$SR^{11}$, —$S(=O)R^{21}$, —$S(=O)_2R^{21}$, —$NHS(=O)_2R^{21}$, —$S(=O)_2NR^{22}R^{23}$, —$C(=O)R^{21}$, —$OC(=O)R^{21}$, —$C(=O)OR^{22}$, —$OC(=O)OR^{22}$, —$C(=O)NR^{22}R^{23}$, —$OC(=O)NR^{22}R^{23}$, —$NR^{22}R^{23}$, —$NO_2$, —$NHS(=O)_2R^{21}$, —$NR^{22}C(=O)NR^{22}R^{23}$, —$NR^{22}C(=O)R^{21}$, —$NR^{22}C(=O)OR^{21}$, halogen, substituted or unsubstituted $C_1$-$C_8$ alkyl, substituted or unsubstituted $C_2$-$C_8$ alkenyl, substituted or unsubstituted $C_2$-$C_8$ alkynyl, or substituted or unsubstituted $C_1$-$C_8$ heteroalkyl. In some embodiments of Formula (I), (Ia), (Ib), (Iaa), (Iab), (Iba), (Ibb), (II), (IIa), (IIb), (IIaa) (IIab), (IIba), or (IIbb), R³ is —$OR^{11}$, —$SR^{11}$, substituted or unsubstituted $C_1$-$C_8$ alkyl, substituted or unsubstituted $C_2$-$C_8$ alkenyl, substituted or unsubstituted $C_2$-$C_8$ alkynyl, or substituted or unsubstituted $C_1$-$C_8$ heteroalkyl. In some embodiments of Formula (I), (Ia), (Ib), (Iaa), (Iab), (Iba), (Ibb), (II), (IIa), (IIb), (IIaa) (IIab), (IIba), or (IIbb), R³ is —$OR^{11}$, —$SR^{11}$, —$S(=O)R^{21}$, —$S(=O)_2R^{21}$, —$NHS(=O)_2R^{21}$, —$S(=O)_2NR^{22}R^{23}$, —$C(=O)R^{21}$, —$OC(=O)R^{21}$, —$C(=O)OR^{22}$, —$OC(=O)OR^{22}$, —$C(=O)NR^{22}R^{23}$, —$OC(=O)NR^{22}R^{23}$, —$NR^{22}R^{23}$, —$NO_2$, —$NHS(=O)_2R^{21}$, —$NR^{22}C(=O)NR^{22}R^{23}$, —$NR^{22}C(=O)R^{21}$, —$NR^{22}C(=O)OR^{21}$. In some embodiments of Formula (I), (Ia), (Ib), (Iaa), (Iab), (Iba), (Ibb), (II), (IIa), (IIb), (IIaa) (IIab), (IIba), or (IIbb), $R^3$ is —$OR^{11}$. In some embodiments of Formula (I), (Ia), (Ib), (Iaa), (Iab), (Iba), (Ibb), (II), (IIa), (IIb), (IIaa) (IIab), (IIba), or (IIbb), $R^3$ is —$SR^{11}$.

In some embodiments, $R^3$ is —$OR^{11}$, —$SR^{11}$, —$NR^{22}R^{23}$, substituted or unsubstituted $C_1$-$C_8$ alkyl, or substituted or unsubstituted monocyclic heteroaryl. In some embodiments of Formula (I), (Ia), (Ib), (Iaa), (Iab), (Iba), (Ibb), (II), (IIa), (IIb), (IIaa) (IIab), (IIba), or (IIbb), $R^3$ is

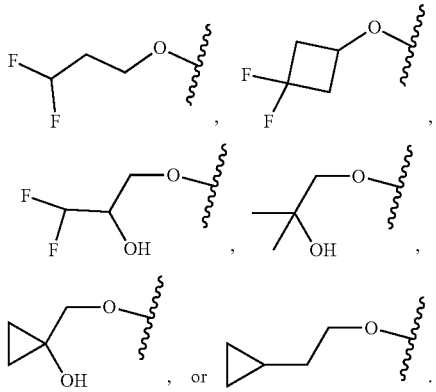

In some embodiments of Formula (I), (Ia), (Ib), (Iaa), (Iab), (Iba), (Ibb), (II), (IIa), (IIb), (IIaa) (IIab), (IIba), or (IIbb), $R^3$ is

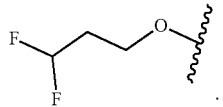

In some embodiments of Formula (I), (Ia), (Ib), (Iaa), (Iab), (Iba), (Ibb), (II), (IIa), (IIb), (IIaa) (IIab), (IIba), or (IIbb), $R^3$ is

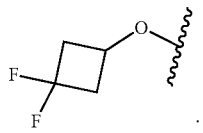

In some embodiments of Formula (I), (Ia), (Ib), (Iaa), (Iab), (Iba), (Ibb), (II), (IIa), (IIb), (IIaa) (IIab), (IIba), or (IIbb), $R^3$ is

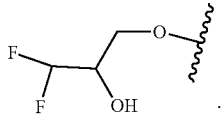 [SMILES: *OCC(O)C(F)F]

In some embodiments of Formula (I), (Ia), (Ib), (Iaa), (Iab), (Iba), (Ibb), (II), (IIa), (IIb), (IIaa) (IIab), (IIba), or (IIbb), $R^3$ is

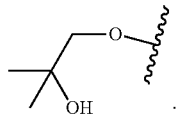

In some embodiments of Formula (I), (Ia), (Ib), (Iaa), (Iab), (Iba), (Ibb), (II), (IIa), (IIb), (IIaa) (IIab), (IIba), or (IIbb), $R^3$ is

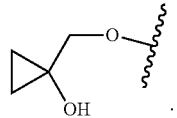

In some embodiments of Formula (I), (Ia), (Ib), (Iaa), (Iab), (Iba), (Ibb), (II), (IIa), (IIb), (IIaa) (IIab), (IIba), or (IIbb), $R^3$ is

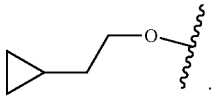 [SMILES: *OCCC1CC1]

In some embodiments of Formula (I), (Ia), (Ib), (Iaa), (Iab), (Iba), (Ibb), (II), (IIa), (IIb), (IIaa) (IIab), (IIba), or (IIbb), $R^{11}$ is substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted phenyl, substituted or unsubstituted naphthyl, substituted or unsubstituted monocyclic heteroaryl, or substituted or unsubstituted bicyclic heteroaryl.

In some embodiments of Formula (I), (Ia), (Ib), (Iaa), (Iab), (Iba), (Ibb), (II), (IIa), (IIb), (IIaa) (IIab), (IIba), or (IIbb), $R^{11}$ is substituted or unsubstituted $C_1$-$C_6$ alkyl or substituted or unsubstituted $C_3$-$C_6$ cycloalkyl. In some embodiments of Formula (I), (Ia), (Ib), (Iaa), (Iab), (Iba), (Ibb), (II), (IIa), (IIb), (IIaa) (IIab), (IIba), or (IIbb), $R^{11}$ is substituted or unsubstituted $C_1$-$C_6$ alkyl. In some embodiments of Formula (I), (Ia), (Ib), (Iaa), (Iab), (Iba), (Ibb), (II), (IIa), (IIb), (IIaa) (IIab), (IIba), or (IIbb), $R^{11}$ is substituted or unsubstituted $C_3$-$C_6$ cycloalkyl.

In some embodiments of Formula (I), (Ia), (Ib), (Iaa), (Iab), (Iba), (Ibb), (II), (IIa), (IIb), (IIaa) (IIab), (IIba), or (IIbb), $R^{11}$ is substituted $C_1$-$C_4$ alkyl.

In some embodiments of Formula (I), (Ia), (Ib), (Iaa), (Iab), (Iba), (Ibb), (II), (IIa), (IIb), (IIaa) (IIab), (IIba), or (IIbb), $R^{11}$ is substituted with one or more substituents selected from cyano, oxime, oxo, halogen, —CN, —$NH_2$, —NH($CH_3$), —N($CH_3$)$_2$, —OH, —$CO_2$H, —$CO_2$($C_1$-$C_4$ alkyl), —C(=O)$NH_2$, —C(=O)NH($C_1$-$C_4$ alkyl), —C(=O)N($C_1$-$C_4$ alkyl)$_2$, —S(=O)$_2$$NH_2$, —S(=O)$_2$NH ($C_1$-$C_4$ alkyl), —S(=O)$_2$N($C_1$-$C_4$ alkyl)$_2$, —S$C_1$-$C_4$ alkyl, —S(=O)$C_1$-$C_4$ alkyl, —S(=O)$_2$($C_1$-$C_4$ alkyl), mono-$C_{1-6}$ alkylamino, di-$C_{1-6}$ alkylamino, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{1-6}$ alkoxy, substituted or unsubstituted $C_{3-7}$ cycloalkyl, substituted or unsubstituted $C_{2-8}$ heterocycloalkyl, heteroaryl, substituted or unsubstituted heterocycloalkyl-$C_{1-6}$ alkyl, substituted or unsubstituted $C_{1-6}$ alkyl-heterocycloalkyl, substituted or unsubstituted C$_{1-6}$ alkyl-aryl, substituted or unsubstituted C$_{1-6}$ alkyl-heteroaryl, substituted or unsubstituted C$_{1-6}$ alkoxy-aryl, substituted or unsubstituted C$_{1-6}$ alkoxy-heterocycloalkyl, and substituted or unsubstituted C$_{1-6}$ alkoxy-heteroaryl. In some embodiments of Formula (I), (Ia), (Ib), (Iaa), (Iab), (Iba), (Ibb), (II), (IIa), (IIb), (IIaa) (IIab), (IIba), or (IIbb), R$^{11}$ is substituted with one or more substituents selected from halogen, —OH, C$_1$-C$_4$ alkyl, C$_3$-C$_6$ cycloalkyl, C$_1$-C$_4$ fluoroalkyl, C$_1$-C$_4$ heteroalkyl, C$_1$-C$_4$ alkoxy, or C$_1$-C$_4$ fluoroalkoxy. In some embodiments of Formula (I), (Ia), (Ib), (Iaa), (Iab), (Iba), (Ibb), (II), (IIa), (IIb), (IIaa) (IIab), (IIba), or (IIbb), R$^{11}$ is substituted with one or more substituents selected from halogen, —OH, and C$_3$-C$_6$ cycloalkyl.

In some embodiments of Formula (I), (Ia), (Ib), (Iaa), (Iab), (Iba), (Ibb), (II), (IIa), (IIb), (IIaa) (IIab), (IIba), or (IIbb), R$^{11}$ is substituted with one or more F.

In some embodiments of Formula (I), (Ia), (Ib), (Iaa), (Iab), (Iba), (Ibb), (II), (IIa), (IIb), (IIaa) (IIab), (IIba), or (IIbb), R$^{11}$ is

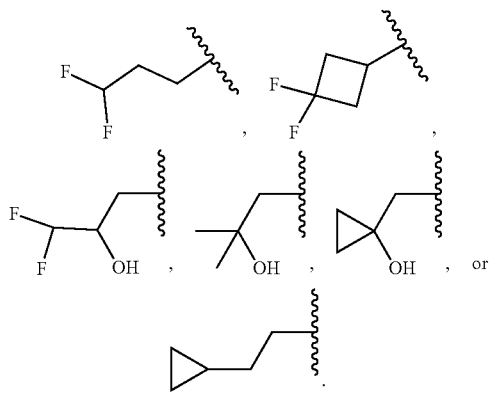

In some embodiments of Formula (I), (Ia), (Ib), (Iaa), (Iab), (Iba), (Ibb), (II), (IIa), (IIb), (IIaa) (IIab), (IIba), or (IIbb), R$^{11}$ is

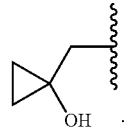

In some embodiments of Formula (I), (Ia), (Ib), (Iaa), (Iab), (Iba), (Ibb), (II), (IIa), (IIb), (IIaa) (IIab), (IIba), or (IIbb), R$^{11}$ is

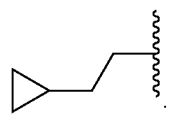

In some embodiments of Formula (I), (Ia), (Ib), (Iaa), (Iab), (Iba), (Ibb), (II), (IIa), (IIb), (IIaa) (IIab), (IIba), or (IIbb), R$^{11}$ is

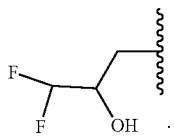

In some embodiments of Formula (I), (Ia), (Ib), (Iaa), (Iab), (Iba), (Ibb), (II), (IIa), (IIb), (IIaa) (IIab), (IIba), or (IIbb), R$^{11}$ is

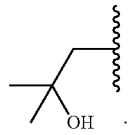

In some embodiments of Formula (I), (Ia), (Ib), (Iaa), (Iab), (Iba), (Ibb), (II), (IIa), (IIb), (IIaa) (IIab), (IIba), or (IIbb), R$^{11}$ is

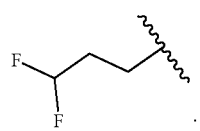 [SMILES: *CCC(F)F]

In some embodiments of Formula (I), (Ia), (Ib), (Iaa), (Iab), (Iba), (Ibb), (II), (IIa), (IIb), (IIaa) (IIab), (IIba), or (IIbb), R$^{11}$ is

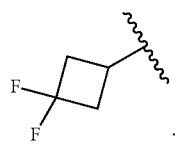 [SMILES: *C1CC(F)(F)C1]

In some embodiments of Formula (I), (Ia), (Ib), (Iaa), (Iab), (Iba), (Ibb), (II), (IIa), (IIb), (IIaa) (IIab), (IIba), or (IIbb), R$^{21}$, R$^{22}$, and R$^{23}$ are each independently selected from hydrogen and C$_1$-C$_4$ alkyl. In some embodiments, R$^{21}$, R$^{22}$, and R$^{23}$ are each independently selected from C$_1$-C$_4$ alkyl. In some embodiments of Formula (I), (Ia), (Ib), (Iaa), (Iab), (Iba), (Ibb), (II), (IIa), (IIb), (IIaa) (IIab), (IIba), or (IIbb), R$^{21}$ is selected from hydrogen and C$_1$-C$_4$ alkyl. In some embodiments of Formula (I), (Ia), (Ib), (Iaa), (Iab), (Iba), (Ibb), (II), (IIa), (IIb), (IIaa) (IIab), (IIba), or (IIbb), R$^{21}$ is hydrogen. In some embodiments of Formula (I), (Ia), (Ib), (Iaa), (Iab), (Iba), (Ibb), (II), (IIa), (IIb), (IIaa) (IIab), (IIba), or (IIbb), R$^{22}$ is selected from hydrogen and C$_1$-C$_4$ alkyl. In some embodiments, of Formula (I), (Ia), (Ib), (Iaa), (Iab), (Iba), (Ibb), (II), (IIa), (IIb), (IIaa) (IIab), (IIba), or (IIbb) R$^{22}$ is hydrogen. In some embodiments of Formula (I), (Ia), (Ib), (Iaa), (Iab), (Iba), (Ibb), (II), (IIa), (IIb), (IIaa) (IIab), (IIba), or (IIbb), and R$^{23}$ is selected from hydrogen and C$_1$-C$_4$ alkyl. In some embodiments of Formula (I), (Ia), (Ib), (Iaa), (Iab), (Iba), (Ibb), (II), (IIa), (IIb), (IIaa) (IIab), (IIba), or (IIbb), and R$^{23}$ is hydrogen.

In some embodiments of Formula (I), (Ia), (Ib), (Iaa), (Iab), (Iba), (Ibb), (II), (IIa), (IIb), (IIaa) (IIab), (IIba), or (IIbb), the compounds made in the examples below are made from racemic starting materials (and/or intermediates) and separated into the individual enantiomers by chiral chromatography as final products or intermediates. Unless otherwise stated, it is understood that the absolute configuration of the separated intermediates and final compounds as drawn is arbitrarily assigned and was not determined.

In some embodiments of Formula (I), (Ia), (Ib), (Iaa), (Iab), (Iba), (Ibb), (II), (IIa), (IIb), (IIaa) (IIab), (IIba), or (IIbb), the compound described herein is

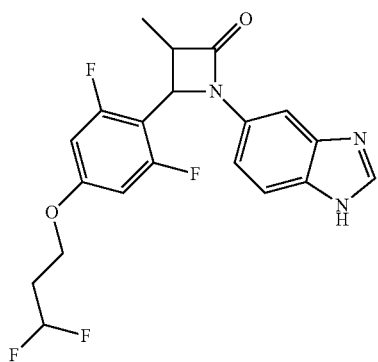 [SMILES: CC1C(=O)N(c2ccc3[nH]cnc3c2)C1c1c(F)cc(OCCC(F)F)cc1F]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

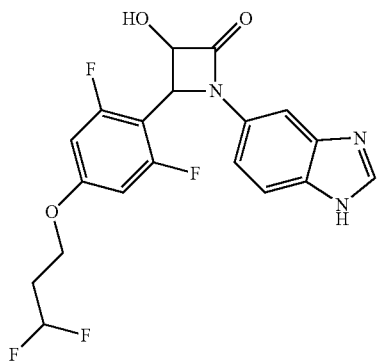 [SMILES: O=C1C(O)C(c2c(F)cc(OCCC(F)F)cc2F)N1c1ccc2[nH]cnc2c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

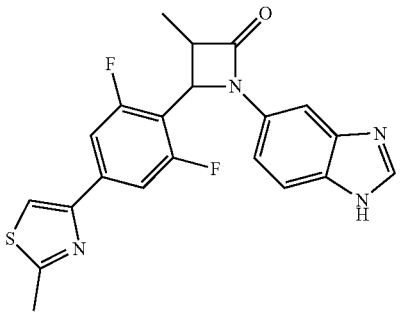 [SMILES: Cc1nc(-c2cc(F)c(C3C(C)C(=O)N3c3ccc4[nH]cnc4c3)c(F)c2)cs1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

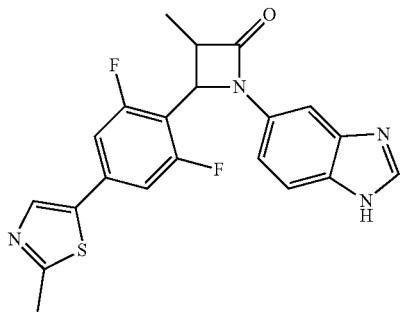 [SMILES: Cc1ncc(-c2cc(F)c(C3C(C)C(=O)N3c3ccc4[nH]cnc4c3)c(F)c2)s1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

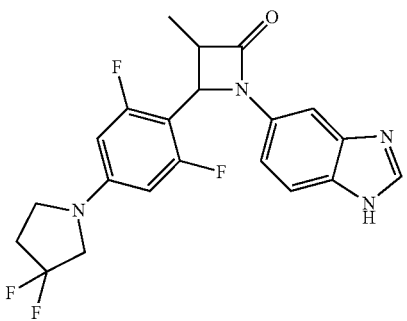 [SMILES: CC1C(=O)N(c2ccc3[nH]cnc3c2)C1c1c(F)cc(N2CCC(F)(F)C2)cc1F]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

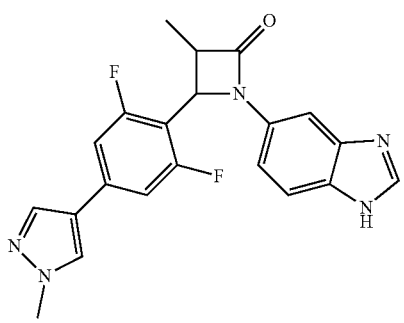 [SMILES: CC1C(=O)N(c2ccc3[nH]cnc3c2)C1c1c(F)cc(-c2cnn(C)c2)cc1F]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

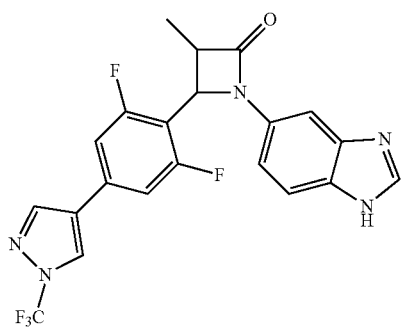

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

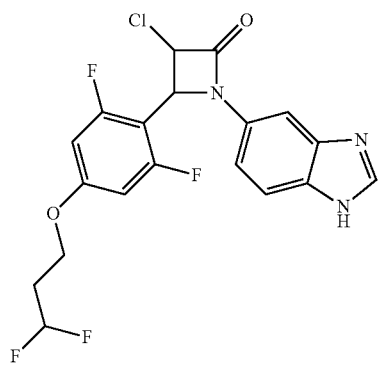

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

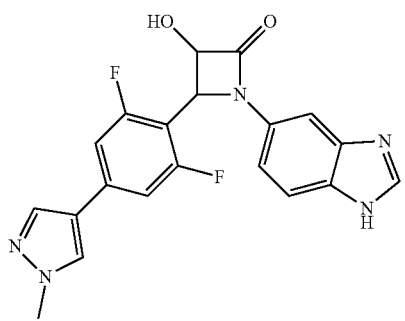

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

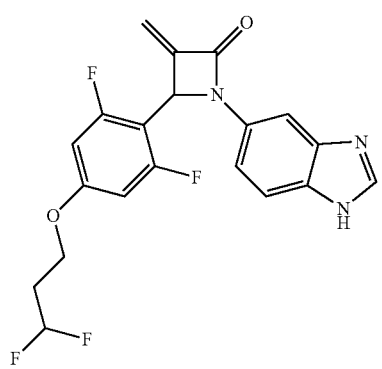

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

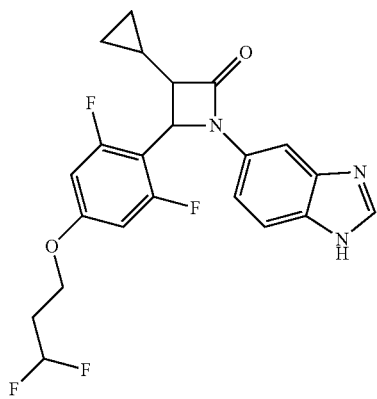

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

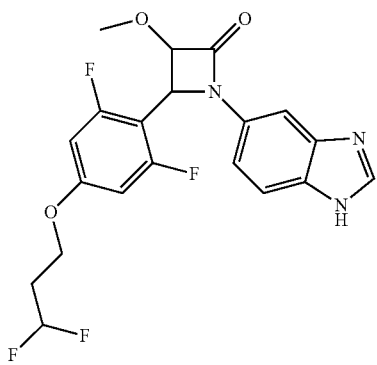 [SMILES: COC1C(=O)N(c2ccc3[nH]cnc3c2)C1c1c(F)cc(OCCC(F)F)cc1F]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

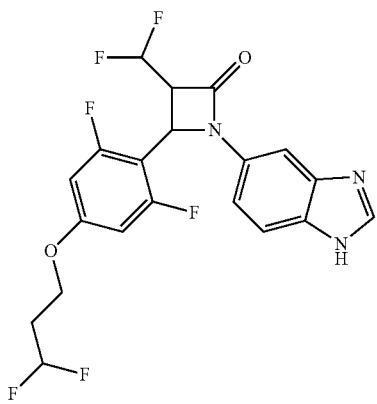 [SMILES: O=C1C(C(F)F)C(c2c(F)cc(OCCC(F)F)cc2F)N1c1ccc2[nH]cnc2c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

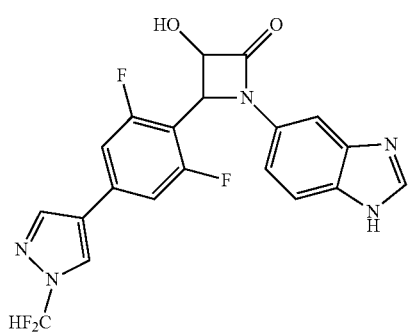

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

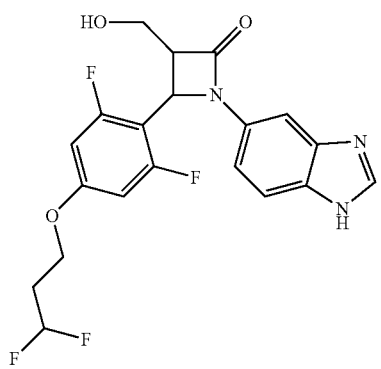

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

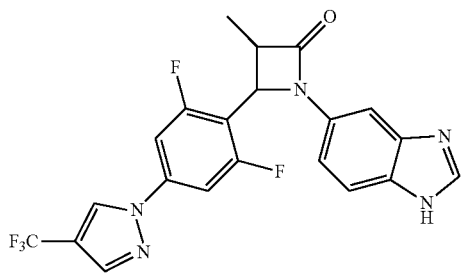 [SMILES: CC1C(=O)N(c2ccc3[nH]cnc3c2)C1c1c(F)cc(-n2cc(C(F)(F)F)cn2)cc1F]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

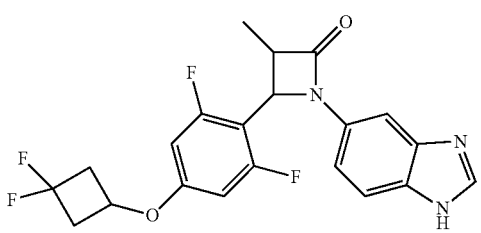 [SMILES: CC1C(=O)N(c2ccc3[nH]cnc3c2)C1c1c(F)cc(OC2CC(F)(F)C2)cc1F]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

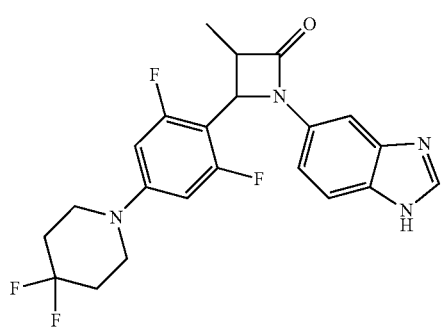 [SMILES: CC1C(=O)N(c2ccc3[nH]cnc3c2)C1c1c(F)cc(N2CCC(F)(F)CC2)cc1F]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

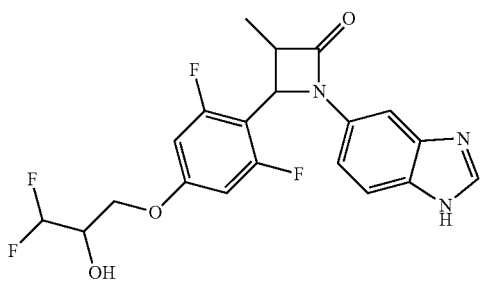 [SMILES: CC1C(=O)N(c2ccc3[nH]cnc3c2)C1c1c(F)cc(OCC(O)C(F)F)cc1F]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

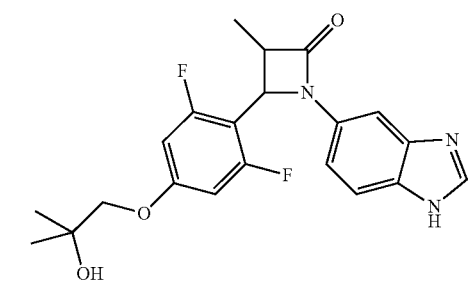 [SMILES: CC1C(=O)N(c2ccc3[nH]cnc3c2)C1c1c(F)cc(OCC(C)(C)O)cc1F]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

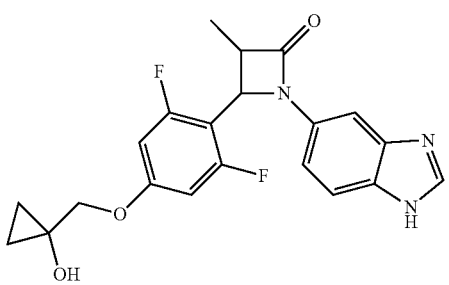 [SMILES: CC1C(=O)N(c2ccc3[nH]cnc3c2)C1c1c(F)cc(OCC2(O)CC2)cc1F]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

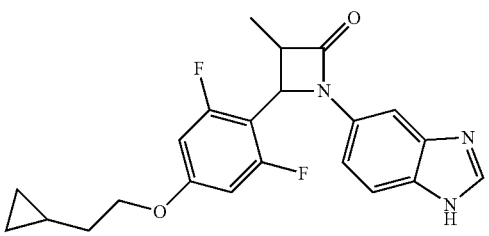 [SMILES: CC1C(=O)N(c2ccc3[nH]cnc3c2)C1c1c(F)cc(OCCC2CC2)cc1F]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or Ibb), the compound described herein is

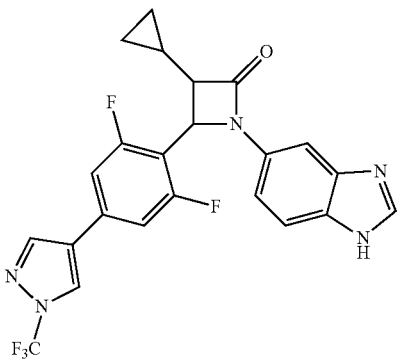

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

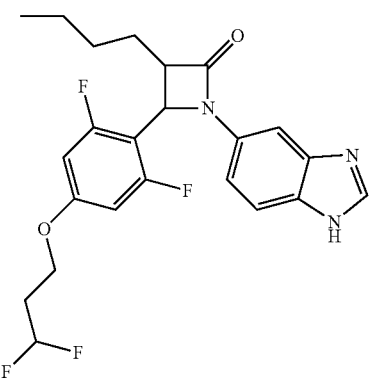 [SMILES: CCCCC1C(=O)N(c2ccc3[nH]cnc3c2)C1c1c(F)cc(OCCC(F)F)cc1F]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

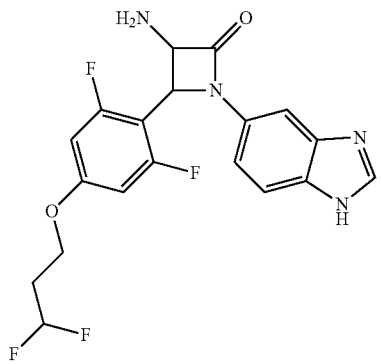 [SMILES: NC1C(=O)N(c2ccc3[nH]cnc3c2)C1c1c(F)cc(OCCC(F)F)cc1F]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

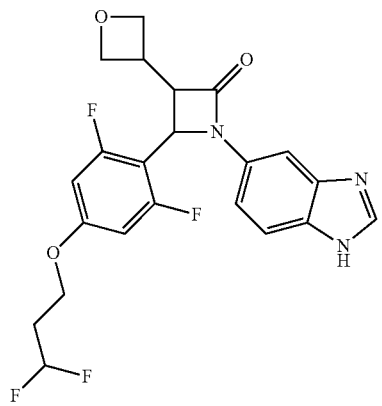

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

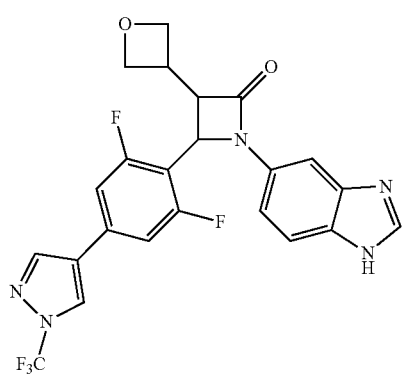 [SMILES: O=C1C(C2COC2)C(c2c(F)cc(-c3cnn(C(F)(F)F)c3)cc2F)N1c1ccc2[nH]cnc2c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

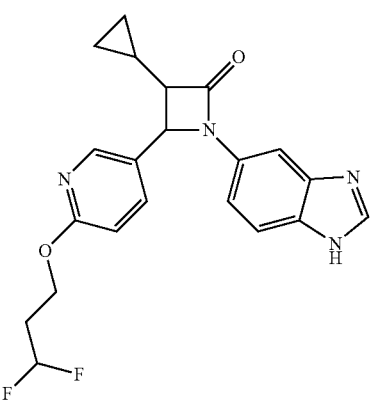 [SMILES: O=C1C(C2CC2)C(c2ccc(OCCC(F)F)nc2)N1c1ccc2[nH]cnc2c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

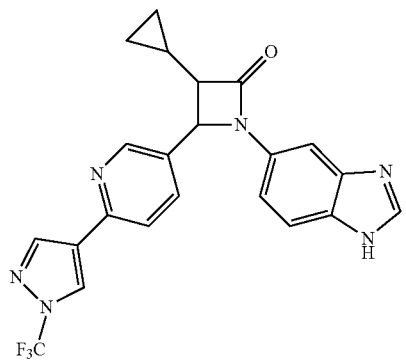

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

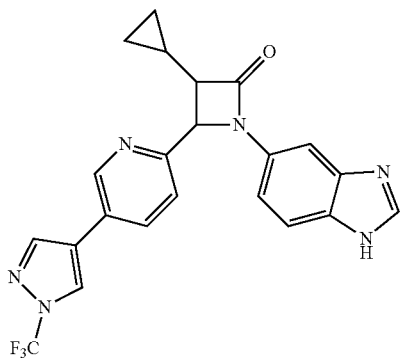 [SMILES: O=C1C(C2CC2)C(c2ccc(-c3cnn(C(F)(F)F)c3)cn2)N1c1ccc2[nH]cnc2c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

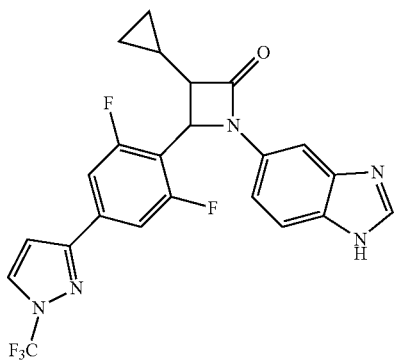 [SMILES: O=C1C(C2CC2)C(c2c(F)cc(-c3ccn(C(F)(F)F)n3)cc2F)N1c1ccc2[nH]cnc2c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

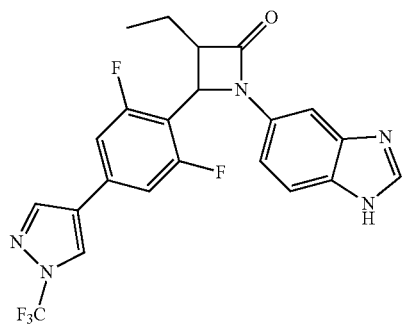

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

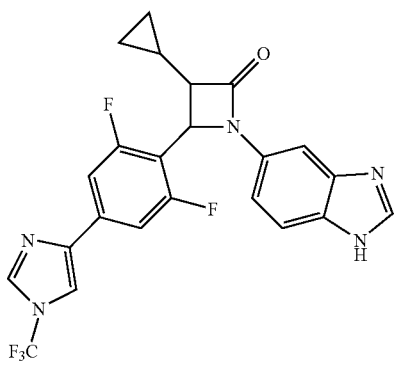 [SMILES: O=C1C(C2CC2)C(c2c(F)cc(-c3cn(C(F)(F)F)cn3)cc2F)N1c1ccc2[nH]cnc2c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

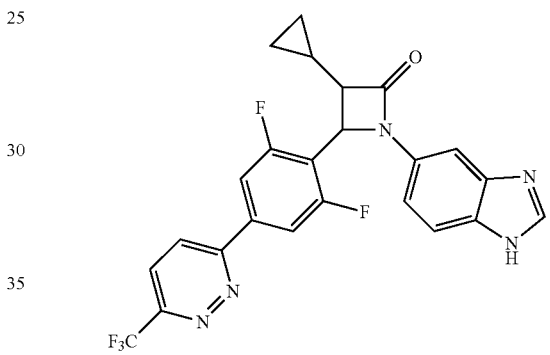

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

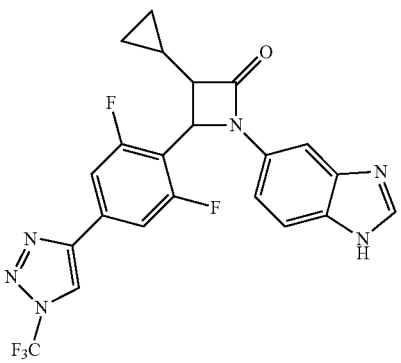

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

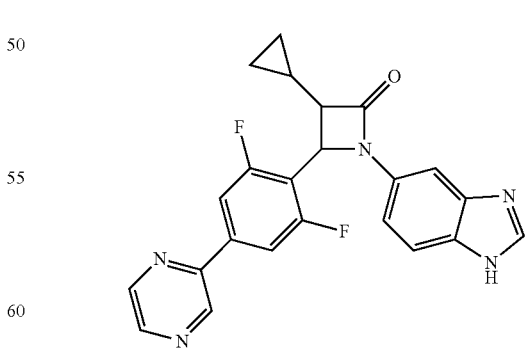

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

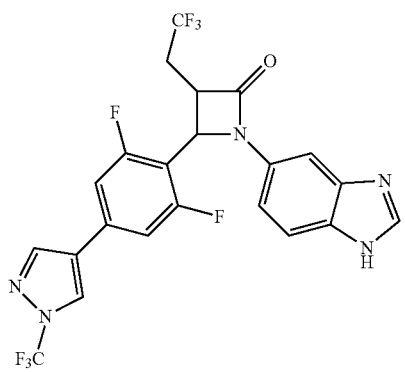 [SMILES: O=C1C(CC(F)(F)F)C(c2c(F)cc(-c3cnn(C(F)(F)F)c3)cc2F)N1c1ccc2[nH]cnc2c1]

or a pharmaceutically acceptable salt or solvate thereof. In some embodiments of Formula (I), (Ia), (Ib), (Iaa), (Iab), (Iba), (Ibb), (II), (Ia), (IIb), (IIaa) (IIab), (IIba), or (IIbb), the compound described herein is

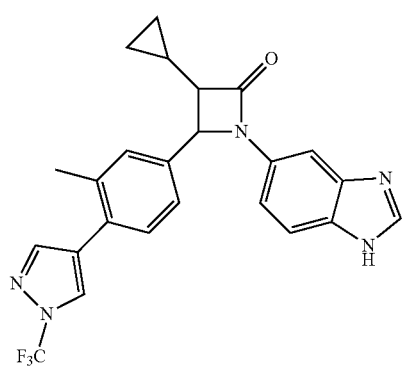 [SMILES: Cc1cc(C2C(C3CC3)C(=O)N2c2ccc3[nH]cnc3c2)ccc1-c1cnn(C(F)(F)F)c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

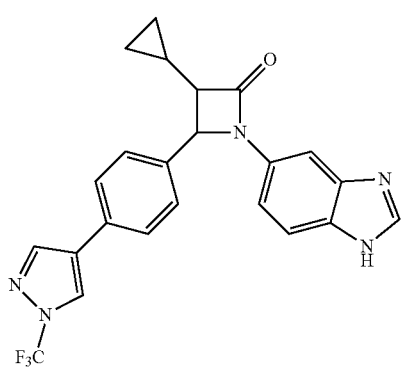

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

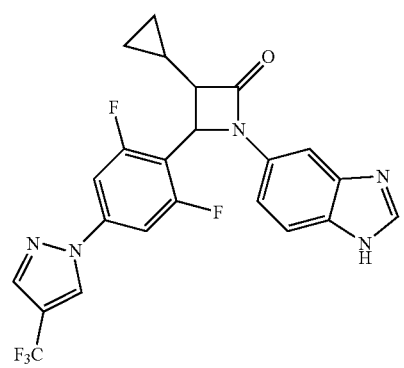 [SMILES: O=C1C(C2CC2)C(c2c(F)cc(-n3cc(C(F)(F)F)cn3)cc2F)N1c1ccc2[nH]cnc2c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

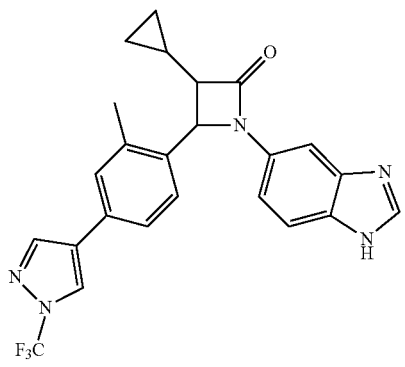

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

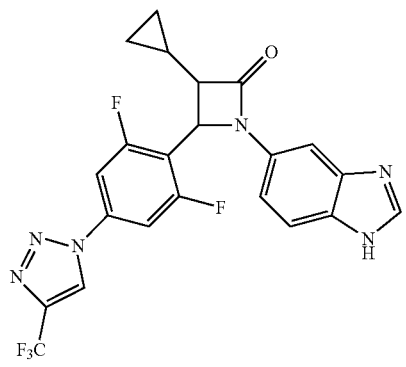

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

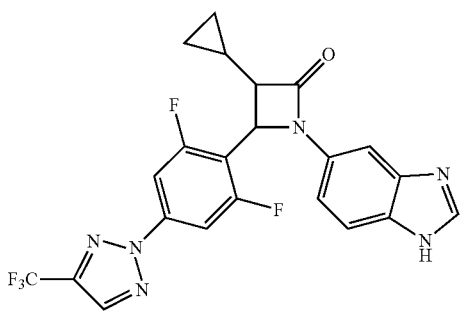 [SMILES: O=C1C(C2CC2)C(c2c(F)cc(-n3ncc(C(F)(F)F)n3)cc2F)N1c1ccc2[nH]cnc2c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

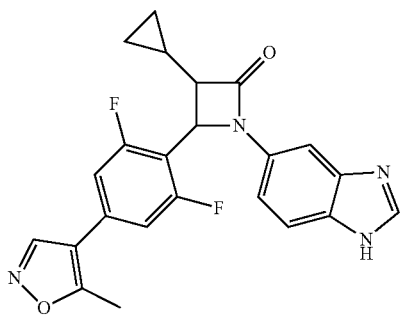

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

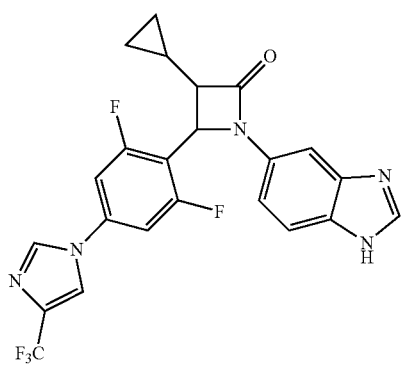 [SMILES: O=C1C(C2CC2)C(c2c(F)cc(-n3cnc(C(F)(F)F)c3)cc2F)N1c1ccc2[nH]cnc2c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

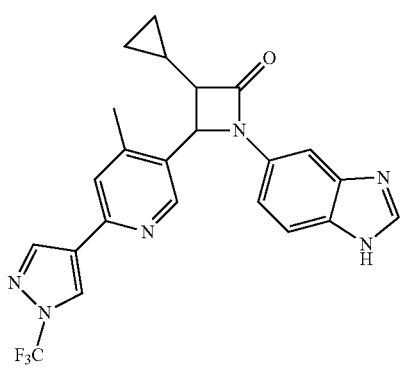

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

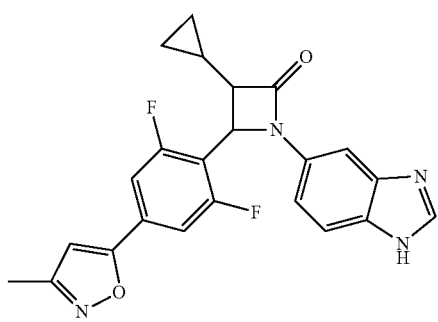 [SMILES: Cc1cc(-c2cc(F)c(C3C(C4CC4)C(=O)N3c3ccc4[nH]cnc4c3)c(F)c2)on1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

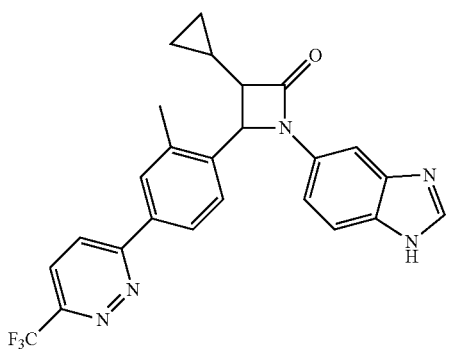 [SMILES: Cc1cc(-c2ccc(C(F)(F)F)nn2)ccc1C1C(C2CC2)C(=O)N1c1ccc2[nH]cnc2c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

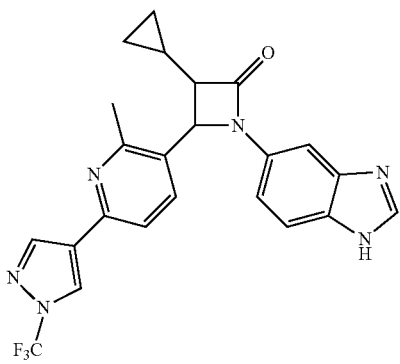 [SMILES: Cc1nc(-c2cnn(C(F)(F)F)c2)ccc1C1C(C2CC2)C(=O)N1c1ccc2[nH]cnc2c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

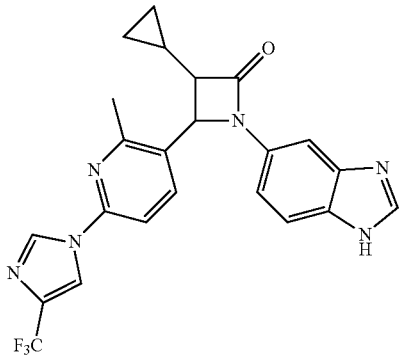

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

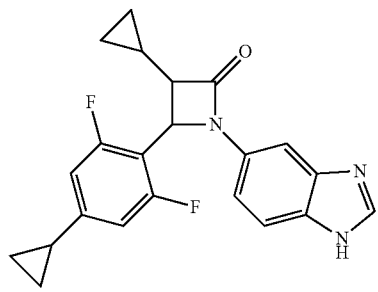 [SMILES: O=C1C(C2CC2)C(c2c(F)cc(C3CC3)cc2F)N1c1ccc2[nH]cnc2c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

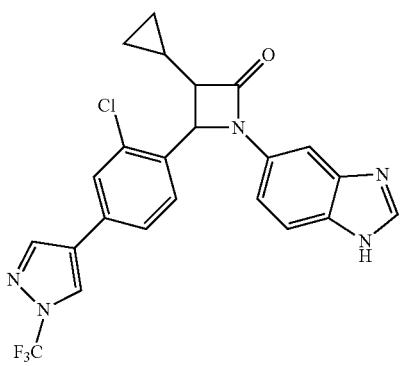

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

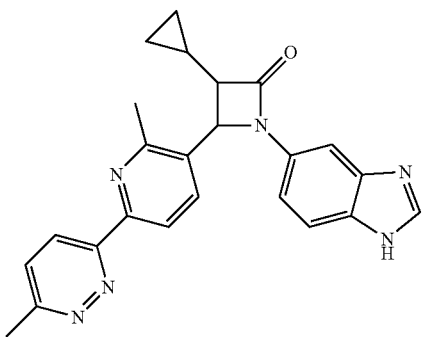 [SMILES: Cc1ccc(-c2ccc(C3C(C4CC4)C(=O)N3c3ccc4[nH]cnc4c3)c(C)n2)nn1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

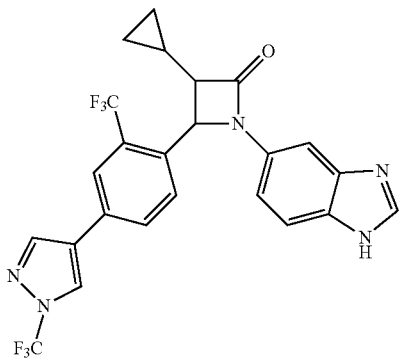 [SMILES: O=C1C(C2CC2)C(c2ccc(-c3cnn(C(F)(F)F)c3)cc2C(F)(F)F)N1c1ccc2[nH]cnc2c1]

or a pharmaceutically acceptable salt or solvate thereof.

In some embodiments of Formula (I), (Ia), (Ib), (Iaa), (Iab), (Iba), (Ibb), (II), (IIa), (IIb), (IIaa) (IIab), (IIba), or (IIbb), the compound described herein is

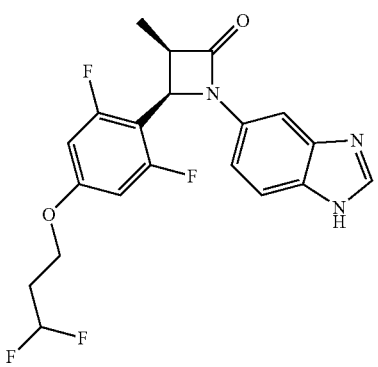 [SMILES: C[C@H]1C(=O)N(c2ccc3[nH]cnc3c2)[C@H]1c1c(F)cc(OCCC(F)F)cc1F]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

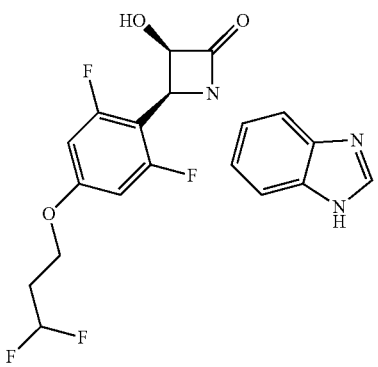

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

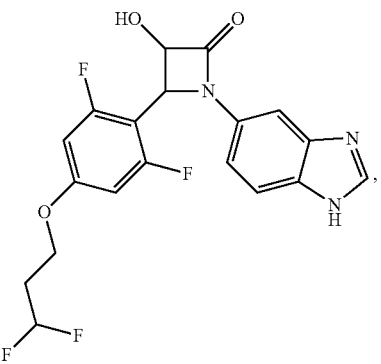 [SMILES: O=C1C(O)C(c2c(F)cc(OCCC(F)F)cc2F)N1c1ccc2[nH]cnc2c1]

a stereoisomer, or a pharmaceutically acceptable salt or solvate thereof. In some embodiments of Formula (I), (Ia),
(Ib), (Iaa), (Iab), (Iba), (Ibb), (II), (IIa), (IIb), (IIaa) (IIab), (IIba), or (IIbb), the compound described herein is

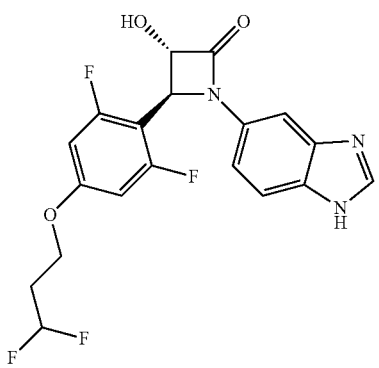 [SMILES: O=C1[C@@H](O)[C@H](c2c(F)cc(OCCC(F)F)cc2F)N1c1ccc2[nH]cnc2c1]

or a pharmaceutically acceptable salt or solvate thereof. In some embodiments of Formula (I), (Ia), (Ib), (Iaa), (Iab), (Iba), (Ibb), (II), (Ia), (Ib), (IIaa) (IIab), (IIba), or (IIbb), the compound described herein is

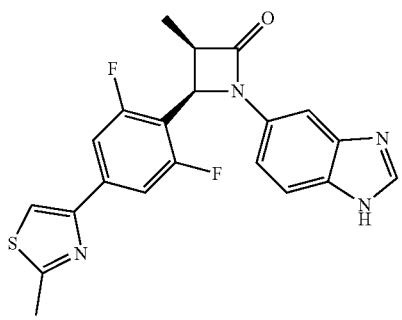 [SMILES: Cc1nc(-c2cc(F)c([C@H]3[C@@H](C)C(=O)N3c3ccc4[nH]cnc4c3)c(F)c2)cs1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

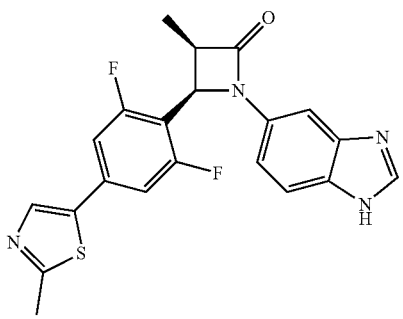

or a pharmaceutically acceptable salt or solvate thereof. In some embodiments of Formula (I), (Ia), (Ib), (a), (Iab), (Iba), (Ibb), (II), (IIa), (IIb), (IIaa) (IIab), (IIba), or (IIbb), the compound described herein is

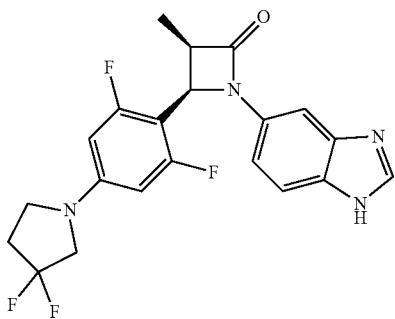 [SMILES: C[C@H]1C(=O)N(c2ccc3[nH]cnc3c2)[C@H]1c1c(F)cc(N2CCC(F)(F)C2)cc1F]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

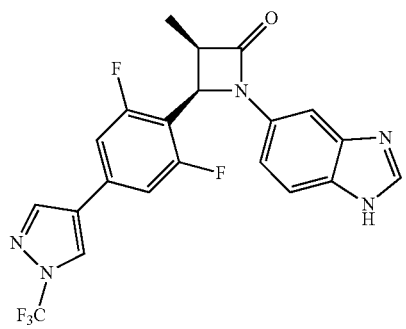

or a pharmaceutically acceptable salt or solvate thereof. In some embodiments of Formula (I), (Ia), (Ib), (Iaa) (Iab), (Iba), (Ibb), (Ia), (Ia), (IIb), (IIaa) (IIab), (IIba), or (IIbb), the compound described herein is

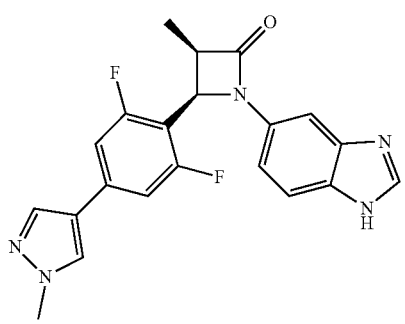 [SMILES: C[C@H]1C(=O)N(c2ccc3[nH]cnc3c2)[C@H]1c1c(F)cc(-c2cnn(C)c2)cc1F]

or a pharmaceutically acceptable salt or solvate thereof. In some embodiments of Formula (I), (Ia) (Ib), (Iaa), (Iab), (Iba), (Ibb), (II), (IIa), (IIb), (IIaa) (IIab), (IIba), or (IIbb), the compound described herein is

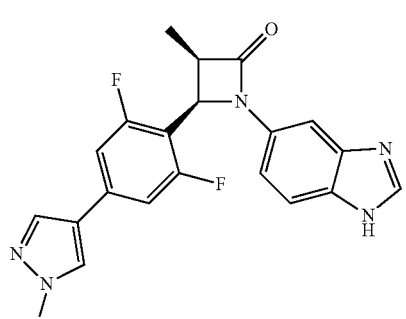

or a pharmaceutically acceptable salt or solvate thereof. In some embodiments of Formula (I), (Ia), (Ib), (Iaa), (Iab), (Iba), (Ibb), (II), (IIa), (Ib), (IIaa) (IIab), (IIba), or (IIbb), the compound described herein is

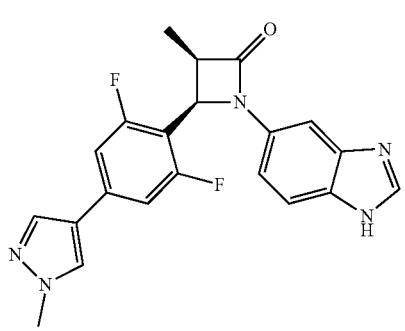 [SMILES: C[C@H]1C(=O)N(c2ccc3[nH]cnc3c2)[C@H]1c1c(F)cc(-c2cnn(C)c2)cc1F]

or a pharmaceutically acceptable salt or solvate thereof. In some embodiments of Formula (I), (Ia), (Ib) (Iaa), (Iab), (Iba), (Ibb), (II), (IIa), (IIb), (IIaa) (IIab), (IIba), or (IIbb), the compound described herein is

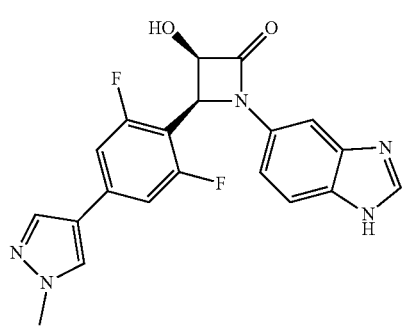 [SMILES: Cn1cc(-c2cc(F)c([C@H]3[C@@H](O)C(=O)N3c3ccc4[nH]cnc4c3)c(F)c2)cn1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

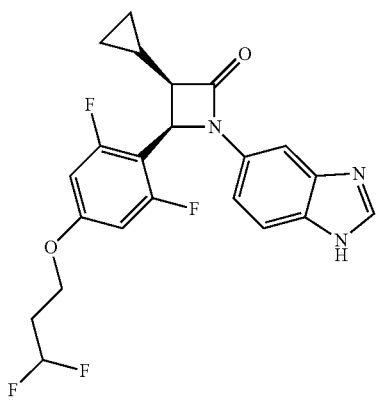 [SMILES: O=C1[C@H](C2CC2)[C@H](c2c(F)cc(OCCC(F)F)cc2F)N1c1ccc2[nH]cnc2c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

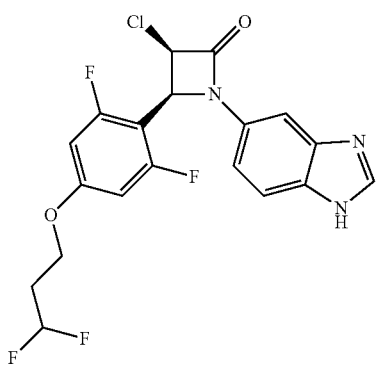 [SMILES: O=C1[C@H](Cl)[C@H](c2c(F)cc(OCCC(F)F)cc2F)N1c1ccc2[nH]cnc2c1]

or a pharmaceutically acceptable salt or solvate thereof. In some embodiments of Formula (I), (Ia), (Ib) (Iaa), (Iab), (Iba), (Ibb), (II), (IIa), (IIb), (IIaa) (IIab), (IIba), or (IIbb), the compound described herein is

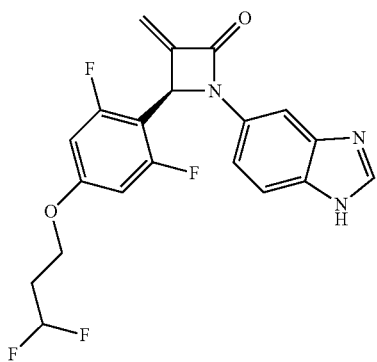

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

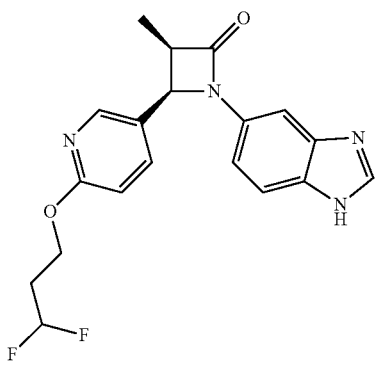 [SMILES: C[C@H]1C(=O)N(c2ccc3[nH]cnc3c2)[C@H]1c1ccc(OCCC(F)F)nc1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

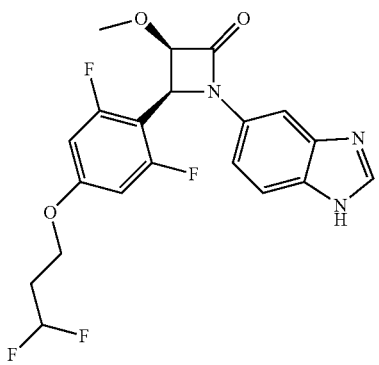 [SMILES: CO[C@H]1C(=O)N(c2ccc3[nH]cnc3c2)[C@H]1c1c(F)cc(OCCC(F)F)cc1F]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

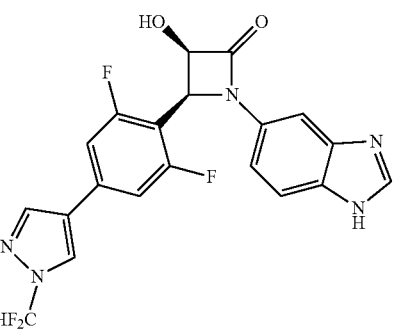

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb),

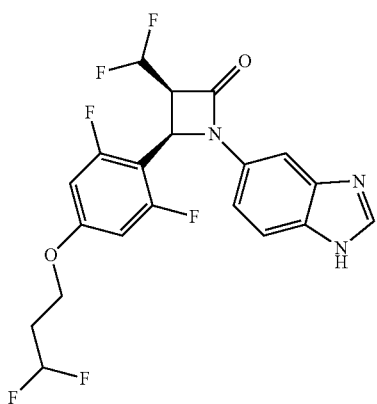 [SMILES: O=C1[C@H](C(F)F)[C@H](c2c(F)cc(OCCC(F)F)cc2F)N1c1ccc2[nH]cnc2c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

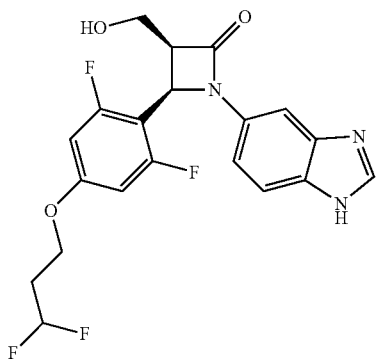 [SMILES: O=C1[C@H](CO)[C@H](c2c(F)cc(OCCC(F)F)cc2F)N1c1ccc2[nH]cnc2c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

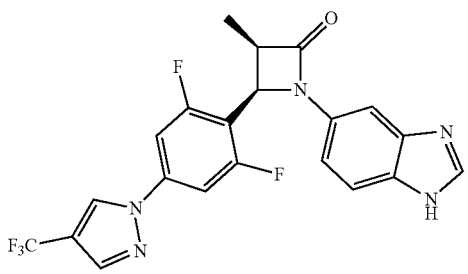 [SMILES: C[C@H]1C(=O)N(c2ccc3[nH]cnc3c2)[C@H]1c1c(F)cc(-n2cc(C(F)(F)F)cn2)cc1F]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

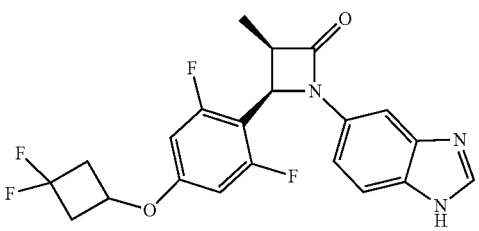 [SMILES: C[C@H]1C(=O)N(c2ccc3[nH]cnc3c2)[C@H]1c1c(F)cc(OC2CC(F)(F)C2)cc1F]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

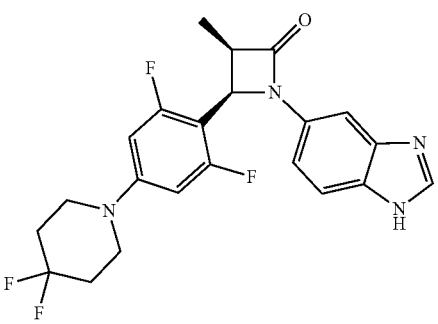 [SMILES: C[C@H]1C(=O)N(c2ccc3[nH]cnc3c2)[C@H]1c1c(F)cc(N2CCC(F)(F)CC2)cc1F]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

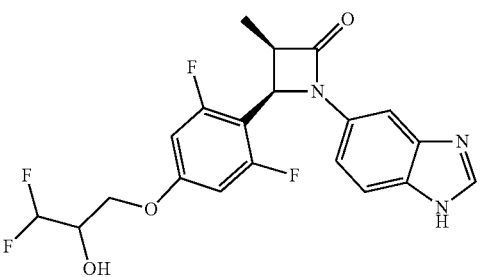 [SMILES: C[C@H]1C(=O)N(c2ccc3[nH]cnc3c2)[C@H]1c1c(F)cc(OCC(O)C(F)F)cc1F]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

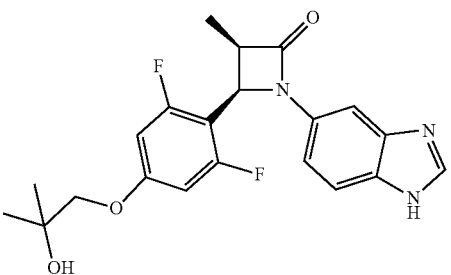 [SMILES: C[C@H]1C(=O)N(c2ccc3[nH]cnc3c2)[C@H]1c1c(F)cc(OCC(C)(C)O)cc1F]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

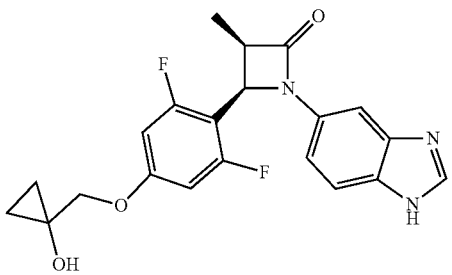 [SMILES: C[C@H]1C(=O)N(c2ccc3[nH]cnc3c2)[C@H]1c1c(F)cc(OCC2(O)CC2)cc1F]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

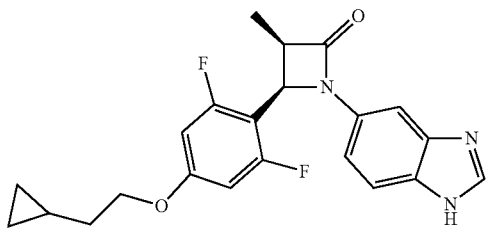 [SMILES: C[C@H]1C(=O)N(c2ccc3[nH]cnc3c2)[C@H]1c1c(F)cc(OCCC2CC2)cc1F]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

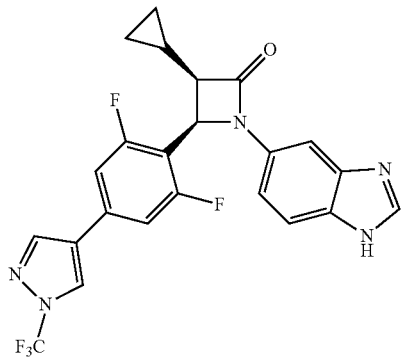

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

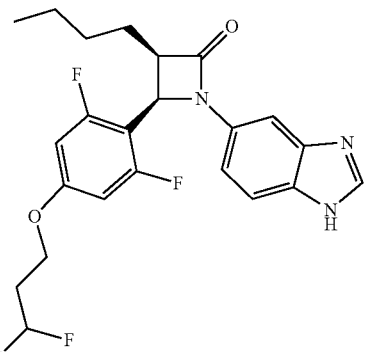

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

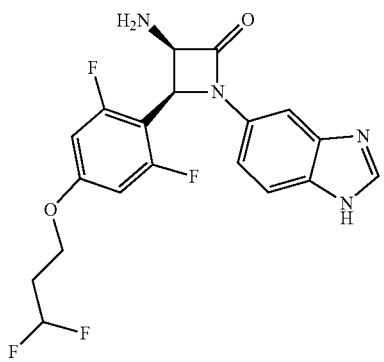 [SMILES: N[C@H]1C(=O)N(c2ccc3[nH]cnc3c2)[C@H]1c1c(F)cc(OCCC(F)F)cc1F]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

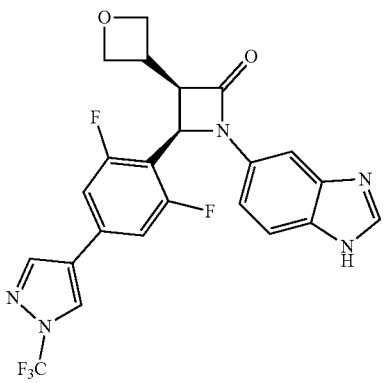 [SMILES: O=C1[C@H](C2COC2)[C@H](c2c(F)cc(-c3cnn(C(F)(F)F)c3)cc2F)N1c1ccc2[nH]cnc2c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

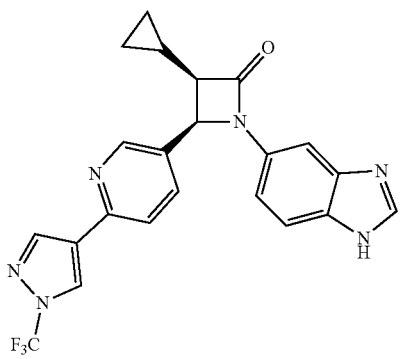 [SMILES: O=C1[C@H](C2CC2)[C@H](c2ccc(-c3cnn(C(F)(F)F)c3)nc2)N1c1ccc2[nH]cnc2c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

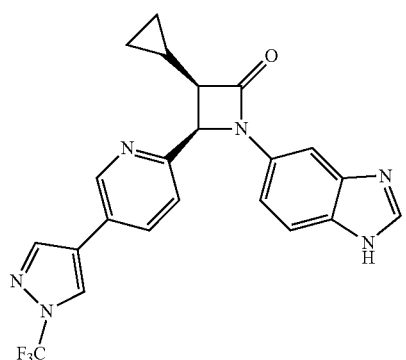

or a pharmaceutically acceptable salt or solvate thereof. In some embodiments of Formula (I), (Ia), (Ib), (Iaa) (Iab), (Iba), (Ibb), (II), (IIa), (IIb), (IIaa) (IIab), (IIba), or (IIbb), the compound described herein is

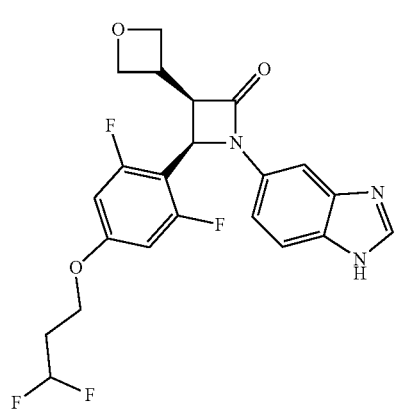 [SMILES: O=C1[C@H](C2COC2)[C@H](c2c(F)cc(OCCC(F)F)cc2F)N1c1ccc2[nH]cnc2c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

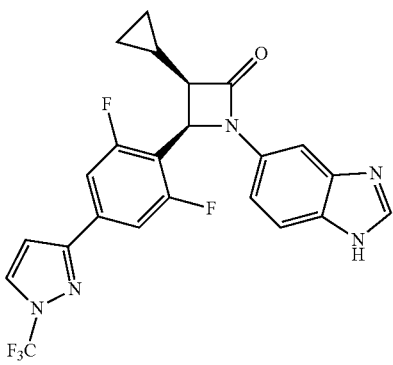

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

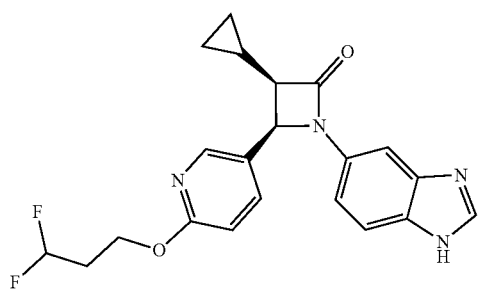 [SMILES: O=C1[C@H](C2CC2)[C@H](c2ccc(OCCC(F)F)nc2)N1c1ccc2[nH]cnc2c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

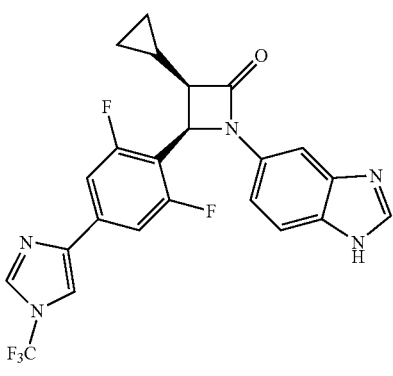

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

101

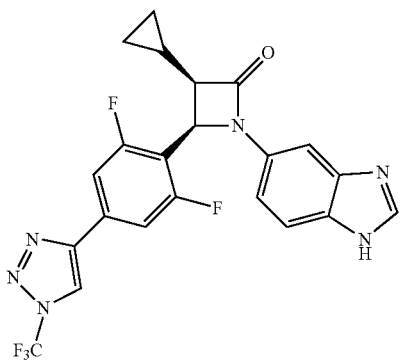 [SMILES: O=C1[C@H](C2CC2)[C@H](c2c(F)cc(-c3cn(C(F)(F)F)nn3)cc2F)N1c1ccc2[nH]cnc2c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (Ibb), the compound described herein is

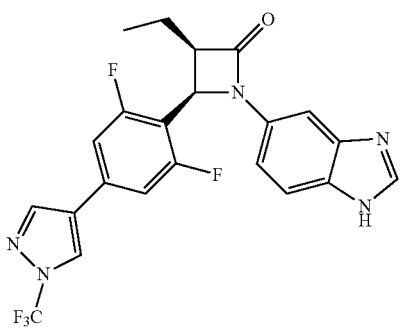 [SMILES: CC[C@H]1C(=O)N(c2ccc3[nH]cnc3c2)[C@H]1c1c(F)cc(-c2cnn(C(F)(F)F)c2)cc1F]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

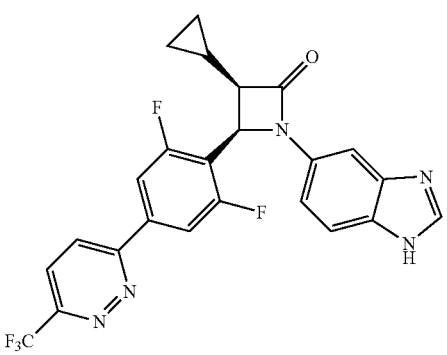 [SMILES: O=C1[C@H](C2CC2)[C@H](c2c(F)cc(-c3ccc(C(F)(F)F)nn3)cc2F)N1c1ccc2[nH]cnc2c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

102

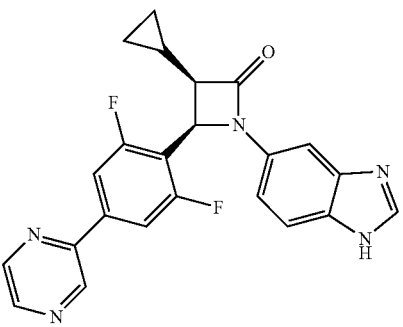 [SMILES: O=C1[C@H](C2CC2)[C@H](c2c(F)cc(-c3cnccn3)cc2F)N1c1ccc2[nH]cnc2c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

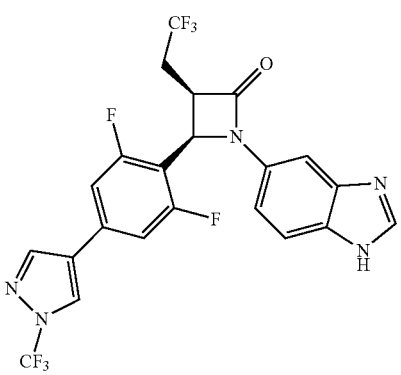 [SMILES: O=C1[C@H](CC(F)(F)F)[C@H](c2c(F)cc(-c3cnn(C(F)(F)F)c3)cc2F)N1c1ccc2[nH]cnc2c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

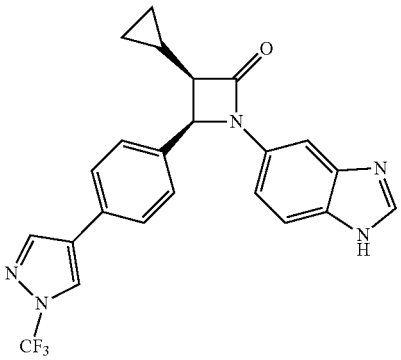

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

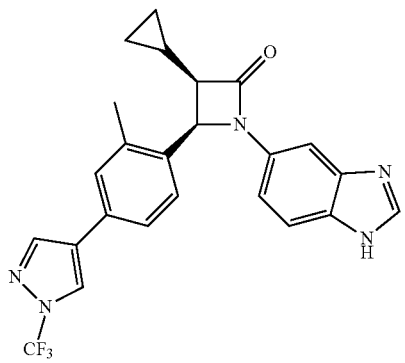 [SMILES: Cc1cc(-c2cnn(C(F)(F)F)c2)ccc1[C@H]1[C@@H](C2CC2)C(=O)N1c1ccc2[nH]cnc2c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

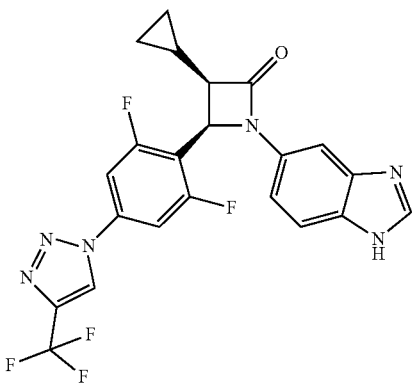

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

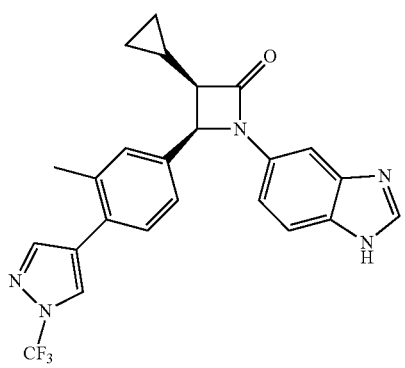 [SMILES: Cc1cc([C@H]2[C@@H](C3CC3)C(=O)N2c2ccc3[nH]cnc3c2)ccc1-c1cnn(C(F)(F)F)c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

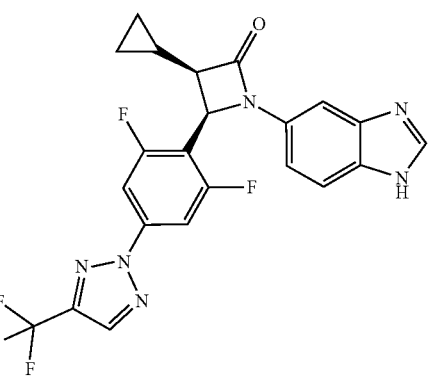

or a pharmaceutically acceptable salt or solvate thereof. In some embodiments of Formula (I), (Ia), (Ib), (Iaa), (Iab), (Iba), (Ibb), (II), (Ia), (Ib), (IIaa) (IIab), (IIba), or (IIbb), the compound described herein is

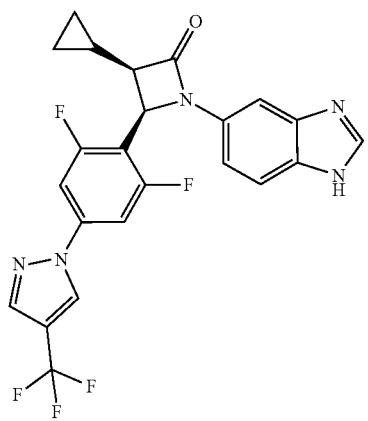 [SMILES: O=C1[C@H](C2CC2)[C@H](c2c(F)cc(-n3cc(C(F)(F)F)cn3)cc2F)N1c1ccc2[nH]cnc2c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

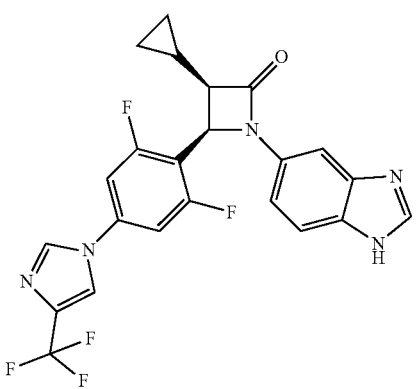 [SMILES: O=C1[C@H](C2CC2)[C@H](c2c(F)cc(-n3cnc(C(F)(F)F)c3)cc2F)N1c1ccc2[nH]cnc2c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

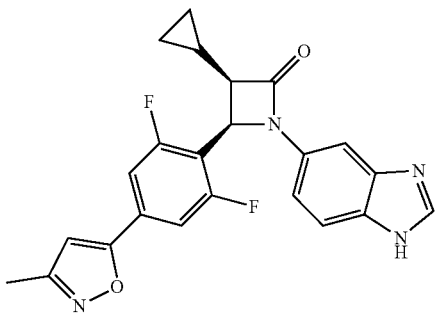 [SMILES: Cc1cc(-c2cc(F)c([C@H]3[C@@H](C4CC4)C(=O)N3c3ccc4[nH]cnc4c3)c(F)c2)on1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

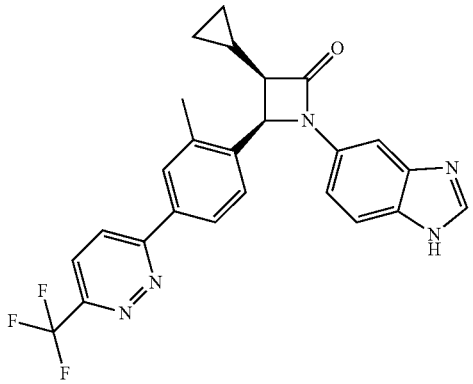

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

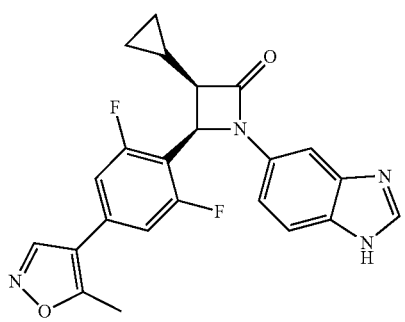 [SMILES: Cc1oncc1-c1cc(F)c([C@H]2[C@@H](C3CC3)C(=O)N2c2ccc3[nH]cnc3c2)c(F)c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

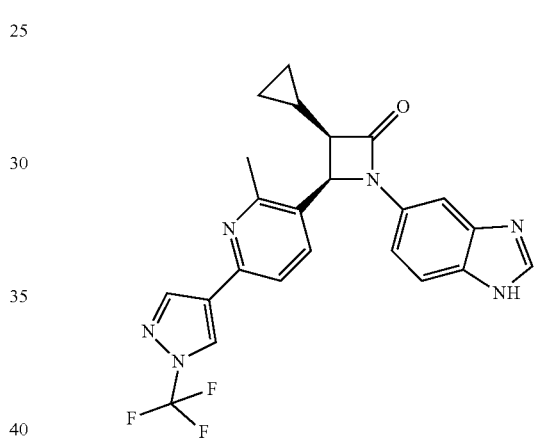

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

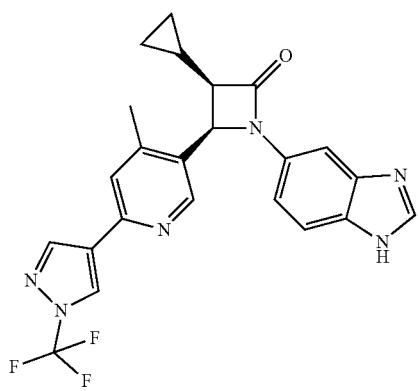 [SMILES: Cc1cc(-c2cnn(C(F)(F)F)c2)ncc1[C@H]1[C@@H](C2CC2)C(=O)N1c1ccc2[nH]cnc2c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

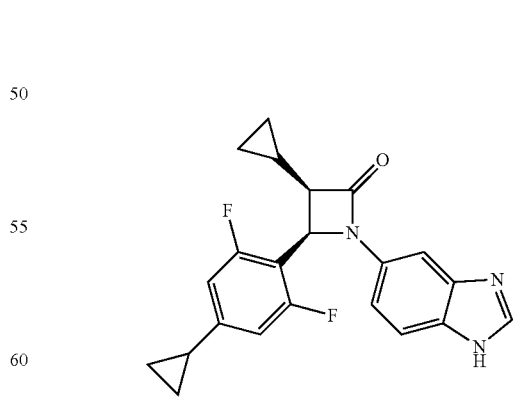

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

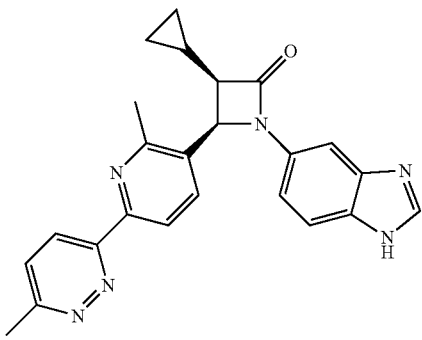 [SMILES: Cc1ccc(-c2ccc([C@H]3[C@@H](C4CC4)C(=O)N3c3ccc4[nH]cnc4c3)c(C)n2)nn1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

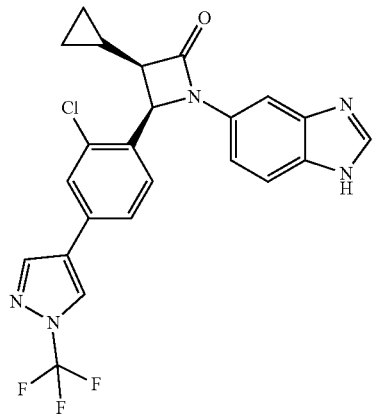

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

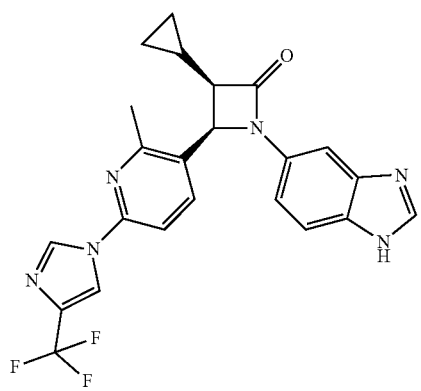 [SMILES: Cc1nc(-n2cnc(C(F)(F)F)c2)ccc1[C@H]1[C@@H](C2CC2)C(=O)N1c1ccc2[nH]cnc2c1]

or a pharmaceutically acceptable salt or solvate thereof. In some embodiments of Formula (I), (Ia), (Ib), (Iaa), (Iab), (Iba), (Ibb), (II), (IIa), (IIb), (IIaa) (IIab), (IIba), or (IIbb), the compound described herein is

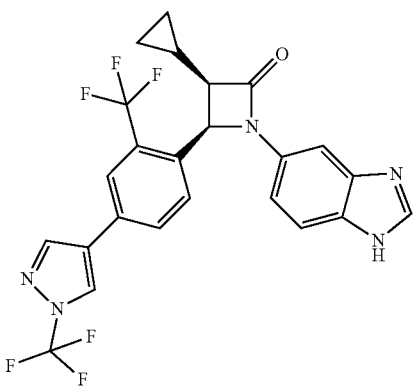 [SMILES: O=C1[C@H](C2CC2)[C@H](c2ccc(-c3cnn(C(F)(F)F)c3)cc2C(F)(F)F)N1c1ccc2[nH]cnc2c1]

or a pharmaceutically acceptable salt or solvate thereof.

Non-limiting examples of compounds described herein, are compounds presented in Table 1 and pharmaceutically acceptable salts or solvates thereof.

TABLE 1

| Com. ID | Structure | Comments |
| --- | --- | --- |
| 2 | 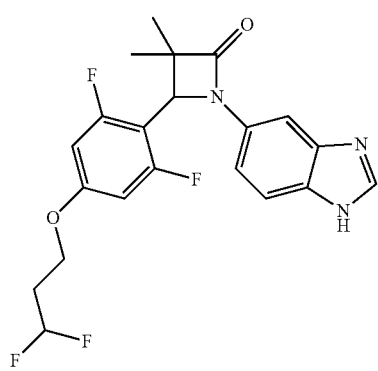 [SMILES: CC1(C)C(=O)N(c2ccc3[nH]cnc3c2)C1c1c(F)cc(OCCC(F)F)cc1F] | Racemic |

TABLE 1-continued
| Com. ID | Structure | Comments |
|---|---|---|
| 3 | 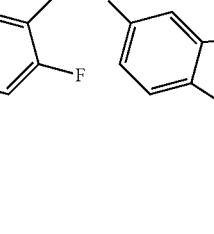 | Racemic |
| 4 | 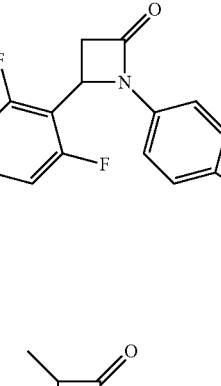 | Racemic |
| 7 | 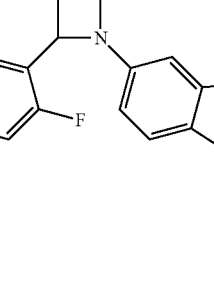 | Racemic |
| 7A | 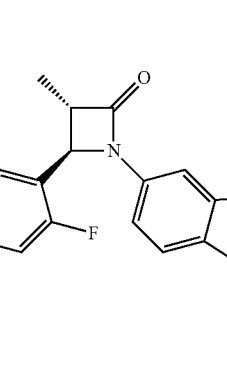 | Chiral |

TABLE 1-continued

| Com. ID | Structure | Comments |
|---------|-----------|----------|
| 7B | 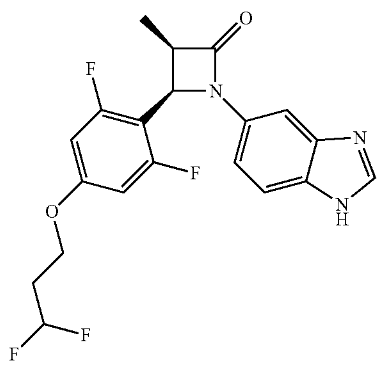 [SMILES: C[C@H]1C(=O)N(c2ccc3[nH]cnc3c2)[C@H]1c1c(F)cc(OCCC(F)F)cc1F] | Chiral |
| 8 | 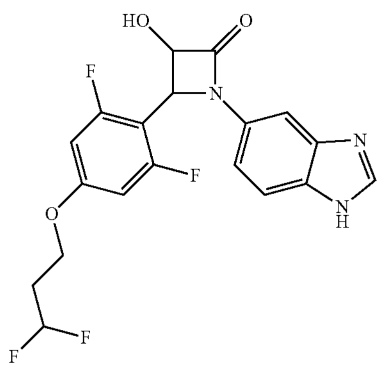 | Racemic |
| 8A | 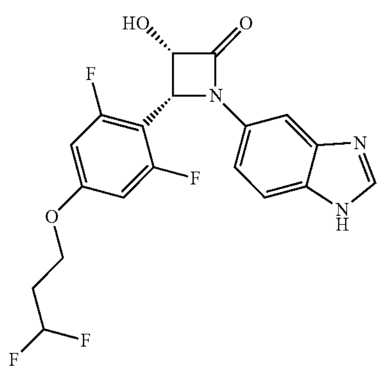 | Chiral |
| 8B | 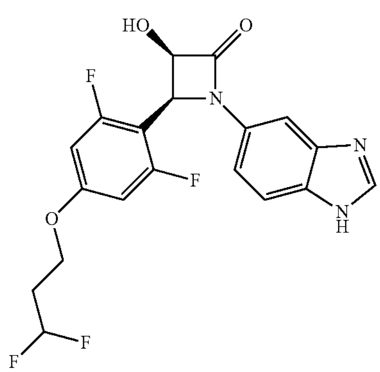 | Chiral |

TABLE 1-continued

| Com. ID | Structure | Comments |
| --- | --- | --- |
| 8TR | 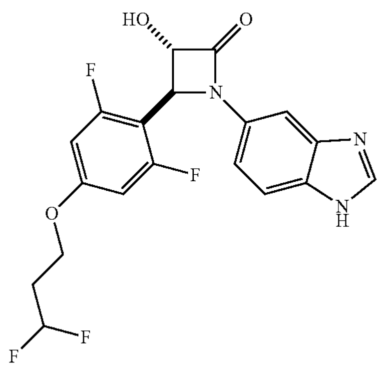 [SMILES: O=C1[C@@H](O)[C@H](c2c(F)cc(OCCC(F)F)cc2F)N1c1ccc2[nH]cnc2c1] | Trans and racemic |
| 9 | 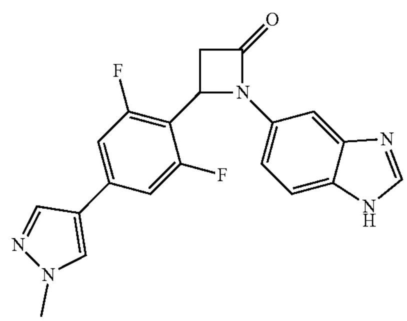 [SMILES: Cn1cc(-c2cc(F)c(C3CC(=O)N3c3ccc4[nH]cnc4c3)c(F)c2)cn1] | Racemic |
| 10CR | 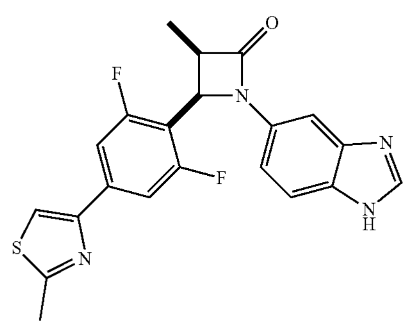 [SMILES: Cc1nc(-c2cc(F)c([C@H]3[C@@H](C)C(=O)N3c3ccc4[nH]cnc4c3)c(F)c2)cs1] | cis and racemic |
| 11CR | 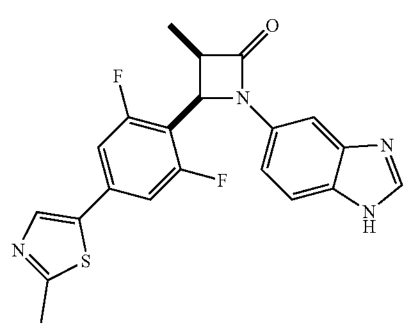 [SMILES: Cc1ncc(-c2cc(F)c([C@H]3[C@@H](C)C(=O)N3c3ccc4[nH]cnc4c3)c(F)c2)s1] | cis and racemic |

TABLE 1-continued

| Com. ID | Structure | Comments |
|---|---|---|
| 12CR | 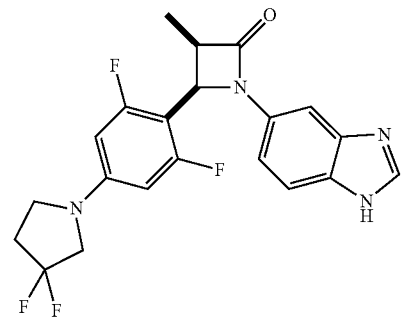 [SMILES: C[C@H]1C(=O)N(c2ccc3[nH]cnc3c2)[C@H]1c1c(F)cc(N2CCC(F)(F)C2)cc1F] | cis and racemic |
| 13 | 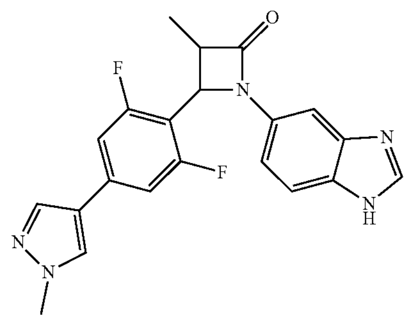 [SMILES: CC1C(=O)N(c2ccc3[nH]cnc3c2)C1c1c(F)cc(-c2cnn(C)c2)cc1F] | Racemic |
| 13A | 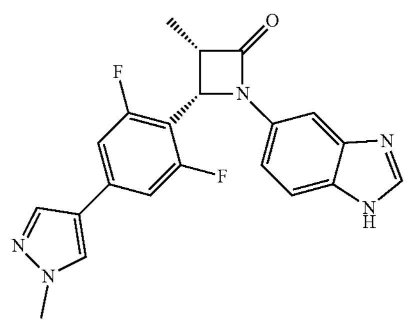 [SMILES: C[C@@H]1C(=O)N(c2ccc3[nH]cnc3c2)[C@@H]1c1c(F)cc(-c2cnn(C)c2)cc1F] | Chiral |
| 13B | 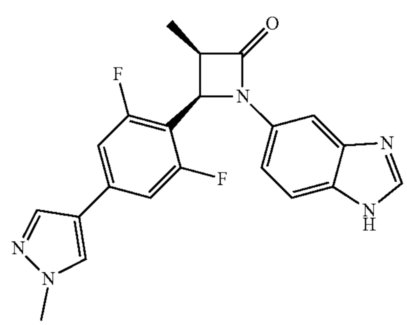 [SMILES: C[C@H]1C(=O)N(c2ccc3[nH]cnc3c2)[C@H]1c1c(F)cc(-c2cnn(C)c2)cc1F] | Chiral |
| 14 | 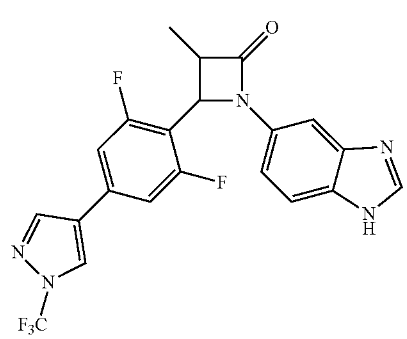 [SMILES: CC1C(=O)N(c2ccc3[nH]cnc3c2)C1c1c(F)cc(-c2cnn(C(F)(F)F)c2)cc1F] | Racemic |

TABLE 1-continued
| Com. ID | Structure | Comments |
|---|---|---|
| 14A | 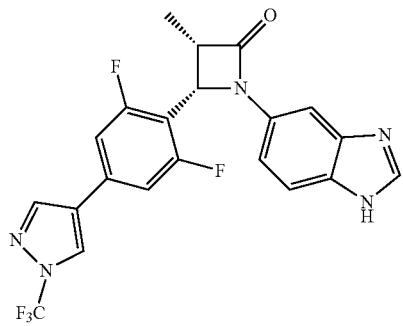 [SMILES: C[C@@H]1C(=O)N(c2ccc3[nH]cnc3c2)[C@@H]1c1c(F)cc(-c2cnn(C(F)(F)F)c2)cc1F] | Chiral |
| 14B | 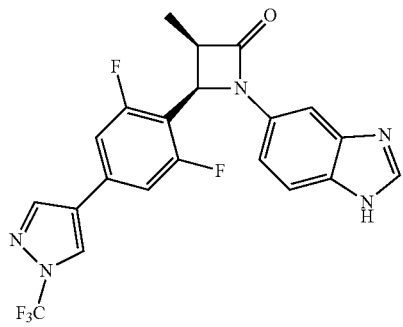 [SMILES: C[C@H]1C(=O)N(c2ccc3[nH]cnc3c2)[C@H]1c1c(F)cc(-c2cnn(C(F)(F)F)c2)cc1F] | Chiral |
| 15 | 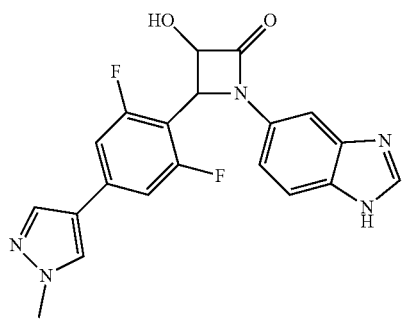 [SMILES: Cn1cc(-c2cc(F)c(C3C(O)C(=O)N3c3ccc4[nH]cnc4c3)c(F)c2)cn1] | Racemic |
| 15TR | 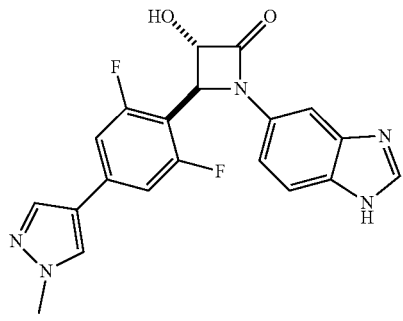 [SMILES: Cn1cc(-c2cc(F)c([C@H]3[C@H](O)C(=O)N3c3ccc4[nH]cnc4c3)c(F)c2)cn1] | Trans and racemic |

TABLE 1-continued

| Com. ID | Structure | Comments |
| --- | --- | --- |
| 15A | 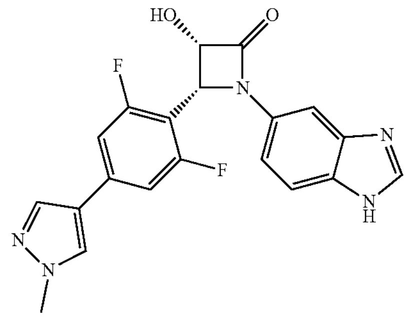 | Chiral |
| 15B | 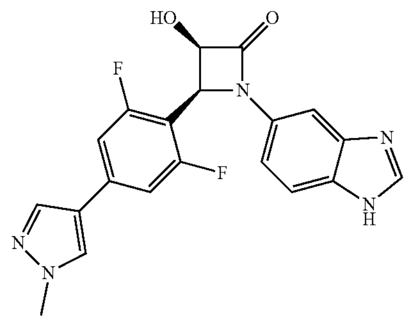 [SMILES: Cn1cc(-c2cc(F)c([C@H]3[C@@H](O)C(=O)N3c3ccc4[nH]cnc4c3)c(F)c2)cn1] | Chiral |
| 16CR | 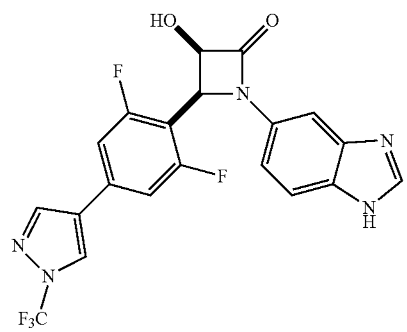 [SMILES: O=C1[C@H](O)[C@H](c2c(F)cc(-c3cnn(C(F)(F)F)c3)cc2F)N1c1ccc2[nH]cnc2c1] | cis and racemic |
| 16TR | 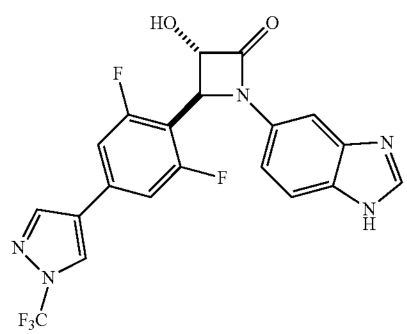 [SMILES: O=C1[C@@H](O)[C@H](c2c(F)cc(-c3cnn(C(F)(F)F)c3)cc2F)N1c1ccc2[nH]cnc2c1] | trans and racemic |

TABLE 1-continued
| Com. ID | Structure | Comments |
|---|---|---|
| 17A | 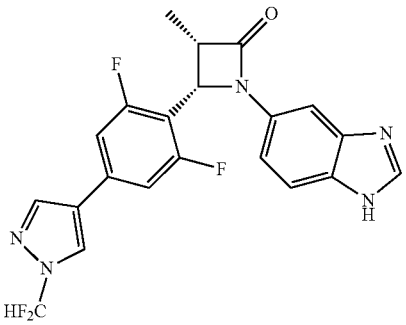 | Chiral |
| 17B | 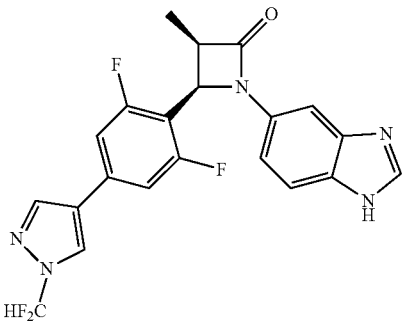 | Chiral |
| 18 | 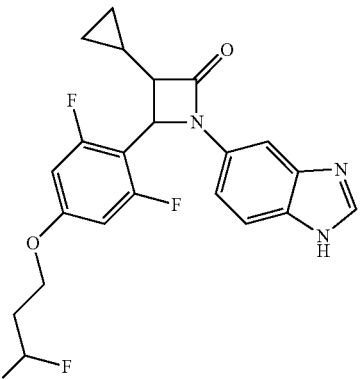 | Racemic |
| 18A | 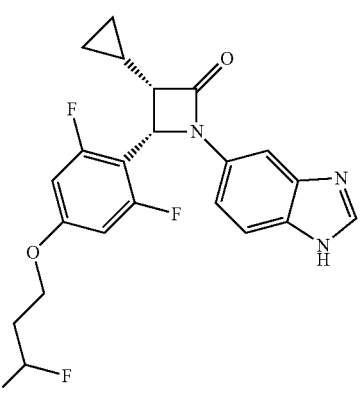 | Chiral |

TABLE 1-continued

| Com. ID | Structure | Comments |
|---|---|---|
| 18B | 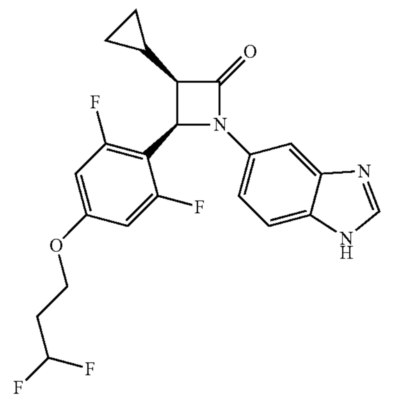 [SMILES: O=C1[C@H](C2CC2)[C@H](c2c(F)cc(OCCC(F)F)cc2F)N1c1ccc2[nH]cnc2c1] | Chiral |
| 20CR | 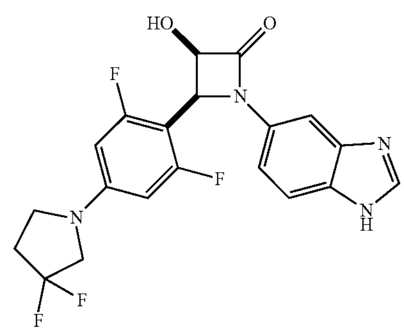 [SMILES: O=C1[C@H](O)[C@H](c2c(F)cc(N3CCC(F)(F)C3)cc2F)N1c1ccc2[nH]cnc2c1] | cis and racemic |
| 21B | 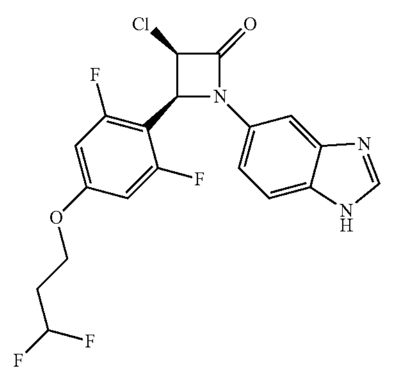 | chiral |
| 22 | 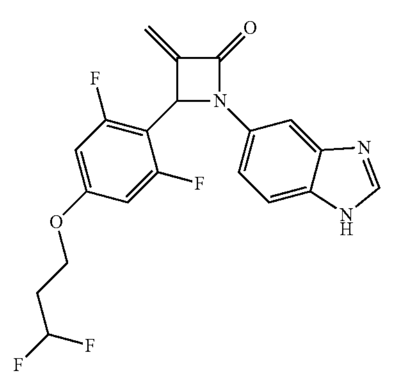 [SMILES: C=C1C(=O)N(c2ccc3[nH]cnc3c2)C1c1c(F)cc(OCCC(F)F)cc1F] | Racemic |

TABLE 1-continued

| Com. ID | Structure | Comments |
|---|---|---|
| 22A | 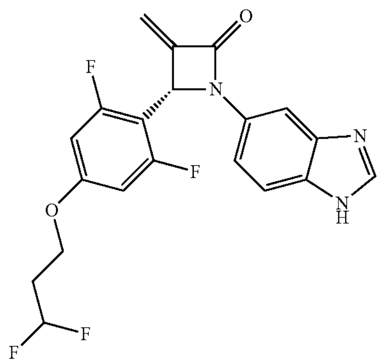 | chiral |
| 22B | 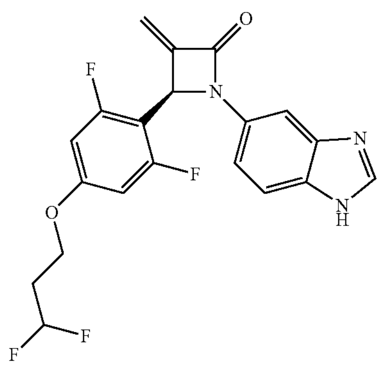 [SMILES: C=C1C(=O)N(c2ccc3[nH]cnc3c2)[C@H]1c1c(F)cc(OCCC(F)F)cc1F] | chiral |
| 23 | 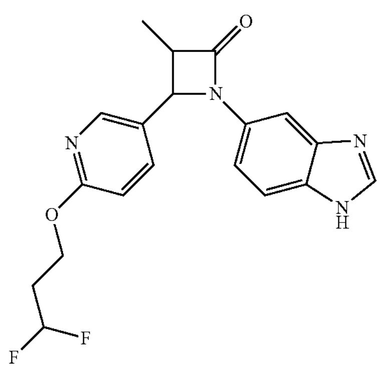 [SMILES: CC1C(=O)N(c2ccc3[nH]cnc3c2)C1c1ccc(OCCC(F)F)nc1] | racemic |
| 23CR | 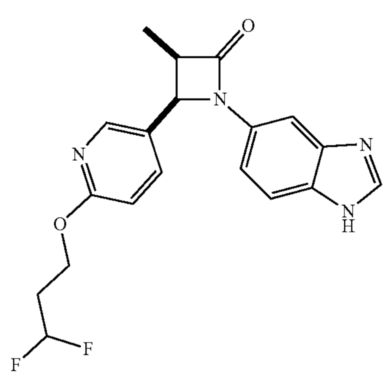 [SMILES: C[C@H]1C(=O)N(c2ccc3[nH]cnc3c2)[C@H]1c1ccc(OCCC(F)F)nc1] | cis and racemic |

TABLE 1-continued
| Com. ID | Structure | Comments |
|---------|-----------|----------|
| 23B | 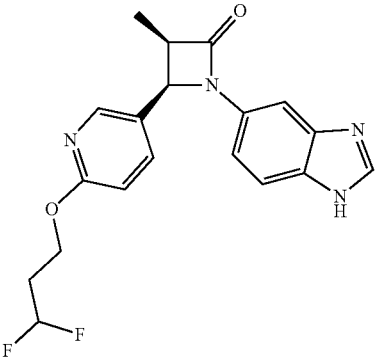 [SMILES: C[C@H]1C(=O)N(c2ccc3[nH]cnc3c2)[C@H]1c1ccc(OCCC(F)F)nc1] | Chiral |
| 24B | 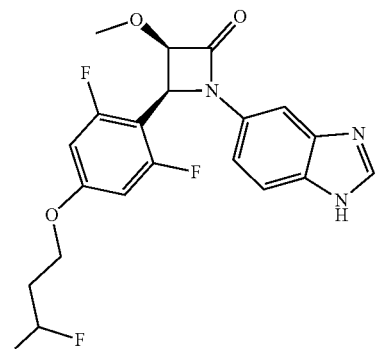 | Chiral |
| 25 | 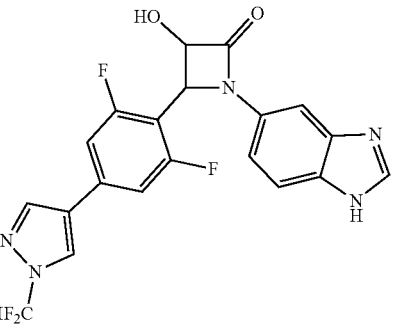 | Racemic |
| 25CR | 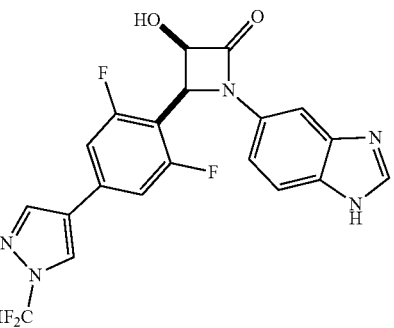 | cis and racemic |

TABLE 1-continued

| Com. ID | Structure | Comments |
|---|---|---|
| 25TR | 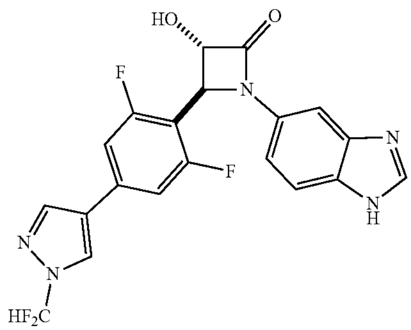 | trans and racemic |
| 25B | 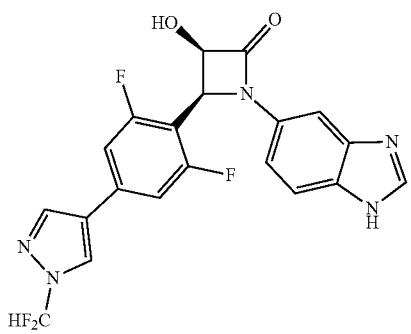 | Chiral |
| 26B | 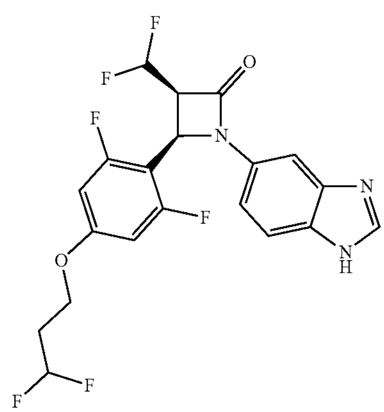 [SMILES: O=C1[C@H](C(F)F)[C@H](c2c(F)cc(OCCC(F)F)cc2F)N1c1ccc2[nH]cnc2c1] | Chiral |
| 27B | 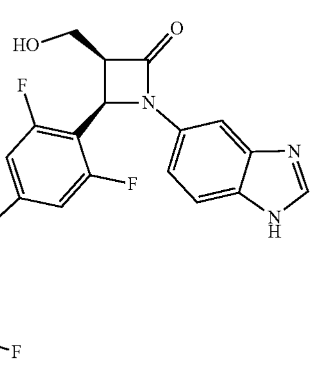 | Chiral |

TABLE 1-continued

| Com. ID | Structure | Comments |
|---|---|---|
| 28CR | 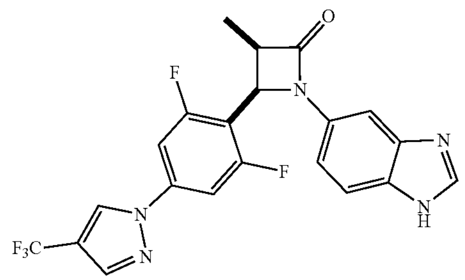 [SMILES: C[C@H]1C(=O)N(c2ccc3[nH]cnc3c2)[C@H]1c1c(F)cc(-n2cc(C(F)(F)F)cn2)cc1F] | cis and racemic |
| 28TR | 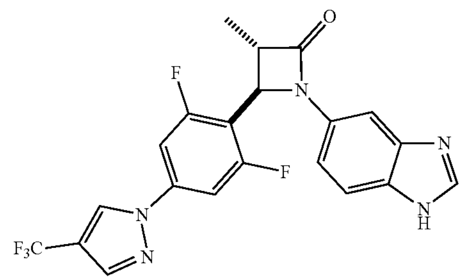 [SMILES: C[C@@H]1C(=O)N(c2ccc3[nH]cnc3c2)[C@H]1c1c(F)cc(-n2cc(C(F)(F)F)cn2)cc1F] | trans and racemic |
| 29B | 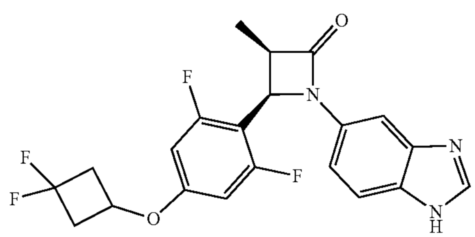 [SMILES: C[C@H]1C(=O)N(c2ccc3[nH]cnc3c2)[C@H]1c1c(F)cc(OC2CC(F)(F)C2)cc1F] | Chiral |
| 30 | 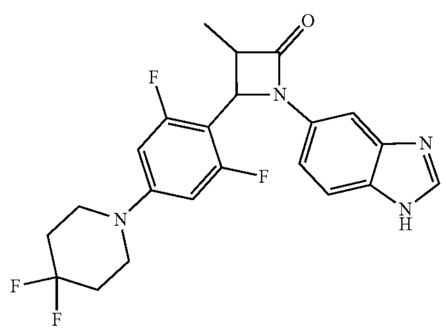 [SMILES: CC1C(=O)N(c2ccc3[nH]cnc3c2)C1c1c(F)cc(N2CCC(F)(F)CC2)cc1F] | Racemic |
| 30A | 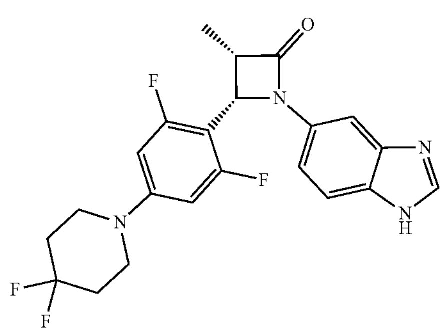 [SMILES: C[C@@H]1C(=O)N(c2ccc3[nH]cnc3c2)[C@@H]1c1c(F)cc(N2CCC(F)(F)CC2)cc1F] | Chiral |

TABLE 1-continued
| Com. ID | Structure | Comments |
|---|---|---|
| 30B | 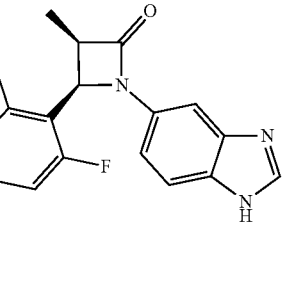 | Chiral |
| 31B | 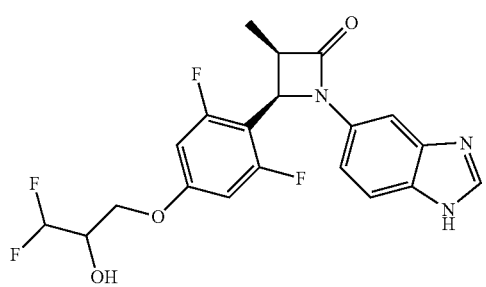 [SMILES: C[C@H]1C(=O)N(c2ccc3[nH]cnc3c2)[C@H]1c1c(F)cc(OCC(O)C(F)F)cc1F] | Chiral |
| 32 | 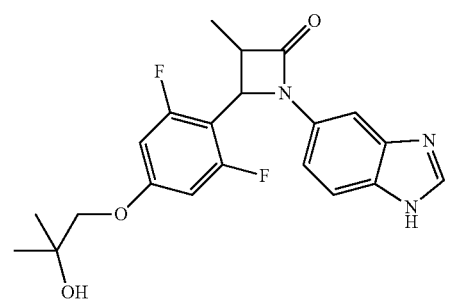 [SMILES: CC1C(=O)N(c2ccc3[nH]cnc3c2)C1c1c(F)cc(OCC(C)(C)O)cc1F] | Racemic |
| 32A | 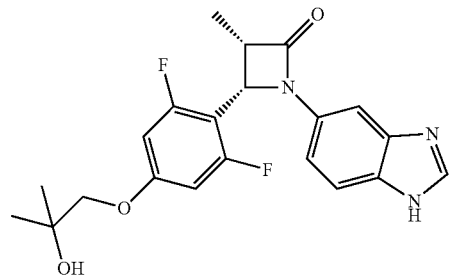 [SMILES: C[C@@H]1C(=O)N(c2ccc3[nH]cnc3c2)[C@@H]1c1c(F)cc(OCC(C)(C)O)cc1F] | Chiral |
| 32B | 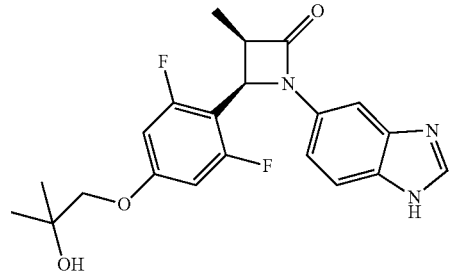 [SMILES: C[C@H]1C(=O)N(c2ccc3[nH]cnc3c2)[C@H]1c1c(F)cc(OCC(C)(C)O)cc1F] | Chiral |

TABLE 1-continued

| Com. ID | Structure | Comments |
|---|---|---|
| 33B | 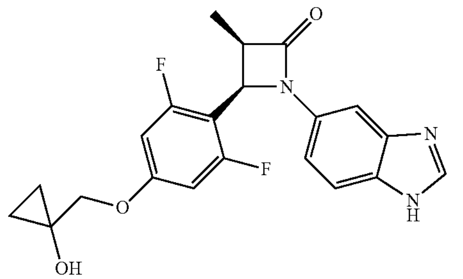 [SMILES: C[C@H]1C(=O)N(c2ccc3[nH]cnc3c2)[C@H]1c1c(F)cc(OCC2(O)CC2)cc1F] | Chiral |
| 34CR | 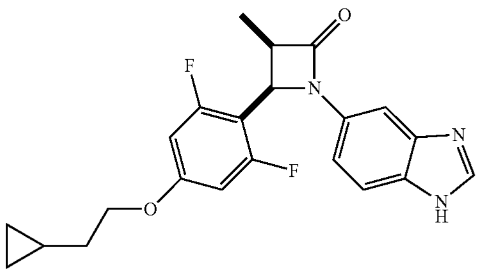 [SMILES: C[C@H]1C(=O)N(c2ccc3[nH]cnc3c2)[C@H]1c1c(F)cc(OCCC2CC2)cc1F] | cis and racemic |
| 34TR | 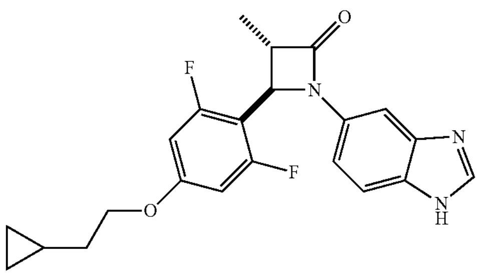 [SMILES: C[C@@H]1C(=O)N(c2ccc3[nH]cnc3c2)[C@H]1c1c(F)cc(OCCC2CC2)cc1F] | trans and racemic |
| 35A | 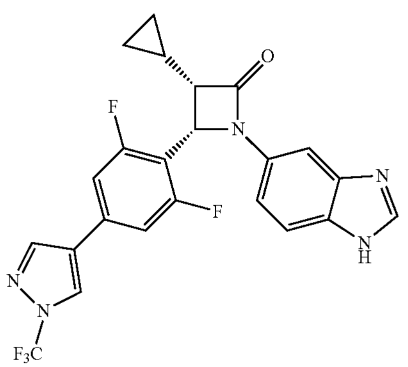 [SMILES: O=C1[C@@H](C2CC2)[C@@H](c2c(F)cc(-c3cnn(C(F)(F)F)c3)cc2F)N1c1ccc2[nH]cnc2c1] | Chiral |
| 35B | 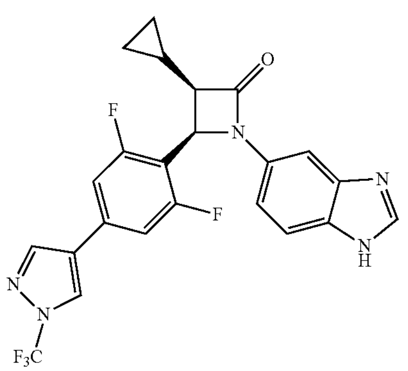 | Chiral |

TABLE 1-continued

| Com. ID | Structure | Comments |
|---|---|---|
| 36B | 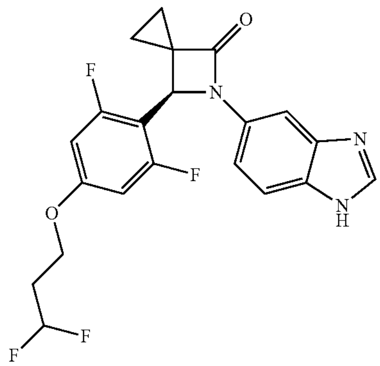 [SMILES: O=C1N(c2ccc3[nH]cnc3c2)[C@@H](c2c(F)cc(OCCC(F)F)cc2F)C12CC2] | Chiral |
| 37B | 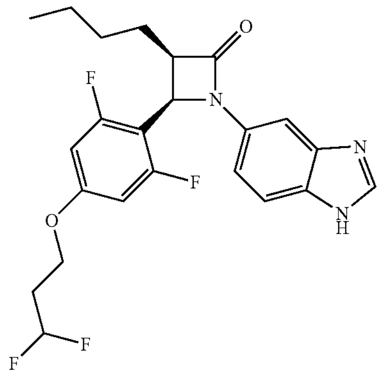 [SMILES: CCCC[C@H]1C(=O)N(c2ccc3[nH]cnc3c2)[C@H]1c1c(F)cc(OCCC(F)F)cc1F] | Chiral |
| 38B | 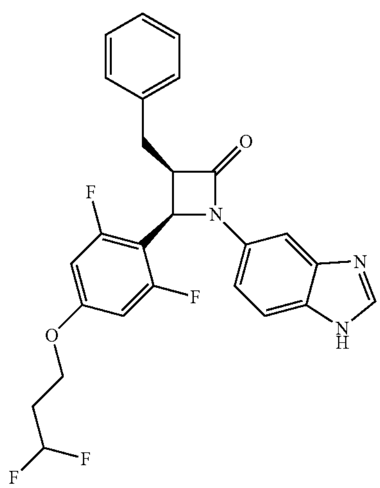 [SMILES: O=C1[C@H](Cc2ccccc2)[C@H](c2c(F)cc(OCCC(F)F)cc2F)N1c1ccc2[nH]cnc2c1] | Chiral |
| 39B | 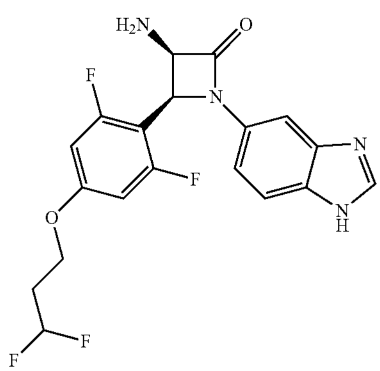 [SMILES: N[C@H]1C(=O)N(c2ccc3[nH]cnc3c2)[C@H]1c1c(F)cc(OCCC(F)F)cc1F] | Chiral |

TABLE 1-continued

| Com. ID | Structure | Comments |
|---------|-----------|----------|
| 40B | 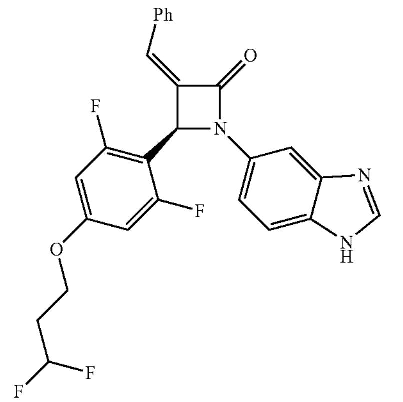 [SMILES: O=C1/C(=C\c2ccccc2)[C@H](c2c(F)cc(OCCC(F)F)cc2F)N1c1ccc2[nH]cnc2c1] | Chiral |
| 41B | 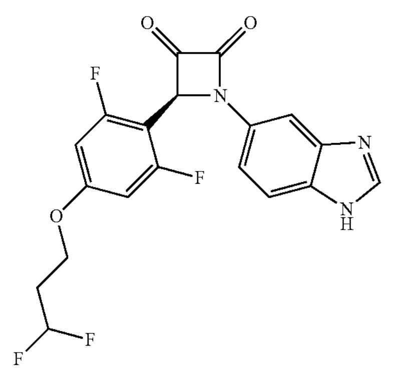 [SMILES: O=C1C(=O)N(c2ccc3[nH]cnc3c2)[C@H]1c1c(F)cc(OCCC(F)F)cc1F] | Chiral |
| 42B | 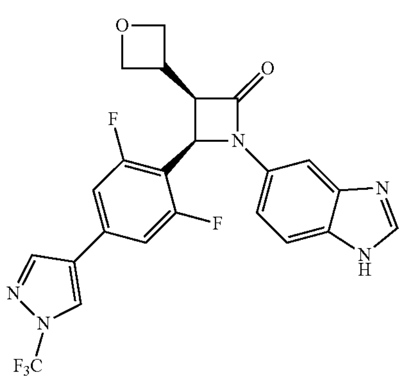 [SMILES: O=C1[C@H](C2COC2)[C@H](c2c(F)cc(-c3cnn(C(F)(F)F)c3)cc2F)N1c1ccc2[nH]cnc2c1] | Chiral |
| 42A | 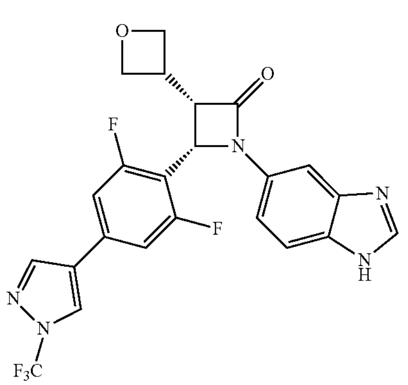 [SMILES: O=C1[C@@H](C2COC2)[C@@H](c2c(F)cc(-c3cnn(C(F)(F)F)c3)cc2F)N1c1ccc2[nH]cnc2c1] | Chiral |

TABLE 1-continued
| Com. ID | Structure | Comments |
|---|---|---|
| 43A | 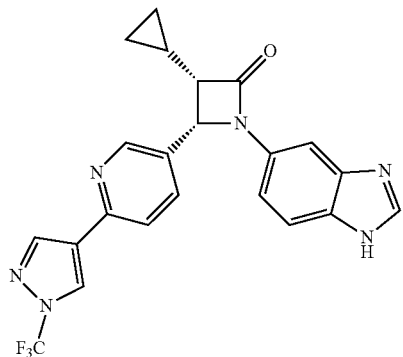 [SMILES: O=C1[C@@H](C2CC2)[C@@H](c2ccc(-c3cnn(C(F)(F)F)c3)nc2)N1c1ccc2[nH]cnc2c1] | Chiral |
| 43B | 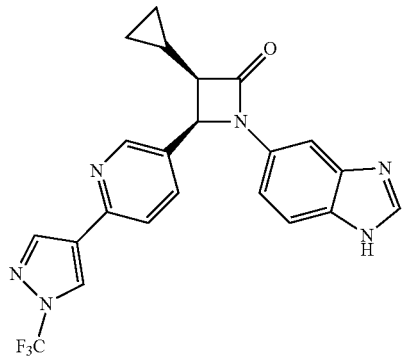 [SMILES: O=C1[C@H](C2CC2)[C@H](c2ccc(-c3cnn(C(F)(F)F)c3)nc2)N1c1ccc2[nH]cnc2c1] | Chiral |
| 44B | 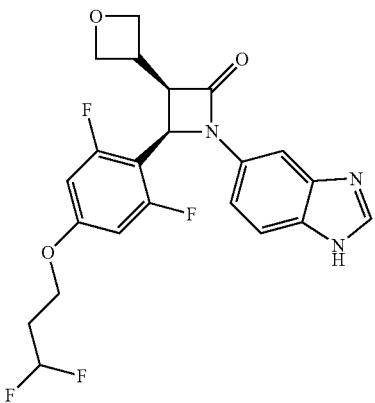 [SMILES: O=C1[C@H](C2COC2)[C@H](c2c(F)cc(OCCC(F)F)cc2F)N1c1ccc2[nH]cnc2c1] | chiral |
| 45A | 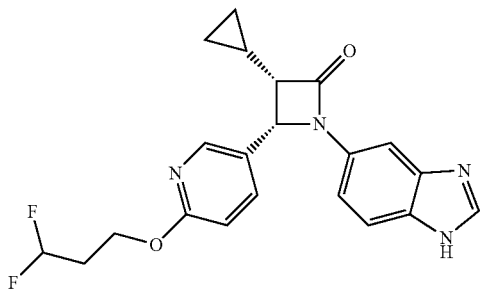 [SMILES: O=C1[C@@H](C2CC2)[C@@H](c2ccc(OCCC(F)F)nc2)N1c1ccc2[nH]cnc2c1] | chiral |

TABLE 1-continued

| Com. ID | Structure | Comments |
|---------|-----------|----------|
| 45B | 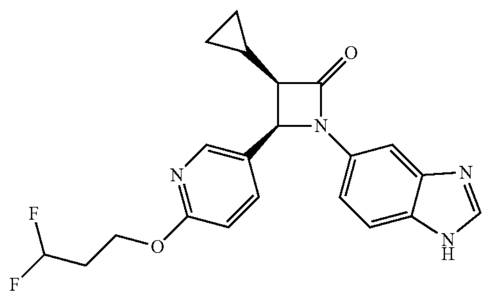 [SMILES: O=C1[C@H](C2CC2)[C@H](c2ccc(OCCC(F)F)nc2)N1c1ccc2[nH]cnc2c1] | chiral |
| 46A | 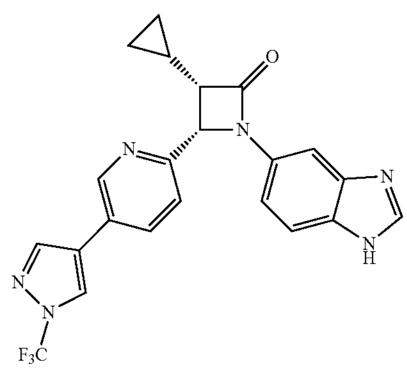 [SMILES: O=C1[C@@H](C2CC2)[C@@H](c2ccc(-c3cnn(C(F)(F)F)c3)cn2)N1c1ccc2[nH]cnc2c1] | chiral |
| 46B | 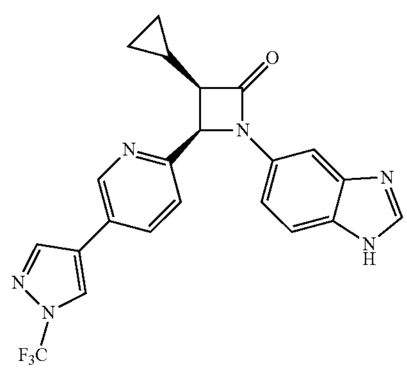 [SMILES: O=C1[C@H](C2CC2)[C@H](c2ccc(-c3cnn(C(F)(F)F)c3)cn2)N1c1ccc2[nH]cnc2c1] | chiral |
| 47B | 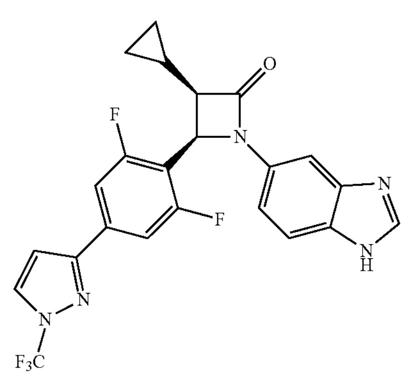 [SMILES: O=C1[C@H](C2CC2)[C@H](c2c(F)cc(-c3ccn(C(F)(F)F)n3)cc2F)N1c1ccc2[nH]cnc2c1] | chiral |

TABLE 1-continued

| Com. ID | Structure | Comments |
|---|---|---|
| 48A | 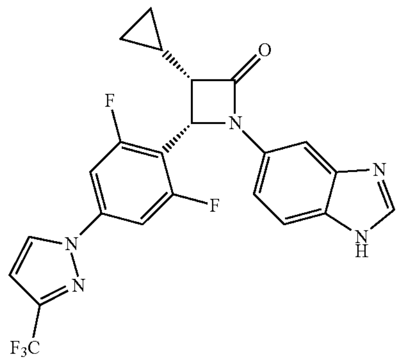 [SMILES: O=C1[C@@H](C2CC2)[C@@H](c2c(F)cc(-n3ccc(C(F)(F)F)n3)cc2F)N1c1ccc2[nH]cnc2c1] | chiral |
| 48B | 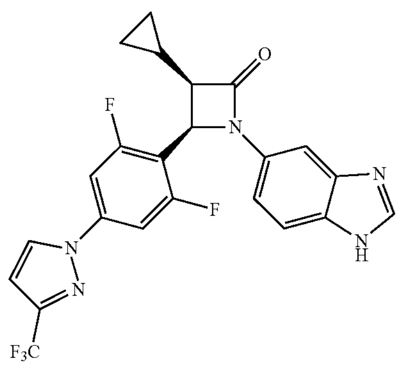 [SMILES: O=C1[C@H](C2CC2)[C@H](c2c(F)cc(-n3ccc(C(F)(F)F)n3)cc2F)N1c1ccc2[nH]cnc2c1] | chiral |
| 49B | 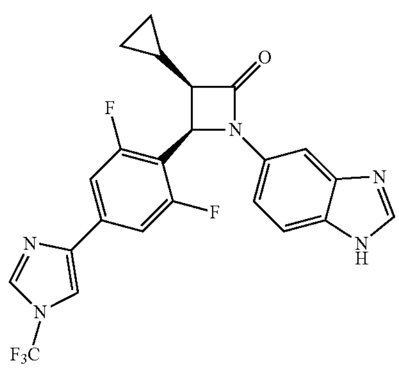 [SMILES: O=C1[C@H](C2CC2)[C@H](c2c(F)cc(-c3cn(C(F)(F)F)cn3)cc2F)N1c1ccc2[nH]cnc2c1] | chiral |
| 50A | 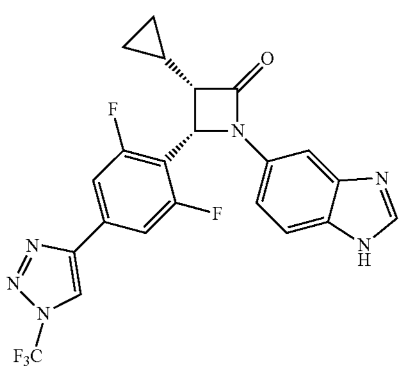 [SMILES: O=C1[C@@H](C2CC2)[C@@H](c2c(F)cc(-c3cn(C(F)(F)F)nn3)cc2F)N1c1ccc2[nH]cnc2c1] | chiral |

TABLE 1-continued
| Com. ID | Structure | Comments |
|---|---|---|
| 50B | 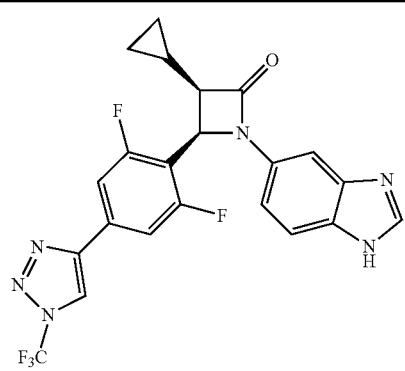 | chiral |
| 51A | 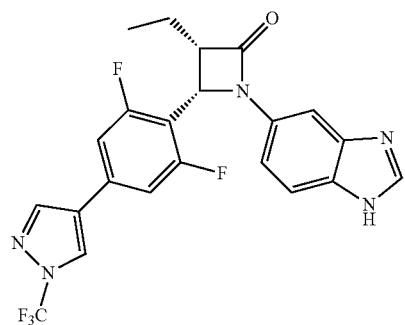 [SMILES: CC[C@@H]1C(=O)N(c2ccc3[nH]cnc3c2)[C@@H]1c1c(F)cc(-c2cnn(C(F)(F)F)c2)cc1F] | chiral |
| 51B | 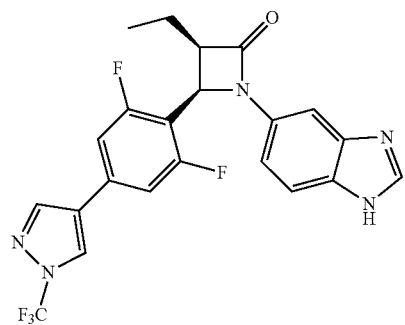 [SMILES: CC[C@H]1C(=O)N(c2ccc3[nH]cnc3c2)[C@H]1c1c(F)cc(-c2cnn(C(F)(F)F)c2)cc1F] | chiral |
| 52A | 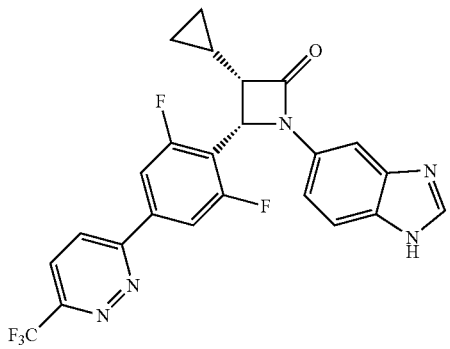 [SMILES: O=C1[C@@H](C2CC2)[C@@H](c2c(F)cc(-c3ccc(C(F)(F)F)nn3)cc2F)N1c1ccc2[nH]cnc2c1] | chiral |

TABLE 1-continued
| Com. ID | Structure | Comments |
|---|---|---|
| 52B | 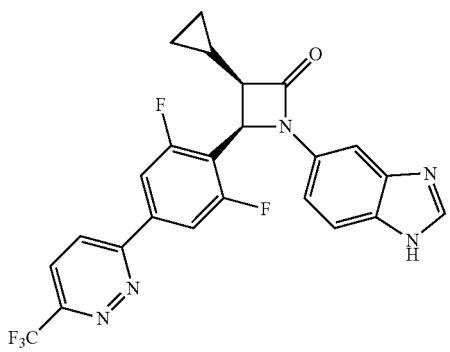 [SMILES: O=C1[C@H](C2CC2)[C@H](c2c(F)cc(-c3ccc(C(F)(F)F)nn3)cc2F)N1c1ccc2[nH]cnc2c1] | chiral |
| 53A | 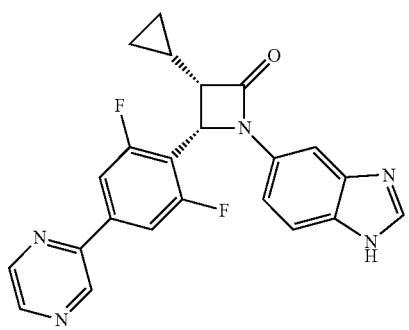 [SMILES: O=C1[C@@H](C2CC2)[C@@H](c2c(F)cc(-c3cnccn3)cc2F)N1c1ccc2[nH]cnc2c1] | chiral |
| 53B | 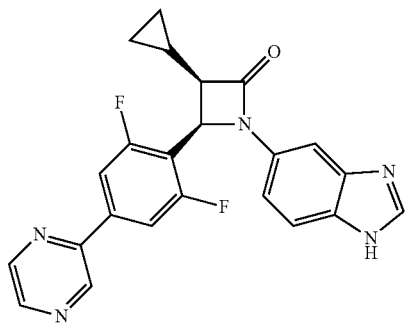 [SMILES: O=C1[C@H](C2CC2)[C@H](c2c(F)cc(-c3cnccn3)cc2F)N1c1ccc2[nH]cnc2c1] | chiral |
| 54B | 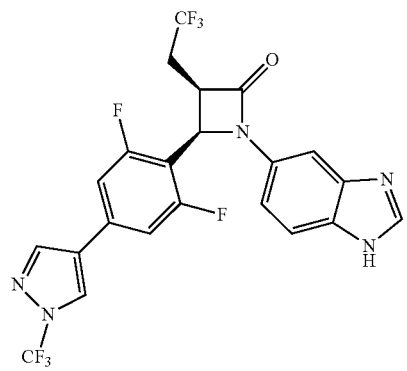 [SMILES: O=C1[C@H](CC(F)(F)F)[C@H](c2c(F)cc(-c3cnn(C(F)(F)F)c3)cc2F)N1c1ccc2[nH]cnc2c1] | chiral |

TABLE 1-continued
| Com. ID | Structure | Comments |
|---|---|---|
| 55A | 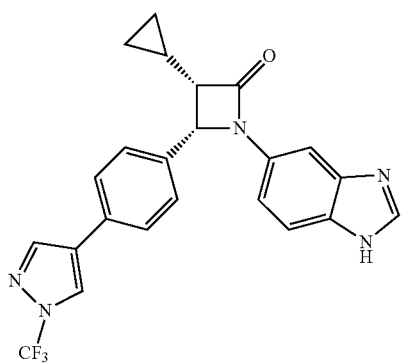 [SMILES: O=C1[C@@H](C2CC2)[C@@H](c2ccc(-c3cnn(C(F)(F)F)c3)cc2)N1c1ccc2[nH]cnc2c1] | chiral |
| 55B | 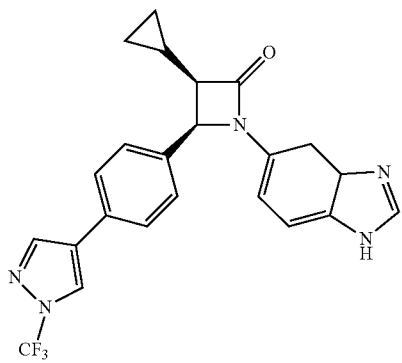 | chiral |
| 56A | 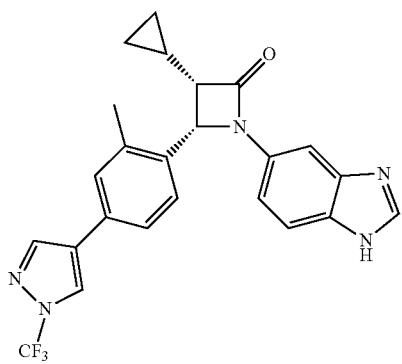 | chiral |
| 56B | 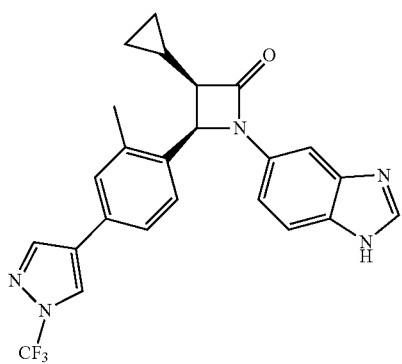 [SMILES: Cc1cc(-c2cnn(C(F)(F)F)c2)ccc1[C@H]1[C@@H](C2CC2)C(=O)N1c1ccc2[nH]cnc2c1] | chiral |

TABLE 1-continued
| Com. ID | Structure | Comments |
|---|---|---|
| 57A | 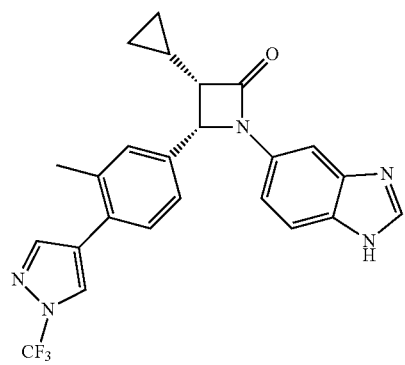 | chiral |
| 57B | 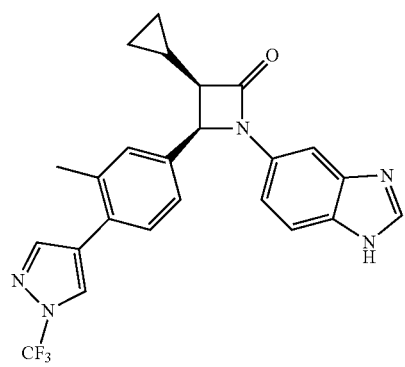 [SMILES: Cc1cc([C@H]2[C@@H](C3CC3)C(=O)N2c2ccc3[nH]cnc3c2)ccc1-c1cnn(C(F)(F)F)c1] | chiral |
| 58B | 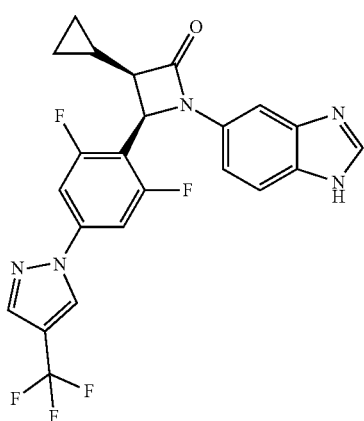 [SMILES: O=C1[C@H](C2CC2)[C@H](c2c(F)cc(-n3cc(C(F)(F)F)cn3)cc2F)N1c1ccc2[nH]cnc2c1] | chiral |
| 59B | 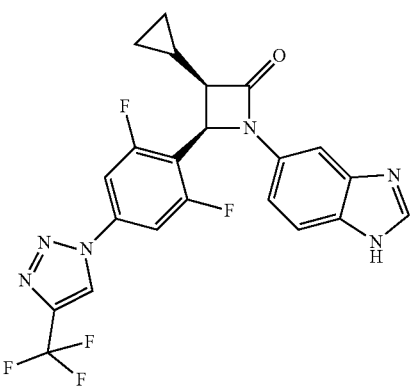 [SMILES: O=C1[C@H](C2CC2)[C@H](c2c(F)cc(-n3cnc(C(F)(F)F)c3)cc2F)N1c1ccc2[nH]cnc2c1] | chiral |

TABLE 1-continued
| Com. ID | Structure | Comments |
|---|---|---|
| 60B | 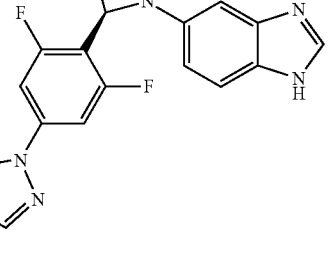 | chiral |
| 61B | 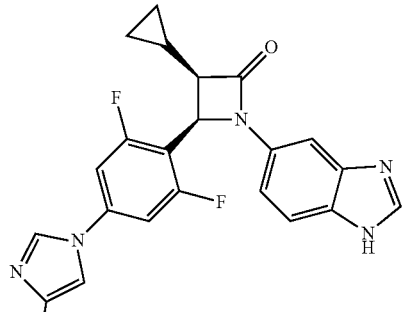 | chiral |
| 62B | 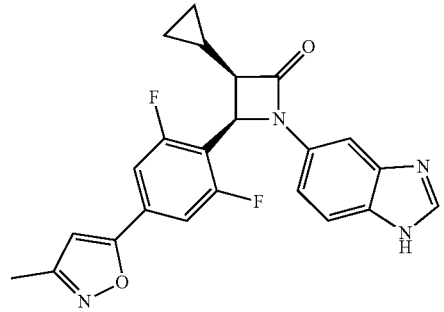 [SMILES: Cc1cc(-c2cc(F)c([C@H]3[C@@H](C4CC4)C(=O)N3c3ccc4[nH]cnc4c3)c(F)c2)on1] | chiral |
| 63B | 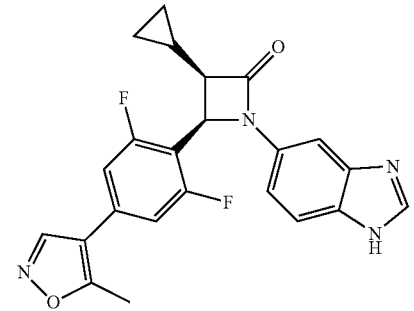 [SMILES: Cc1oncc1-c1cc(F)c([C@H]2[C@@H](C3CC3)C(=O)N2c2ccc3[nH]cnc3c2)c(F)c1] | chiral |

TABLE 1-continued
| Com. ID | Structure | Comments |
|---|---|---|
| 64B | 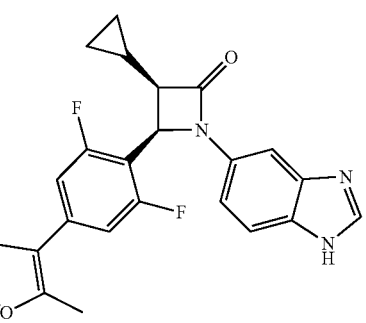 | chiral |
| 65B | 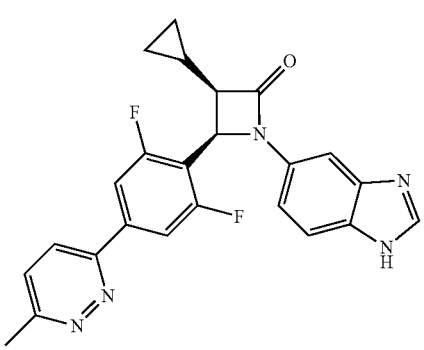 [SMILES: Cc1ccc(-c2cc(F)c([C@H]3[C@@H](C4CC4)C(=O)N3c3ccc4[nH]cnc4c3)c(F)c2)nn1] | chiral |
| 66A | 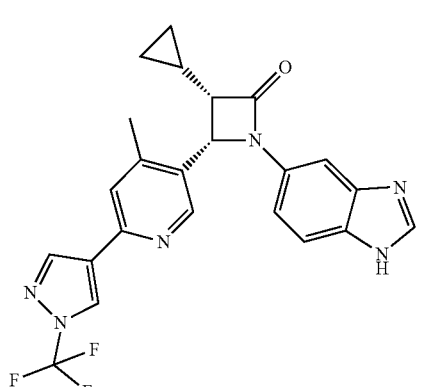 | chiral |
| 66B | 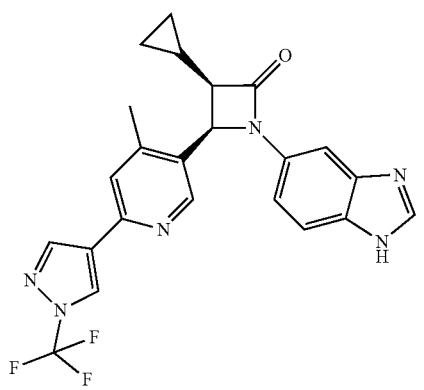 [SMILES: Cc1cc(-c2cnn(C(F)(F)F)c2)ncc1[C@H]1[C@@H](C2CC2)C(=O)N1c1ccc2[nH]cnc2c1] | chiral |

TABLE 1-continued
| Com. ID | Structure | Comments |
|---|---|---|
| 67A | 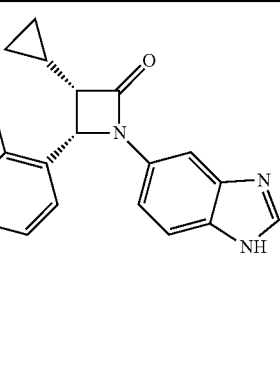 | chiral |
| 67B | 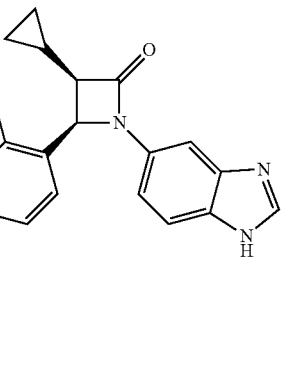 | chiral |
| 68A | 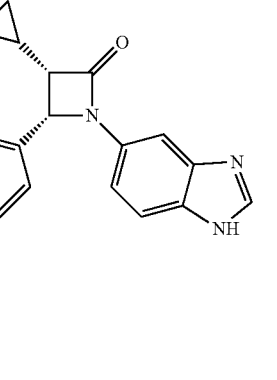 | chiral |
| 68B | 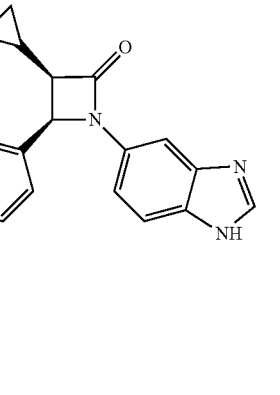 | chiral |

TABLE 1-continued
| Com. ID | Structure | Comments |
|---|---|---|
| 69A | 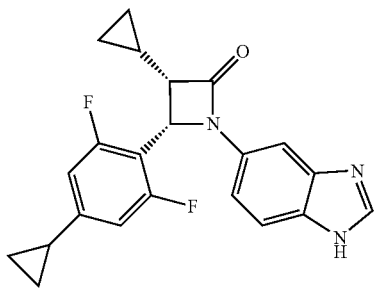 [SMILES: O=C1[C@@H](C2CC2)[C@@H](c2c(F)cc(C3CC3)cc2F)N1c1ccc2[nH]cnc2c1] | chiral |
| 69B | 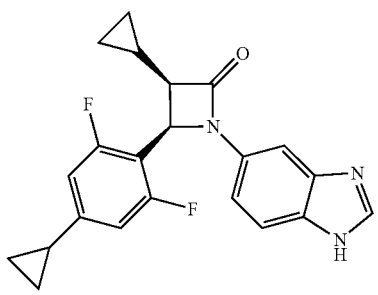 [SMILES: O=C1[C@H](C2CC2)[C@H](c2c(F)cc(C3CC3)cc2F)N1c1ccc2[nH]cnc2c1] | chiral |
| 70A | 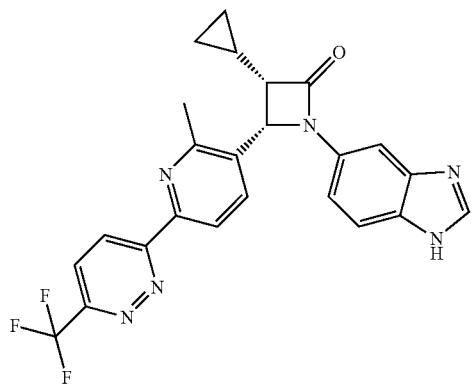 [SMILES: Cc1nc(-c2ccc(C(F)(F)F)nn2)ccc1[C@@H]1[C@H](C2CC2)C(=O)N1c1ccc2[nH]cnc2c1] | chiral |
| 70B | 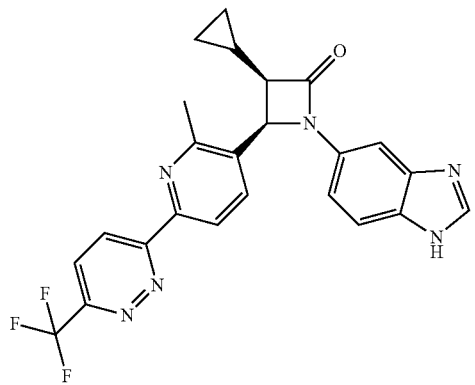 [SMILES: Cc1nc(-c2ccc(C(F)(F)F)nn2)ccc1[C@H]1[C@@H](C2CC2)C(=O)N1c1ccc2[nH]cnc2c1] | chiral |

TABLE 1-continued
| Com. ID | Structure | Comments |
|---------|-----------|----------|
| 71A | 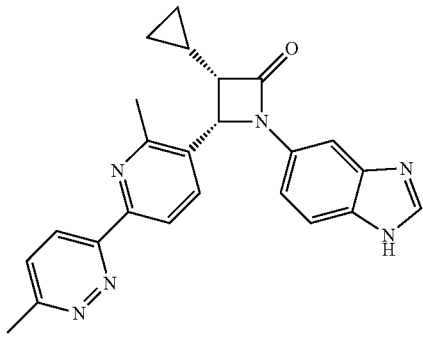 [SMILES: Cc1ccc(-c2ccc([C@@H]3[C@H](C4CC4)C(=O)N3c3ccc4[nH]cnc4c3)c(C)n2)nn1] | chiral |
| 71B | 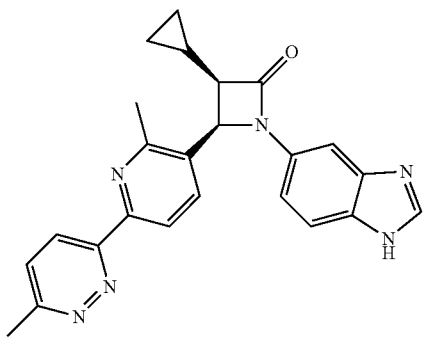 [SMILES: Cc1ccc(-c2ccc([C@H]3[C@@H](C4CC4)C(=O)N3c3ccc4[nH]cnc4c3)c(C)n2)nn1] | chiral |
| 72A | 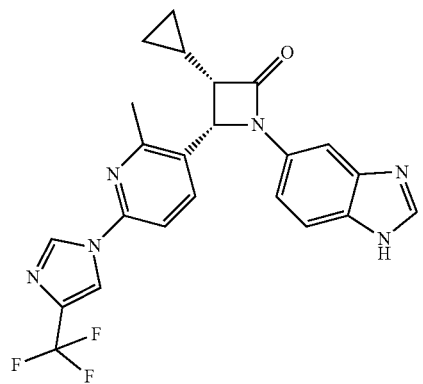 [SMILES: Cc1nc(-n2cnc(C(F)(F)F)c2)ccc1[C@@H]1[C@H](C2CC2)C(=O)N1c1ccc2[nH]cnc2c1] | chiral |
| 72B | 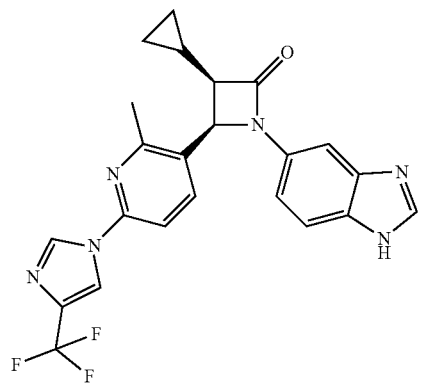 [SMILES: Cc1nc(-n2cnc(C(F)(F)F)c2)ccc1[C@H]1[C@@H](C2CC2)C(=O)N1c1ccc2[nH]cnc2c1] | chiral |

TABLE 1-continued
| Com. ID | Structure | Comments |
|---|---|---|
| 73A | 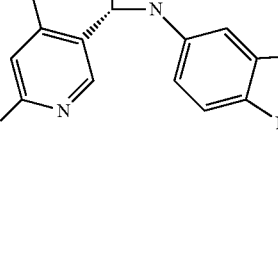 | chiral |
| 73B | 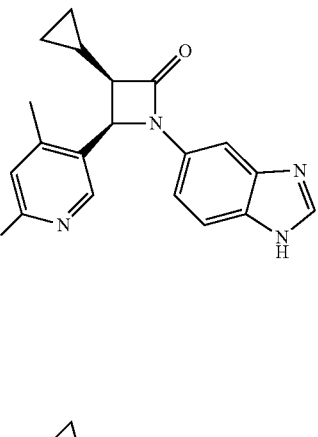 | chiral |
| 74A | 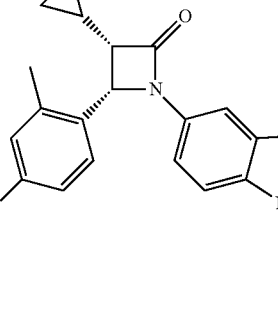 | chiral |
| 74B | 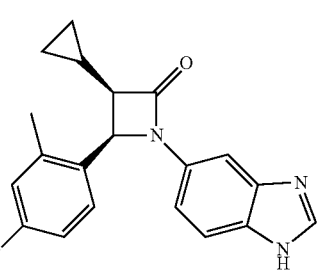 | chiral |

TABLE 1-continued
| Com. ID | Structure | Comments |
|---------|-----------|----------|
| 75A | 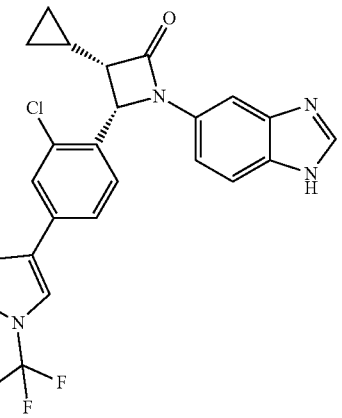 | chiral |
| 75B | 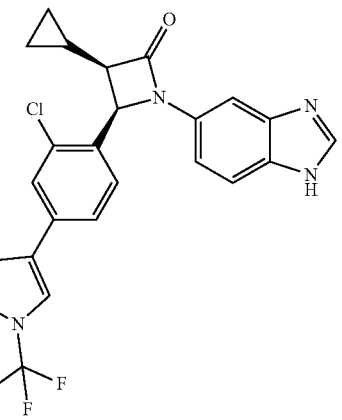 | chiral |
| 76A | 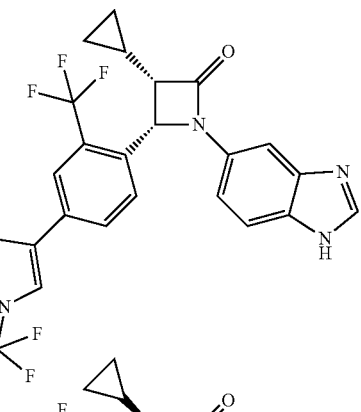 | chiral |
| 76B | 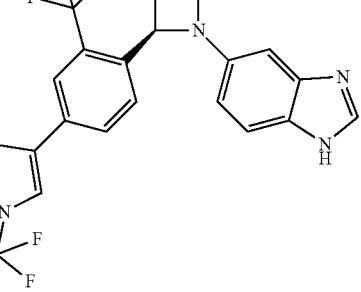 | chiral |

In some embodiments, a compound described herein is in a racemic form. For example, a compound in the racemic form such as

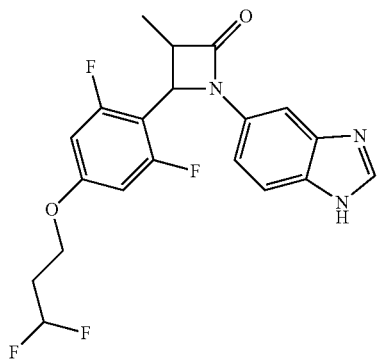 [SMILES: CC1C(=O)N(c2ccc3[nH]cnc3c2)C1c1c(F)cc(OCCC(F)F)cc1F]

(compound 7) can encompass four stereoisomers, including

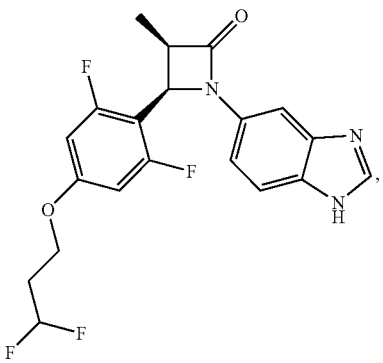

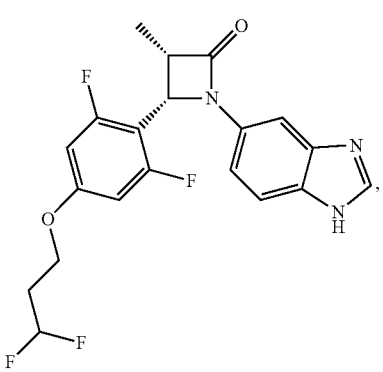

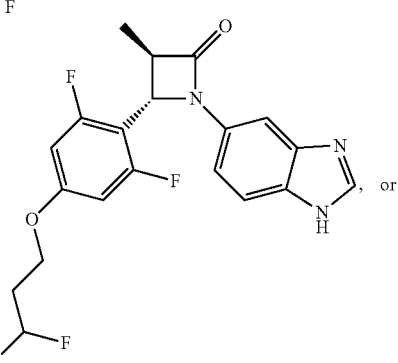

, or

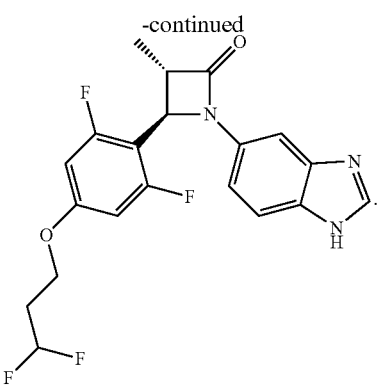

In some embodiments, provided herein is a compound in a cis and racemic form. For example, the compound 7 in cis and racemic form encompasses two stereoisomers, including

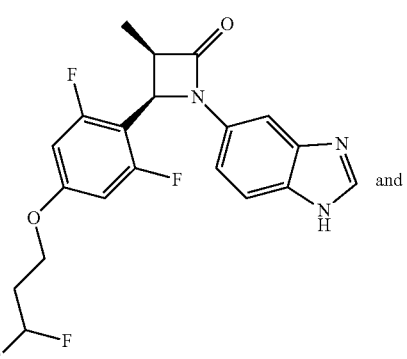

and

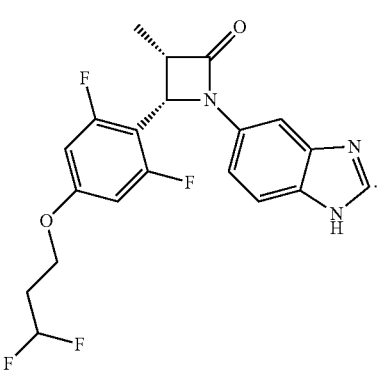

In some embodiments, provided herein is a compound in a trans and racemic form. For example, the compound 7 in trans and racemic form encompasses two stereoisomers, including

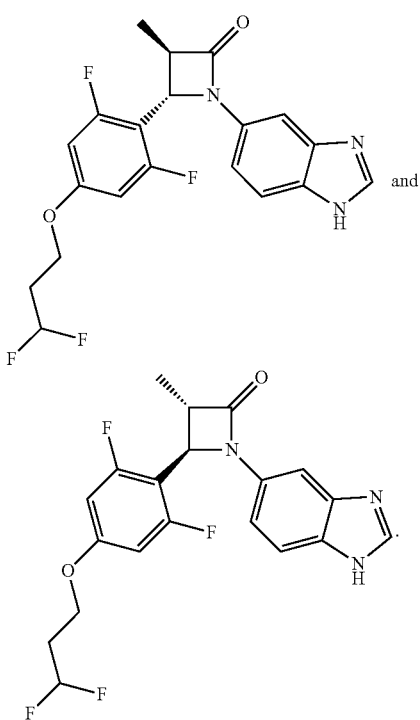

For another example, a compound in the racemic form such as

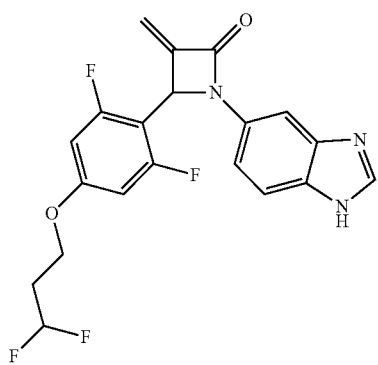 [SMILES: C=C1C(=O)N(c2ccc3[nH]cnc3c2)C1c1c(F)cc(OCCC(F)F)cc1F]

(Compound 22) can encompass two stereoisomers, including

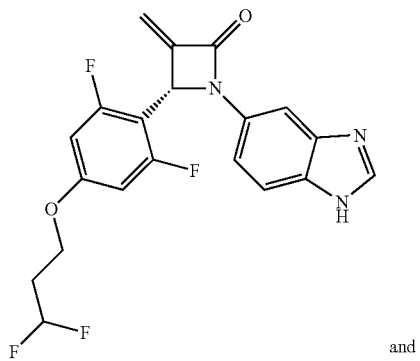

and

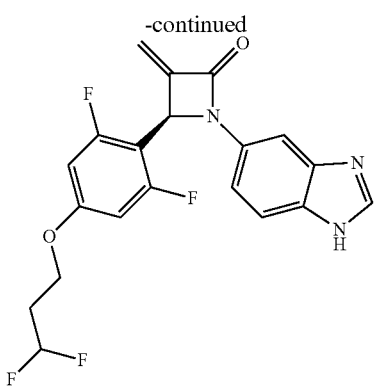

-continued

In some embodiments, described herein is a compound having a structure selected from Table 1, and exists in its racemic form. In some embodiments, described herein is a compound having a structure selected from Table 1, and exists in its cis and racemic form. In some embodiments, described herein is a compound having a structure selected from Table 1, and exists in its trans and racemic form. In some embodiments, described herein is a compound having a structure selected from Table 1, and is stereochemically pure. A person of skill would appreciate that, all stereoisomers and racemic forms of compounds disclosed in Table 1 are encompassed by the present disclosure.

In some embodiments, the compound of Formula (I), (Ia), (Ib), (II), (IIa), or (IIb) is not racemic. In some embodiments, the compound of the present disclosure is substantially free of other isomers. In some embodiments, the compound is a single isomer substantially free of other isomers. In some embodiments, the compound comprises 25% or less of other isomers. In some embodiments, the compound comprises 20% or less of other isomers. In some embodiments, the compound comprises 15% or less of other isomers. In some embodiments, the compound comprises 10% or less of other isomers. In some embodiments, the compound comprises 5% or less of other isomers. In some embodiments, the compound comprises 1% or less of other isomers. In some embodiments, the compound of the present disclosure has a stereochemical purity of at least 75%. In some embodiments, the compound has a stereochemical purity of at least 80%. In some embodiments, the compound has a stereochemical purity of at least 85%. In some embodiments, the compound has a stereochemical purity of at least 90%. In some embodiments, the compound has a stereochemical purity of at least 95%. In some embodiments, the compound has a stereochemical purity of at least 96%. In some embodiments, the compound has a stereochemical purity of at least 97%. In some embodiments, the compound has a stereochemical purity of at least 98%. In some embodiments, the compound has a stereochemical purity of at least 99%. In some embodiments, the compound is stereochemically pure.

Included in the present disclosure are salts, particularly pharmaceutically acceptable salts, of the compounds described herein. The compounds of the present invention that possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counterion, e.g., a halide such as bromide, chloride, or fluoride, particularly bromide.

Chemical entities having carbon-carbon double bonds or carbon-nitrogen double bonds may exist in Z- or E-form (or cis- or trans-form). Furthermore, some chemical entities may exist in various tautomeric forms. Unless otherwise specified, compounds described herein are intended to include all Z-, E- and tautomeric forms as well.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

The compounds of the present disclosure optionally contain unnatural proportions of atomic isotopes at one or more atoms that constitute such compounds. For example, the compounds may be labeled with isotopes, such as for example, deuterium ($^2H$), tritium ($^3H$), iodine-125 ($^{125}I$) or carbon-14 ($^{14}C$). Isotopic substitution with $^2H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, and $^{125}I$ are all contemplated. All isotopic variations of the compounds of the present invention, whether radioactive or not, are encompassed within the scope of the present invention.

In some embodiments of a compound disclosed herein, one or more of $R^1$, $R^2$, $R^3$, $R^4$, $R^5$, $R^6$, $R^7$, $R^{10a}$, $R^{10b}$, $R^{12a}$,

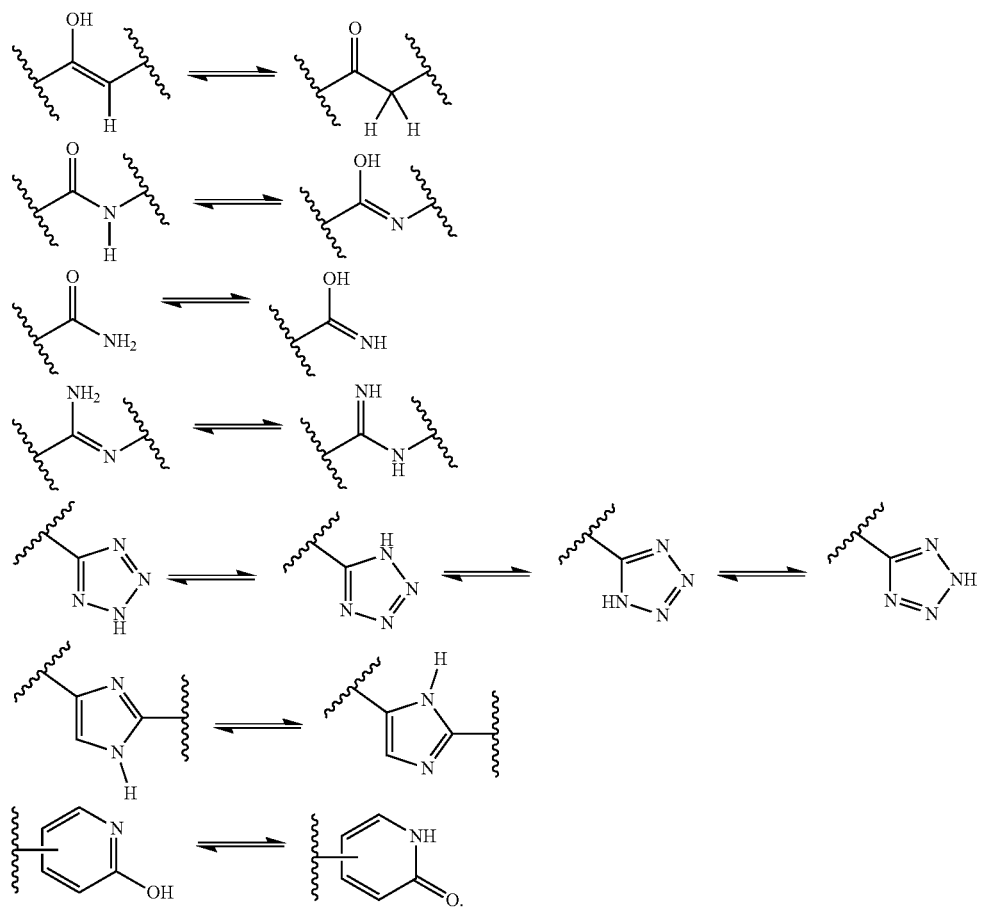

The compounds disclosed herein, in some embodiments, are used in different enriched isotopic forms, e.g., enriched in the content of $^2H$, $^3H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, compounds described herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

$R^{12b}$, $R^{21}$, $R^{22}$, $R^{23}$, and $R^{31}$ groups comprise deuterium at a percentage higher than the natural abundance of deuterium.

In some embodiments of a compound disclosed herein, one or more hydrogens are replaced with one or more deuteriums in one or more of the following groups $R^1$, $R^2$, $R^3$, $R^4$, $R^5$, $R^6$, $R^7$, $R^{10a}$, $R^{10b}$, $R^{12a}$, $R^{12b}$, $R^{21}$, $R^{22}$, $R^{23}$, and $R^{31}$.

In some embodiments of a compound disclosed herein, the abundance of deuterium in each of $R^1$, $R^2$, $R^3$, $R^4$, $R^5$, $R^6$, $R^7$, $R^{10a}$, $R^{10b}$, $R^{12a}$, $R^{12b}$, $R^{21}$, $R^{22}$, $R^{23}$, and $R^{31}$ is independently at least 1%, at least 10%, at least 20%, at least 30%, at least 40%, at least 50%, at least 60%, at least 70%, at least 80%, at least 90%, or 100% of a total number of hydrogen and deuterium.

In some embodiments of a compound disclosed herein, one or more hydrogens of Ring Q are replaced with one or more deuteriums.

In certain embodiments, the compounds disclosed herein have some or all of the $^1$H atoms replaced with $^2$H atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6 (10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64 (1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Compounds of the present invention also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

The compounds described herein may in some cases exist as diastereomers, enantiomers, or other stereoisomeric forms. Where absolute stereochemistry is not specified, the compounds presented herein include all diastereomeric, enantiomeric, and epimeric forms as well as the appropriate mixtures thereof. Separation of stereoisomers may be performed by chromatography or by forming diastereomers and separating by recrystallization, or chromatography, or any combination thereof (Jean Jacques, Andre Collet, Samuel H. Wilen, "Enantiomers, Racemates and Resolutions", John Wiley And Sons, Inc., 1981, herein incorporated by reference for this disclosure). Stereoisomers may also be obtained by stereoselective synthesis.

The methods and compositions described herein include the use of amorphous forms as well as crystalline forms (also known as polymorphs). The compounds described herein may be in the form of pharmaceutically acceptable salts. As well, in some embodiments, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

In certain embodiments, compounds or salts of the compounds may be prodrugs, e.g., wherein a hydroxyl in the parent compound is presented as an ester or a carbonate, or carboxylic acid present in the parent compound is presented as an ester. The term "prodrug" is intended to encompass compounds which, under physiologic conditions, are converted into pharmaceutical agents of the present disclosure. One method for making a prodrug is to include one or more selected moieties which are hydrolyzed under physiologic conditions to reveal the desired molecule. In other embodiments, the prodrug is converted by an enzymatic activity of the host animal such as specific target cells in the host animal. For example, esters or carbonates (e.g., esters or carbonates of alcohols or carboxylic acids and esters of phosphonic acids) are preferred prodrugs of the present disclosure.

Prodrug forms of the herein described compounds, wherein the prodrug is metabolized in vivo to produce a compound as set forth herein are included within the scope of the claims. In some cases, some of the herein-described compounds may be a prodrug for another derivative or active compound.

Prodrugs are often useful because, in some situations, they may be easier to administer than the parent drug. They may, for instance, be bioavailable by oral administration whereas the parent is not. Prodrugs may help enhance the cell permeability of a compound relative to the parent drug. The prodrug may also have improved solubility in pharmaceutical compositions over the parent drug. Prodrugs may be designed as reversible drug derivatives, for use as modifiers to enhance drug transport to site-specific tissues or to increase drug residence inside of a cell.

In some embodiments, the design of a prodrug increases the lipophilicity of the pharmaceutical agent. In some embodiments, the design of a prodrug increases the effective water solubility. See, e.g., Fedorak et al., *Am. J Physiol.*, 269:G210-218 (1995); McLoed et al., *Gastroenterol*, 106: 405-413 (1994); Hochhaus et al., *Biomed. Chrom.*, 6:283-286 (1992); J. Larsen and H. Bundgaard, *Int. J. Pharmaceutics*, 37, 87 (1987); J. Larsen et al., *Int. J. Pharmaceutics*, 47, 103 (1988); Sinkula et al., *J. Pharm. Sci.*, 64:181-210 (1975); T. Higuchi and V. Stella, Pro-drugs as Novel Delivery Systems, Vol. 14 of the A.C.S. Symposium Series; and Edward B. Roche, *Bioreversible Carriers in Drug Design*, American Pharmaceutical Association and Pergamon Press, 1987, all incorporated herein for such disclosure). According to another embodiment, the present disclosure provides methods of producing the above-defined compounds. The compounds may be synthesized using conventional techniques. Advantageously, these compounds are conveniently synthesized from readily available starting materials.

Synthetic chemistry transformations and methodologies useful in synthesizing the compounds described herein are known in the art and include, for example, those described in R. Larock, *Comprehensive Organic Transformations* (1989); T. W. Greene and P. G. M. Wuts, *Protective Groups in Organic Synthesis*, 2d. Ed. (1991); L. Fieser and M. Fieser, *Fieser and Fieser's Reagents for Organic Synthesis* (1994); and L. Paquette, ed., *Encyclopedia of Reagents for Organic Synthesis* (1995).

C. Pharmaceutical Compositions

Provided herein, in certain embodiments, are compositions comprising a therapeutically effective amount of any compound or salt of any one of Formulas (I), (Ia), (Ib), (Iaa), (Iab), (Iba), (Ibb), (II), (IIa), (IIb), (IIaa), (IIab), (IIba), and (IIbb), (also referred to herein as "a pharmaceutical agent").

Pharmaceutical compositions may be formulated using one or more physiologically acceptable carriers including excipients and auxiliaries which facilitate processing of the pharmaceutical agent into preparations which are used pharmaceutically. Proper formulation is dependent upon the route of administration chosen. A summary of pharmaceutical compositions is found, for example, in Remington: The Science and Practice of Pharmacy, Nineteenth Ed (Easton, Pa., Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999).

The compositions and methods of the present disclosure may be utilized to treat an individual in need thereof. In certain embodiments, the individual is a mammal such as a human, or a non-human mammal. When administered to an animal, such as a human, the composition or the pharmaceutical agent, is preferably administered as a pharmaceutical composition comprising, for example, a pharmaceutical agent and a pharmaceutically acceptable carrier or excipient. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration, e.g., routes, such as injection or implantation, that circumvent transport or diffusion through an epithelial barrier, the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule, granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable excipient can contain physiologically acceptable agents that act, for example, to stabilize, increase solubility or to increase the absorption of a compound such as a pharmaceutical agent. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable excipient, including a physiologically acceptable agent, depends, for example, on the route of administration of the composition. The preparation or pharmaceutical composition can be a self-emulsifying drug delivery system or a self microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

A pharmaceutical composition (preparation) can be administered to a subject by any of a number of routes of administration including, for example, orally, for example, drenches as in aqueous or non-aqueous solutions or suspensions, tablets, capsules, including sprinkle capsules and gelatin capsules, boluses, powders, granules, pastes for application to the tongue; absorption through the oral mucosa, e.g., sublingually; anally, rectally or vaginally, for example, as a pessary, cream or foam parenterally, including intramuscularly, intravenously, subcutaneously or intrathecally as, for example, a sterile solution or suspension; nasally: intraperitoneally; subcutaneously; transdermally, for example, as a patch applied to the skin; and topically, for example, as a cream, ointment or spray applied to the skin, or as an eye drop. The compound may also be formulated for inhalation. In certain embodiments, a compound may be simply dissolved or suspended in sterile water.

A pharmaceutical composition may be a sterile aqueous or non-aqueous solution, suspension or emulsion, e.g., a microemulsion. The excipients described herein are examples and are in no way limiting. An effective amount or therapeutically effective amount refers to an amount of the one or more pharmaceutical agents administered to a subject, either as a single dose or as part of a series of doses, which is effective to produce a desired therapeutic effect.

Subjects may generally be monitored for therapeutic effectiveness using assays and methods suitable for the condition being treated, which assays will be familiar to those having ordinary skill in the art and are described herein. Pharmacokinetics of a pharmaceutical agent, or one or more metabolites thereof, that is administered to a subject may be monitored by determining the level of the pharmaceutical agent or metabolite in a biological fluid, for example, in the blood, blood fraction, e.g., serum, and/or in the urine, and/or other biological sample or biological tissue from the subject. Any method practiced in the art and described herein to detect the agent may be used to measure the level of the pharmaceutical agent or metabolite during a treatment course.

The dose of a pharmaceutical agent described herein for treating a disease or disorder may depend upon the subject's condition, that is, stage of the disease, severity of symptoms caused by the disease, general health status, as well as age, gender, and weight, and other factors apparent to a person skilled in the medical art. Pharmaceutical compositions may be administered in a manner appropriate to the disease to be treated as determined by persons skilled in the medical arts. In addition to the factors described herein and above related to use of pharmaceutical agent for treating a disease or disorder, suitable duration and frequency of administration of the pharmaceutical agent may also be determined or adjusted by such factors as the condition of the patient, the type and severity of the patient's disease, the particular form of the active ingredient, and the method of administration. Optimal doses of an agent may generally be determined using experimental models and/or clinical trials. The optimal dose may depend upon the body mass, weight, or blood volume of the subject. The use of the minimum dose that is sufficient to provide effective therapy is usually preferred. Design and execution of pre-clinical and clinical studies for a pharmaceutical agent, including when administered for prophylactic benefit, described herein are well within the skill of a person skilled in the relevant art. When two or more pharmaceutical agents are administered to treat a disease or disorder, the optimal dose of each pharmaceutical agent may be different, such as less than when either agent is administered alone as a single agent therapy. In certain particular embodiments, two pharmaceutical agents in combination may act synergistically or additively, and either agent may be used in a lesser amount than if administered alone. An amount of a pharmaceutical agent that may be administered per day may be, for example, between about 0.01 mg/kg and 100 mg/kg, e.g., between about 0.1 to 1 mg/kg, between about 1 to 10 mg/kg, between about 10-50 mg/kg, between about 50-100 mg/kg body weight. In other embodiments, the amount of a pharmaceutical agent that may be administered per day is between about 0.01 mg/kg and 1000 mg/kg, between about 100-500 mg/kg, or between about 500-1000 mg/kg body weight. The optimal dose, per day or per course of treatment, may be different for the disease or disorder to be treated and may also vary with the administrative route and therapeutic regimen.

Pharmaceutical compositions comprising a pharmaceutical agent can be formulated in a manner appropriate for the delivery method by using techniques routinely practiced in the art. The composition may be in the form of a solid, e.g., tablet, capsule, semi-solid, e.g., gel, liquid, or gas, e.g., aerosol. In other embodiments, the pharmaceutical composition is administered as a bolus infusion.

Pharmaceutical acceptable excipients are well known in the pharmaceutical art and described, for example, in Rowe et al., Handbook of Pharmaceutical Excipients: A Comprehensive Guide to Uses, Properties, and Safety, $5^{th}$ Ed., 2006, and in *Remington: The Science and Practice of Pharmacy* (Gennaro, 21V Ed. Mack Pub. Co., Easton, PA (2005)). Exemplary pharmaceutically acceptable excipients include sterile saline and phosphate buffered saline at physiological pH. Preservatives, stabilizers, dyes, buffers, and the like may be provided in the pharmaceutical composition. In addition, antioxidants and suspending agents may also be used. In general, the type of excipient is selected based on the mode of administration, as well as the chemical composition of the active ingredient(s). Alternatively, compositions described herein may be formulated as a lyophilizate. A composition described herein may be lyophilized or otherwise formulated as a lyophilized product using one or more appropriate excipient solutions for solubilizing and/or diluting the pharmaceutical agent(s) of the composition upon administration. In other embodiments, the pharmaceutical agent may be encapsulated within liposomes using technology known and practiced in the art. In certain particular embodiments, a pharmaceutical agent is not formulated within liposomes for application to a stent that is used for treating highly, though not totally, occluded arteries. Pharmaceutical compositions may be formulated for any appropriate manner of administration described herein and in the art.

A pharmaceutical composition, e.g., for oral administration or for injection, infusion, subcutaneous delivery, intramuscular delivery, intraperitoneal delivery or other method, may be in the form of a liquid. A liquid pharmaceutical composition may include, for example, one or more of the following: a sterile diluent such as water, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral composition can be enclosed in ampoules, disposable syringes or multiple dose vials made of glass or plastic. The use of physiological saline is preferred, and an injectable pharmaceutical composition is preferably sterile. In another embodiment, for treatment of an ophthalmological condition or disease, a liquid pharmaceutical composition may be applied to the eye in the form of eye drops. A liquid pharmaceutical composition may be delivered orally.

For oral formulations, at least one of the pharmaceutical agents described herein can be used alone or in combination with appropriate additives to make tablets, powders, granules or capsules, and if desired, with diluents, buffering agents, moistening agents, preservatives, coloring agents, and flavoring agents. The pharmaceutical agents may be formulated with a buffering agent to provide for protection of the compound from low pH of the gastric environment and/or an enteric coating. A pharmaceutical agent included in a pharmaceutical composition may be formulated for oral delivery with a flavoring agent, e.g., in a liquid, solid or semi-solid formulation and/or with an enteric coating.

A pharmaceutical composition comprising any one of the pharmaceutical agents described herein may be formulated for sustained or slow release, also called timed release or controlled release. Such compositions may generally be prepared using well known technology and administered by, for example, oral, rectal, intradermal, or subcutaneous implantation, or by implantation at the desired target site. Sustained-release formulations may contain the compound dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of pharmaceutical agent contained within a sustained release formulation depends upon the site of implantation, the rate and expected duration of release, and the nature of the condition, disease or disorder to be treated or prevented.

In certain embodiments, the pharmaceutical compositions comprising a pharmaceutical agent are formulated for transdermal, intradermal, or topical administration. The compositions can be administered using a syringe, bandage, transdermal patch, insert, or syringe-like applicator, as a powder/talc or other solid, liquid, spray, aerosol, ointment, foam, cream, gel, paste. This preferably is in the form of a controlled release formulation or sustained release formulation administered topically or injected directly into the skin adjacent to or within the area to be treated, e.g., intradermally or subcutaneously. The active compositions can also be delivered via iontophoresis. Preservatives can be used to prevent the growth of fungi and other microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetypyridinium chloride, chlorobutanol, phenol, phenylethyl alcohol, thimerosal, and combinations thereof.

Pharmaceutical compositions comprising a pharmaceutical agent can be formulated as emulsions for topical application. An emulsion contains one liquid distributed in the body of a second liquid. The emulsion may be an oil-in-water emulsion or a water-in-oil emulsion. Either or both of the oil phase and the aqueous phase may contain one or more surfactants, emulsifiers, emulsion stabilizers, buffers, and other excipients. The oil phase may contain other oily pharmaceutically approved excipients. Suitable surfactants include, but are not limited to, anionic surfactants, non-ionic surfactants, cationic surfactants, and amphoteric surfactants. Compositions for topical application may also include at least one suitable suspending agent, antioxidant, chelating agent, emollient, or humectant.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. Liquid sprays may be delivered from pressurized packs, for example, via a specially shaped closure. Oil-in-water emulsions can also be used in the compositions, patches, bandages and articles. These systems are semisolid emulsions, micro-emulsions, or foam emulsion systems.

In some embodiments, the pharmaceutical agent described herein can be formulated as in inhalant. Inhaled methods can deliver medication directly to the airway. The pharmaceutical agent can be formulated as aerosols, microspheres, liposomes, or nanoparticles. The pharmaceutical agent can be formulated with solvents, gases, nitrates, or any combinations thereof. Compositions described herein are optionally formulated for delivery as a liquid aerosol or inhalable dry powder. Liquid aerosol formulations are optionally nebulized predominantly into particle sizes that can be delivered to the terminal and respiratory bronchioles. Liquid aerosol and inhalable dry powder formulations are preferably delivered throughout the endobronchial tree to the terminal bronchioles and eventually to the parenchymal tissue.

Aerosolized formulations described herein are optionally delivered using an aerosol forming device, such as a jet, vibrating porous plate or ultrasonic nebulizer, preferably selected to allow the formation of aerosol particles having with a mass medium average diameter predominantly between 1 to 5. Further, the formulation preferably has balanced osmolarity ionic strength and chloride concentration, and the smallest aerosolizable volume able to deliver effective dose of the pharmaceutical agent. Additionally, the aerosolized formulation preferably does not negatively impair the functionality of the airways and does not cause undesirable side effects.

Aerosolization devices suitable for administration of aerosol formulations described herein include, for example, jet, vibrating porous plate, ultrasonic nebulizers and energized dry powder inhalers, that are able to nebulize the formulation into aerosol particle size predominantly in the size range from 1-5. Predominantly in this application means that at least 70% but preferably more than 90% of all generated aerosol particles are within 1-5 range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AeroNeb™ and AeroDose™ vibrating porous plate nebulizers (AeroGen, Inc., Sunnyvale, California), Sidestream® nebulizers (Medic-Aid Ltd., West Sussex, England), Pari LC® and Pari LC Star® jet nebulizers (Pari Respiratory Equipment, Inc., Richmond, Virginia), and Aerosonic™ (DeVilbiss Medizinische Produkte (Deutschland) GmbH, Heiden, Germany) and UltraAire® (Omron Healthcare, Inc., Vernon Hills, Illinois) ultrasonic nebulizers.

In some embodiments, the pharmaceutical agent(s) can be formulated with oleaginous bases or ointments to form a semisolid composition with a desired shape. In addition to the pharmaceutical agent, these semisolid compositions can contain dissolved and/or suspended bactericidal agents, preservatives and/or a buffer system. A petrolatum component that may be included may be any paraffin ranging in viscosity from mineral oil that incorporates isobutylene, colloidal silica, or stearate salts to paraffin waxes. Absorption bases can be used with an oleaginous system. Additives may include cholesterol, lanolin (lanolin derivatives, beeswax, fatty alcohols, wool wax alcohols, low HLB (hydrophobel-lipophobe balance) emulsifiers, and assorted ionic and nonionic surfactants, singularly or in combination.

Controlled or sustained release transdermal or topical formulations can be achieved by the addition of time-release additives, such as polymeric structures, matrices, that are available in the art. For example, the compositions may be administered through use of hot-melt extrusion articles, such as bioadhesive hot-melt extruded film. The formulation can comprise a cross-linked polycarboxylic acid polymer formulation. A cross-linking agent may be present in an amount that provides adequate adhesion to allow the system to remain attached to target epithelial or endothelial cell surfaces for a sufficient time to allow the desired release of the compound.

An insert, transdermal patch, bandage or article can comprise a mixture or coating of polymers that provide release of the pharmaceutical agents at a constant rate over a prolonged period of time. In some embodiments, the article, transdermal patch or insert comprises water-soluble pore forming agents, such as polyethylene glycol (PEG) that can be mixed with water insoluble polymers to increase the durability of the insert and to prolong the release of the active ingredients.

Transdermal devices (inserts, patches, bandages) may also comprise a water insoluble polymer. Rate controlling polymers may be useful for administration to sites where pH change can be used to effect release. These rate controlling polymers can be applied using a continuous coating film during the process of spraying and drying with the active compound. In one embodiment, the coating formulation is used to coat pellets comprising the active ingredients that are compressed to form a solid, biodegradable insert.

A polymer formulation can also be utilized to provide controlled or sustained release. Bioadhesive polymers described in the art may be used. By way of example, a sustained-release gel and the compound may be incorporated in a polymeric matrix, such as a hydrophobic polymer matrix. Examples of a polymeric matrix include a microparticle. The microparticles can be microspheres, and the core may be of a different material than the polymeric shell. Alternatively, the polymer may be cast as a thin slab or film, a powder produced by grinding or other standard techniques, or a gel such as a hydrogel. The polymer can also be in the form of a coating or part of a bandage, stent, catheter, vascular graft, or other device to facilitate delivery of the pharmaceutical agent. The matrices can be formed by solvent evaporation, spray drying, solvent extraction and other methods known to those skilled in the art.

Kits with unit doses of one or more of the agents described herein, usually in oral or injectable doses, are provided. Such kits may include a container containing the unit dose, an informational package insert describing the use and attendant benefits of the drugs in treating disease, and optionally an appliance or device for delivery of the composition.

D. Methods of Treatment

The compounds described herein can be used in the preparation of medicaments for the prevention or treatment of diseases or conditions. In addition, a method for treating any of the diseases or conditions described herein in a subject in need of such treatment, involves administration of pharmaceutical compositions containing at least one compound described herein, or a pharmaceutically acceptable salt, pharmaceutically acceptable prodrug, or pharmaceutically acceptable solvate thereof, in therapeutically effective amounts to said subject.

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but can nevertheless be determined in a manner recognized in the field according to the particular circumstances surrounding the case, including, e.g., the specific agent being administered, the route of administration, the condition being treated, and the subject or host being treated. In general, however, doses employed for adult human treatment will typically be in the range of about 0.02-about 5000 mg per day, in some embodiments, about 1-about 1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-recloseable containers. Alternatively, multiple-dose recloseable containers can be used, in which case it is typical to include a preservative in the composition. By way of example only, formulations for parenteral injection may be presented in unit dosage form, which include, but are not limited to ampoules, or in multi-dose containers, with an added preservative.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

In one aspect, a compound described herein or a pharmaceutically acceptable salt or solvate thereof, has a brain/blood AUC of at most about 0.0001, 0.001, 0.01, 0.1, 0.2, 0.3, 0.4, 0.5, 0.6, 0.7, 0.8, 0.9, 1, 2, 5, or 10. The values and properties of brain penetration for compounds described herein can be determined by any suitable methods known in the art, such as in vivo assays or in vitro assays, e.g., Caco-2 permeability assay, and MDR1-MDCK assay.

Glutaminyl-peptide cyclotransferase-like protein (QPCTL) is located on the cell organelle called Golgi apparatus and has been identified as a crucial regulator of the CD47/SIRPα axis. CD47 expression is frequently observed on cancer cells in both hematological malignancies and solid tumors, including NHL, acute myeloid leukemia, myelodysplastic syndrome, as well as glioblastoma, gastric cancer, breast cancer, colon cancer, hepatocellular carcinoma, and prostate cancer. Cancer cells use CD47, meditated by SIRPα to evade the detection by the immune system and subsequent destruction by macrophages. The N terminus of the CD47 protein contains a pyroglutamate residue that is essential to create a high affinity SIRPα binding site, and this modification shortly after protein synthesis has been shown to depend on QPCTL protein. Inhibition of QPCTL with pharmacological tools or bioengineered knockout methods have been shown to cause a reduction or loss of the binding between CD47 and SIRPα, as well as an increased antibody-dependent cellular phagocytosis and neutrophils-induced cytotoxicity.

In addition to the engagement of CD47/SIRPα axis, QPCTL also pyroglutamates the C-C Motif chemokine ligand proteins, CCL2, CCL7, CCL8 and CCL13, which are the ligands of the chemokine receptor CCR2 responsible for directing the migration of myeloid cell lineage including monocytes/macrophages and dendritic cells. The modification of CCL chemokine family members by QPCTL increases this chemokine stability against degradation and enhances CCR2 activation and signal transductions. CCL2/CCR2 axis has been implicated in cancer cell survival, migration and metastasis via recruitment of immune cells into the tumor microenvironment. A downregulation of CCL2/CCR2 signaling transduction by inhibiting QPCLT thus could be used to attenuate the biological functions of the CCL2/CCR2 signaling in cancer pathogenesis.

In one aspect, the disclosure provides a method of modulating glutaminyl-peptide cyclotransferase-like protein (QPCTL) activity in a subject, comprising administering to the subject a compound described herein, or a pharmaceutically acceptable salt or solvate thereof.

In one aspect, the disclosure provides a method of inhibiting glutaminyl-peptide cyclotransferase-like protein (QPCTL) activity in a subject, comprising administering to the subject a compound described herein, or a pharmaceutically acceptable salt or solvate thereof.

In one aspect, the disclosure provides a method of treating cancer in a subject in need thereof, the method comprising administering a therapeutically effective amount of a compound described herein, or a pharmaceutically acceptable salt or solvate thereof, or a pharmaceutical composition described herein.

In one aspect, the disclosure provides a method of treating a disease or condition in a subject in need thereof, comprising administering to the subject a therapeutically effective amount of a compound described herein, or a pharmaceutically acceptable salt or solvate thereof, or a pharmaceutical composition of described herein. In some embodiments, the disease or condition is associated with an aberrant glutaminyl-peptide cyclotransferase-like protein (QPCTL) activity. In some embodiments, the disease or condition that is associated with an aberrant QPCTL activity is cancer.

In some embodiments, the cancer is leukemia, acute myeloid leukemia (AML), chronic myeloid leukemia, acute lymphoblastic leukemia (ALL), non-Hodgkin lymphoma (NHL), Hodgkin lymphoma (HL), multiple myeloma (MM), or myelodysplastic syndrome (MDS).

In some embodiments, the cancer is leukemia. In some embodiments, the cancer is acute myeloid leukemia (AML). In some embodiments, the cancer is chronic myeloid leukemia. In some embodiments, the cancer is acute lymphoblastic leukemia (ALL). In some embodiments, the cancer is non-Hodgkin lymphoma (NHL). In some embodiments, the cancer is Hodgkin lymphoma (HL). In some embodiments, the cancer is multiple myeloma (MM). In some embodiments, the cancer is or myelodysplastic syndrome (MDS).

In some embodiments, the cancer is a solid cancer or a metastatic cancer. In some embodiments, the cancer is a solid cancer. In some embodiments, the cancer is a metastatic cancer.

In some embodiments, the cancer is a skin cancer, ocular cancer, gastrointestinal cancer, thyroid cancer, breast cancer, ovarian cancer, central nervous system cancer, laryngeal cancer, cervical cancer, lymphatic system cancer, genitourinary tract cancer, bone cancer, biliary tract cancer, endometrial cancer, liver cancer, lung cancer, prostate cancer, or colon cancer.

In certain embodiments, the invention provides a method of treating or preventing a disease, state or condition in a patient in need thereof comprising administering to the patient an effective amount of a compound of any one of embodiments of the invention or a pharmaceutically acceptable salt thereof. The disease, state or condition may be selected from the group consisting of colorectal cancer, gastric cancer, breast cancer, lung cancer, pancreatic cancer, prostate cancer, multiple myeloma, chronic myelogenous leukemia, cancer metastasis, fibrosis and psychiatric disorders.

In one aspect, described herein is a method of treating a disease or condition in a subject in need thereof, the method comprising administering a therapeutically effective amount of a herein described compound, or a pharmaceutically acceptable salt or solvate thereof, or a herein described pharmaceutical composition to the subject, wherein the disease or condition is a disease that engages innate immune system. In some embodiments, the disease is atherosclerosis, a fibrotic disease, ischemia-reperfusion injury, or an infectious disease caused by pathogens. In some embodiments, the disease is a fibrotic disease selected from liver fibrosis, pulmonary fibrosis, renal fibrosis, and scleroderma.

In one aspect, described herein is a method of treating a disease or condition in a subject in need thereof, the method comprising administering a therapeutically effective amount of a herein described compound, or a pharmaceutically acceptable salt or solvate thereof, or a herein described pharmaceutical composition to the subject, wherein the disease or condition is a chronic kidney disease (CKD). In some embodiments, the chronic kidney disease is diabetic nephropathy. Diabetic nephropathy, a complication of diabetes and a leading cause of CKD, is typically characterized by damage to the capillaries supplying the kidney glomeruli, which leads to declining filtering efficiency in the kidney and progressive loss in renal function that can lead to end-stage renal disease, with patients requiring dialysis or a kidney transplant. In some embodiments, the diabetic nephropathy is caused by diabetes type or diabetes type 2. In some embodiments, the chronic kidney disease is Focal Segmental Glomerulosclerosis (FSGS). FSGS is a chronic, progressive form of kidney disease characterized by scarring (sclerosis) of the glomeruli. The scarring may happen due to an infection, a drug such as anabolic steroids, or a systemic disease such as diabetes, HIV infection, sickle cell disease or lupus.

In one aspect, described herein is a method of treating a disease or condition in a subject in need thereof, the method comprising administering a compound of Formula (I), (Ia), (Ib), (Iaa), (Iab), (Iba), (Ibb), (II), (IIa), (IIb), (IIaa) (IIab), (IIba), or (IIbb), a stereoisomer thereof, or a salt or solvate thereof. In one aspect, described herein is a method of treating a disease or condition in a subject in need thereof, the method comprising administering a therapeutically effective amount of a herein described compound, or a pharmaceutically acceptable salt or solvate thereof, or a herein described pharmaceutical composition to the subject, wherein the disease or condition is Kennedy's disease, duodenal cancer with or without *Helicobacter pylori* infections, colorectal cancer, Zolliger-Ellison syndrome, gastric cancer with or without *Helicobacter pylori* infections, pathogenic psychotic conditions, schizophrenia, infertility, neoplasia, inflammatory host responses, cancer, malign metastasis, melanoma, psoriasis, impaired humoral and cell-mediated immune responses, leukocyte adhesion and migration processes in the endothelium, impaired food intake, impaired sleep-wakefulness, impaired homeostatic regulation of energy metabolism, impaired autonomic function, impaired hormonal balance or impaired regulation of body fluids, multiple sclerosis, the Guillain-Barre syndrome, chronic inflammatory demyelinizing polyradiculoneuropathy, mild cognitive impairment, Alzheimer's disease, Familial British Dementia, Familial Danish Dementia, neurodegeneration in Down Syndrome, Huntington's disease, rheumatoid arthritis, atherosclerosis, pancreatitis and restenosis. In some embodiments, the disease or condition is a chronic kidney disease (CKD). In some embodiments, the disease or condition is an immuno-oncology disease. In some embodiments, the disease or condition is a tumor. In some embodiments, the disease or condition is a kidney disease. In some embodiments, the disease or condition is FSGS. In some embodiments, the FSGS is a primary FSGS. In some embodiments, the FSGS is a secondary FSGS. In some embodiments, the FSGS is a genetic FSGS. In some embodiments, the underlying cause of FSGS cannot be determined. In some embodiments, the disease or condition is a diabetic nephropathy. In some embodiments, the disease or condition is a stage 1 diabetic nephropathy. In some embodiments, the disease or condition is a stage 2 diabetic nephropathy. In some embodiments, the disease or condition is a stage 4 diabetic nephropathy. In some embodiments, the disease or condition is a stage 4 diabetic nephropathy. In some embodiments, the subject has diabetes. In some embodiments, the subject has type I diabetes. In some embodiments, the subject has type II diabetes.

In some embodiments, the method comprises administering a second therapeutic agent. In some embodiments, the second therapeutic agent is a monoclonal antibody. In some embodiments, the monoclonal antibody is an anti-CD20 antibody. In some embodiments, the monoclonal antibody is selected from edrecolomab, rituximab, gemtuzumab ozogamicin, alemtuzumab, ibritumomab tiuxetan, tositumomab, cetuximab, bevacizumab, and trastuzumab. In some embodiments, the second therapeutic agent is an epithermal growth factor receptor (EGFR) inhibitor. In some embodiments, the second therapeutic agent is edrecolomab. In some embodiments, the second therapeutic agent is rituximab. In some embodiments, the second therapeutic agent is gemtuzumab ozogamicin. In some embodiments, the second therapeutic agent is alemtuzumab. In some embodiments, the second therapeutic agent is ibritumomab tiuxetan. In some embodiments, the second therapeutic agent is tositumomab. In some embodiments, the second therapeutic agent is cetuximab. In some embodiments, the second therapeutic agent is bevacizumab. In some embodiments, the second therapeutic agent is trastuzumab.

In some embodiments, the second therapeutic agent is an immune checkpoint inhibitor. In some embodiments, the immune checkpoint inhibitor is a CTLA-4 inhibitor, a PD-1 inhibitor, or a PD-L1 inhibitor. In some embodiments, the immune checkpoint inhibitor is Ipilimumab, Nivolumab, Pembrolizumab, Atezolizumab, Avelumab, Durvalumab or Cemiplimab.

EXAMPLES

The following examples are offered to illustrate, but not to limit the claimed invention. The following examples further illustrate the invention but, of course, should not be construed as in any way limiting its scope.

The following synthetic schemes are provided for purposes of illustration, not limitation. The following examples illustrate the various methods of making compounds described herein. It is understood that one skilled in the art may be able to make these compounds by similar methods or by combining other methods known to one skilled in the art. It is also understood that one skilled in the art would be able to make, in a similar manner as described below by using the appropriate starting materials and modifying the synthetic route as needed. In general, starting materials and reagents can be obtained from commercial vendors or synthesized according to sources known to those skilled in the art or prepared as described herein.

The compounds and salts of Formulas (I), (Ia), (Ib), (Iaa), (Iab), (Iba), (Ibb), (II), (IIa), (IIb), (IIaa), (IIab), (IIba), and (IIbb), can be synthesized according to one or more illustrative schemes herein and/or techniques known in the art. Materials used herein are either commercially available or prepared by synthetic methods generally known in the art. These schemes are not limited to the compounds listed in the examples or by any particular substituents, which are employed for illustrative purposes. Although various steps are described and depicted in the synthesis schemes below, the steps in some cases may be performed in a different order than the order shown below. Numberings or R groups in each scheme do not necessarily correspond to that of the claims or other schemes or tables herein.

As used herein in the examples and specification, the same structure may be given different numberings at different examples and/or sections of the specification.

Example 1: Synthesis of Compounds 7A and 7B

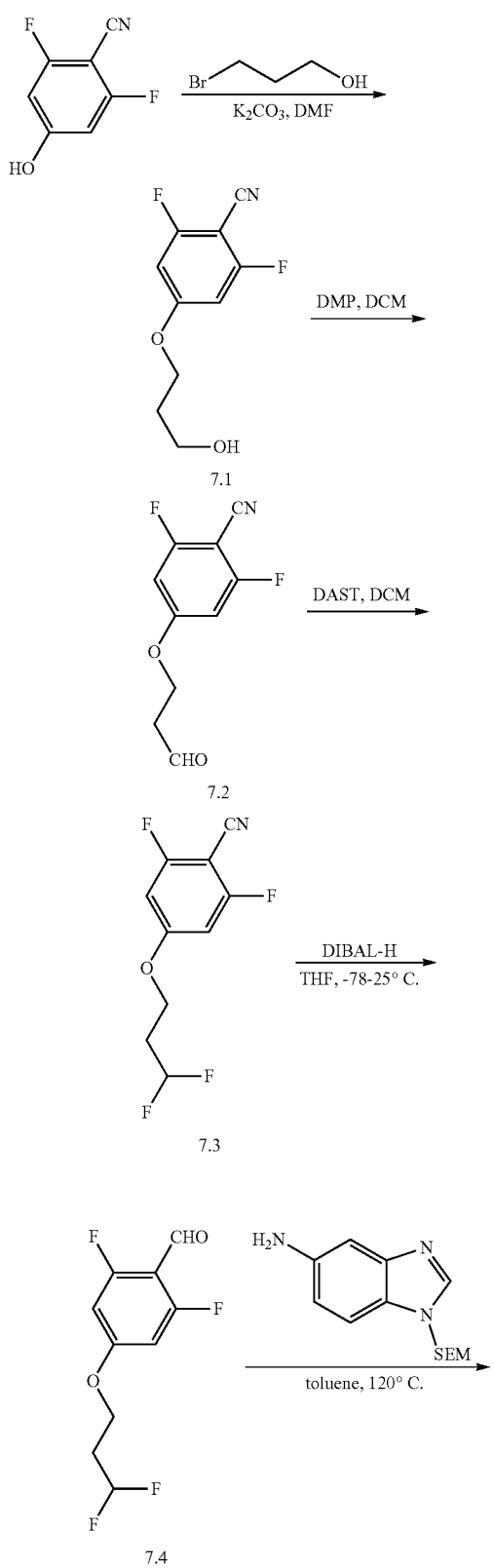

Scheme 1.

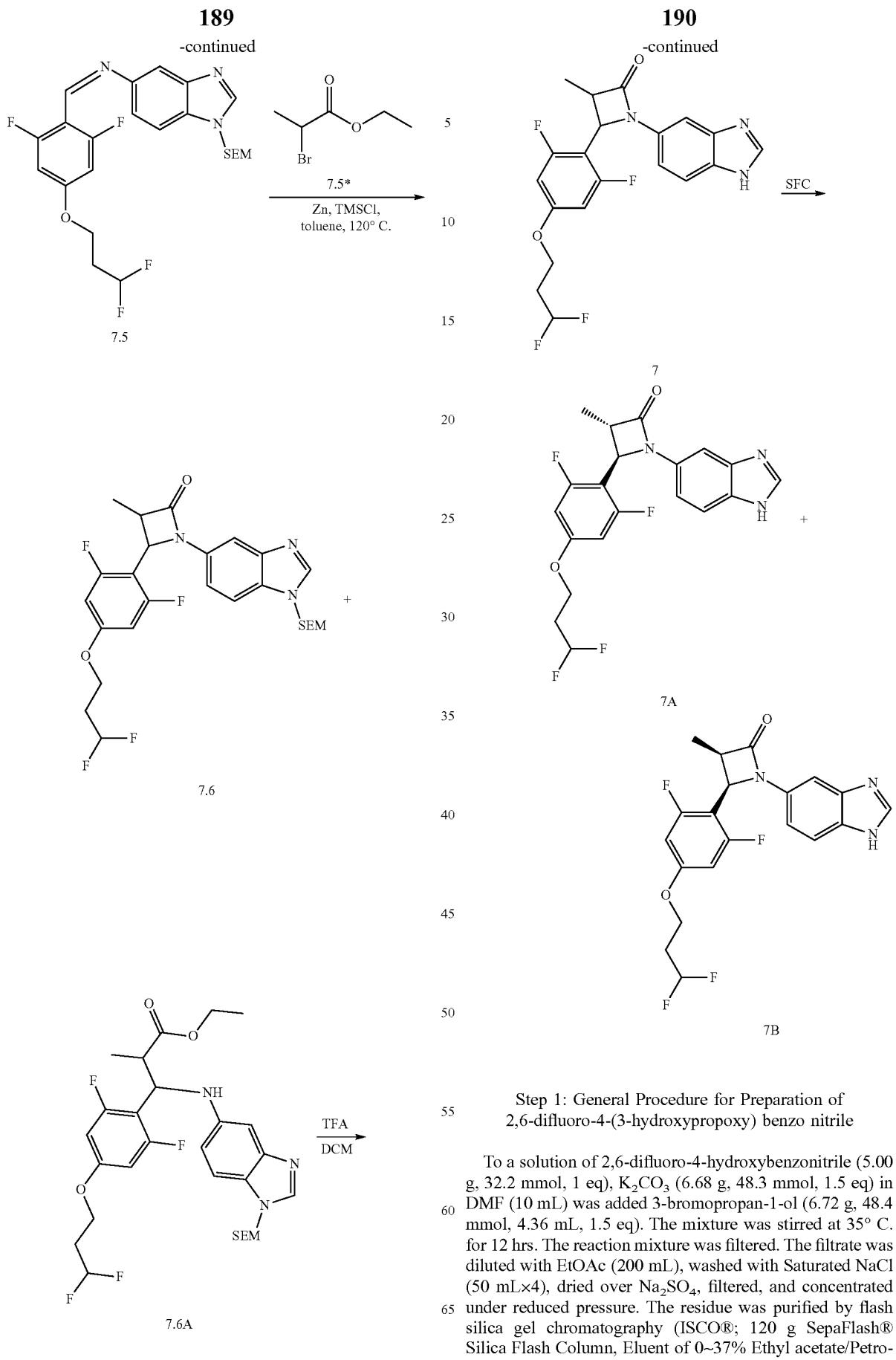

Step 1: General Procedure for Preparation of 2,6-difluoro-4-(3-hydroxypropoxy) benzo nitrile To a solution of 2,6-difluoro-4-hydroxybenzonitrile (5.00 g, 32.2 mmol, 1 eq), K$_2$CO$_3$ (6.68 g, 48.3 mmol, 1.5 eq) in DMF (10 mL) was added 3-bromopropan-1-ol (6.72 g, 48.4 mmol, 4.36 mL, 1.5 eq). The mixture was stirred at 35° C. for 12 hrs. The reaction mixture was filtered. The filtrate was diluted with EtOAc (200 mL), washed with Saturated NaCl (50 mL×4), dried over Na$_2$SO$_4$, filtered, and concentrated under reduced pressure. The residue was purified by flash silica gel chromatography (ISCO®; 120 g SepaFlash® Silica Flash Column, Eluent of 0~37% Ethyl acetate/Petroleum ether gradient @ 85 mL/min). The target compound (5.5 g, 23.20 mmol, 71.98% yield) was obtained as a colorless oil.

LCMS: Retention time: 0.834 min, (M+H)$^+$=214.1, 10-80AB_2 min_Agilent.

$^1$HNMR: (400 MHz, DMSO-d$_6$) δ=7.11-7.05 (m, 2H), 4.61 (t, J=5.2 Hz, 1H), 4.17 (t, J=6.4 Hz, 2H), 3.57-3.49 (m, 2H), 1.90-1.82 (m, 2H).

Step 2: General Procedure for Preparation of 2,6-difluoro-4-(3-oxopropoxy)benzonitrile To a solution of 2,6-difluoro-4-(3-hydroxypropoxy) benzonitrile (1.00 g, 4.69 mmol, 1 eq) in DCM (30 mL) was added DMP (2.98 g, 7.04 mmol, 2.18 mL, 1.5 eq). The mixture was stirred at 0° C. for 1 hour. The reaction mixture was quenched by addition saturated aqueous Na$_2$S$_2$O$_3$ (30 mL). The organic layer were washed with aqueous NaHCO$_3$ (30 mL), dried over Na$_2$SO$_4$, filtered and concentrated under reduced pressure to give a residue. The residue was purified by flash silica gel chromatography (ISCO®; 20 g SepaFlash® Silica Flash Column, Eluent of 0~30% Ethyl acetate/ Petroleum ether gradient @ 20 mL/min). The target compound (500 mg, 2.11 mmol, 44.92% yield) was obtained as a yellow solid.

LCMS: Retention time: 0.791 min, (M+H)=212.1, 10-80AB_2 min_Agilent.

Step 3: General Procedure for Preparation of 4-(3,3-difluoropropoxy)-2,6-difluoro benzonitrile To a solution of 2,6-difluoro-4-(3-oxopropoxy)benzonitrile (310 mg, 1.47 mmol, 1 eq) in DCM (10 mL) was added DAST (473 mg, 2.94 mmol, 388 µL, 2 eq) at 0° C. under N$_2$. The mixture was stirred at 25° C. for 1 hour. The reaction mixture was quenched by addition water (10 mL), diluted with water (50 mL) and extracted with EtOAc (50 mL×3). The combined organic layers were washed with brine (30 mL), dried over Na$_2$SO$_4$, filtered and concentrated under reduced pressure to give a residue. The residue was purified by flash silica gel chromatography (ISCO®; 4 g SepaFlash® Silica Flash Column, Eluent of 0~20% Ethyl acetate/Petroleum ether gradient @ 20 mL/min). The target compound (120 mg, 515 µmol, 35.06% yield) was obtained as a colorless oil.

LCMS: Retention time: 1.005 min, (M+H)=234.1, 10-80AB_2 min_220&254.

$^1$HNMR: (400 MHz, DMSO-d$_6$) δ=7.16-7.14 (m, 1H), 7.13-7.11 (m, 1H), 6.40-6.07 (m, 1H), 4.27 (t, J=6.0 Hz, 2H), 2.43-2.28 (m, 2H).

Step 4: General Procedure for Preparation of 4-(3,3-difluoropropoxy)-2,6-difluoro benzaldehyde To a solution of 4-(3,3-difluoropropoxy)-2,6-difluoro benzonitrile (9.50 g, 40.7 mmol, 1 eq) in DCM (100 mL) was added DIBAL-H (1 M, 57.0 mL, 1.4 eq) at −78° C. under N$_2$. The mixture was stirred at 25° C. for 12 hours. The reaction mixture was quenched by addition saturated aqueous potassium sodium 2, 3-dihydroxysuccinate 200 mL and extracted with DCM (150 mL×3). The combined organic layers were washed with brine (100 mL), dried over Na$_2$SO$_4$, filtered and concentrated under reduced pressure to give a residue. The residue was purified by flash silica gel chromatography (ISCO®; 110 g SepaFlash® Silica Flash Column, Eluent of 0~15% Ethyl acetate/Petroleum ether gradient @ 85 mL/min). The target compound (5.1 g, 20.82 mmol, 51.11% yield) was obtained as a white solid.

LCMS: Retention time: 1.080 min, (M+H)=237.2, 10-80AB_2 min_220&254.

$^1$HNMR: (400 MHz, DMSO-d$_6$) δ=10.07 (s, 1H), 6.96-6.88 (m, 2H), 6.43-6.06 (m, 1H), 4.27 (t, J=6.0 Hz, 2H), 2.41-2.29 (m, 2H).

Step 5: General Procedure for Preparation of 1-(4-(3,3-difluoropropoxy)-2,6-difluorophenyl)-N-(1-((2-(trimethylsilyl)ethoxy)methyl)-1H-benzo[d]imidazol-5-yl)methanimine To a solution of 4-(3,3-difluoropropoxy)-2,6-difluorobenzaldehyde (1.17 g, 4.94 mmol, 1 eq) in toluene (50 mL) was added 1-((2-(trimethylsilyl)ethoxy)methyl)-1H-benzo[d]imidazol-5-amine (1.30 g, 4.94 mmol, 1 eq). The mixture was stirred at 120° C. for 12 hours. The mixture was concentrated under reduced pressure to give a residue. The residue was purified by flash silica gel chromatography (ISCO®; 20 g SepaFlash® Silica Flash Column, Eluent of 0~100% Ethyl acetate/Petroleum ether gradient @ 25 mL/min). The target compound (1.80 g, 3.74 mmol, 75.74% yield) was obtained as an orange oil.

$^1$HNMR: (400 MHz, DMSO-d$_6$) δ=8.63 (d, J=2.0 Hz, 1H), 8.37 (d, J=9.6 Hz, 1H), 7.67 (dd, J=6.4, 8.4 Hz, 1H), 7.56-7.51 (m, 1H), 7.24-7.18 (m, 1H), 6.97-6.89 (m, 2H), 6.46-6.05 (m, 1H), 5.65 (d, J=7.2 Hz, 2H), 4.25 (t, J=6.4 Hz, 2H), 3.57-3.46 (m, 2H), 2.43-2.31 (m, 2H), 0.84 (t, J=8.0 Hz, 2H), −0.09 (d, J=3.6 Hz, 9H).

Step 6: General Procedure for Preparation of 4-(4-(3,3-difluoropropoxy)-2,6-difluorophenyl)-3-methyl-1-(1-((2-(trimethylsilyl)ethoxy)methyl)-1H-benzo[d]imidazole-5-yl)azetidin-2-one To a solution of Zn (54.3 mg, 831 µmol, 2 eq) in toluene (20 mL) was added TMS-Cl (31.6 mg, 291 µmol, 36.9 µL, 0.7 eq) under Ar. The mixture was stirred under reflux (120° C.) for 0.25 hrs. After cooling to 25° C., then Compound 7.5* (128 mg, 706 µmol, 92.0 µL, 1.7 eq) and Compound 7.5 (200 mg, 415 µmol, 1 eq) was added. The resulting mixture was refluxed (120° C.) for 12 hrs. The reaction mixture was concentrated under reduced pressure to give a residue. The residue was purified by flash silica gel chromatography (ISCO®; 4 g SepaFlash® Silica Flash Column, Eluent of 0~75% Ethyl acetate/Petroleum ether gradient @ 20 mL/min). A mixture (180 mg, 334.81 µmol, 80.61% yield) of Compound 7.6 and Compound 7.6A was obtained as a yellow solid.

LCMS: Retention time: 1.191 min, (M+H)=538.3, 10-80AB_2 min_220&254.

Step 7: General Procedure for Preparation of 1-(1H-benzo[d]imidazol-5-yl)-4-(4-(3,3-difluoropropoxy)-2,6-difluorophenyl)-3-methylazetidin-2-one To a solution of Compound 7.6 (180 mg, 335 µmol, 1 eq) was added TBAF (1 M, 4.50 mL, 13.4 eq). The mixture was stirred at 25° C. for 12 hrs. The reaction mixture was poured into water (10 mL) and extracted with EtOAc (10 mL×3). The combined organic layers were dried over Na$_2$SO$_4$, filtered, and concentrated under reduced pressure to give a residue. The residue was added a solution of TFA (2.77 g, 24.3 mmol, 1.8 mL, 72.6 eq) and DCM (0.2 mL). The mixture was stirred at 25° C. for 2 hrs. The reaction mixture was concentrated under reduced pressure to give a residue. The residue was purified by prep-HPLC (column: Phenomenex Gemini-NX 80*40 mm*3 um; mobile phase: [water (0.05% NH$_3$H$_2$O)-ACN]; B %: 33%-63%, 8 min). Compound 7 (30.72 mg, 71.55 μmol, 21.37% yield) was obtained as a white solid.

LCMS: Retention time: 0.943 min, (M+H)=408.2, 10-80AB_2 min_220&254.

$^1$HNMR: (400 MHz, DMSO-d$_6$) δ=12.61-12.24 (m, 1H), 8.23-8.06 (m, 1H), 7.62-7.01 (m, 3H), 6.92-6.70 (m, 2H), 6.37-6.02 (m, 1H), 5.64-5.01 (m, 1H), 4.24-4.05 (m, 2H), 3.92-3.46 (m, 1H), 2.35-2.19 (m, 2H), 1.43-0.96 (m, 3H).

Step 8: General Procedure for Preparation of (3S, 4R)-1-(1H-benzo[d]imidazol-5-yl)-4-(4-(3,3-difluoropropoxy)-2,6-difluorophenyl)-3-methylazetidin-2-one (Compound 7A) and (3R,4R)-1-(1H-benzo[d]imidazol-5-yl)-4-(4-(3,3-difluoropropoxy)-2,6-difluorophenyl)-3-methylazetidin-2-one (Compound 7B)

Compound 7 was separated by SFC (column: Phenomenex-Cellulose-2 (250 mm*30 mm, 10 um); mobile phase: [0.1% NH$_3$H$_2$O EtOH]; B %: 30%-30%, min). Compound 7A (17.80 mg, 41.24 μmol, 7.00% yield) as a white solid and Compound 7B (10.63 mg, 24.15 μmol, 4.10% yield) as a white solid were obtained.

Compound 7A: SFC: Retention time: 5.117 min. LCMS: Retention time: 0.805 min, (M+H)=408.1, 5-95AB_220&254_Agilent. $^1$HNMR: (400 MHz, DMSO-d$_6$) δ=12.55-12.29 (m, 1H), 8.20-8.10 (m, 1H), 7.59-7.45 (m, 1H), 7.40-7.27 (m, 1H), 7.26-7.00 (m, 1H), 6.87-6.76 (m, 2H), 6.37-6.03 (m, 1H), 5.09-5.04 (m, 1H), 4.13 (t, J=6.0 Hz, 2H), 3.57-3.44 (m, 1H), 2.33-2.20 (m, 2H), 1.40 (d, J=7.2 Hz, 3H).

Compound 7B: SFC: Retention time: 6.271 min. LCMS: Retention time: 0.802 min, (M+H)=408.1, 5-95AB_220&254_Agilent. $^1$HNMR: (400 MHz, DMSO-d$_6$) δ=12.54-12.15 (m, 1H), 8.18-8.11 (m, 1H), 7.61-7.43 (m, 1H), 7.42-7.31 (m, 1H), 7.30-7.03 (m, 1H), 6.96-6.59 (m, 2H), 6.39-6.03 (m, 1H), 5.59 (d, J=6.0 Hz, 1H), 4.14 (t, J=6.0 Hz, 2H), 3.92-3.83 (m, 1H), 2.35-2.24 (m, 2H), 1.00 (d, J=7.2 Hz, 3H.

Example 2: Synthesis of Compound 9

Scheme 2.

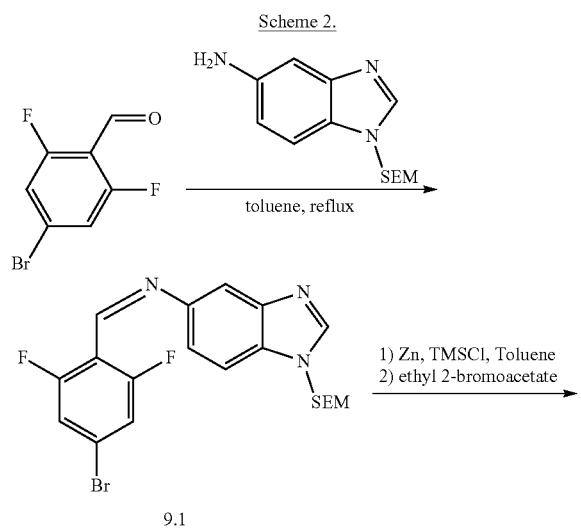

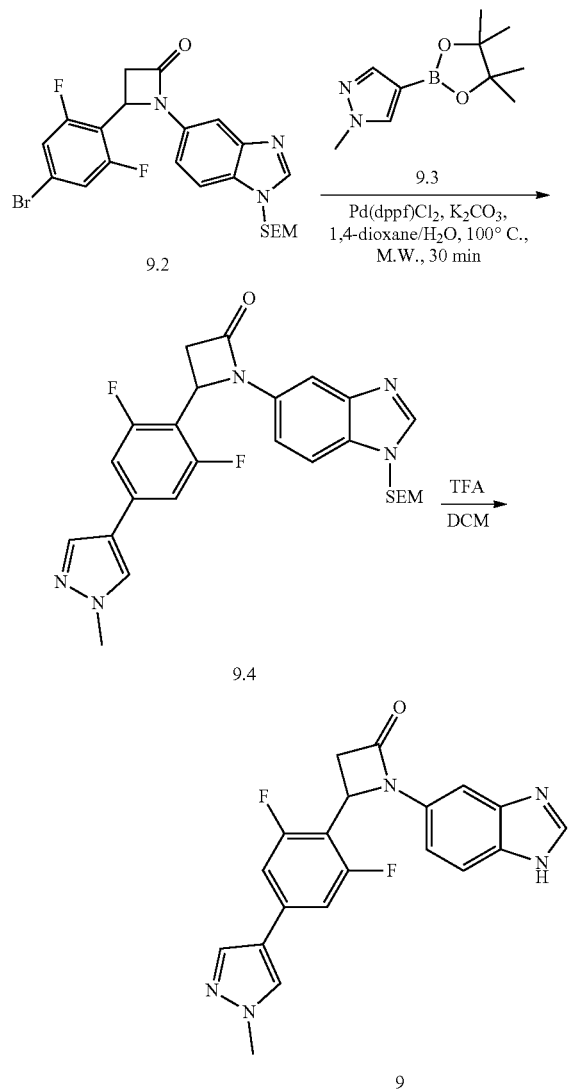

Step 1: General Procedure for Preparation of 1-(4-bromo-2,6-difluorophenyl)-N-(1-((2-(trimethylsilyl)ethoxy)methyl)-1H-benzo[d]imidazol-5-yl)methanimine A mixture of 4-bromo-2,6-difluorobenzaldehyde (2.68 g, 12.15 mmol, 1 eq), 1-((2-(trimethylsilyl)ethoxy)methyl)-1H-benzo[d]imidazol-5-amine (3.2 g, 12.15 mmol, 1 eq) in toluene (40 mL) was degassed and purged with N$_2$ for 3 times, and then the mixture was stirred at 120° C. for 12 hrs under N$_2$ atmosphere. The mixture was concentrated under reduced pressure and purified by flash silica gel chromatography (ISCO®; 40 g SepaFlash® Silica Flash Column, Eluent of 0~60% Ethyl acetate/Petroleum ether gradient @ 60 mL/min) to afford the target compound (4.7 g, 10.08 mmol, 82.95% yield) as a brown oil was obtained.

$^1$HNMR: (400 MHz, DMSO-d$_6$) 8.70 (s, 1H), 8.40 (d, J=6.4 Hz, 1H), 7.79-7.53 (m, 4H), 7.39-7.19 (m, 1H), 5.66 (d, J=7.2 Hz, 2H), 3.58-3.41 (m, 2H), 0.84 (t, J=8.0 Hz, 2H), 0.11--0.30 (m, 9H).

Step 2: General Procedure for Preparation of 4-(4-bromo-2,6-difluorophenyl)-1-(1-((2-(trimethylsilyl)ethoxy)methyl)-1H-benzo[d]imidazol-5-yl)azetidin-2-one To a mixture of Zn (28.04 mg, 428.82 μmol, 2 eq) in Toluene (5 mL) was added TMS-Cl (16.31 mg, 150.09 μmol, 19.05 μL, 0.7 eq) in one portion at 25° C. under Ar. The mixture was stirred at 120° C. for 15 min and then cooled to 25° C. Ethyl 2-bromoacetate (60.87 mg, 364.50 μmol, 40.31 μL, 1.7 eq) and 1-(4-bromo-2,6-difluorophenyl)-N-(1-((2-(trimethylsilyl)ethoxy)methyl)-1H-benzo[d]imidazol-5-yl)methanimine (100 mg, 214.41 μmol, 1 eq) was added. The mixture was stirred at 120° C. for 12 hours. The mixture was concentrated under reduced pressure. The residue was purified by flash silica gel chromatography (ISCO®; 4 g SepaFlash® Silica Flash Column, Eluent of 0~60% Ethyl acetate/Petroleum ether gradient @ 18 mL/min) to afford the target compound (62 mg, 121.94 μmol, 56.87% yield) as a brown oil.

LCMS: Retention time: 0.940 min, (M+H)=509.9, 5-95AB_1.5 min_220&254_Shimadzu.

Step 3: General Procedure for Preparation of 4-(2,6-difluoro-4-(1-methyl-1H-pyrazol-4-yl)phenyl)-1-(1-((2-(trimethylsilyl)ethoxy)methyl)-1H-benzo[d]imidazol-5-yl) azetidine-2-one 4-(4-Bromo-2,6-difluorophenyl)-1-(1-((2-(trimethylsilyl)ethoxy)methyl)-1H-benzo[d]imidazol-5-yl)azetidin-2-one (30 mg, 59.01 μmol, 1 eq), 1-methyl-4-(4,4,5,5-tetramethyl-1,3,2-dioxaborolan-2-yl)-1H-pyrazole (14.73 mg, 70.81 μmol, 1.2 eq) and $K_2CO_3$ (24.47 mg, 177.02 μmol, 3 eq), Pd(dppf)Cl$_2$ (4.32 mg, 5.90 μmol, 0.1 eq) were taken up into a microwave tube in dioxane (2 mL) and $H_2O$ (0.4 mL) under $N_2$. The sealed tube was heated at 100° C. for 30 min under microwave. The mixture was filtered. The filtrate was concentrated under reduced pressure to afford the target compound (40 mg, crude) as a brown solid was obtained and used into the next step without further purification.

LCMS: Retention time: 3.257 min, (M+H)=510.3, 10-80AB_7 min_220&254.

Step 4: General Procedure for Preparation of 1-(1H-benzo[d]imidazol-5-yl)-4-(2,6-difluoro-4-(1-methyl-1H-pyrazol-4-yl)phenyl)azetidin-2-one To a solution of 4-(2,6-difluoro-4-(1-methyl-1H-pyrazol-4-yl)phenyl)-1-(1-((2-(trimethylsilyl)ethoxy)methyl)-1H-benzo[d]imidazol-5-yl) azetidine-2-one Compound 9.4 (40.00 mg, 78.49 μmol, 1 eq) in DCM (2 mL) was added TFA (1 mL). The mixture was stirred at 25° C. for 0.5 hr. The mixture was filtered. The filtrate was concentrated under reduced pressure and purified by prep-HPLC (column: Phenomenex Gemini-NX C18 75*30 mm*3 um; mobile phase: [water (0.225% FA)-ACN]; B %: 10%-30%, 7 min) to afford Compound 9 (1 mg, 2.64 μmol, 3.36% yield) as a white solid.

LCMS: Retention time: 0.734 min, (M+H)=380.0, 5-95AB_1.5 min_220&254_Shimadzu.

Example 3: Synthesis of Compound 4

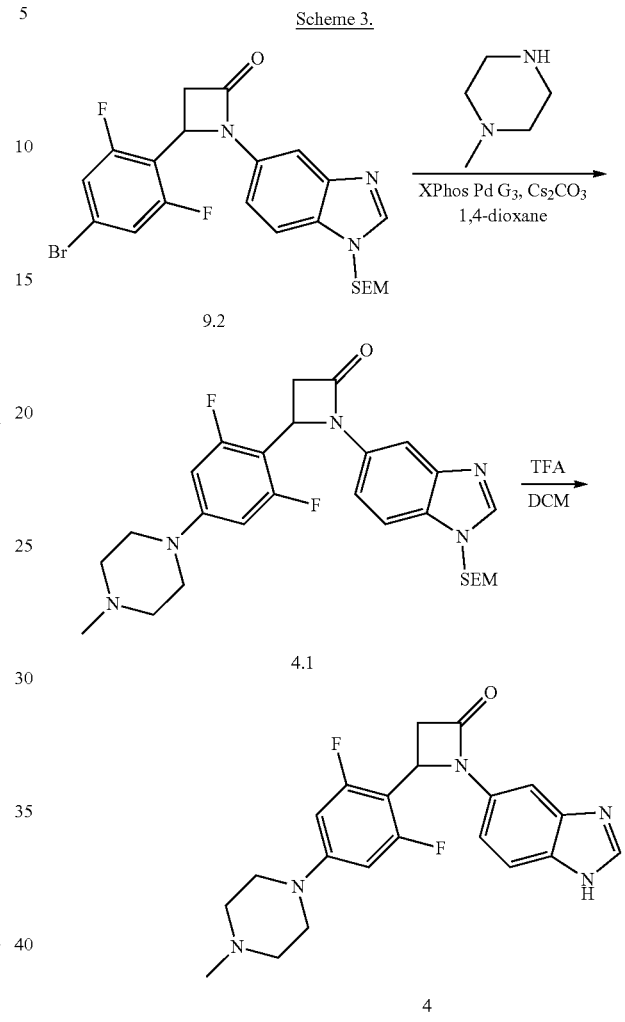

Scheme 3.

Step 1: General Procedure for Preparation of 4-(2,6-difluoro-4-(4-methylpiperazin-1-yl)phenyl)-1-(1-((2-(trimethylsilyl)ethoxy)methyl)-1H-benzo[d]imidazol-5-yl) azetidin-2-one 4-(4-Bromo-2,6-difluorophenyl)-1-(1-((2-(trimethylsilyl)ethoxy)methyl)-1H-benzo[d]imidazol-5-yl)azetidin-2-one Compound 9.2 (250 mg, 491.71 μmol, 1 eq), 1-methylpiperazine (59.10 mg, 590.05 μmol, 65.45 μL, 1.2 eq), $Cs_2CO_3$ (320.42 mg, 983.42 μmol, 2 eq) and 1,4-dioxane (2 mL) were added to a 10 mL round-bottomed flask before sparged with $N_2$ for 5 min, then treated with Xphos-Pd-G3 (41.62 mg, 49.17 μmol, 0.1 eq). The mixture was sparged with $N_2$ for another 5 minutes and then stirred at 100° C. for 3 hours. The mixture was filtered, and the filtrate was concentrated under reduced pressure. The residue was purified by prep-TLC (SiO$_2$, THF:MeOH=4:1, R$_f$=0.3). The target compound (60 mg, crude) was obtained as a white solid.

LCMS: Retention time: 2.083 min, (M+H)$^+$=528.2, 10-80CD_3 min_220&254.

Step 2: General Procedure for Preparation of 1-(1H-benzo[d]imidazol-5-yl)-4-(2,6-difluoro-4-(4-methylpiperazin-1-yl)phenyl)azetidin-2-one To a solution of 4-(2,6-difluoro-4-(4-methylpiperazin-1-yl)phenyl)-1-(1-((2-(trimethylsilyl)ethoxy)methyl)-1H-benzo[d]imidazol-5-yl)azetidin-2-one Compound 4.1 (40 mg, 75.80 μmol, 1 eq) in DCM (1 mL) was added TFA (1.54 g, 13.51 mmol, 1.00 mL, 178.17 eq). The mixture was stirred at 40° C. for 1.5 hours. The reaction mixture was combined with another batch of the reaction mixture (0.5 equivalents) and concentrated under reduced pressure to afford the crude product. The crude product was basified to pH=9~10 with $NH_3 \cdot H_2O$ and purified by prep-HPLC (column: Phenomenex Gemini-NX 80*40 mm*3 um; mobile phase: [water (0.05% $NH_3 \cdot H_2O$)-ACN]; B %: 34%-64%, 8 min). Compound 4 (1.07 mg, 2.06 μmol, 1.81% yield) was obtained as a white solid.

LCMS: Retention time: 1.464 min, $(M+H)^+$=398.1, 10-80CD_3 min_220&254.

$^1$H NMR: (400 MHz, DMSO-$d_6$) δ=12.48-12.31 (m, 1H), 8.18-8.12 (m, 1H), 7.59-7.42 (m, 1H), 7.39-7.26 (m, 1H), 7.25-7.03 (m, 1H), 6.65 (d, J=12.8 Hz, 2H), 5.42-5.32 (m, 1H), 3.61-3.52 (m, 1H), 3.20-3.15 (m, 4H), 3.11-3.03 (m, 1H), 2.41-2.33 (m, 4H), 2.18 (s, 3H).

Example 4: Synthesis of Compound 2

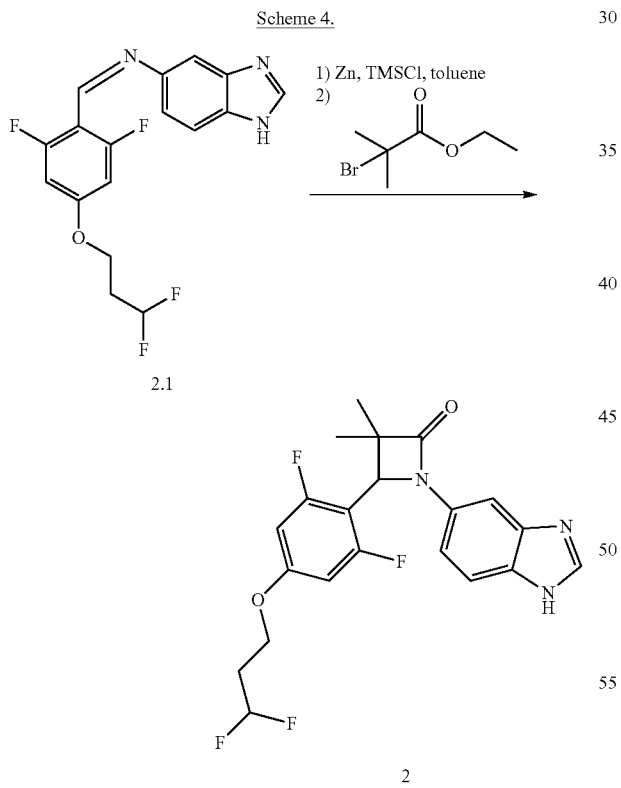

General Procedure for Preparation of 1-(1H-benzo[d]imidazol-5-yl)-4-(4-(3,3-difluoropropoxy)-2,6-difluorophenyl)-3,3-dimethylazetidin-2-one To a mixture of Zn (37.23 mg, 569.32 μmol, 2 eq) in Toluene (5 mL) was added TMS-Cl (21.65 mg, 199.26 μmol, 25.29 μL, 0.7 eq) in one portion at 25° C. under Ar. The mixture was stirred at 120° C. for 15 min and then cooled to 25° C. (Z)—N-(1H-benzo[d]imidazol-5-yl)-1-(4-(3,3-difluoropropoxy)-2,6-difluorophenyl)methanimine (100 mg, 284.66 μmol, 1 eq) and ethyl 2-bromo-2-methylpropanoate (94.39 mg, 483.92 μmol, 70.97 μL, 1.7 eq) was added and the mixture was stirred at 120° C. for 12 hours. The mixture was concentrated under reduced pressure and purified by prep-HPLC (column: Phenomenex Gemini-NX C18 75*30 mm*3 um; mobile phase: [water (0.225% FA)-ACN]; B %: 23%-43%, 7 min). Compound 2 (25.26 mg, 59.94 μmol, 21.06% yield) as a white solid was obtained.

LCMS: Retention time: 2.750 min, $(M+H)^+$=422.2, 10-80AB_7 min_220&254.

$^1$H NMR: (400 MHz, DMSO-$d_6$) δ=12.81-11.97 (m, 1H), 8.34-8.12 (m, 1H), 7.52 (s, 1H), 7.45-7.05 (m, 2H), 7.00-6.57 (m, 2H), 6.39-6.02 (m, 1H), 5.23 (s, 1H), 4.13 (t, J=6.4 Hz, 2H), 2.37-2.21 (m, 2H), 1.46 (s, 3H), 0.99 (s, 3H).

Example 5: Synthesis of Compound 3

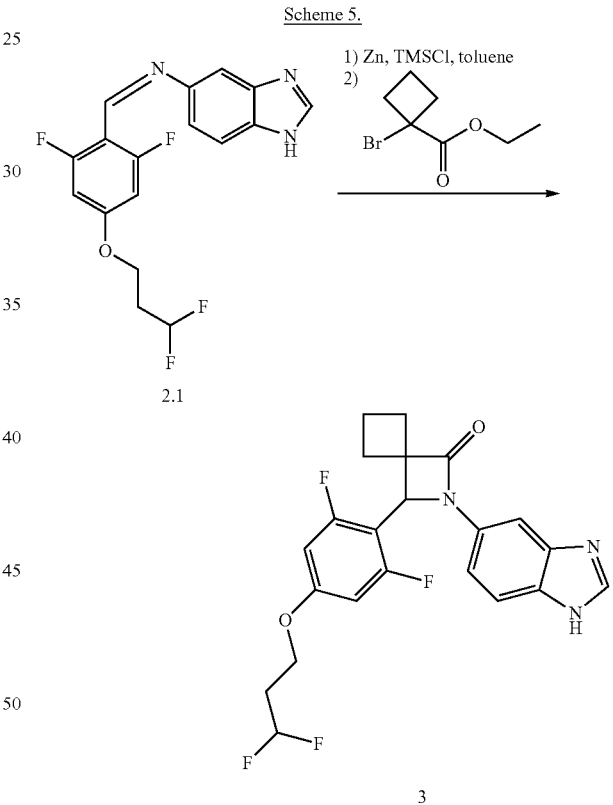

General Procedure for Preparation of 2-(1H-benzo[d]imidazol-5-yl)-3-(4-(3,3-difluoropropoxy)-2,6-difluorophenyl)-2-azaspiro[3.3]heptan-1-one To a mixture of Zn (37.23 mg, 569.32 μmol, 2 eq) in Toluene (5 mL) was added TMS-Cl (21.65 mg, 199.26 μmol, 25.29 μL, 0.7 eq) in one portion at 25° C. under Ar. The mixture was stirred at 120° C. for 15 min and then cooled to 25° C. (Z)—N-(1H-benzo[d]imidazol-5-yl)-1-(4-(3,3-difluoropropoxy)-2,6-difluorophenyl)methanimine Compound 2.1 (100 mg, 284.66 μmol, 1 eq) and ethyl 1-bromocyclobutane-1-carboxylate (100.20 mg, 483.92 μmol, 78.28 μL, 1.7 eq) was added and the mixture was stirred at 120° C. for 12 hours. The mixture was concentrated under reduced pressure and purified by prep-HPLC (column: Phenomenex Gemini-NX C18 75*30 mm*3 um; mobile phase: [water (0.225% FA)-ACN]; B %: 20%-50%, 7 min). Compound 3 (24.35 mg, 56.18 μmol, 19.74% yield) as a white solid was obtained.

LCMS: Retention time: 2.886 min, (M+H)+=434.2, 10-80AB_7 min_220&254.

$^1$H NMR: (400 MHz, DMSO-d$_6$) δ=12.62-12.14 (m, 1H), 8.15 (s, 1H), 7.63-7.43 (m, 1H), 7.41-7.03 (m, 2H), 7.02-6.57 (m, 2H), 6.40-6.02 (m, 1H), 5.36 (s, 1H), 4.24-4.05 (m, 2H), 2.49-2.44 (m, 2H), 2.37-2.20 (m, 3H), 2.02-1.70 (m, 3H).

Example 6: Synthesis of Compound 11CR

Scheme 6.

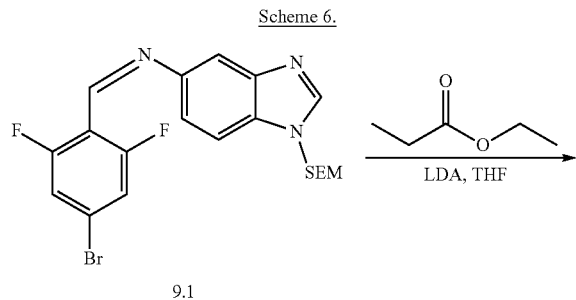

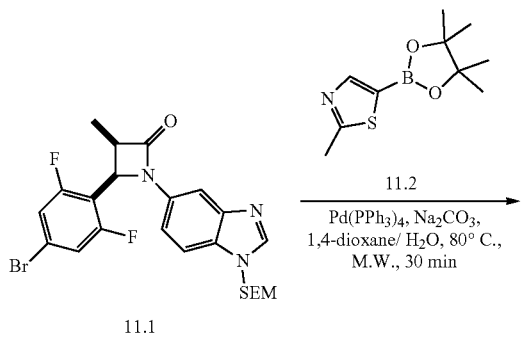

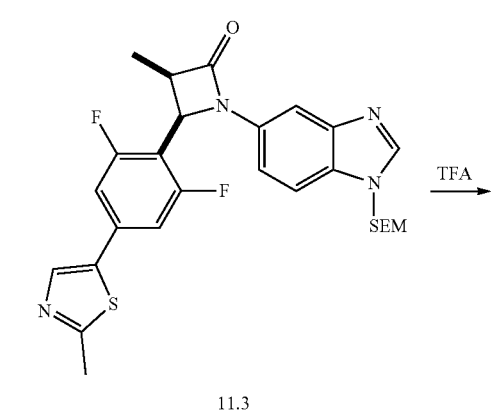

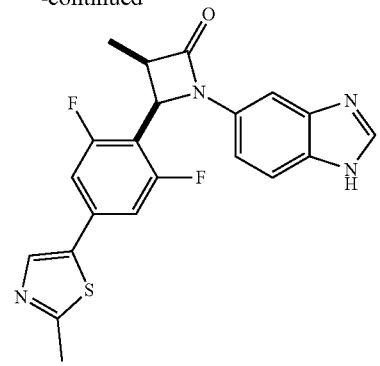

11CR

Step 1: General Procedure for Preparation of (cis and racemic)-4-(4-bromo-2,6-difluorophenyl)-3-methyl-1-(1-((2-(trimethylsilyl)ethoxy)methyl)-1H-benzo[d]imidazole-5-yl)azetidin-2-one To a solution of N-isopropylpropan-2-amine (282.05 mg, 2.79 mmol, 393.92 μL, 1.3 eq) in THF (4 mL) was added n-BuLi (2.5 M, 1.03 mL, 1.2 eq) at −70° C. under N$_2$. The mixture was stirred at −70° C. for 1 h. A mixture of (Z)-1-(4-bromo-2,6-difluorophenyl)-N-(1-((2-(trimethylsilyl)ethoxy)methyl)-1H-benzo[d]imidazol-5-yl)methanimine (218.98 mg, 2.14 mmol, 246.05 μL, 1 eq) in THF (1 mL) was added at −70° C. under N$_2$ and the mixture was stirred at −70° C. for 1 h. A mixture of ethyl propionate (1 g, 2.14 mmol, 1 eq) in THF (1 mL) was added at −70° C. under N$_2$ and the mixture was stirred at 20° C. for 12 h. Aqueous HCl (10 mL, 1M) was added and the mixture was extracted with ethyl acetate (20 mL*3). The combined organic extracts were washed with brine (30 mL), dried over anhydrous Na$_2$SO$_4$, filtered and concentrated under reduced pressure. The residue was purified by flash column chromatography on silica gel (ISCO®; 20 g SepaFlash® Silica Flash Column, Eluent of 0~100% Ethyl acetate/Petroleum ether gradient @ 40 mL/min) to afford the target compound (900 mg, crude) as a brown oil.

LCMS: Retention time: 0.952 min, (M+H)=523.7, 5-95AB_1.5 min_220&254_Shimadzu.

Step 2: General Procedure for Preparation of (cis and racemic)-4-(2,6-difluoro-4-(2-methylthiazol-5-yl)phenyl)-3-methyl-1-(1-((2-(trimethylsilyl)ethoxy)methyl)-1H-benzo[d]imidazol-5-yl)azetidin-2-one (3R,4R)-4-(4-Bromo-2,6-difluorophenyl)-3-methyl-1-(1-((2-(trimethylsilyl)ethoxy)methyl)-1H-benzo[d]imidazol-5-yl)azetidin-2-one (100 mg, 191.40 μmol, 1 eq), 2-methyl-5-(4,4,5,5-tetramethyl-1,3,2-dioxaborolan-2-yl)thiazole (64.63 mg, 287.11 μmol, 1.5 eq), Na$_2$CO$_3$ (60.86 mg, 574.21 μmol, 3 eq) and Pd(PPh$_3$)$_4$ (22.12 mg, 19.14 μmol, 0.1 eq) were taken up into a microwave tube in dioxane (3 mL) and H$_2$O (0.6 mL) under N$_2$. The sealed tube was heated at 80° C. for 30 min under microwave. The mixture was filtered. The filtrate was concentrated under reduced pressure and purified by flash silica gel chromatography (ISCO®; 4 g SepaFlash® Silica Flash Column, Eluent of 0~60% Ethyl acetate/Petroleum ether gradient @ 18 mL/min) to afford the target compound (90 mg, crude) as a yellow oil.

LCMS: Retention time: 1.119 min, (M+H)=541.3, 10-80AB_2 min_220&254.

Step 3: General Procedure for Preparation of (cis and racemic)-1-(1H-benzo[d]imidazol-5-yl)-4-(2,6-difluoro-4-(2-methylthiazol-5-yl)phenyl)-3-methyl-azetidin-2-one To a solution of cis and racemic)-4-(2,6-difluoro-4-(2-methylthiazol-5-yl)phenyl)-3-methyl-1-(1-((2-(trimethylsilyl)ethoxy)methyl)-1H-benzo[d]imidazol-5-yl)azetidin-2-one (90 mg, 166.45 µmol, 1 eq) in DCM (2 mL) was added TFA (1 mL). The mixture was stirred at 25° C. for 0.5 hr. The mixture was concentrated under reduced pressure and adjusted to pH 7 with saturated NaHCO$_3$. The mixture was extracted with ethyl acetate (20 mL*3). The combined organic extracts were washed with brine (30 mL), dried over anhydrous Na$_2$SO$_4$, filtered, and concentrated under reduced pressure. The residue was purified by prep-HPLC (column: Phenomenex Gemini-NX 80*40 mm*3 um; mobile phase: [water (0.05% NH$_3$H$_2$O)-ACN]; B %: 27%-57%, 8 min) to afford Compound 11CR (10 mg, 24.36 µmol, 14.64% yield) as a white solid (in cis and racemic form).

LCMS: Retention time: 0.656 min, (M+H)=411.2, 5-95AB_220&254_Agilent.

$^1$H NMR: (400 MHz, DMSO-d$_6$) δ=8.22-8.18 (m, 1H), 8.14 (s, 1H), 7.59-7.33 (m, 4H), 7.23-7.13 (m, 1H), 5.68 (d, J=6.0 Hz, 1H), 4.02-3.88 (m, 1H), 2.67 (s, 3H), 1.03 (d, J=7.6 Hz, 3H).

Example 7: Synthesis of Compound 10CR

Scheme 7.

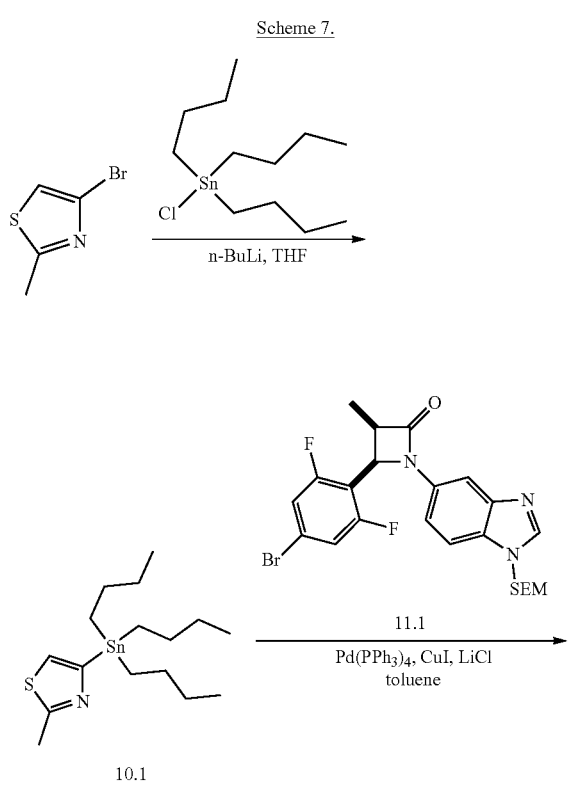

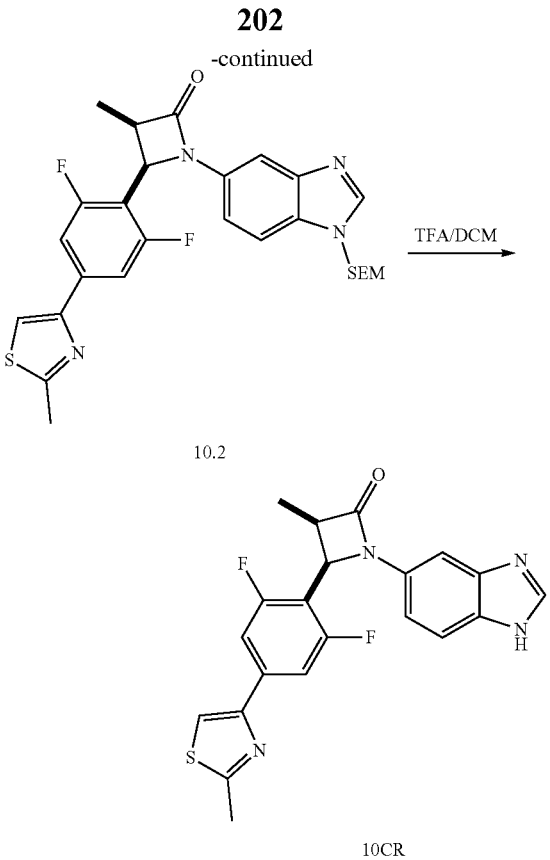

Step 1: General Procedure for Preparation of 2-methyl-4-(tributylstannyl)thiazole To a 4-bromo-2-methylthiazole (2.00 g, 11.2 mmol, 1 eq) in THF (40 mL) was added n-BuLi (1 M, 13.5 mL, 1.2 eq) and at −78° C. under N$_2$. The mixture was stirred at −78° C. for 1 hr. A mixture of tributylchlorostannane (6.25 g, 19.2 mmol, 5.17 mL, 1.71 eq) in THF (20 mL) was added dropwise at −78° C. The resulting mixture was stirred at −78° C. for 1 hr. The reaction mixture was quenched by addition aqueous NH$_4$Cl (20 mL), diluted with H$_2$O (100 mL) and extracted with EtOAc (100 mL*3). The combined organic layers were washed with brine (50 mL), dried over Na$_2$SO$_4$, filtered and concentrated under reduced pressure. The residue was purified by flash silica gel chromatography (ISCO®; 20 g SepaFlash® Silica Flash Column, Eluent of 0~10% Ethyl acetate/Petroleum ether gradient @ 30 mL/min). The target compound (1.00 g, 2.29 mmol, 20.41% yield) was obtained as a yellow oil.

LCMS: Retention time: 1.140 min (M+H)=389.4, 5-95AB_1.5 min_220&254_Shimadzu.

$^1$HNMR: (400 MHz, DMSO-d$_6$) δ=7.59-7.54 (m, 1H), 2.69 (s, 3H), 1.61-1.43 (m, 6H), 1.33-1.25 (m, 6H), 1.17-1.01 (m, 6H), 0.86 (t, J=7.2 Hz, 9H).

Step 2: General Procedure for Preparation of (cis and racemic)-4-(2,6-difluoro-4-(2-methylthiazol-4-yl)phenyl)-3-methyl-1-(1-((2-(trimethylsilyl)ethoxy)methyl)-1H-benzo[d]imidazol-5-yl)azetidin-2-one A mixture of 2-methyl-4-(tributylstannyl)thiazole (156 mg, 402 µmol, 1.5 eq), (3R,4R)-4-(4-bromo-2,6-difluorophenyl)-3-methyl-1-(1-((2-(trimethylsilyl)ethoxy)methyl)-

1H-benzo[d]imidazol-5-yl)azetidin-2-one Compound 11.1 (140 mg, 268 μmol, 1 eq), Pd(PPh$_3$)$_4$ (31.0 mg, 26.8 μmol, 0.1 eq), CuI (51.0 mg, 268 μmol, 1 eq) and LiCl (17.0 mg, 402 μmol, 8.23 μL, 1.5 eq) in toluene (3 mL) was degassed and purged with N$_2$ for 3 times. The mixture was stirred at 120° C. for 12 hours under N$_2$ atmosphere. The reaction mixture was concentrated under reduced pressure and purified by flash silica gel chromatography (ISCO®; 4 g SepaFlash® Silica Flash Column, Eluent of 0~70% Ethyl acetate/ Petroleum ether gradient @ 12 mL/min). The target compound (110 mg, 116.71 μmol, 43.55% yield) was obtained as a white solid.

LCMS: Retention time: 0.907 min, (M+H)=541.2, 5-95AB_1.5 min_220&254_Shimadzu.

Step 3: General Procedure for Preparation of (cis and racemic)-1-(1H-benzo[d]imidazol-5-yl)-4-(2,6-difluoro-4-(2-methylthiazol-4-yl)phenyl)-3-methyl-azetidin-2-one To a solution of Compound 10.2 (110 mg, 203 μmol, 1 eq) in DCM (0.4 mL) was added TFA (3.08 g, 27.0 mmol, 2 mL, 133 eq). The mixture was stirred at 25° C. for 12 hrs. The reaction mixture was concentrated under reduced pressure and purified by prep-HPLC (column: Phenomenex Gemini-NX C18 75*30 mm*3 um; mobile phase: [water (0.225% FA)-ACN]; B %: 15%-45%, 7 min). Compound 10CR (15.97 mg, 37.50 μmol, 18.43% yield) was obtained as a white solid (in cis and racemic form).

LCMS: Retention time: 0.774 min, (M+H)=411.0, 5-95AB_1.5 min_220&254_Shimadzu.

$^1$HNMR: (400 MHz, DMSO-d$_6$) δ=12.37-11.82 (m, 1H), 8.13 (s, 1H), 8.08 (s, 1H), 7.54-7.49 (m, 1H), 7.46-7.36 (m, 3H), 7.27-7.16 (m, 1H), 5.67 (d, J=6.0 Hz, 1H), 3.99-3.90 (m, 1H), 2.68 (s, 3H), 1.06 (d, J=7.6 Hz, 3H).

Example 8: Synthesis of Compound 12CR

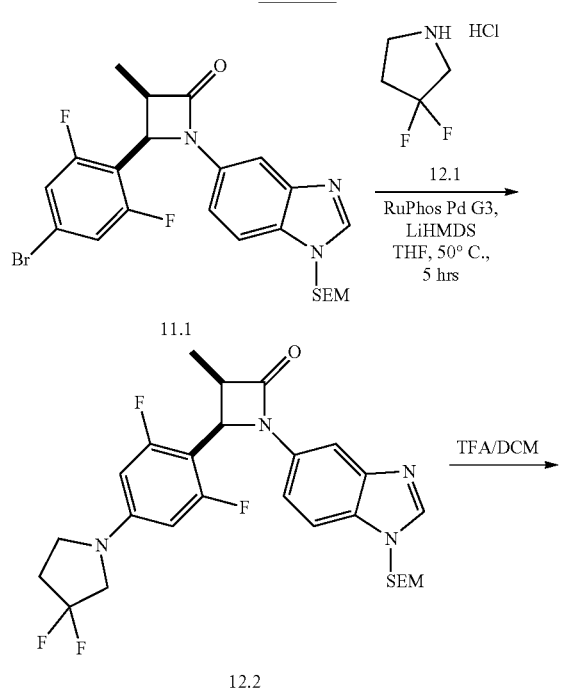

Scheme 8.

11.1

12.2

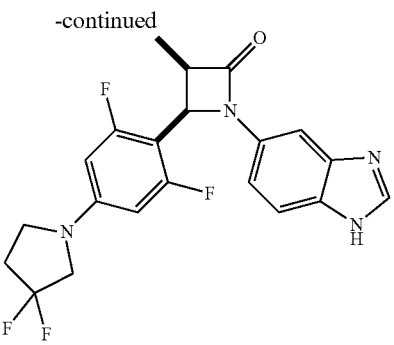

12CR

Step 1: General Procedure for Preparation of (cis and racemic)-4-(4-(3,3-difluoropyrrolidinp-1-yl)-2, 6-difluorophenyl)-3-methyl-1-(1-((2-(trimethylsilyl) ethoxy) methyl)-1H-benzo[d]imidazol-5-yl)azetidin-2-one A mixture of Compound 11.1 (130 mg, 248.82 μmol, 1 eq), Compound 12.1 (71.44 mg, 497.65 μmol, 2 eq, HCl) and RuPhos Pd G3 (83.24 mg, 99.53 μmol, 0.4 eq), LiHMDS (1 M, 1.24 mL, 5 eq) in THF (8 mL) was degassed and purged with N$_2$ for 3 times and then the mixture was stirred at 50° C. for 5 hrs. The mixture was concentrated under reduced pressure and purified by flash column chromatography on silica gel (ISCO®; 12 g SepaFlash® Silica Flash Column, Eluent of 0~100% Ethyl acetate/Petroleum ether gradient @ 30 mL/min) to afford Compound 12.2 (100 mg, 182.27 μmol, 73.25% yield) as a brown oil.

LCMS: Retention time: 1.005 min, (M+H)$^+$=549.0, 5-95AB_1.5 min_220&254_Shimadzu.

Step 2: General Procedure for Preparation of (cis and racemic)-1-(1H-benzo[d]imidazol-5-yl)-4-(4-(3, 3-difluoropyrrolidin-1-yl)-2,6-difluorophenyl)-3-methylazetidin-2-one To a solution of Compound 12.2 (100 mg, 182.27 μmol, 1 eq) in DCM (2 mL) was added TFA (1 mL). The mixture was stirred at 25° C. for 0.5 hr. The mixture was concentrated under reduced pressure to give a residue and adjusted to pH 7 with saturated NaHCO$_3$. The mixture was extracted with ethyl acetate (20 mL*3). The combined organic extracts were washed with brine (30 mL), dried over anhydrous Na$_2$SO$_4$, filtered, and concentrated under reduced pressure. The residue was purified by prep-HPLC (column: Phenomenex Gemini-NX 80*40 mm*3 um; mobile phase: [water (0.05% NH$_3$H$_2$O)-ACN]; B %: 34%-64%, 8 min) to afford Compound 12CR (5 mg, 11.95 μmol, 6.56% yield) as white solid (in cis and racemic form).

LCMS: Retention time: 0.952 min, (M+H)$^+$=419.2, 10-80AB_2 min_220&254.

$^1$H NMR: (400 MHz, DMSO-d$_6$) δ=12.55-12.18 (m, 1H), 8.20-8.07 (m, 1H), 7.61-7.44 (m, 1H), 7.42-7.31 (m, 1H), 7.29-7.02 (m, 1H), 6.55-6.12 (m, 2H), 5.53 (d, J=5.6 Hz, 1H), 3.90-3.78 (m, 1H), 3.77-3.64 (m, 2H), 3.51-3.40 (m, 2H), 2.60-2.53 (m, 2H), 1.01 (br d, J=7.6 Hz, 3H).

Example 9: Synthesis of Compound 13A and 13B

Scheme 9.

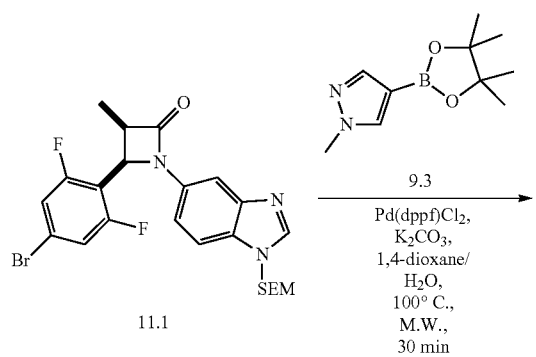

11.1

9.3

Pd(dppf)Cl$_2$,
K$_2$CO$_3$,
1,4-dioxane/
H$_2$O,
100° C.,
M.W.,
30 min

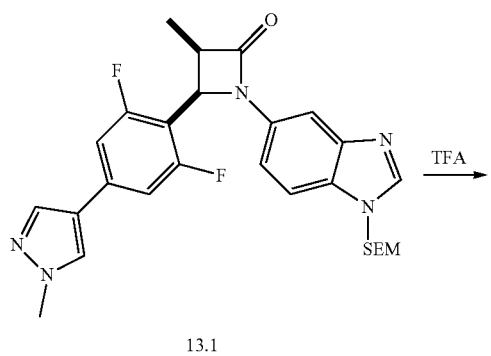

13.1

TFA

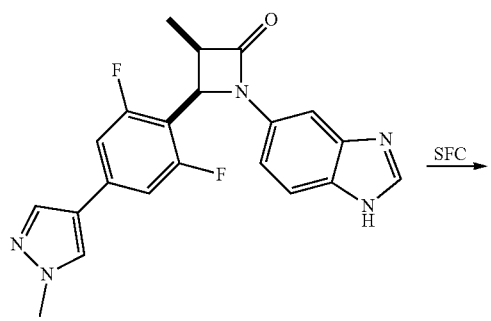

13

SFC

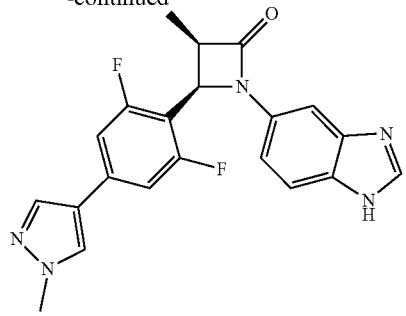

13B

Step 1: General Procedure for Preparation of (cis and racemic)-4-(2,6-difluoro-4-(1-methyl-1H-pyrazol-4-yl)phenyl)-3-methyl-1-(1-((2-(trimethylsilyl)ethoxy)methyl)-1H-benzo[d]imidazol-5-yl)azetidin-2-one Compound 9.3 (43.01 mg, 206.72 μmol, 1.2 eq), Compound 11.1 (90 mg, 172.26 μmol, 1 eq) and K$_2$CO$_3$ (71.43 mg, 516.79 μmol, 3 eq), Pd(dppf)Cl$_2$ (12.60 mg, 17.23 μmol, 0.1 eq) were taken up into a microwave tube in dioxane (2 mL) and H$_2$O (0.4 mL) under N$_2$. The sealed tube was heated at 100° C. for 30 min under microwave. The mixture was filtered. The filtrate was concentrated under reduced pressure. Compound 13.1 (90 mg, crude) was obtained as a brown oil and used into the next step without further purification.

LCMS: Retention time: 3.358 min, (M+H)=524.3, 10-80AB_7 min_220&254.

Step 2: General Procedure for Preparation of (cis and racemic)-1-(1H-benzo[d]imidazol-5-yl)-4-(2,6-difluoro-4-(1-methyl-1H-pyrazol-4-yl)phenyl)-3-methylazetidin-2-one To a solution of Compound 13.1 (90 mg, 171.87 μmol, 1 eq) in DCM (2 mL) was added TFA (1 mL). The mixture was stirred at 25° C. for 0.5 hr. The mixture was filtered. The filtrate was concentrated under reduced pressure and purified by prep-HPLC (column: Phenomenex Gemini-NX C18 75*30 mm*3 um; mobile phase: [water (0.225% FA)-ACN]; B %: 5%-35%, 7 min). Compound 13 (18 mg, 45.76 μmol, 26.62% yield) was obtained as a white solid (in cis and racemic form).

LCMS: Retention time: 0.846 min, (M+H)=394.2, 10-80AB_2 min_220&254.

$^1$H NMR: (400 MHz, DMSO-d$_6$) δ=13.51-10.97 (m, 1H), 8.25 (s, 1H), 7.97 (s, 1H), 7.84-7.02 (m, 5H), 5.64 (d, J=5.8 Hz, 1H), 3.97-3.88 (m, 1H), 3.84 (s, 3H), 1.03 (d, J=7.5 Hz, 3H).

Step 3: General Procedure for Preparation of (3S,4S)-1-(1H-benzo[d]imidazol-5-yl)-4-(2,6-difluoro-4-(1-methyl-1H-pyrazol-4-yl)phenyl)-3-methylazetidin-2-one (Compound 13A) and (3R,4R)-1-(1H-benzo[d]imidazol-5-yl)-4-(2,6-difluoro-4-(1-methyl-1H-pyrazol-4-yl)phenyl)-3-methylazetidin-2-one (Compound 13B)

Compound 13 (15 mg, 38.13 μmol) was purified by SFC (column: DAICEL CHIRALPAK AD (250 mm*30 mm, 10 um); mobile phase: [0.1% NH$_3$·H$_2$O ETOH]; B %: 35%-35%, min) to afford Compound 13A (4.84 mg, 12.30 μmol, 32.27% yield) as a white solid and Compound 13B (5.28 mg, 13.42 μmol, 35.20% yield) as a white solid.

Compound 13A: SFC: Retention time: 1.743 min. LCMS: Retention time: 0.745 min, (M+H)=394.1, 5-95AB_1.5 min_220&254_Shimadzu. $^1$H NMR: (400 MHz, DMSO-d$_6$) δ=12.60-12.10 (m, 1H), 8.25 (s, 1H), 8.19-8.09 (m, 1H), 7.97 (s, 1H), 7.61-7.00 (m, 5H), 5.64 (d, J=6.0 Hz, 1H), 3.99-3.88 (m, 1H), 3.84 (s, 3H), 1.03 (d, J=7.6 Hz, 3H).

Compound 13B: SFC: Retention time: 1.935 min. LCMS: Retention time: 0.752 $^1$H NMR: (400 MHz, DMSO-d$_6$) δ=12.43-11.65 (m, 1H), 8.18 (s, 1H), 8.07 (s, 1H), 7.90 (s, 1H), 7.60-7.45 (m, 1H), 7.42 (s, 1H), 7.35-7.03 (m, 3H), 5.63 (d, J=6.0 Hz, 1H), 4.01-3.87 (m, 1H), 3.85 (s, 3H), 1.06 (d, J=7.2 Hz, 3H).

Example 10: Synthesis of Compounds 14A and 14B

Scheme 10.

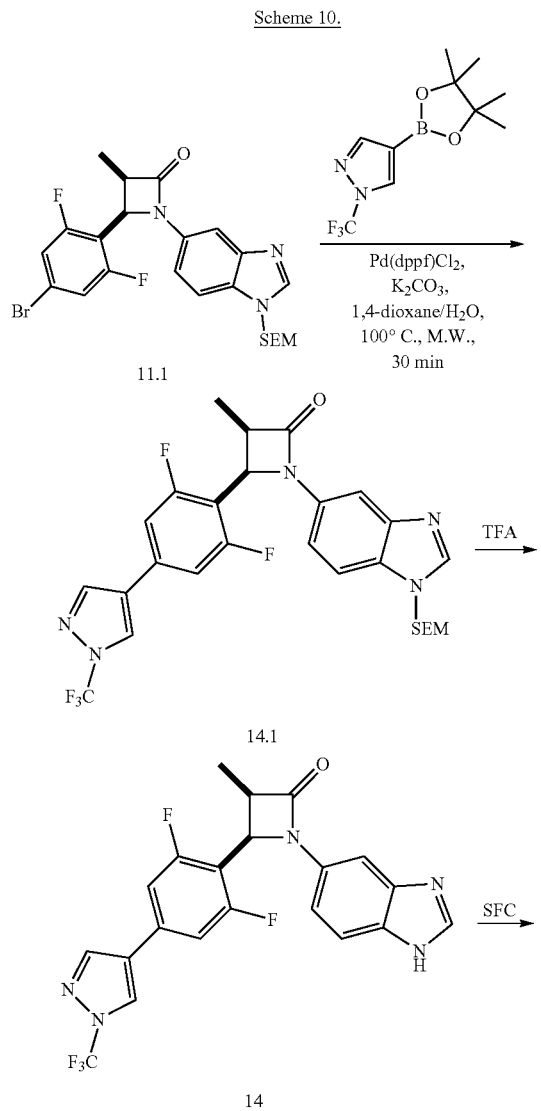

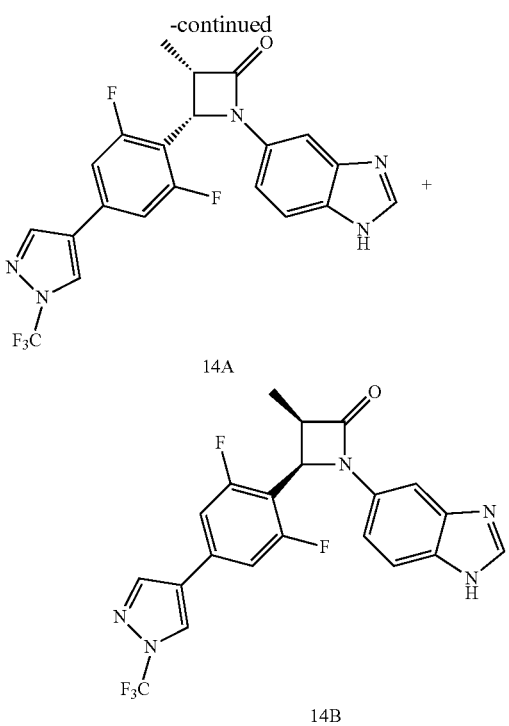

Step 1: General Procedure for Preparation of (cis and racemic)-4-(2,6-difluoro-4-(1-(trifluoromethyl)-1H-pyrazol-4-yl)phenyl)-3-methyl-1-(1-((2-(trimethylsilyl)ethoxy) methyl)-1H-benzo[d]imidazol-5-yl) azetidin-2-one Compound 11.1 (100 mg, 191.40 μmol, 1 eq), 4-(4,4,5,5-tetramethyl-1,3,2-dioxaborolan-2-yl)-1-(trifluoromethyl)-1H-pyrazole (75.23 mg, 287.11 μmol, 1.5 eq), K$_2$CO$_3$ (79.36 mg, 574.21 μmol, 3 eq) and Pd(dppf)Cl$_2$ (14.01 mg, 19.14 μmol, 0.1 eq) were taken up into a microwave tube in dioxane (3 mL) and H$_2$O (0.6 mL) under N$_2$. The sealed tube was heated at 100° C. for 30 min under microwave. The mixture was filtered. The filtrate was concentrated under reduced pressure and purified by flash silica gel chromatography (ISCO®; 4 g SepaFlash® Silica Flash Column, Eluent of 0~60% Ethyl acetate/Petroleum ether gradient @ 18 mL/min). Compound 14.1 (100 mg, 173.12 μmol, 90.45% yield) as a yellow oil was obtained.

LCMS: Retention time: 1.158 min, (M+H)=578.3, 10-80AB_7 min_220&254.

Step 2: General Procedure for Preparation of (cis and racemic)-1-(1H-benzo[d]imidazol-5-yl)-4-(2,6-difluoro-4-(1-(trifluoromethyl)-1H-pyrazol-4-yl) phenyl)-3-methyl azetidin-2-one To a solution of Compound 14.1 (100 mg, 173.12 μmol, 1 eq) in DCM (2 mL) was added TFA (1 mL). The mixture was stirred at 25° C. for 0.5 hr. The mixture was concentrated under reduced pressure to give a residue and adjusted to pH 7 with saturated NaHCO$_3$. The mixture was extracted with ethyl acetate (20 mL*3). The combined organic extracts were washed with brine (30 mL), dried over anhydrous Na$_2$SO$_4$, filtered, and concentrated under reduced pressure. The residue was purified by prep-HPLC (column: Phenomenex Gemini-NX 80*40 mm*3 um; mobile phase:

[water (0.05% NH₃·H₂O)-ACN]; B %: 34%-64%, 8 min). Compound 14 (11.49 mg, 25.68 μmol, 14.84% yield) was obtained as a white solid (in cis and racemic form).

LCMS: Retention time: 0.707 min, (M+H)=448.1, 5-95AB_220&254_Agilent.

$^1$H NMR: (400 MHz, DMSO-$d_6$) δ=12.57-12.15 (m, 1H), 9.12 (s, 1H), 8.56 (s, 1H), 8.24-8.08 (m, 1H), 7.78-7.04 (m, 5H), 5.69 (d, J=5.6 Hz, 1H), 4.07-3.80 (m, 1H), 1.03 (d, J=7.6 Hz, 3H).

Step 3: General Procedure for Preparation of (3S, 4S)-1-(1H-benzo[d]imidazol-5-yl)-4-(2,6-difluoro-4-(1-(trifluoromethyl)-1H-pyrazol-4-yl)phenyl)-3-methylazetidin-2-one (Compound 14A) and (3R, 4R)-1-(1H-benzo[d]imidazol-5-yl)-4-(2,6-difluoro-4-(1-(trifluoromethyl)-1H-pyrazol-4-yl)phenyl)-3-methylazetidin-2-one (Compound 14B)

Compound 14 (40 mg, 89.41 μmol, 1 eq) was purified by SFC (column: Phenomenex-Cellulose-2 (250 mm*30 mm, 5 um); mobile phase: [0.1% NH₃·H₂O ETOH]; B %: 25%-25%, min) to afford Compound 14A (11.71 mg, 26.18 μmol, 29.28% yield) as a white solid and Compound 14B (12.01 mg, 26.85 μmol, 30.03% yield) as a white solid.

Compound 14A: SFC: Retention time: 3.351 min. LCMS: Retention time: 0.814 min, (M+H)=448.3, 5-95AB_1.5 min_220&254_Shimadzu. $^1$H NMR (400 MHz, DMSO-$d_6$) δ=12.52-12.15 (m, 1H), 9.12 (s, 1H), 8.55 (s, 1H), 8.19-8.11 (m, 1H), 7.69-7.39 (m, 3H), 7.38-7.27 (m, 1H), 7.10 (dd, J=2.0, 8.4 Hz, 1H), 5.69 (d, J=6.0 Hz, 1H), 4.04-3.81 (m, 1H), 1.03 (d, J=7.6 Hz, 3H).

Compound 14B: SFC: Retention time: 3.897 min. LCMS: Retention time: 0.809 min, (M+H)=448.0, 5-95AB_1.5 min_220&254_Shimadzu. $^1$H NMR (400 MHz, DMSO-$d_6$) δ=12.67-12.11 (m, 1H), 9.12 (s, 1H), 8.55 (s, 1H), 8.15 (s, 1H), 7.81-7.01 (m, 5H), 5.69 (d, J=6.0 Hz, 1H), 4.08-3.80 (m, 1H), 1.03 (d, J=7.6 Hz, 3H).

Example 11: Synthesis of Compounds 8A and 8B

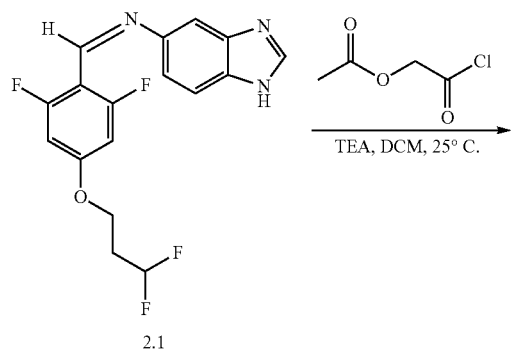

Scheme 11.

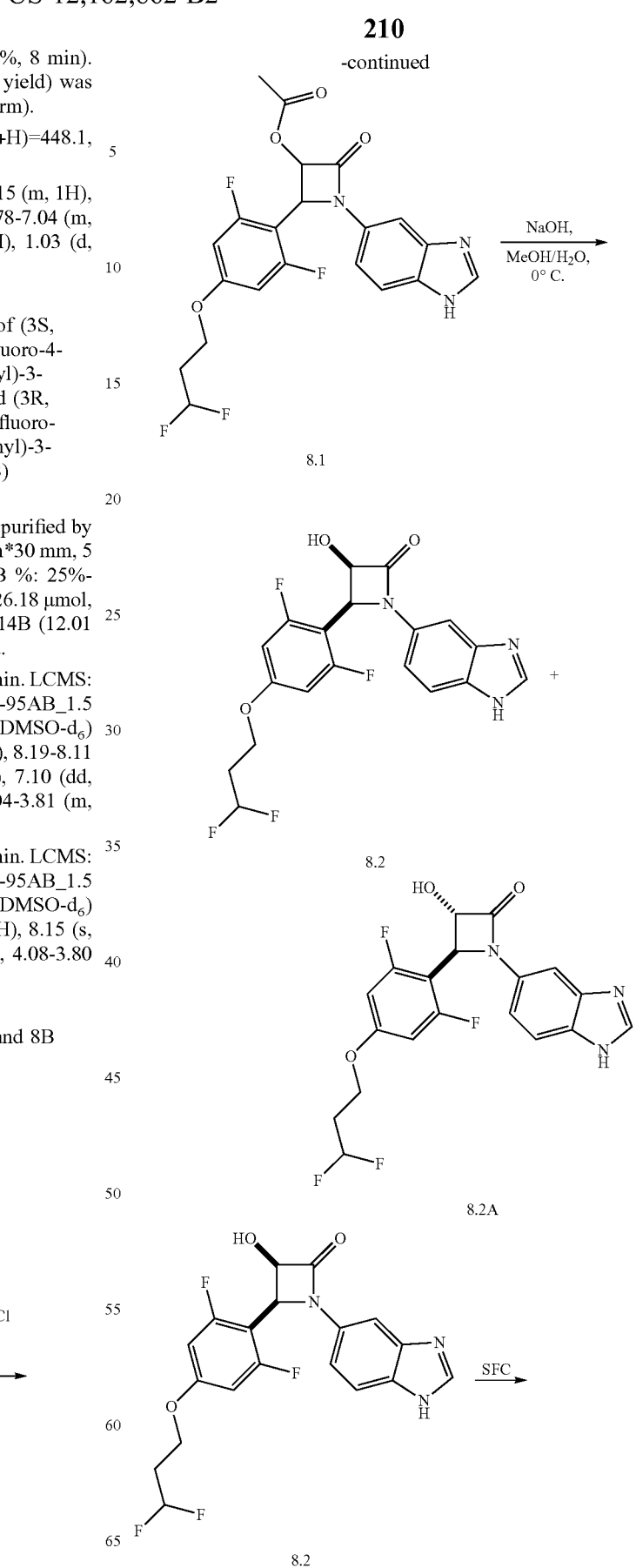

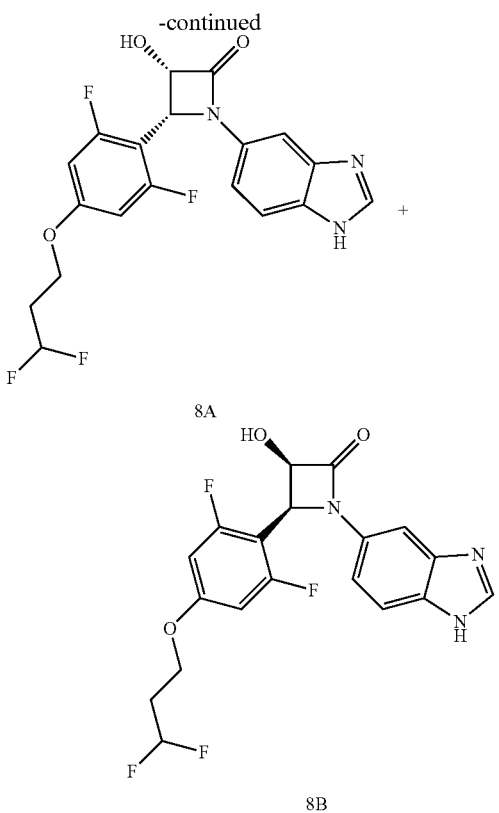

Step 1: General Procedure for Preparation of 1-(1H-benzo[d]imidazol-5-yl)-2-(4-(3,3-difluoropropoxy)-2,6-difluorophenyl)-4-oxoazetidin-3-yl acetate 2-Chloro-2-oxoethyl acetate (150.80 mg, 1.10 mmol, 118.74 µL, 3.88 eq) was added dropwise to a solution of (Z)—N-(1H-benzo[d]imidazol-5-yl)-1-(4-(3,3-difluoropropoxy)-2,6-difluorophenyl)methanimine (100 mg, 284.66 µmol, 1 eq) and TEA (86.41 mg, 853.98 µmol, 118.86 µL, 3 eq) in DCM (1 mL) at 25° C. The reaction mixture was stirred for 1 hour at 25° C. The mixture was diluted with ethyl acetate (20 mL) and washed with saturated aqueous NaHCO$_3$ (5 mL×2), brine (20 mL), dried over anhydrous Na$_2$SO$_4$, filtered and concentrated under reduced pressure. The residue was purified by flash silica gel chromatography (ISCO®; 12 g SepaFlash® Silica Flash Column, Eluent of 0~100% Ethyl acetate/Petroleum ether gradient @35 mL/min). The target compound (40 mg, 244.59 µmol, 28.64% yield) was obtained as a brown solid.

LCMS: Retention time: 0.884-0.901 min, (M+H)$^+$=452.2, 10-80AB_2 min_220&254.

Step 2: General Procedure for Preparation of (cis and racemic)-1-(1H-benzo[d]imidazol-5-yl)-4-(4-(3,3-difluoropropoxy)-2,6-difluorophenyl)-3-hydroxyazetidin-2-one and (trans and racemic)-1-(1H-benzo[d]imidazol-5-yl)-4-(4-(3,3-difluoropropoxy)-2,6-difluorophenyl)-3-hydroxyazetidin-2-one To a solution of Compound 8.1 (15 mg, 33.23 µmol, 1 eq) in MeOH (0.5 mL) and H$_2$O (0.5 mL) was added NaOH (13.29 mg, 33.23 µmol, 85.97 µL, 10% purity, 1 eq) at 0° C. The mixture was stirred at 0° C. for 5 min. FA (0.25 mL) was added to the mixture and the mixture was concentrated under reduced pressure to afford the crude product. The residue was purified by prep-HPLC (column: Boston Green ODS 150*30 mm*5 um; mobile phase: [water (0.225% FA)-ACN]; B %: 15%-45%, 7 min) to afford Compound 8.2 (0.57 mg, 1.39 µmol, 4.19% yield) as a white solid (in cis and racemic form) and Compound 8.2A (1.93 mg, 4.71 µmol, 14.19% yield) as a white solid (in trans and racemic form).

Compound 8.2: LCMS: Retention time: 0.780 min, (M+H)$^+$=410.2, 10-80AB_2 MIN_220&254. $^1$HNMR: (400 MHz, CD$_3$OD) δ=8.12 (s, 1H), 7.62-7.49 (m, 2H), 7.40-7.28 (m, 1H), 6.71-6.54 (m, 2H), 6.27-5.90 (m, 1H), 5.67 (d, J=4.8 Hz, 1H), 5.32 (d, J=4.8 Hz, 1H), 4.13 (t, J=6.4 Hz, 2H), 2.52-2.16 (m, 2H).

Compound 8.2A: LCMS: Retention time: 0.823 min, (M+H)$^+$=410.2, 10-80AB_2 MIN_220&254.
$^1$HNMR: (400 MHz, CD$_3$OD) δ=8.14 (s, 1H), 7.54 (d, J=8.8 Hz, 1H), 7.50-7.46 (m, 1H), 7.30 (d, J=8.8 Hz, 1H), 6.67 (d, J=10.8 Hz, 2H), 6.24-5.90 (m, 1H), 5.24-5.16 (m, 1H), 5.11-5.04 (m, 1H), 4.12 (t, J=6.0 Hz, 2H), 2.37-2.20 (m, 2H).

Step 3: General Procedure for Preparation of (3S,4R)-1-(1H-benzo[d]imidazol-5-yl)-4-(4-(3,3-difluoropropoxy)-2,6-difluorophenyl)-3-hydroxyazetidin-2-one (Compound 8A) and (3R,4S)-1-(1H-benzo[d]imidazol-5-yl)-4-(4-(3,3-difluoropropoxy)-2,6-difluorophenyl)-3-hydroxyazetidin-2-one (Compound 8B)

Compound 8.2 (35 mg, 85.50 µmol, 1 eq) was purified by prep-SFC (column: DAICEL CHIRALPAK AD (250 mm*30 mm, 10 um); mobile phase: [0.1% NH$_3$·H$_2$O ETOH]; B %: 40%-40%, min) to afford Compound 8A (11.51 mg, 26.90 µmol, 31.46% yield) as a white solid and Compound 8B (12.57 mg, 30.14 µmol, 35.25% yield) as a white solid.

Compound 8A: SFC: Retention time: 1.355 min. LCMS: Retention time: 0.805 min, (M+H)$^+$=409.9, 5-95AB_1.5 min_220&254_Shimadzu. $^1$HNMR: (400 MHz, DMSO-d$_6$) δ=12.58-12.19 (m, 1H), 8.27-8.07 (m, 1H), 7.63-7.06 (m, 3H), 6.93-6.54 (m, 2H), 6.43-6.02 (m, 2H), 5.58 (d, J=4.8 Hz, 1H), 5.32-5.23 (m, 1H), 4.22-4.08 (m, 2H), 2.37-2.22 (m, 2H).

Compound 8B: SFC: Retention time: 2.668 min. LCMS: Retention time: 0.803 min, (M+H)$^+$=409.9, 5-95AB_1.5 min_220&254_Shimadzu. $^1$HNMR: (400 MHz, DMSO-d$_6$) δ=12.61-12.16 (m, 1H), 8.22-8.10 (m, 1H), 7.64-7.06 (m, 3H), 6.75 (br s, 2H), 6.43-6.01 (m, 2H), 5.58 (d, J=4.8 Hz, 1H), 5.32-5.24 (m, 1H), 4.17-4.10 (m, 2H), 2.38-2.21 (m, 2H).

Example 12: Synthesis of Compound 15A and 15B

Scheme 12.

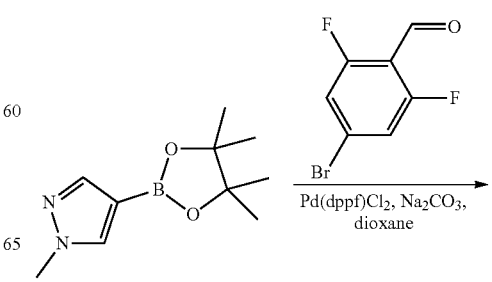

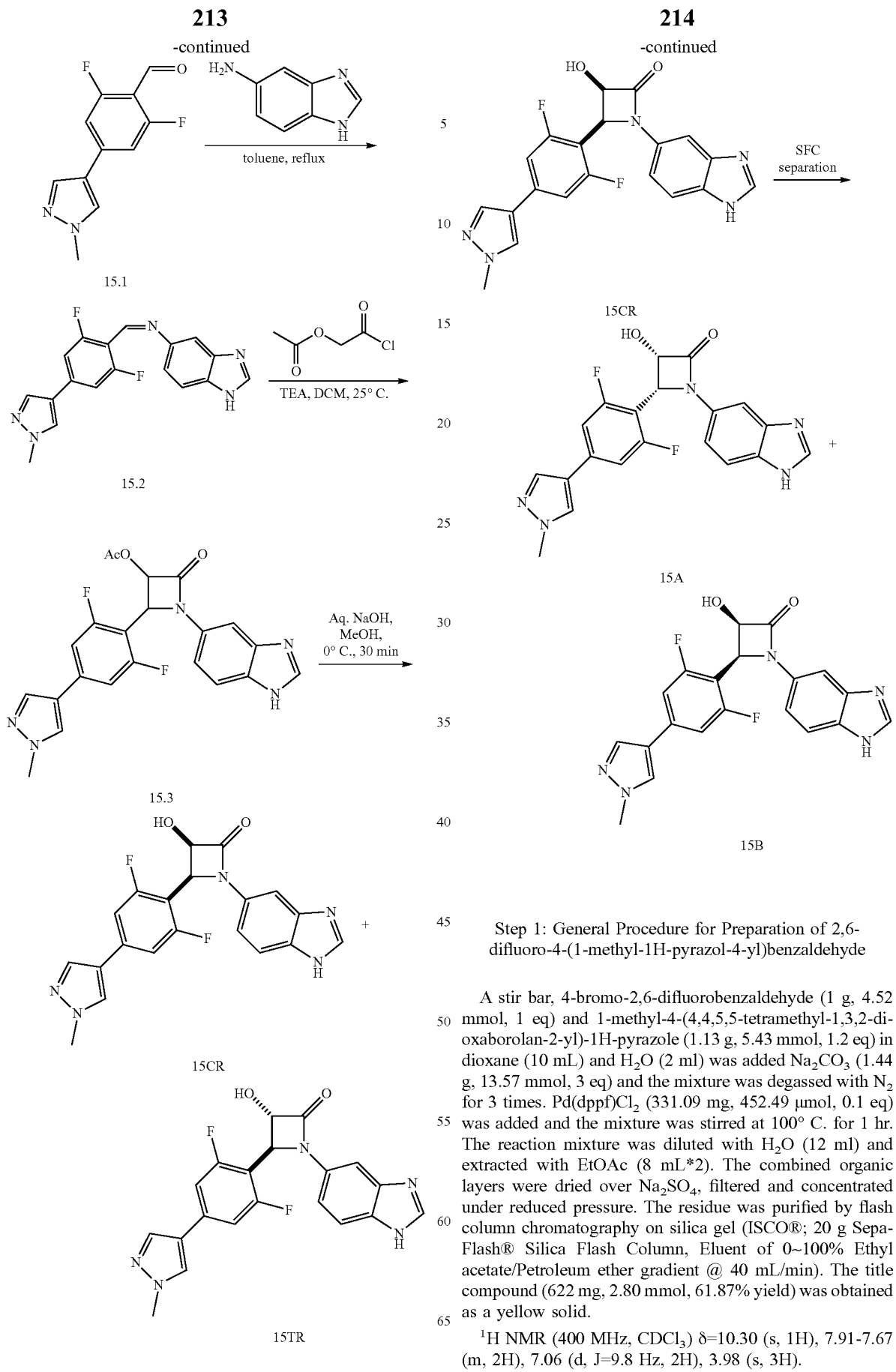

Step 1: General Procedure for Preparation of 2,6-difluoro-4-(1-methyl-1H-pyrazol-4-yl)benzaldehyde A stir bar, 4-bromo-2,6-difluorobenzaldehyde (1 g, 4.52 mmol, 1 eq) and 1-methyl-4-(4,4,5,5-tetramethyl-1,3,2-dioxaborolan-2-yl)-1H-pyrazole (1.13 g, 5.43 mmol, 1.2 eq) in dioxane (10 mL) and $H_2O$ (2 ml) was added $Na_2CO_3$ (1.44 g, 13.57 mmol, 3 eq) and the mixture was degassed with $N_2$ for 3 times. Pd(dppf)$Cl_2$ (331.09 mg, 452.49 μmol, 0.1 eq) was added and the mixture was stirred at 100° C. for 1 hr. The reaction mixture was diluted with $H_2O$ (12 ml) and extracted with EtOAc (8 mL*2). The combined organic layers were dried over $Na_2SO_4$, filtered and concentrated under reduced pressure. The residue was purified by flash column chromatography on silica gel (ISCO®; 20 g SepaFlash® Silica Flash Column, Eluent of 0~100% Ethyl acetate/Petroleum ether gradient @ 40 mL/min). The title compound (622 mg, 2.80 mmol, 61.87% yield) was obtained as a yellow solid.

$^1$H NMR (400 MHz, CDCl$_3$) δ=10.30 (s, 1H), 7.91-7.67 (m, 2H), 7.06 (d, J=9.8 Hz, 2H), 3.98 (s, 3H).

Step 2: General Procedure for Preparation of N-(1H-benzo[d]imidazol-5-yl)-1-(2,6-difluoro-4-(1-methyl-1H-pyrazol-4-yl)phenyl)methanimine To a solution of 2,6-difluoro-4-(1-methyl-1H-pyrazol-4-yl)benzaldehyde (622 mg, 2.80 mmol, 1 eq) in toluene (10 mL) was added 1H-benzo[d]imidazol-5-amine (372.74 mg, 2.80 mmol, 1 eq) and the mixture was stirred at 120° C. for 12 hours under $N_2$. The mixture was concentrated under reduced pressure to remove the solvent. The crude product was purified by re-crystallization from EtOAc (12 mL) at 25° C. and filtered. The filter cake was collected to afford the title compound (920 mg, 2.73 mmol, 97.43% yield) as a yellow solid.

$^1$HNMR: (400 MHz, DMSO-$d_6$) δ=8.69 (s, 1H), 8.40 (s, 1H), 8.25 (s, 1H), 8.11 (s, 1H), 7.62 (br d, J=6.4 Hz, 1H), 7.52 (br d, J=10.5 Hz, 3H), 7.27-7.17 (m, 1H), 3.89 (s, 3H).

Step 3: General Procedure for Preparation of 1-(1H-benzo[d]imidazol-5-yl)-2-(2,6-difluoro-4-(1-methyl-1H-pyrazol-4-yl)phenyl)-4-oxoazetidin-3-ylacetate 2-Chloro-2-oxoethyl acetate (157.04 mg, 1.15 mmol, 123.66 μL, 3.88 eq) was added dropwise to a solution of (Z)—N-(1H-benzo[d]imidazol-5-yl)-1-(2,6-difluoro-4-(1-methyl-1H-pyrazol-4-yl)phenyl)methanimine (100 mg, 296.45 μmol, 1 eq) and TEA (89.99 mg, 889.35 μmol, 123.79 μL, 3 eq) in DCM (1.5 mL) at 25° C. The reaction mixture was stirred for 1 hour at 25° C. The mixture was concentrated under reduced pressure and purified by flash silica gel chromatography (ISCO®; 5 g SepaFlash® Silica Flash Column, Eluent of 0~100% Ethyl acetate/Petroleum ether gradient @ 35 mL/min). The title compound (120 mg, 403.27 μmol, 54.41% yield) was obtained as a light yellow solid.

LCMS: Retention time: 0.758 min, (M+H)$^+$=438.1, 5-95AB_1.5 min_220&254.

Step 4: General Procedure for Preparation of (cis and racemic)-1-(1H-benzo[d]imidazol-5-yl)-4-(2,6-difluoro-4-(1-methyl-1H-pyrazol-4-yl)phenyl)-3-hydroxyazetidin-2-one (Compound 1029) and (trans and racemic)-1-(1H-benzo[d]imidazol-5-yl)-4-(2,6-difluoro-4-(1-methyl-1H-pyrazol-4-yl)phenyl)-3-hydroxyazetidin-2-one To a solution of Compound 15.3 (250 mg, 571.56 μmol, 1 eq) in MeOH (1 mL) and $H_2O$ (1 mL) was added NaOH (228.62 mg, 571.56 μmol, 228.62 μL, 10% purity, 1 eq) at 0° C. The mixture was stirred at 0° C. for 5 min. The residue was acidified with FA to pH=5~6 and the mixture was concentrated under reduced pressure to afford the crude product. The residue was purified by prep-HPLC (column: Phenomenex Gemini-NX C18 75*30 mm*3 um; mobile phase: [water (0.225% FA)-ACN]; B %: 0%-30%, 7 min) to afford Compound 15CR (8.15 mg, 19.08 μmol, 3.34% yield) as a white solid (in cis and racemic form) and Compound 15TR (4.00 mg, 9.23 μmol, 1.61% yield) as a white solid (in trans and racemic form).

Compound 15CR: LCMS: Retention time: 0.877 min, (M+H)$^+$=396.2, 0-60AB_2 min_220&254. $^1$HNMR: (400 MHz, DMSO-$d_6$) δ=12.31 (br. s., 1H), 8.25 (s, 1H), 8.15 (s, 1H), 7.96 (s, 1H), 7.64-7.07 (m, 5H), 6.41 (d, J=6.0 Hz, 1H), 5.63 (d, J=4.8 Hz, 1H), 5.38-5.28 (m, 1H), 3.84 (s, 3H).

Compound 15TR: LCMS: Retention time: 0.925 min, (M+H)$^+$=396.2, 0-60AB_2 min_220&254. $^1$HNMR: (400 MHz, DMSO-$d_6$) δ=12.68-12.23 (m, 1H), 8.26 (s, 1H), 8.22-8.12 (m, 1H), 7.98 (s, 1H), 7.64-7.03 (m, 5H), 6.86-6.72 (m, 1H), 5.17-5.12 (m, 1H), 5.07-5.00 (m, 1H), 3.84 (s, 3H).

Step 5: General Procedure for Preparation of (3S,4R)-1-(1H-benzo[d]imidazol-5-yl)-4-(2,6-difluoro-4-(1-methyl-1H-pyrazol-4-yl)phenyl)-3-hydroxyazetidin-2-one (Compound 15A) and (3R,4S)-1-(1H-benzo[d]imidazol-5-yl)-4-(2,6-difluoro-4-(1-methyl-1H-pyrazol-4-yl)phenyl)-3-hydroxyazetidin-2-one (Compound 15B)

Compound 15CR (7 mg, 17.71 μmol, 1 eq) was prep-SFC (column: DAICEL CHIRALPAK IG (250 mm*30 mm, 10 um); mobile phase: [0.1% $NH_3 \cdot H_2O$ ETOH]; B %: %-60%, min) to afford Compound 15A (2.56 mg, 6.48 μmol, 36.57% yield) as a white solid and Compound 15B (2.89 mg, 7.04 μmol, 39.74% yield) as a white solid.

Compound 15A: SFC: Retention time: 1.831 min. LCMS: Retention time: 0.871 min, (M+H)$^+$=396.2, 0-60AB_2 min 220&254.

Compound 15B: SFC: Retention time: 4.851 min. LCMS: Retention time: 0.870 min, (M+H)$^+$=396.2, 0-60AB_2 min_220&254.

Example 13: Synthesis of Compounds 16CR and 16TR

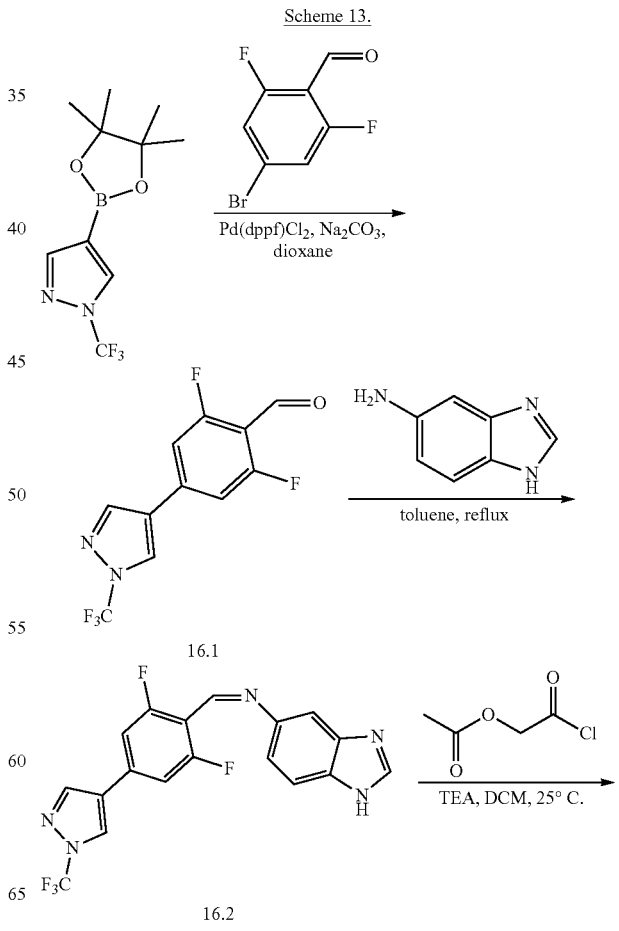

Scheme 13.

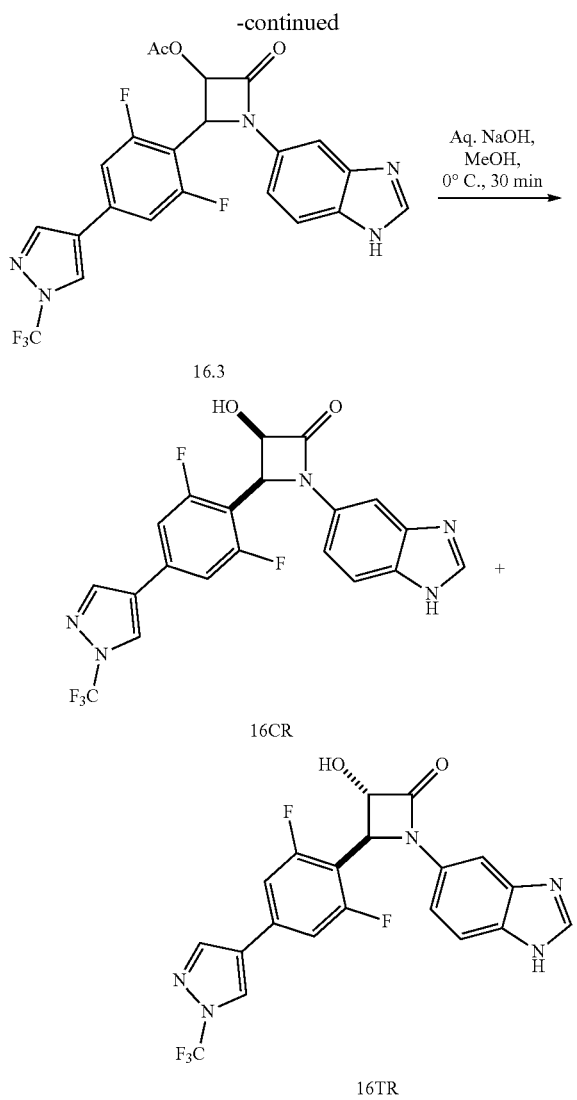

16.3

16CR

16TR

Step 1: General Procedure for Preparation of 2,6-difluoro-4-(1-(trifluoromethyl)-1H-pyrazol-4-yl)benzaldehyde To a mixture of 4-bromo-2,6-difluorobenzaldehyde (30 mg, 135.75 µmol, 1 eq), -(4,4,5,5-tetramethyl-1,3,2-dioxaborolan-2-yl)-1-(trifluoromethyl)-1H-pyrazole (35.57 mg, 135.75 µmol, 1 eq), K$_2$CO$_3$ (56.28 mg, 407.25 µmol, 3 eq) in dioxane (0.5 mL) and H$_2$O (0.1 mL) was added Pd(dppf)Cl$_2$ (9.93 mg, 13.58 µmol, 0.1 eq) under N$_2$ atmosphere. The suspension was degassed and purged with N$_2$ for 3 times. The mixture was stirred under N$_2$ at 100° C. for 0.5 hours under MW. The reaction mixture was concentrated under reduced pressure and purified by flash silica gel chromatography (ISCO®; 4 g SepaFlash® Silica Flash Column, Eluent of 0~10% Ethyl acetate/Petroleum ether gradient @ 12 mL/min). 2,6-difluoro-4-(1-(trifluoromethyl)-1H-pyrazol-4-yl)benzaldehyde (10 mg, 36.21 µmol, 26.67% yield) was obtained as a white solid.

$^1$HNMR: (400 MHz, DMSO-d$_6$) δ=10.19 (s, 1H), 9.29 (s, 1H), 8.67 (s, 1H), 7.84-7.67 (m, 2H).

Step 2: General Procedure for Preparation of N-(1H-benzo[d]imidazol-5-yl)-1-(2,6-difluoro-4-(1-(trifluoromethyl)-1H-pyrazol-4-yl)phenyl)methanimine A mixture of 2,6-difluoro-4-(1-(trifluoromethyl)-1H-pyrazol-4-yl)benzaldehyde (200 mg, 724.21 µmol, 1 eq), 1H-benzo[d]imidazol-5-amine (96.43 mg, 724.21 µmol, 1 eq) in toluene (10 mL) was degassed and purged with N$_2$ for 3 times and then the mixture was stirred at 120° C. for 12 hours under N$_2$ atmosphere. The mixture was concentrated under reduced pressure to give a residue. The residue was slurried in PE:EA=1:1 (30 mL) and filtered. The solid was collected. N-(1H-benzo[d]imidazol-5-yl)-1-(2,6-difluoro-4-(1-(trifluoromethyl)-1H-pyrazol-4-yl)phenyl)methanimine (250 mg, 638.90 µmol, 88.22% yield) was obtained as a white solid.

$^1$HNMR: (400 MHz, DMSO-d$_6$) δ=12.52 (br s, 1H), 9.25 (s, 1H), 8.72 (br s, 1H), 8.67 (s, 1H), 8.24 (br s, 1H), 7.75 (d, J=10.3 Hz, 2H), 7.71-7.12 (m, 3H).

Step 3: General Procedure for Preparation of 1-(1H-benzo[d]imidazol-5-yl)-2-(2,6-difluoro-4-(1-(trifluoromethyl)-1H-pyrazol-4-yl)phenyl)-4-oxoazetidin-3-yl acetate 2-Chloro-2-oxoethyl acetate (41.87 mg, 306.67 µmol, 32.97 µL, 2 eq) was added dropwise to a solution of (Z)—N-(1H-benzo[d]imidazol-5-yl)-1-(2,6-difluoro-4-(1-(trifluoromethyl)-1H-pyrazol-4-yl)phenyl)methanimine (60 mg, 153.34 µmol, 1 eq) and TEA (46.55 mg, 460.01 µmol, 64.03 µL, 3 eq) in DCM (1.5 mL) at 25° C. The reaction mixture was stirred for 1 hour at 25° C. The reaction mixture was combined with another batch of reaction mixture (2 equivalents). The combined mixture was concentrated under reduced pressure and purified by flash silica gel chromatography (ISCO®; 4 g Sepa Flash® Silica Flash Column, Eluent of 0~100% Ethyl acetate/Petroleum ether gradient @ 55 mL/min). The title compound (35 mg, crude) was obtained as a yellow solid.

LCMS: Retention time: 1.785 min, (M+H)$^+$=492.2, 10-80CD_3 min_220&254.

Step 4: General Procedure for Preparation of (cis and racemic)-1-(1H-benzo[d]imidazol-5-yl)-4-(2,6-difluoro-4-(1-methyl-1H-pyrazol-4-yl)phenyl)-3-hydroxyazetidin-2-one and (trans and racemic)-1-(1H-benzo[d]imidazol-5-yl)-4-(2,6-difluoro-4-(1-methyl-1H-pyrazol-4-yl)phenyl)-3-hydroxyazetidin-2-one To a solution of Compound 16.3 (10 mg, 20.35 µmol, 1 eq) in MeOH (1 mL) and H$_2$O (1 mL) was added NaOH (16.28 mg, 40.70 µmol, 16.28 µL, 10% purity, 2 eq) at 0° C. The mixture was stirred at 0° C. for 5 min. The mixture was diluted with ethyl acetate (20 mL) and washed with H$_2$O (5 mL×2), brine (20 mL), dried over anhydrous Na$_2$SO$_4$, filtered and concentrated under reduced pressure. The residue was purified by prep-HPLC (column: Phenomenex Gemini-NX 80*40 mm*3 um; mobile phase: [water (0.05% NH$_3$·H$_2$O)-ACN]; B %: 30%-60%, 8 min) to afford Compound 16CR (0.51 mg, 1.14 µmol, 5.58% yield) as a white solid (in cis and racemic form) and Compound 16TR (0.40 mg, 0.861 µmol, 4.23% yield) as a white solid (in trans and racemic form).

Compound 16CR: LCMS: Retention time: 1.564 min, (M+H)$^+$=450.1, 10-80CD_3 min_220&254. $^1$HNMR: (400

MHz, DMSO-$d_6$) δ=12.61-12.24 (m, 1H), 9.12 (s, 1H), 8.55 (s, 1H), 8.20-8.14 (m, 1H), 7.68-7.10 (m, 5H), 6.50-6.42 (m, 1H), 5.67 (d, J=5.2 Hz, 1H), 5.38-5.31 (m, 1H).

Compound 16TR: LCMS: Retention time: 1.595 min, (M+H)$^+$=450.0, 10-80CD_3 min_220&254. $^1$HNMR: (400 MHz, DMSO-$d_6$) δ=12.57-12.19 (m, 1H), 9.28-9.01 (m, 1H), 8.69-8.45 (m, 1H), 8.21-8.13 (m, 1H), 7.70-7.03 (m, 5H), 6.87-6.80 (m, 1H), 5.20-5.17 (m, 1H), 5.09-5.04 (m, 1H).

Example 14: Synthesis of Compounds 17A and 17B

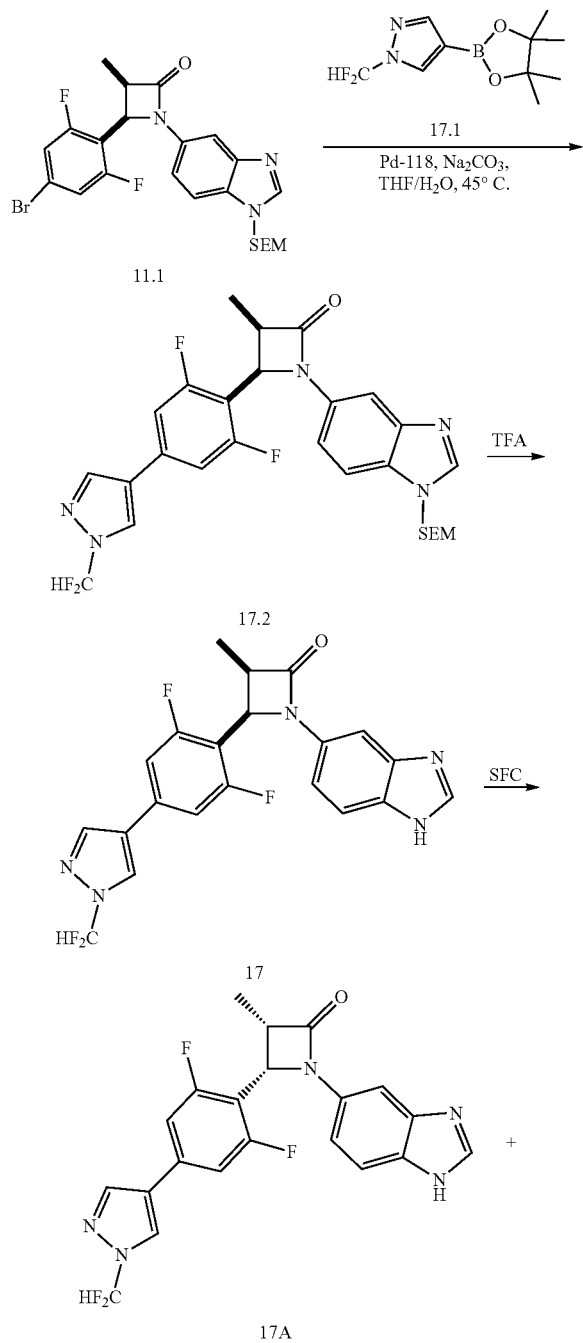

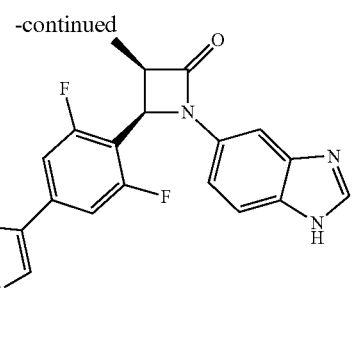

Step 1: General Procedure for Preparation of (cis and racemic)-4-(4-(1-(difluoromethyl)-1H-pyrazol-4-yl)-2,6-difluorophenyl)-3-methyl-1-(1-((2-(trimethyl silyl)ethoxy)methyl)-1H-benzo[d]imidazol-5-yl)azetidin-2-one A stir bar, (3R,4R)-4-(4-bromo-2,6-difluorophenyl)-3-methyl-1-(1-((2-(trimethylsilyl)ethoxy)methyl)-1H-benzo[d]imidazol-5-yl)azetidin-2-one (2 g, 3.83 mmol, 1 eq), 1-(difluoromethyl)-4-(4,4,5,5-tetramethyl-1,3,2-dioxaborolan-2-yl)-1H-pyrazole (1.40 g, 5.74 mmol, 1.5 eq), Na$_2$CO$_3$ (405.73 mg, 3.83 mmol, 1 eq) in H$_2$O (3 mL) and THF (18 mL) were added to a 100 mL round-bottomed flask of before sparged with N$_2$ for 5 minutes, then treated with dichloro[1,1'-bis(di-tert-butylphosphino)ferrocene]palladium(II) (374.24 mg, 574.21 μmol, 0.15 eq). The mixture was sparged with N$_2$ for another 5 minutes and then stirred at 45° C. for 3 hr. The reaction mixture was filtered, and the filtrate was concentrated under reduced pressure. The residue was purified by flash silica gel chromatography (ISCO®; 12 g SepaFlash® Silica Flash Column, Eluent of 0~50% Ethyl acetate/Petroleum ether gradient @ 80 mL/min). The title compound (1.2 g, 1.76 mmol, 46.02% yield) was obtained as a yellow oil.

LCMS: Retention time: 1.121 min, (M+H)=560.3, 10-80AB_2 min_Agilent.

Step 2: General Procedure for Preparation of (cis and racemic)-1-(1H-benzo[d]imidazol-5-yl)-4-(4-(1-(difluoromethyl)-1H-pyrazol-4-yl)-2,6-difluorophenyl)-3-methyl azetidin-2-one To a solution of (cis and racemic)-4-(4-(1-(difluoromethyl)-1H-pyrazol-4-yl)-2,6-difluorophenyl)-3-methyl-1-(1-((2-(trimethyl silyl)ethoxy)methyl)-1H-benzo[d]imidazol-5-yl)azetidin-2-one (1.2 g, 2.14 mmoL, 1 eq) in DCM (10 mL) was added TFA (5 mL). The mixture was stirred at 25° C. for 8 hrs. The reaction mixture was diluted with DCM (50 mL), basified with aqueous NaHCO$_3$ (1N) to pH=8~9 and extracted with DCM (100 mL×3). The organic layer was dried over anhydrous Na$_2$SO$_4$, filtered and concentrated under reduced pressure to give the crude product as a yellow oil. The residue was purified by prep-HPLC (column: Phenomenex Genimi NX 80*40 mm*3 um; mobile phase: [water (0.05% NH$_3$·H$_2$O)-ACN]; B %: 35%-65%, 8 min). The title compound (60 mg, 139.74 μmoL, 6.52% yield) was obtained as a white solid.

LCMS: Retention time: 0.893 min, (M+H)=430.2, 10-80AB_2 min_Agilent.

¹HNMR: (400 MHz, DMSO-d₆) δ=12.68-12.10 (m, 1H), 8.87 (s, 1H), 8.37 (s, 1H), 8.20-8.10 (m, 1H), 8.02-7.67 (m, 1H), 7.56 (br d, J=8.5 Hz, 1H), 7.50-7.40 (m, 1H), 7.37-7.27 (m, 1H), 7.10 (d, J=10.6 Hz, 1H), 5.70-5.65 (m, 1H), 5.67 (d, J=6.0 Hz, 1H), 4.04-3.85 (m, 1H), 1.02 (d, J=7.5 Hz, 3H).

Step 3: General Procedure for Preparation of (3S, 4S)-1-(1H-benzo[d]imidazol-5-yl)-4-(4-(1-(difluoromethyl)-1H-pyrazol-4-yl)-2,6-difluorophenyl)-3-methylazetidin-2-one (Compound 17A) and (3R, 4R)-1-(1H-benzo[d]imidazol-5-yl)-4-(4-(1-(difluoromethyl)-1H-pyrazol-4-yl)-2,6-difluorophenyl)-3-methylazetidin-2-one (Compound 17B)

Compound 17 (40 mg) was purified by SFC (column: DAICEL CHIRALPAK AD (250 mm*30 mm, 10 um); mobile phase: [0.1% NH₃·H₂O ETOH]; B %: 25%-25%, min) to afford Compound 17A (12.83 mg, 29.53 μmoL, 41.31% yield) as a white solid and Compound 17B (15.12 mg, 34.38 μmoL, 48.10% yield) as a white solid.

Compound 17A: SFC: Retention time: 1.437 min. LCMS: Retention time: 0.709 min, (M+H)=430.1, 5-95AB_220&254_Agilent.M ¹H NMR: (400 MHz, DMSO-d₆) δ=12.54-12.21 (m, 1H), 8.87 (s, 1H), 8.39-8.35 (m, 1H), 8.19-8.12 (m, 1H), 8.02-7.68 (m, 1H), 7.66-7.06 (m, 5H), 5.68 (d, J=5.8 Hz, 1H), 3.99-3.85 (m, 1H), 1.03 (d, J=7.6 Hz, 3H).

Compound 17B: SFC: Retention time: 1.552 min. LCMS: Retention time: 0.792 min (M+H)=430.1, 5-95AB_220&254_Agilent.M ¹H NMR: (400 MHz, DMSO-d₆) δ=12.55-12.19 (m, 1H), 8.89-8.84 (m, 1H), 8.39-8.35 (m, 1H), 8.18-8.11 (m, 1H), 8.02-7.69 (m, 1H), 7.67-7.02 (m, 5H), 5.68 (d, J=5.8 Hz, 1H), 4.02-3.86 (m, 1H), 1.03 (d, J=7.6 Hz, 3H).

Example 15: Synthesis of Compounds 18A and 18B

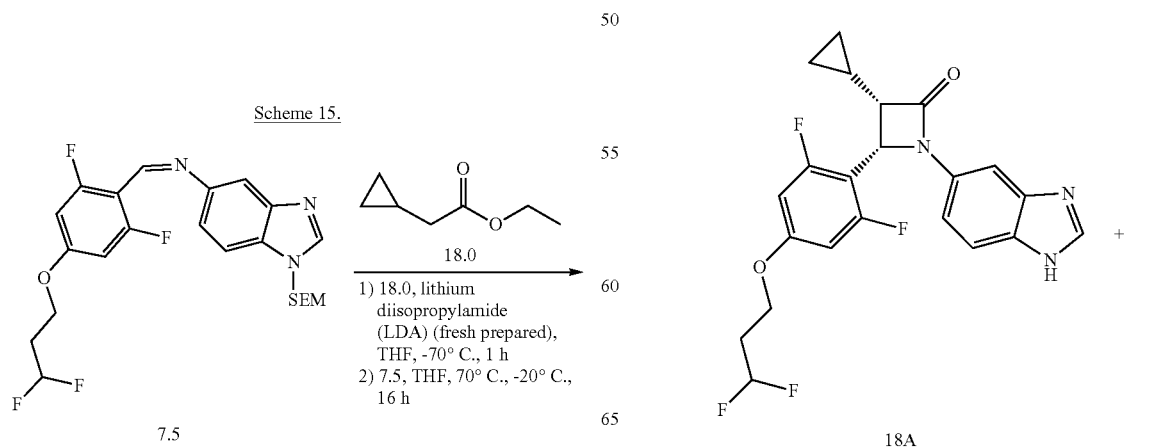

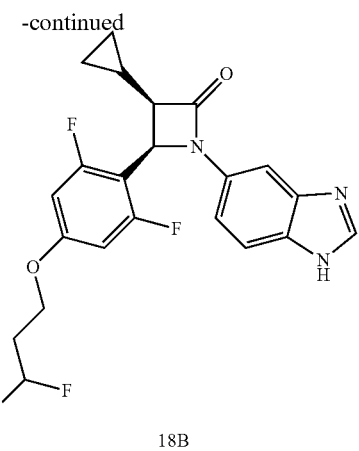

18B

Step 1: General Procedure for Preparation of (cis and racemic)-3-cyclopropyl-4-(4-(3,3-difluoropropoxy)-2,6-difluorophenyl)-1-(1-((2-(trimethylsilyl)ethoxy)methyl)-1H-benzo[d]imidazol-5-yl)azetidin-2-one To a solution of N-isopropylpropan-2-amine (81.95 mg, 809.87 μmol, 114.46 μL, 1.3 eq) in THF (1.5 mL) was added BuLi (2.5 M, 299.03 μL, 1.2 eq) at −70° C. under Ar. The mixture was stirred at −70° C. for 1 h. A mixture of ethyl 2-cyclopropylacetate (79.85 mg, 622.98 μmol, 1 eq) in THF (0.1 mL) was added at −70° C. under Ar and the mixture was stirred at −70° C. for 1 h. A mixture of (Z)-1-(4-(3,3-difluoropropoxy)-2,6-difluorophenyl)-N-(1-((2-(trimethylsilyl)ethoxy)methyl)-1H-benzo[d]imidazol-5-yl)methanimine (300 mg, 622.98 μmol, 1 eq) in THF (0.5 mL) was added at −70° C. under Ar and the mixture was stirred at −20° C. for 16 hrs. The mixture was adjusted to pH=7~8 with aqueous HCl (1N) and extracted with ethyl acetate (20 mL*3). The combined organic extracts were dried over anhydrous Na₂SO₄, filtered and concentrated under reduced pressure. The residue was purified by flash silica gel chromatography (ISCO®; 20 g SepaFlash® Silica Flash Column, Eluent of 0~50% Ethyl acetate/Petroleum ether gradient @ 35 mL/min). The title compound (200 mg, crude) was obtained as a brown solid.

LCMS: Retention time: 3.912 min, (M+H)=564.0, 10-80AB_7 min_220&254_Shimadzu.

Step 2: General Procedure for Preparation of (cis and racemic)-1-(1H-benzo[d]imidazol-5-yl)-3-cyclopropyl-4-(4-(3,3-difluoropropoxy)-2,6-difluorophenyl)azetidin-2-one TFA (1.54 g, 13.51 mmol, 1 mL, 38.06 eq) was added to a mixture of Compound 18.1 (200 mg, 354.83 μmol, 1 eq) and DCM (2 mL) and then the mixture was stirred at 20° C. for 2 hours. The reaction mixture was concentrated to dryness under reduced pressure and diluted with MeOH (5 mL). NH₃/MeOH (7 M, 1 mL) was added. The resultant solution was stirred at room-temperature for 10 min. The resultant solution was concentrated to dryness under reduced pressure and purified by prep-HPLC (column: Welch Xtimate C18 150*30 mm*5 um; mobile phase: [water (NH₃H₂O+NH₄HCO₃)-ACN]; B %: 40%-70%, 9 min). Compound 18CR (15.52 mg, 34.75 μmol, 9.79% yield) was obtained as a white solid (in cis and racemic form).

LCMS: Retention time: 0.846 min, (M+H)=434.2, 5-95AB_220&254.

¹H NMR (400 MHz, DMSO-d₆) δ=8.16 (s, 1H), 7.64-7.05 (m, 3H), 7.00-6.59 (m, 2H), 6.39-6.02 (m, 1H), 5.55 (d, J=5.8 Hz, 1H), 4.14 (t, J=6.0 Hz, 2H), 3.32-3.29 (m, 1H), 2.38-2.23 (m, 2H), 0.75-0.63 (m, 1H), 0.56-0.47 (m, 1H), 0.44-0.36 (m, 1H), 0.25-0.14 (m, 1H), 0.08--0.01 (m, 1H).

Step 3: General Procedure for Preparation of (3S,4S)-1-(1H-benzo[d]imidazol-5-yl)-3-cyclopropyl-4-(4-(3,3-difluoropropoxy)-2,6-difluorophenyl)azetidin-2-one (Compound 18A) and (3R,4R)-1-(1H-benzo[d]imidazol-5-yl)-3-cyclopropyl-4-(4-(3,3-difluoropropoxy)-2,6-difluorophenyl)azetidin-2-one (Compound 18B)

Compound 18CR (14.52 mg, 33.50 μmol, 1 eq) was purified by SFC (column: Phenomenex-Cellulose-2 (250 mm*30 mm, 10 um); mobile phase: [0.1% NH₃·H₂O ETOH]; B %: 40%-40%, min) to afford Compound 18A (4.46 mg, 10.14 μmol, 30.28% yield) as a white solid and Compound 18B (5.76 mg, 12.94 μmol, 38.62% yield) as a white solid.

Compound 18A: SFC: Retention time: 0.918 min. LCMS: Retention time: 0.757 min, (M+H)+=434.2, 5-95AB_220&254_Agilent.

Compound 18B: SFC: Retention time: 1.864 min. LCMS: Retention time: 0.756 min, (M+H)+=434.2, 5-95AB_220&254_Agilent.

Example 16: Synthesis of Compounds 35A and 35B (using similar procedures to compound 11, see Example 6)

Scheme 16.

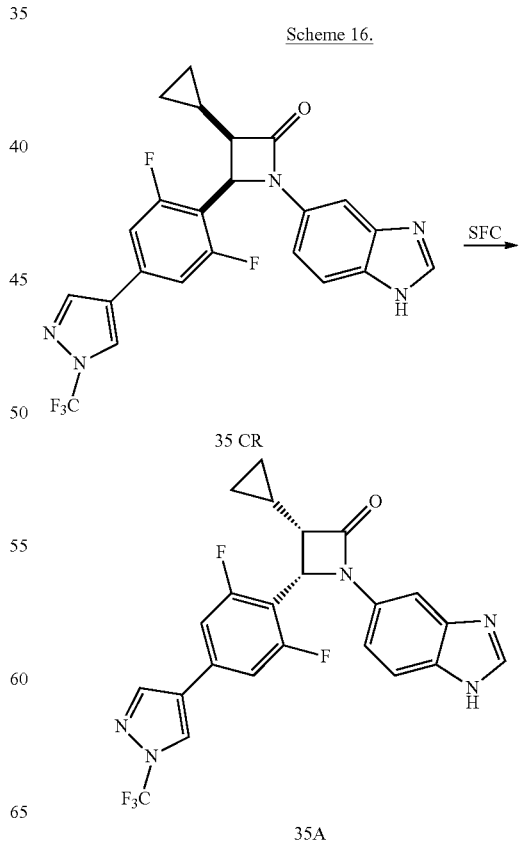

35 CR

35A

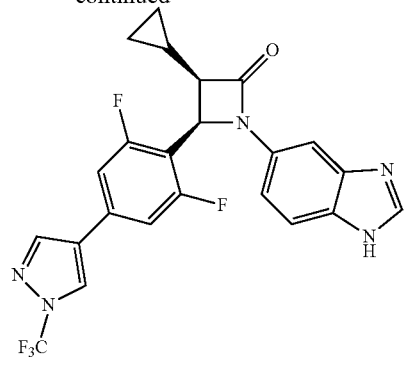

35B (3S,4S)-3-cyclopropyl-4-{2,6-difluoro-4-[1-(trifluoromethyl)pyrazol-4-yl]phenyl}-1-(1H-benzo[d]imidazol-5-yl)azetidin-2-one (Compound 35A) and (3R,4R)-3-cyclopropyl-4-{2,6-difluoro-4-[1-(trifluoromethyl)pyrazol-4-yl]phenyl}-1-(1H-benzo[d]imidazol-5-yl)azetidin-2-one (Compound 35B)

Compound 35A: SFC: Retention time: 1.429 min. LCMS: Retention time: 0.850 min, (M+H)=474.1, 5-95AB_220&254_Agilent. $^1$H NMR (400 MHz, DMSO-$d_6$) δ=12.39 (br s, 1H), 9.12 (s, 1H), 8.56 (s, 1H), 8.17 (s, 1H), 7.79-7.19 (m, 5H), 5.64 (d, J=5.8 Hz, 1H), 3.40-3.39 (m, 1H), 0.76-0.64 (m, 1H), 0.56-0.47 (m, 1H), 0.45-0.37 (m, 1H), 0.23-0.15 (m, 1H), 0.11-0.02 (m, 1H).

Compound 35B: SFC: Retention time: 2.431 min. LCMS: Retention time: 0.852 min, (M+H)=474.1, 5-95AB_220&254_Agilent. $^1$H NMR (400 MHz, DMSO-$d_6$) δ=12.49-12.24 (m, 1H), 9.12 (s, 1H), 8.56 (s, 1H), 8.21-8.12 (m, 1H), 7.81-7.08 (m, 5H), 5.64 (d, J=5.8 Hz, 1H), 3.43-3.42 (m, 1H), 0.75-0.64 (m, 1H), 0.56-0.47 (m, 1H), 0.45-0.37 (m, 1H), 0.24-0.14 (m, 1H), 0.11-0.01 (m, 1H).

Example 16B: Synthesis of Compound 35B

Scheme 16B.

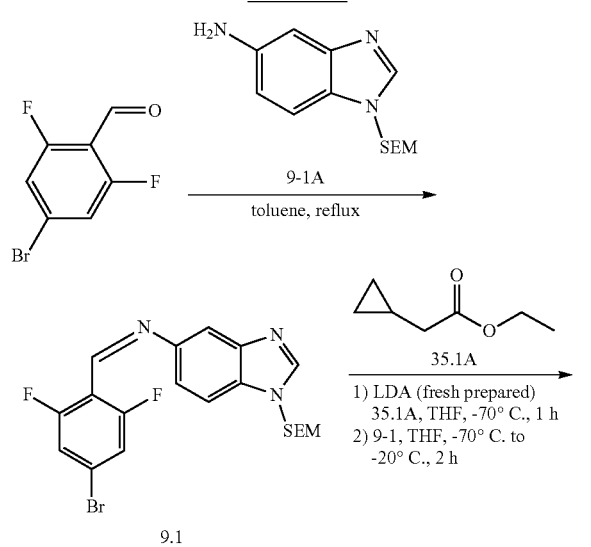

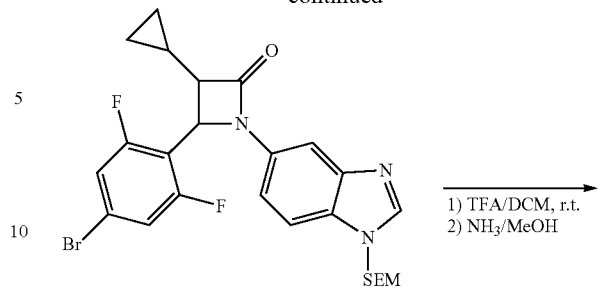

35.1

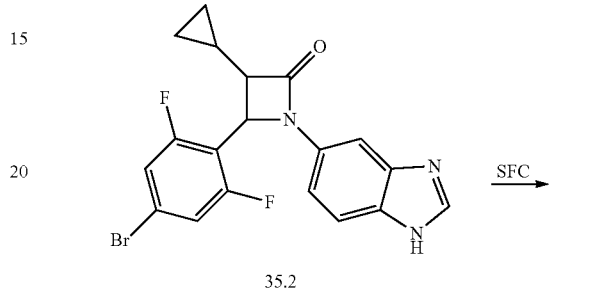

35.2

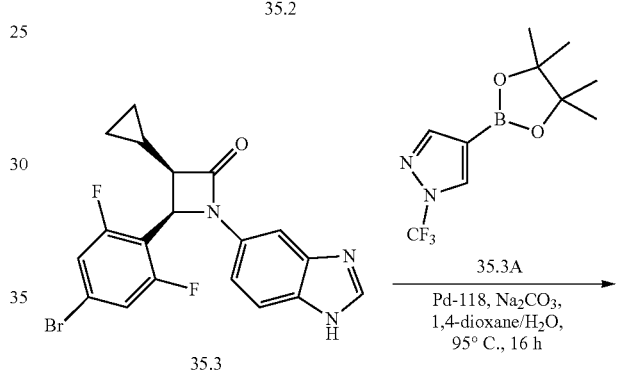

35.3

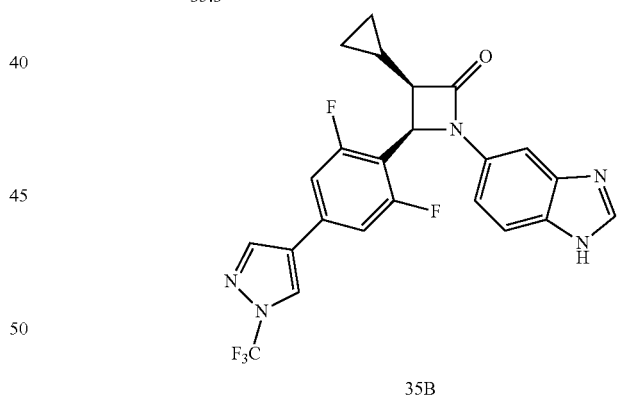

35B

Step 1: General Procedure for Preparation of 1-(4-bromo-2,6-difluorophenyl)-N-(1-((2-(trimethylsilyl)ethoxy)methyl)-1H-benzo[d]imidazol-5-yl)methanimine A mixture of 4-bromo-2,6-difluorobenzaldehyde (2.68 g, 12.15 mmol, 1 eq), Compound 9.1A (3.2 g, 12.15 mmol, 1 eq) in toluene (40 mL) was degassed and purged with N$_2$ for 3 times, and then the mixture was stirred at 120° C. for 12 hrs under N$_2$ atmosphere. The mixture was concentrated under reduced pressure and purified by flash silica gel chromatography (ISCO®; 40 g SepaFlash® Silica Flash Column, Eluent of 0~60% Ethyl acetate/Petroleum ether gradient @ 60 mL/min) to afford Compound 9.1 (4.7 g, 10.08 mmol, 82.95% yield) as a brown oil was obtained.

$^1$HNMR: (400 MHz, DMSO-$d_6$) 8.70 (s, 1H), 8.40 (d, J=6.4 Hz, 1H), 7.79-7.53 (m, 4H), 7.39-7.19 (m, 1H), 5.66 (d, J=7.2 Hz, 2H), 3.58-3.41 (m, 2H), 0.84 (t, J=8.0 Hz, 2H), 0.11--0.30 (m, 9H).

Step 2: General Procedure for Preparation of (racemic)-4-(4-bromo-2,6-difluorophenyl)-3-cyclopropyl-1-(1-((2-(trimethylsilyl)ethoxy)methyl)-1H-benzo[d]imidazol-5-yl)azetidin-2-one To a solution of N-isopropylpropan-2-amine (1.25 g, 12.33 mmol, 1.74 mL, 1.15 eq) in THF (20 mL) was added n-BuLi (2.5 M, 4.50 mL, 1.05 eq) at −70° C. under Ar. The mixture was stirred at −70° C. for 1 hour. Compound 9.1 (1.37 g, 10.72 mmol, 1 eq) in THF (2 mL) was added to the mixture at −70° C. under Ar and the mixture was stirred at −70° C. for 1 hour. Compound 35.1A (5 g, 10.72 mmol, 1 eq) in THF (10 mL) was added to the mixture at −70° C. under Ar and the mixture was stirred at −70 to −20° C. for 2 hours. The mixture was adjusted to pH=7-8 with 2N HCl. $H_2O$ (20 mL) was added and the mixture was extracted with ethyl acetate (80 mL*3). The combined organic extracts were dried over anhydrous $Na_2SO_4$, filtered and concentrated under reduced pressure. The crude was purified by flash silica gel chromatography (ISCO®; 40 g SepaFlash® Silica Flash Column, Eluent of 0~80% Ethyl acetate/Petroleum ether gradient @ 50 mL/min). Compound 35.1 (3.7 g, 6.57 mmol, 61.28% yield) as a brown oil was obtained.

LCMS: Retention time: 0.98 min, (M+H)=548.1&550.1, 5-95AB_220&254_Agilent

Step 3: General Procedure for Preparation of (racemic)-1-(1H-benzo[d]imidazol-5-yl)-4-(4-bromo-2,6-difluorophenyl)-3-cyclopropylazetidin-2-one TFA (10 mL) was added to a mixture of Compound 35.1 (3.7 g, 6.75 mmol, 1 eq) in DCM (20 mL) and the mixture was stirred at 25° C. for 16 hours. The reaction solution was concentrated to dryness under reduced pressure. The crude was diluted with methanol (10 mL) and then ammonia 7 M in methanol (2 mL) was added. The resultant solution was stirred at room-temperature for 2 min. The resultant solution was concentrated, quenched by addition $NaHCO_3$ (50 mL) and extracted with ethyl acetate (30 mL*3). The combined organic layers were dried over $Na_2SO_4$, filtered and concentrated under reduced pressure. The residue was purified by flash silica gel chromatography (ISCO®; 40 g SepaFlash® Silica Flash Column, Eluent of 0~100% Ethyl acetate/Petroleum ether gradient @ 30 mL/min). Compound 35.2 (2.3 g, 4.82 mmol, 71.46% yield) was obtained.

LCMS: Retention time: 0.73 min, (M+H)=418.1&420.1, 5-95AB_220&254_Agilent

Step 4: General Procedure for Preparation of (3R, 4R)-1-(1H-benzo[d]imidazol-5-yl)-4-(4-bromo-2,6-difluorophenyl)-3-cyclopropylazetidin-2-one Compound 35.2 (40 g, 95.64 mmol) was purified by SFC (column: Phenomenex-Cellulose-2 (250 mm*50 mm, 10 um); mobile phase: [0.1% $NH_3·H_2O$ ETOH]; B %: 55%-55%, min). Compound 35.3 (11.5 g, 27.50 mmol, 28.75% yield) was obtained.

LCMS: Retention time: 0.81 min, (M+H)=418.0&420.0, 5-95AB_220&254_Agilent

H NMR (400 MHz, DMSO-$d_6$) δ=12.35 (br s, 1H), 8.16 (s, 1H), 7.75-7.10 (m, 5H), 5.61 (d, J=5.8 Hz, 1H), 3.41-3.37 (m, 1H), 0.70-0.59 (m, 1H), 0.54-0.45 (m, 1H), 0.39 (qd, J=4.8, 9.4 Hz, 1H), 0.24-0.15 (m, 1H), 0.06 (qd, J=4.8, 9.6 Hz, 1H)

Step 5: General Procedure for Preparation of (3R, 4R)-1-(1H-benzo[d]imidazol-5-yl)-3-cyclopropyl-4-(2,6-difluoro-4-(1-(trifluoromethyl)-1H-pyrazol-4-yl)phenyl)azetidin-2-one (Compound 35B)

Compound 35.3 (3.50 g, 8.37 mmol, 1 eq), Compound 35.3A (2.30 g, 8.79 mmol, 1.05 eq), Pd-118 (1.09 g, 1.67 mmol, 0.2 eq), $Na_2CO_3$ (2.22 g, 20.92 mmol, 2.5 eq) and 1,4-dioxane (30 mL), $H_2O$ (6 mL) was degassed and purged with $N_2$ for 3 times, and then the mixture was stirred at 95° C. for 16 hours under $N_2$ atmosphere. The reaction mixture was quenched by addition $H_2O$ (60 mL) and extracted with EA (30 mL*3). The combined organic layers were dried over $Na_2SO_4$, filtered and concentrated under reduced pressure. The residue was purified by flash silica gel chromatography (ISCO®; 20 g SepaFlash® Silica Flash Column, Eluent of 0~100% Ethyl acetate/Petroleum ether gradient @ 30 mL/min) and combined with another Batch (0.57 equivalents). The combined product was further purified by reversed-phase HPLC ($H_2O$/MeCN condition). Compound 35B (3.3 g, 6.82 mmol) was obtained.

LCMS: Retention time: 0.758 min, (M+H)=474.1, 5-95AB_220&254_Agilent $^1$H NMR: (400 MHz, DMSO-$d_6$) δ=12.51-12.25 (m, 1H), 9.13 (s, 1H), 8.56 (s, 1H), 8.22-8.10 (m, 1H), 7.83-7.07 (m, 5H), 5.64 (d, J=5.8 Hz, 1H), 3.43-3.39 (m, 1H), 0.76-0.64 (m, 1H), 0.56-0.47 (m, 1H), 0.45-0.37 (m, 1H), 0.24-0.14 (m, 1H), 0.11-0.02 (m, 1H).

Example 17: Synthesis of Compounds 42A and 42B (Using Similar Procedures to Compound 11, See Example 6)

Scheme 17.

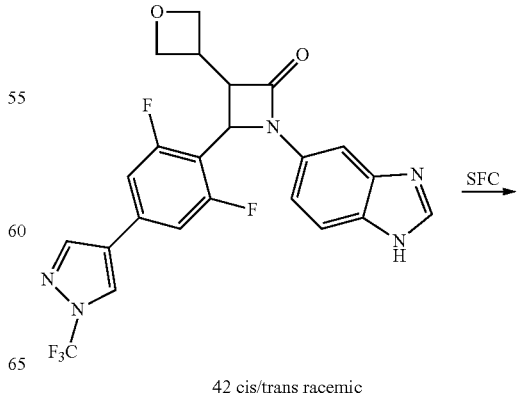

42 cis/trans racemic

-continued

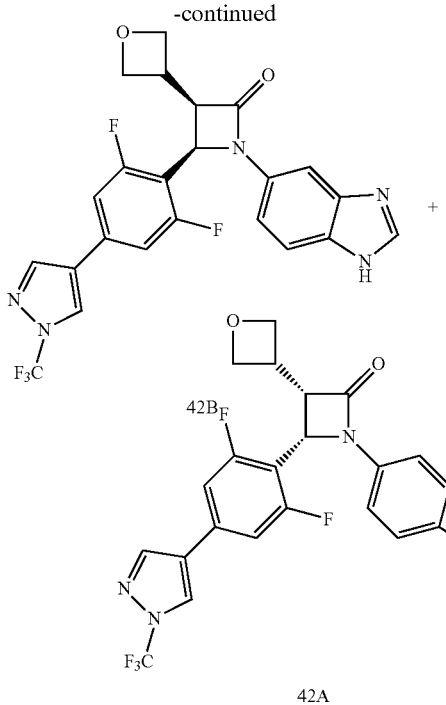

42A (3R,4R)-1-(1H-benzo[d]imidazol-5-yl)-4-(2,6-difluoro-4-(1-(trifluoromethyl)-1H-pyrazol-4-yl)phenyl)-3-(oxetan-3-yl)azetidin-2-one (Compound 42B) and (3S,4S)-1-(1H-benzo[d]imidazol-5-yl)-4-(2,6-difluoro-4-(1-(trifluoromethyl)-1H-pyrazol-4-yl)phenyl)-3-(oxetan-3-yl)azetidin-2-one (Compound 42A)

Compound 42B: SFC: Retention time: 2.033 min. LCMS: Retention time: 0.656 min, (M+H)=490.1, 5-95AB_220&254_Agilent. H NMR: (400 MHz, DMSO-$d_6$) δ=12.32 (br s, 1H), 9.13 (s, 1H), 8.56 (s, 1H), 8.16 (s, 1H), 7.84-7.04 (m, 5H), 5.73 (d, J=5.8 Hz, 1H), 4.70-4.54 (m, 2H), 4.49-4.37 (m, 1H), 4.29-4.13 (m, 2H), 3.19-3.04 (m, 1H).

Compound 42A: SFC: Retention time: 2.865 min. LCMS: Retention time: 0.661 min, (M+H)=490.1, 5-95AB_220&254_Agilent. H NMR: (400 MHz, DMSO-$d_6$) δ=12.86-11.76 (m, 1H), 9.13 (s, 1H), 8.56 (s, 1H), 8.16 (s, 1H), 7.82-7.47 (m, 3H), 7.41 (br s, 1H), 7.18 (br s, 1H), 5.73 (d, J=5.8 Hz, 1H), 4.72-4.52 (m, 2H), 4.48-4.36 (m, 1H), 4.32-4.13 (m, 2H), 3.19-3.02 (m, 1H).

Example 18: Synthesis of Compounds 43A and 43B (Using Similar Procedures to Compound 11, see Example 6)

Scheme 18.

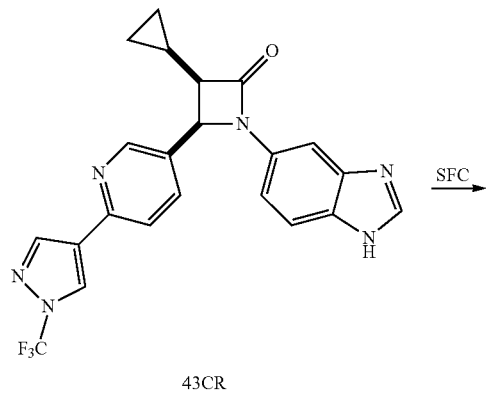

43CR

→ SFC

-continued

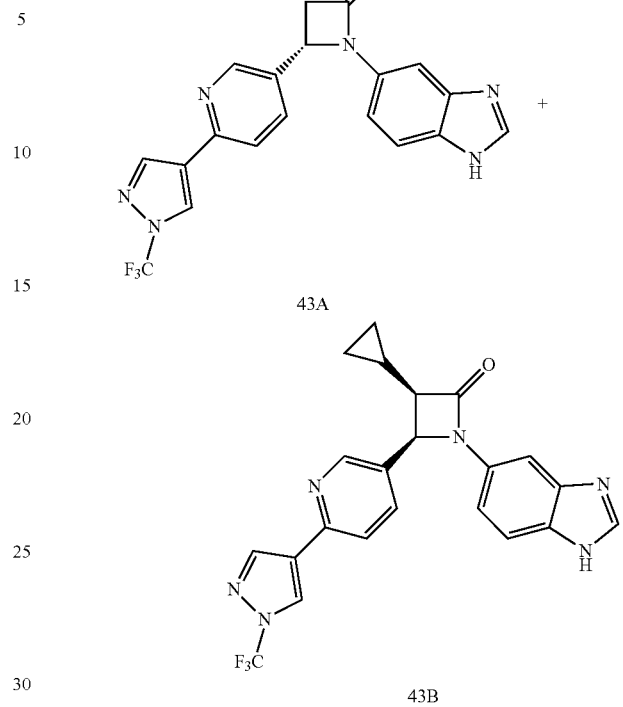

43A

43B (3S,4S)-1-(1H-benzo[d]imidazol-5-yl)-3-cyclopropyl-4-(6-(1-(trifluoromethyl)-1H-pyrazol-4-yl)pyridin-3-yl)azetidin-2-one (Compound 43A) and (3R,4R)-1-(1H-benzo[d]imidazol-5-yl)-3-cyclopropyl-4-(6-(1-(trifluoromethyl)-1H-pyrazol-4-yl)pyridin-3-yl)azetidin-2-one (Compound 43B)

Compound 43A: SFC: Retention time: 3.090 min. LCMS: Retention time: 0.790 min, (M+H)=439.1, 5-95AB_220&254_Agilent. $^1$H NMR (400 MHz, DMSO-$d_6$) δ=12.54-12.27 (m, 1H), 9.07 (s, 1H), 8.61 (br. s., 1H), 8.50 (s, 1H), 8.17 (d, J=11.4 Hz, 1H), 7.89-7.76 (m, 2H), 7.63-7.11 (m, 3H), 5.52 (d, J=5.7 Hz, 1H), 3.52-3.44 (m, 1H), 0.54-0.33 (m, 3H), 0.20-0.05 (m, 2H).

Compound 43B: SFC: Retention time: 3.298 min. LCMS: Retention time: 0.790 min, (M+H)=439.1, 5-95AB_220&254_Agilent. $^1$H NMR (400 MHz, DMSO-$d_6$) δ=12.55-12.25 (m, 1H), 9.07 (s, 1H), 8.61 (br. s., 1H), 8.50 (s, 1H), 8.17 (d, J=11.0 Hz, 1H), 7.88-7.76 (m, 2H), 7.63-7.12 (m, 3H), 5.52 (d, J=5.7 Hz, 1H), 3.52-3.44 (m, 1H), 0.55-0.33 (m, 3H), 0.22-0.04 (m, 2H).

Example 18B: Synthesis of Compounds 43B

Scheme 18B.

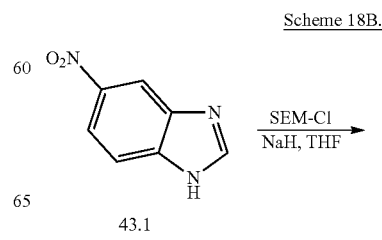

43.1

→ SEM-Cl / NaH, THF

-continued

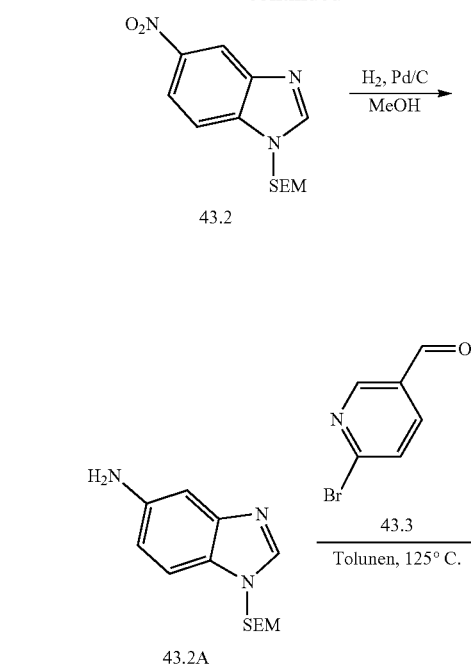

-continued

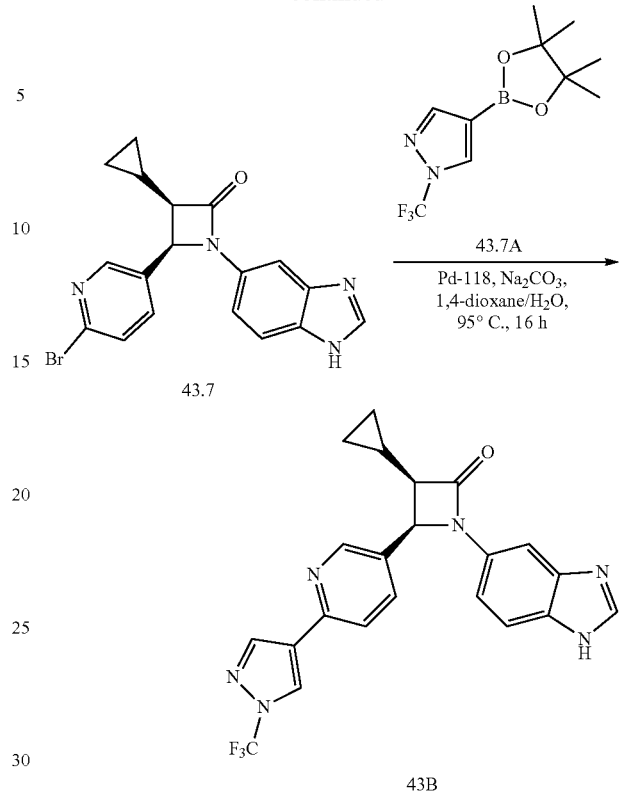

Step 1: General Procedure for Preparation of 5-nitro-1-((2-(trimethylsilyl)ethoxy)methyl)-1H-benzo[d]imidazole (Compound 43.2)

To a solution of Compound 43.1 (50 g, 306.50 mmoL, 1 eq) in THF (500 mL) was added SEM-Cl (62.34 g, 373.93 mmoL, 66.18 mL, 1.22 eq) at 0° C. and the mixture was stirred at 0° C. for 30 min. NaH (14.71 g, 367.80 mmoL, 60% purity, 1.2 eq) was added at 0° C. The mixture was stirred at 25° C. for 12 hours. The mixture was combined with other batch of the mixture (2 equivalents). The combined reaction mixture was quenched by addition water (1.5 L) at 0° C., diluted with ethyl acetate (1 L) and extracted with ethyl acetate 3 L (1 L*3). The combined organic layers were washed with Brine (400 mL*2), dried over anhydrous $Na_2SO_4$, filtered and concentrated under reduced pressure. The residue was purified by column chromatography ($SiO_2$, Petroleum ether/Ethyl acetate=10/1 to 1/1) to afford Compound 43.2 (235 g, 789.12 mmoL, 85.82% yield) as a brown oil.

LCMS: Retention time: 0.860 min, (M+H)=294.2, 5-95AB_220&254_Agilent.M $^1$H NMR (400 MHz, DMSO-$d_6$) δ=8.76-8.68 (m, 1H), 8.66-8.55 (m, 1H), 8.24-8.11 (m, 1H), 7.88 (dd, J=3.2, 8.9 Hz, 1H), 5.92-5.61 (m, 2H), 3.64-3.42 (m, 2H), 0.83 (t, J=8.0 Hz, 2H), −0.11 (d, J=3.0 Hz, 9H).

Step 2: General Procedure for Preparation of 1-((2-(trimethylsilyl)ethoxy)methyl)-1H-benzo[d]imidazol-5-amine To a solution of Compound 43.2 (60 g, 204.50 mmol, 1 eq) in MeOH (500 mL) was added Pd/C (21.76 g, 20.45 mmol, 10% purity, 0.1 eq) under Ar atmosphere. The suspension was degassed and purged with H₂ for 3 times. The mixture was stirred under H₂ (30 Psi) at 25° C. for 16 hours. The mixture was combined with other batch of the mixture (3 equivalents). The combined mixture was filtered and concentrated under reduced pressure to afford Compound 43.2A (200 g, crude) as a brown oil.

H NMR (400 MHz, DMSO-$d_6$) δ=8.15-7.91 (m, 1H), 7.28 (dd, J=8.7, 11.7 Hz, 1H), 6.84-6.66 (m, 1H), 6.65-6.51 (m, 1H), 5.46 (d, J=18.8 Hz, 2H), 5.02 (s, 1H), 4.79 (s, 1H), 3.50-3.41 (m, 2H), 0.83 (q, J=7.5 Hz, 2H), −0.08 (d, J=8.8 Hz, 9H)

Step 3: General Procedure for Preparation of 1-(6-bromopyridin-3-yl)-N-(1-((2-(trimethylsilyl)ethoxy)methyl)-1H-benzo[d]imidazol-5-yl)methanimine To a solution of Compound 43.2A (50 g, 189.82 mmol, 1 eq) in toluene (500 mL) was added Compound 43.3 (35.35 g, 190.05 mmol, 1 eq) and the mixture was stirred at 125° C. for 12 hours under N₂. The reaction mixture was concentrated under reduced pressure. The residue was purified by column chromatography (SiO₂, Petroleum ether/Ethyl acetate=0/1 to 1/1) to afford Compound 43.4 (55 g, 127.49 mmol, 67.17% yield) as a brown oil.

H NMR (400 MHz, DMSO-$d_6$) δ=8.87 (s, 1H), 8.82 (d, J=8.0 Hz, 1H), 8.40 (d, J=4.8 Hz, 1H), 8.27 (dd, J=2.3, 8.3 Hz, 1H), 7.81 (dd, J=4.5, 8.3 Hz, 1H), 7.74-7.64 (m, 2H), 7.43-7.28 (m, 1H), 5.65 (d, J=3.5 Hz, 2H), 3.51 (dt, J=3.1, 8.0 Hz, 2H), 0.84 (t, J=8.0 Hz, 2H), −0.03-−0.14 (m, 9H)

Step 4: General Procedure for Preparation of (cis and racemic)-4-(6-bromopyridin-3-yl)-3-cyclopropyl-1-(1-((2-(trimethylsilyl)ethoxy)methyl)-1H-benzo[d]imidazol-5-yl)azetidin-2-one To a solution of N-isopropylpropan-2-amine (1.35 g, 13.33 mmol, 1.88 mL, 1.15 eq) in THF (20 mL) was added n-BuLi (2.5 M, 4.87 mL, 1.05 eq) at −70° C. under Ar. The mixture was stirred at −70° C. for 1 hour. Compound 43.4A (1.49 g, 11.59 mmol, 1 eq) in THF (2 mL) was added to the mixture at −70° C. under Ar and the mixture was stirred at −70° C. for 1 hour. Compound 43.4 (5 g, 11.59 mmol, 1 eq) in THF (10 mL) was added to the mixture at −70° C. under Ar and the mixture was stirred at −20° C. for 2 hours. The mixture was combined with another batch of the mixture (1 equivalent). The mixture was adjusted to pH=7-8 with HCl (2N). H₂O (15 mL) was added and the mixture was extracted with ethyl acetate (50 mL*3). The combined organic extracts were dried over anhydrous Na₂SO₄, filtered and concentrated under reduced pressure. The crude was purified by flash silica gel chromatography (ISCO®; 40 g SepaFlash® Silica Flash Column, Eluent of 0~80% Ethyl acetate/Petroleum ether gradient @ 80 mL/min) to afford Compound 43.5 (10.5 g, 20.45 mmol, 88.21% yield) as a brown oil.

LCMS: Retention time: 0.921 min, (M+H)=514.9, 5-95AB_1.5 min_220&254_Shimadzu

Step 5: General Procedure for Preparation of (cis and racemic)-1-(1H-benzo[d]imidazol-5-yl)-4-(6-bromopyridin-3-yl)-3-cyclopropylazetidin-2-one To a solution of Compound 43.5 (5 g, 9.74 mmol, 1 eq) in DCM (30 mL) was added TFA (14.09 g, 123.53 mmol, 9.15 mL, 12.69 eq). The mixture was stirred at 25° C. for 4 hours. The mixture was combined with another batch of the mixture (1 equivalent). The reaction mixture was quenched by addition aqueous NaHCO₃ (100 mL) at 0° C., diluted with DCM (50 mL) and extracted with DCM (100 L*2). The combined organic layers were dried over anhydrous Na₂SO₄, filtered and concentrated under reduced pressure. The residue was purified by flash silica gel chromatography (ISCO®; 40 g SepaFlash® Silica Flash Column, Eluent of 0~100% Ethyl acetate/Petroleum ether gradient @ 80 mL/min) to afford Compound 43.6 (5.08 g, 13.26 mmol, 68.07% yield).

LCMS: Retention time: 2.907 min, (M+H)=385.0, 10-80CD_7 min_220&254 Agilent

Step 6: General Procedure for Preparation of (3R, 4R)-1-(1H-benzo[d]imidazol-5-yl)-4-(6-bromopyridin-3-yl)-3-cyclopropylazetidin-2-one Compound 43.6 (25 g, 65.23 mmol, 1 eq) was purified by SFC (column: Phenomenex-Cellulose-2 (250 mm*50 mm, 10 um); mobile phase: [0.1% NH₃·H₂O ETOH]; B %: 55%-55%, min) to afford Compound 43.7 (6 g, 15.66 mmol, 24.00% yield).

LCMS: Retention time: 0.629 min, (M+H)=385.0, 5-95AB_220&254_Agilent

Step 7: General Procedure for Preparation of (3R, 4R)-1-(1H-benzo[d]imidazol-5-yl)-3-cyclopropyl-4-(6-(1-(trifluoromethyl)-1H-pyrazol-4-yl)pyridin-3-yl)azetidin-2-one A mixture of Compound 43.7 (3 g, 7.83 mmol, 1 eq), Compound 43.7A (3.08 g, 11.74 mmol, 1.5 eq), Na₂CO₃ (1.66 g, 15.66 mmol, 2 eq) in H₂O (3 mL) and dioxane (30 mL) was degassed and purged with N₂ for 3 times. Then Pd-118 (765.28 mg, 1.17 mmol, 0.15 eq) was added and the mixture was stirred at 95° C. for 16 hours under N₂ atmosphere. The mixture was combined with another batch of the mixture (1 equivalent). The reaction mixture was diluted with EA (60 mL) and extracted with EA (100 mL*3). The combined organic layers were dried over Na₂SO₄, filtered and concentrated under reduced pressure. The residue was purified by flash silica gel chromatography (ISCO®; 40 g SepaFlash® Silica Flash Column, Eluent of 0~100% Ethyl acetate/Petroleum ether gradient @ 60 mL/min) to afford Compound 43B (5.7 g, 13.00 mmol, 83.05% yield).

LCMS: Retention time: 0.810 min, (M+H)=439.8, 5-95AB_220&254_Agilent

General procedure for purification of (3R,4R)-1-(1H-benzo[d]imidazol-5-yl)-3-cyclopropyl-4-(6-(1-(trifluoromethyl)-1H-pyrazol-4-yl)pyridin-3-yl)azetidin-2-one Compound 43B (3 g, 6.84 mmol) was purified by reversed-phase HPLC column: Phenomenex C18 80*40 mm*3 um; (Mobile phase: A: water (NH₃·H₂O) B: ACN; Gradient condition: from 34% B to 64% B; Flow rate: 80 mL/min) to afford Compound 43B (2.97 g, 6.77 mmol, 99.00% yield).

LCMS: Retention time: 0.742 min, (M+H)=439.0, 5-95AB_1.5 min_220&254 Shimadzu

¹H NMR (400 MHz, DMSO-$d_6$) δ=12.55-12.23 (m, 1H), 9.07 (s, 1H), 8.60 (d, J=2.0 Hz, 1H), 8.50 (s, 1H), 8.17 (s, 1H), 7.86-7.78 (m, 2H), 7.54 (d, J=8.8 Hz, 1H), 7.45 (d,

J=1.6 Hz, 1H), 7.28-7.21 (m, 1H), 5.52 (d, J=5.8 Hz, 1H), 3.39-3.37 (m, 1H), 0.53-0.45 (m, 1H), 0.44-0.35 (m, 2H), 0.19-0.05 (m, 2H).
Example 19: Synthesis of Compounds 22A and 22B
Scheme 19.
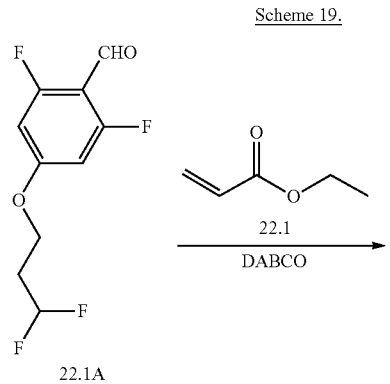
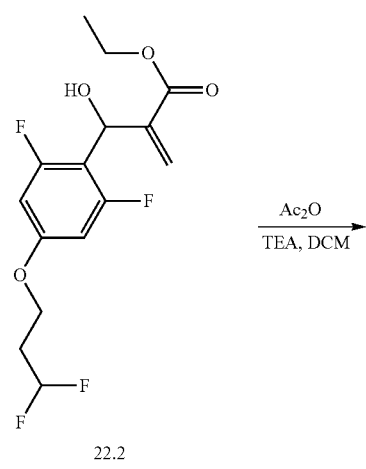
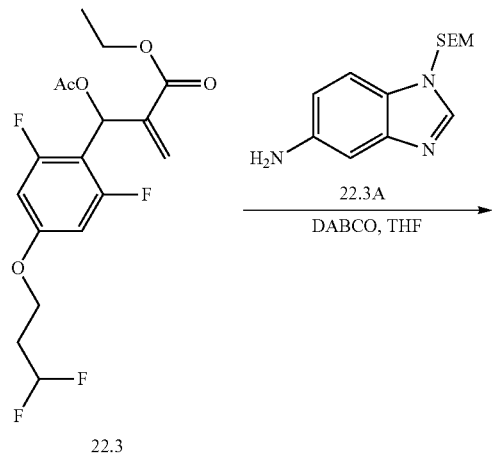
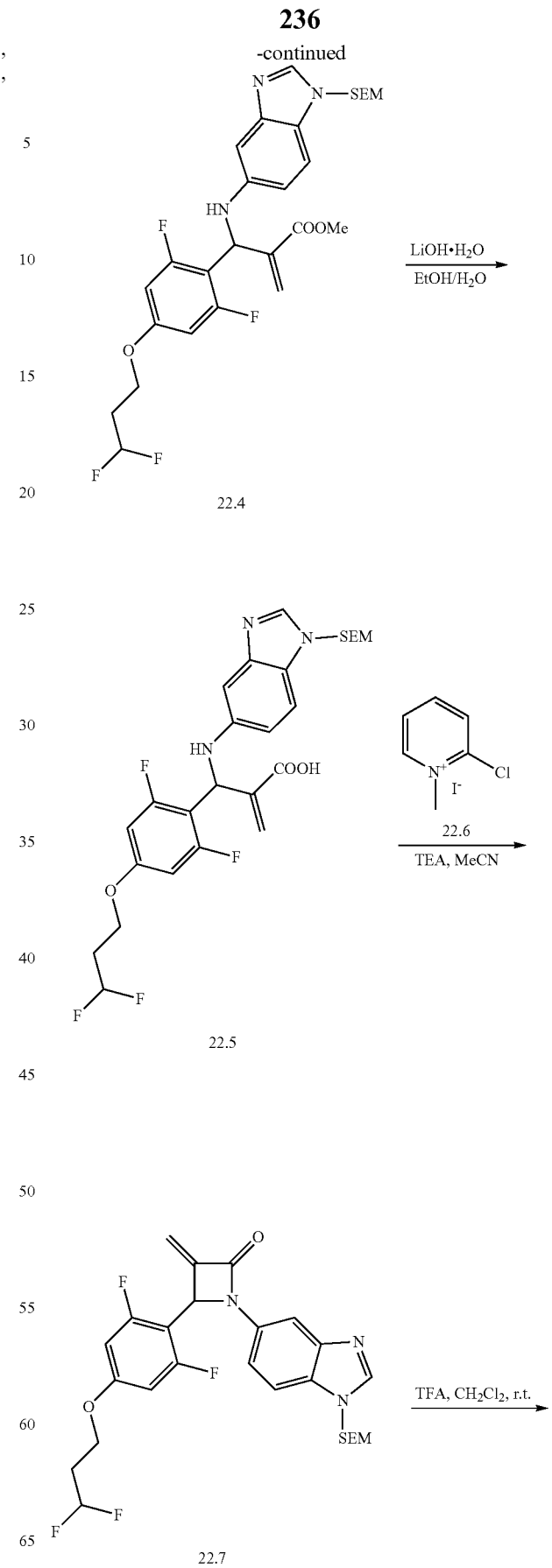

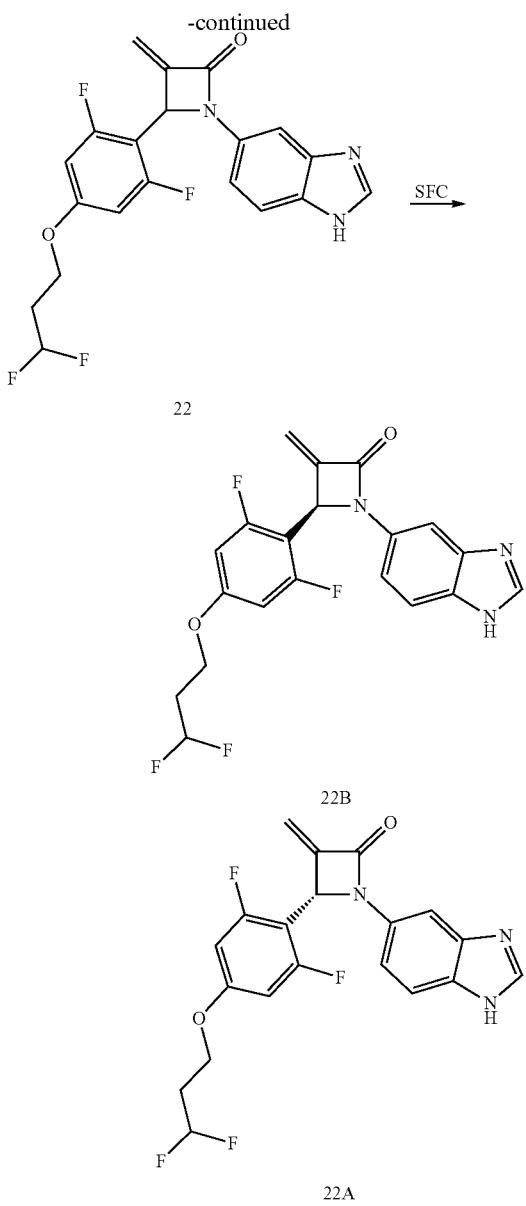

22

22B

22A

Step 1: General Procedure for Preparation of (racemic)-ethyl 2-((4-(3,3-difluoropropoxy)-2,6-difluorophenyl)(hydroxy)methyl)acrylate To a solution of Compound 22.1A (1.6 g, 6.77 mmol, 1 eq) in Compound 22.1 (4.07 g, 40.65 mmol, 4.42 mL, 6 eq) was added DABCO (379.98 mg, 3.39 mmol, 372.52 μL, 0.5 eq). The mixture was stirred at 30° C. for 120 hours. The reaction mixture was poured into water (50 mL) and extracted with EtOAc (50 mL*3). The combined organic layers were washed with brine (20 mL), dried over $Na_2SO_4$, filtered and concentrated under reduced pressure to give the product. The residue was purified by column chromatography ($SiO_2$, Petroleum ether/DCM=0/1 to 1/1). Compound 22.2 (1.5 g, 3.72 mmol, 54.84% yield) as a green oil was obtained.

LCMS: Retention time: 0.861 min, (M+H−18)=318.9, 5-95AB_1.5 min_220&254

Step 2: General Procedure for Preparation of (racemic)-ethyl 2-(acetoxy(4-(3,3-difluoropropoxy)-2,6-difluorophenyl)methyl)acrylate Compound 22.2 (850 mg, 2.53 mmol, 1 eq) was dissolved in DCM (10 mL). TEA (255.77 mg, 2.53 mmol, 351.82 μL, 1 eq) was added and the mixture was cooled to 0° C. Acetyl chloride (595.25 mg, 7.58 mmol, 541.13 μL, 3 eq) was added to the solution slowly. The mixture was stirred at 25° C. for 3 hours. The reaction mixture was concentrated under reduced pressure. The residue was purified by column chromatography ($SiO_2$, Petroleum ether/DCM=0/1 to 2/1). Compound 22.3 (650 mg, 1.62 mmol, 64.10% yield) as a fluorescent green oil was obtained.

LCMS: Retention time: 1.19 min, (M+H−OAc)=319.2, 10-80AB_2 min_220&25

$^1$H NMR: (400 MHz, DMSO-$d_6$) δ=6.80-6.74 (m, 2H), 6.72 (s, 1H), 6.38-6.05 (m, 2H), 5.93 (s, 1H), 4.15 (t, J=6.1 Hz, 2H), 4.11-4.00 (m, 2H), 2.39-2.22 (m, 2H), 2.09 (s, 3H), 1.18-1.11 (m, 3H).

Step 3: General Procedure for Preparation of (racemic)-methyl 2-((4-(3,3-difluoropropoxy)-2,6-difluorophenyl)((1-((2-(trimethylsilyl)ethoxy)methyl)-1H-benzo[d]imidazol-5-yl)amino)methyl)acrylate To a solution of Compound 22.3 (650 mg, 1.72 mmol, 1 eq) in THF (10 mL) was added DABCO (192.72 mg, 1.72 mmol, 188.95 μL, 1 eq) and stirred at 25° C. for 30 min. Compound 22.3A (452.58 mg, 1.72 mmol, 1 eq) was added and stirred for 3 hours at 25° C. The reaction mixture was concentrated under reduced pressure. The residue was purified by column chromatography ($SiO_2$, Petroleum ether/Ethyl acetate=0/1 to 1/2). Compound 22.4 (350 mg, 573.25 μmol, 33.36% yield) as a yellow oil was obtained.

LCMS: Retention time: 0.871 min, (M+H)=582.3, 5-95AB_220&254_Agilent.

Step 4: General Procedure for Preparation of (racemic)-2-((4-(3,3-difluoropropoxy)-2,6-difluorophenyl)((1-((2-(trimethylsilyl)ethoxy)methyl)-1H-benzo[d]imidazol-5-yl)amino)methyl)acrylic acid A mixture of Compound 22.4 (300 mg, 515.75 μmol, 1 eq) and LiOH·$H_2O$ (216.41 mg, 5.16 mmol, 10 eq) in EtOH (10 mL) and $H_2O$ (2 mL) was stirred at 20° C. for 16 hours. The reaction mixture was concentrated under reduced pressure to afford Compound 22.5 (520 mg, crude, Li salt), which was used for the next step without further purification.

Step 5: General Procedure for Preparation of (racemic)-4-(4-(3,3-difluoropropoxy)-2,6-difluorophenyl)-3-methylene-1-(1-((2-(trimethylsilyl)ethoxy)methyl)-1H-benzo[d]imidazol-5-yl)azetidin-2-one A mixture of Compound 22.5 (300 mg, 519.42 μmol, 1 eq, Li salt), Compound 22.6 (265.41 mg, 1.04 mmol, 2 eq), TEA (210.24 mg, 2.08 mmol, 289.19 μL, 4 eq) and $CH_3CN$ (20 mL) was stirred at 90° C. for 16 hours under $N_2$ atmosphere. The reaction mixture was concentrated under reduced pressure. The residue was diluted with $H_2O$ (30 mL) and extracted with EA (20 mL*3). The combined organic layers were dried over $Na_2SO_4$, filtered and concentrated under reduced pressure. Compound 22.7 (160 mg, crude) was obtained.

239

LCMS: Retention time: 0.962 min, (M+H)=536.2, 5-95AB_220&254_Agilent

Step 6: General Procedure for Preparation of (racemic)-1-(1H-benzo[d]imidazol-5-yl)-4-(4-(3,3-difluoropropoxy)-2,6-difluorophenyl)-3-methyleneazetidin-2-one TFA (4.62 g, 40.52 mmol, 3 mL, 135.64 eq) was added to a mixture of Compound 22.7 (160 mg, 298.73 μmol, 1 eq) and DCM (6 mL) and the mixture was stirred at 25° C. for 16 hours. The reaction solution was concentrated to dryness under reduced pressure. The crude product was diluted with methanol (5 mL) and then ammonia (7 M) in methanol (1 mL) was added. The mixture was stirred at room temperature for 10 min. The mixture was concentrated to dryness under reduced pressure and purified by prep-HPLC (column: Boston Prime C18 150*30 mm*5 μm; mobile phase: [water (NH$_3$H$_2$O+NH$_4$HCO$_3$)-ACN]; B %: 40%-70%, 7 min). Compound 22 (17.08 mg, 41.29 μmol, 13.82% yield) was obtained.

LCMS: Retention time: 0.803 min, (M+H)+=406.2, 5-95AB_220&254_Agilent.

HPLC: Retention time: 3.59 min, 10-80AB_8 min.met $^1$H NMR: (400 MHz, DMSO-d$_6$) δ=12.54-12.35 (m, 1H), 8.18 (d, J=12.5 Hz, 1H), 7.64-7.49 (m, 1H), 7.46-7.34 (m, 1H), 7.33-7.07 (m, 1H), 6.83 (d, J=11.0 Hz, 2H), 6.36-6.03 (m, 1H), 5.98 (s, 1H), 5.86-5.78 (m, 1H), 5.44 (s, 1H), 4.14 (t, J=6.1 Hz, 2H), 2.38-2.19 (m, 2H)

Step 7: General Procedure for Preparation of (R)-1-(1H-benzo[d]imidazol-5-yl)-4-(4-(3,3-difluoropropoxy)-2,6-difluorophenyl)-3-methyleneazetidin-2-one (Compound 22B) and (S)-1-(1H-benzo[d]imidazol-5-yl)-4-(4-(3,3-difluoropropoxy)-2,6-difluorophenyl)-3-methyleneazetidin-2-one (Compound 22A)

Compound 22 (16.10 mg) was purified by SFC (column: DAICEL CHIRALCEL OJ (250 mm*30 mm, 10 μm); mobile phase: [0.1% NH$_3$H$_2$O ETOH]; B %: 15%-15%, min) to afford Compound 22A (6.8 mg, 16.51 μmol, 41.56% yield) and Compound 22B (6.14 mg, 15.15 μmol, 38.13% yield).

Compound 22A:

SFC: Retention time: 2.781 min.

LCMS: Retention time: 0.802 min, (M+H)+=406.1, 5-95AB_220&254_Agilent.

HPLC: Retention time: 3.59 min, 10-80AB_8 min.met $^1$H NMR: (400 MHz, DMSO-d$_6$) δ=12.56-12.34 (m, 1H), 8.18 (d, J=12.3 Hz, 1H), 7.64-7.49 (m, 1H), 7.47-7.07 (m, 2H), 6.83 (d, J=11.0 Hz, 2H), 6.37-6.02 (m, 1H), 5.98 (s, 1H), 5.86-5.78 (m, 1H), 5.44 (s, 1H), 4.14 (t, J=6.0 Hz, 2H), 2.37-2.21 (m, 2H)

Compound 22B:

SFC: Retention time: 3.072 min.

LCMS: Retention time: 0.802 min, (M+H)+=406.1, 5-95AB_220&254_Agilent.

HPLC: Retention time: 3.59 min, 10-80AB_8 min.met $^1$H NMR: (400 MHz, DMSO-d$_6$) δ=12.60-12.31 (m, 1H), 8.18 (d, J=12.4 Hz, 1H), 7.63-7.49 (m, 1H), 7.47-7.06 (m, 2H), 6.83 (d, J=11.1 Hz, 2H), 6.37-6.02 (m, 1H), 5.98 (s, 1H), 5.86-5.78 (m, 1H), 5.44 (s, 1H), 4.20-4.08 (m, 2H), 2.37-2.20 (m, 2H).

240

Example 20. Synthesis of Compounds 48A and 48B

Scheme 20.

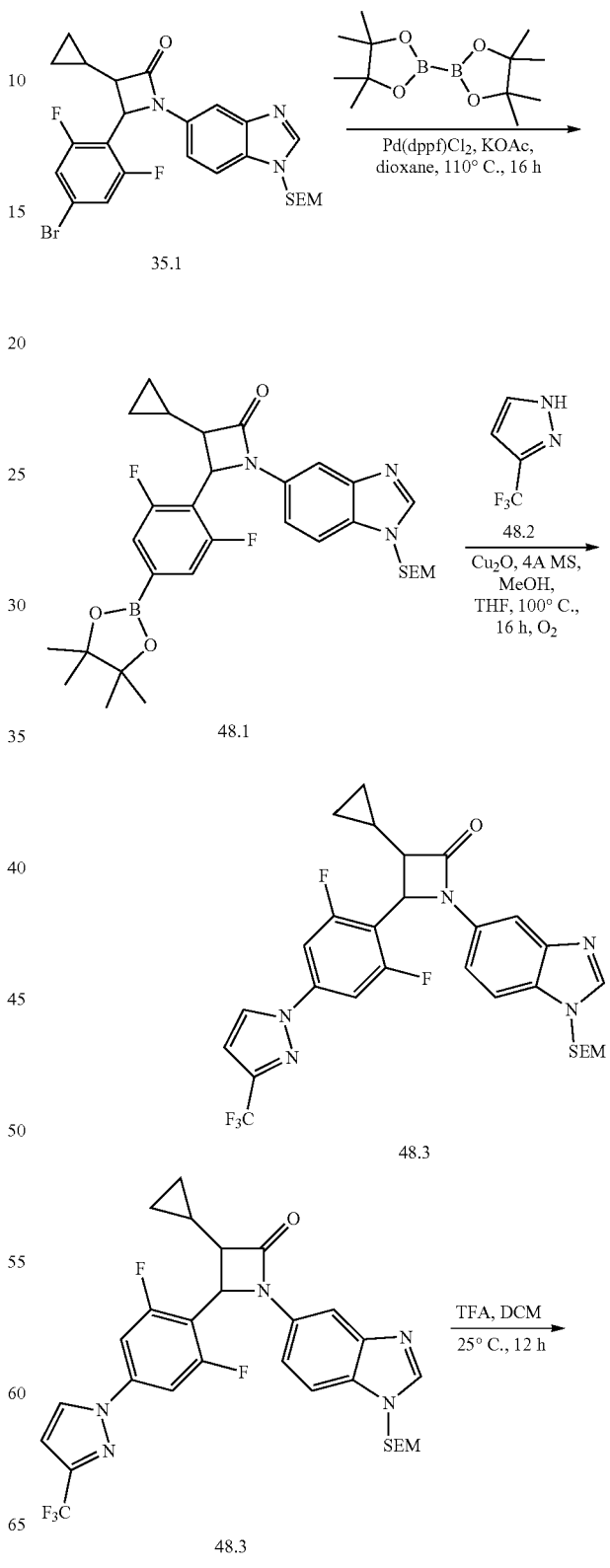

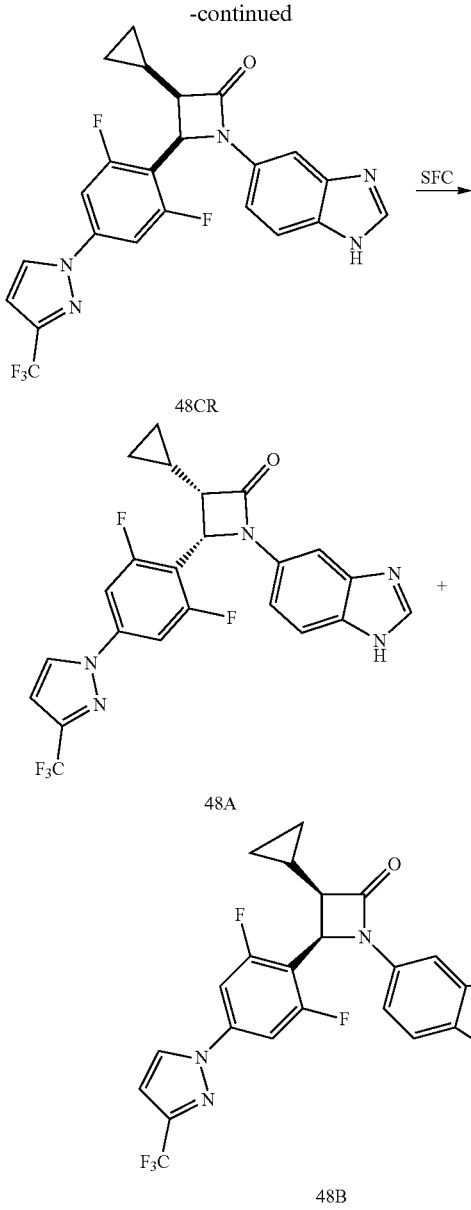

48CR

48A

48B

Step 1: General Procedure for Preparation of (racemic)-3-cyclopropyl-4-(2,6-difluoro-4-(4,4,5,5-tetramethyl-1,3,2-dioxaborolan-2-yl)phenyl)-1-(1-((2-(trimethylsilyl)ethoxy)methyl)-1H-benzo[d]imidazol-5-yl)azetidin-2-one To a solution of Compound 35.1 (1 g, 1.82 mmol, 1 eq), 4,4,5,5-tetramethyl-2-(4,4,5,5-tetramethyl-1,3,2-dioxaborolan-2-yl)-1,3,2-dioxaborolane (925.95 mg, 3.65 mmol, 2 eq) and KOAc (536.79 mg, 5.47 mmol, 3 eq) in dioxane (10 mL) was degassed and purged with $N_2$ for 3 times. Pd(dppf)Cl$_2$ (133.40 mg, 182.32 μmol, 0.1 eq) was added. The mixture was stirred at 110° C. for 16 hours under $N_2$ atmosphere. The reaction mixture was concentrated under reduced pressure. The residue was purified by column chromatography (SiO$_2$, Petroleum ether/Ethyl acetate=1/0 to 1/1). Compound 48.1 (820 mg, 1.38 mmol, 75.52% yield) was obtained.

LCMS: Retention time: 1.232 min, (M+H)=596.4, 10-80AB_2 min_220&25

Step 2: General Procedure for Preparation of (racemic)-3-cyclopropyl-4-(2,6-difluoro-4-(3-(trifluoromethyl)-1H-pyrazol-1-yl)phenyl)-1-(1-((2-(trimethylsilyl)ethoxy)methyl)-1H-benzo[d]imidazol-5-yl)azetidin-2-one To a solution of Compound 48.1 (100 mg, 167.91 μmol, 1 eq) and Compound 48.2 (34.27 mg, 251.86 μmol, 1.5 eq) in MeOH (2 mL) and THF (1 mL) was added Cu$_2$O (24.03 mg, 167.91 μmol, 17.16 μL, 1 eq) and 4AMS (200 mg, 1.00 eq) under $O_2$ condition (15 psi). The mixture was stirred at 100° C. for 16 hours. The reaction mixture was concentrated under reduced pressure. The residue was purified by column chromatography (SiO$_2$, Petroleum ether/Ethyl acetate=1/0 to 1/1). Compound 48.3 (80 mg, crude) was obtained.

Step 3: General Procedure for Preparation of (cis and racemic)-1-(1H-benzo[d]imidazol-5-yl)-3-cyclopropyl-4-(2,6-difluoro-4-(3-(trifluoromethyl)-1H-pyrazol-1-yl)phenyl)azetidin-2-one To a solution of Compound 48.3 (80 mg, 132.53 μmol, 1 eq) in DCM (2 mL) was added TFA (1 mL). The mixture was stirred at 25° C. for 12 hours. The reaction mixture was quenched by addition NaHCO$_3$ (aq) 20 mL at 0° C., diluted with DCM (30 mL) and extracted with DCM 90 mL (30 mL*3). The combined organic layers were dried over anhydrous Na$_2$SO$_4$, filtered and concentrated under reduced pressure. The crude product was purified by reversed-phase HPLC (column: Phenomenex C18 80*40 mm*3 μm; mobile phase: [water (NH$_3$H$_2$O)-ACN]; B %: 46%-76%, 8 min). Compound 48CR (20 mg, 42.25 μmol, 31.88% yield) was obtained.

LCMS: Retention time: 1.005 min, (M+H)=474.2, 10-80AB_2 min_220&25

$^1$H NMR: (400 MHz, DMSO-d$_6$) δ=13.06-11.62 (m, 1H), 8.82 (s, 1H), 8.24 (s, 1H), 7.99-7.61 (m, 2H), 7.56 (d, J=8.8 Hz, 1H), 7.48 (d, J=1.5 Hz, 1H), 7.27-6.93 (m, 3H), 5.68 (d, J=5.8 Hz, 1H), 3.44 (dd, J=5.6, 9.4 Hz, 1H), 0.73-0.63 (m, 1H), 0.56-0.37 (m, 2H), 0.28-0.03 (m, 2H)

Step 4: General Procedure for Preparation of (3S,4S)-1-(1H-benzo[d]imidazol-5-yl)-3-cyclopropyl-4-(2,6-difluoro-4-(3-(trifluoromethyl)-1H-pyrazol-1-yl)phenyl)azetidin-2-one (Compound 48A) and (3R,4R)-1-(1H-benzo[d]imidazol-5-yl)-3-cyclopropyl-4-(2,6-difluoro-4-(3-(trifluoromethyl)-1H-pyrazol-1-yl)phenyl)azetidin-2-one (Compound 48B)

Compound 48CR (15 mg) was purified by SFC (column: Phenomenex-Cellulose-2 (250 mm*30 mm, 10 um); mobile phase: [0.1% NH$_3$H$_2$O MEOH]; B %: 50%-50%, min). Compound 48A (2 mg, 4.22 μmol, 13.33% yield) and Compound 48B (1.91 mg, 4.03 μmol, 12.73% yield) were obtained.

Compound 48A:
SFC: Retention time: 0.932 min.
LCMS: Retention time: 0.773 min, (M+H)=474.1, 5-95AB_220&254_Agilent.M
HPLC: Retention time: 3.645 min 10-80AB_8 min.met
$^1$H NMR: (400 MHz, DMSO-d$_6$) δ=12.91-11.80 (m, 1H), 8.81 (s, 1H), 8.15 (s, 1H), 7.95-7.60 (m, 2H), 7.58-7.43 (m, 2H), 7.30-7.06 (m, 2H), 5.67 (d, J=5.8 Hz, 1H), 3.45-3.41 (m, 1H), 0.76-0.61 (m, 1H), 0.55-0.35 (m, 2H), 0.25-0.03 (m, 2H)

Compound 48B:
SFC: Retention time: 3.031 min.
LCMS: Retention time: 0.774 min, (M+H)=474.0, 5-95AB_220&254_Agilent.M
HPLC: Retention time: 3.644 min, 10-80AB_8 min.met
$^1$H NMR: (400 MHz, DMSO-$d_6$) δ=12.73-11.92 (m, 1H), 8.79 (s, 1H), 8.13 (s, 1H), 7.94-7.58 (m, 2H), 7.56-7.40 (m, 2H), 7.26-7.05 (m, 2H), 5.65 (d, J=5.8 Hz, 1H), 3.43-3.38 (m, 1H), 0.73-0.61 (m, 1H), 0.55-0.35 (m, 2H), 0.28--0.06 (m, 2H).
Example 21. Synthesis of Compounds 50A and 50B
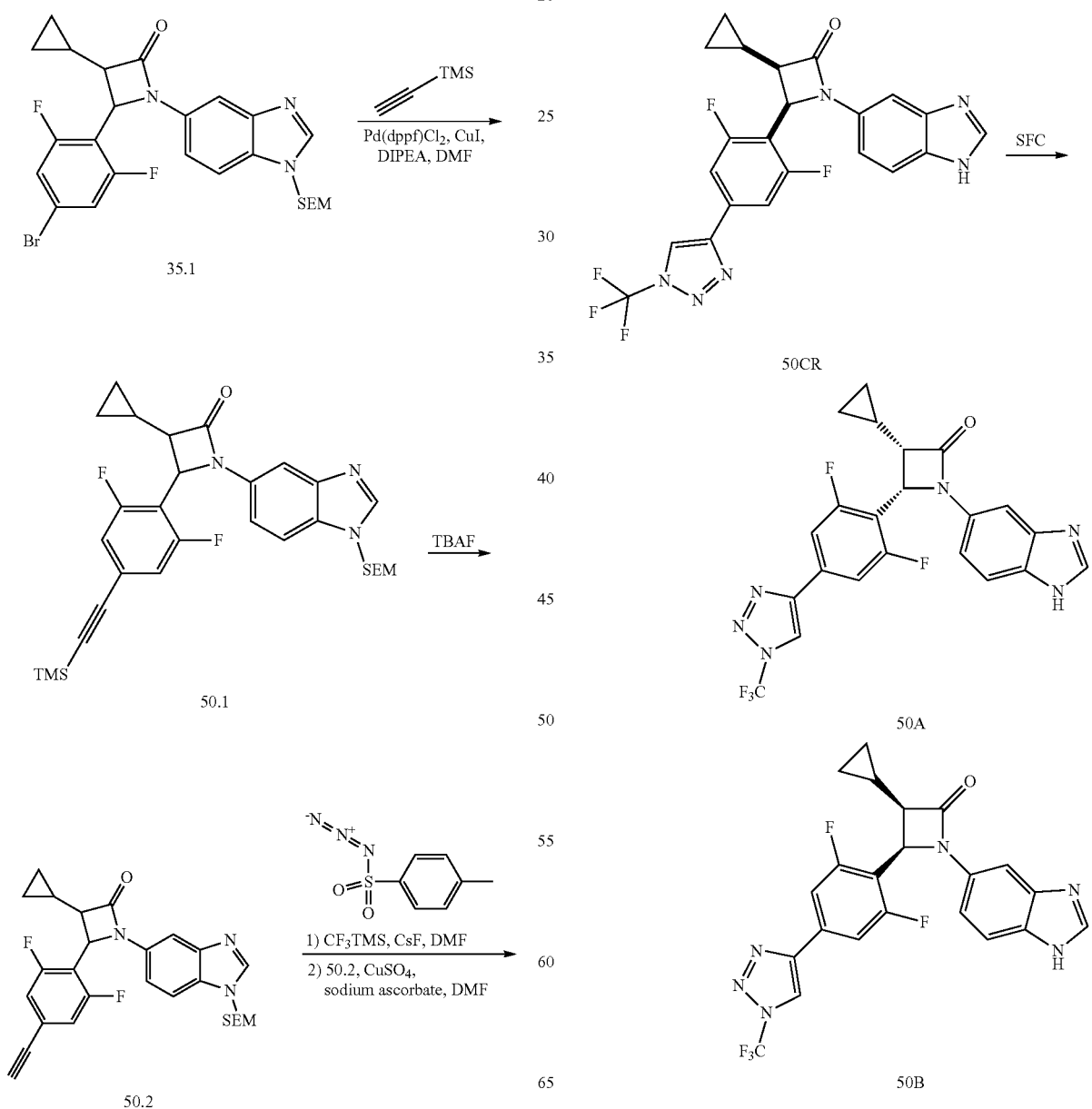
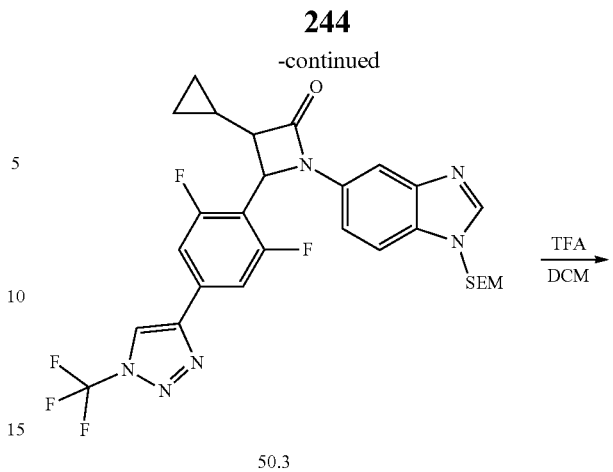

Step 1: General Procedure for Preparation of (racemic)-3-cyclopropyl-4-(2,6-difluoro-4-((trimethylsilyl)ethynyl)phenyl)-1-(1-((2-(trimethylsilyl)ethoxy)methyl)-1H-benzo[d]imidazol-5-yl)azetidin-2-one A mixture of Compound 35.1 (2 g, 3.65 mmol, 1 eq), ethynyl(trimethyl)silane (447.67 mg, 4.56 mmol, 631.41 µL, 1.25 eq), DIPEA (706.90 mg, 5.47 mmol, 952.69 µL, 1.5 eq) were taken up into a microwave tube in DMF (3 mL). The mixture was degassed and purged with $N_2$ for 3 times. CuI (6.94 mg, 36.46 µmol, 0.01 eq) and $Pd(PPh_3)_2Cl_2$ (102.37 mg, 145.85 µmol, 0.04 eq) were added and the mixture was stirred at 100° C. for 2 hours under $N_2$ atmosphere. The reaction mixture was quenched by addition $H_2O$ (40 mL) at 25° C. and extracted with EtOAc (40 mL*3). The combined organic layers were washed with brine (30 mL*3), dried over $Na_2SO_4$, filtered and concentrated under reduced pressure. The residue was purified by flash silica gel chromatography (ISCO®; 25 g SepaFlash® Silica Flash Column, Eluent of 0~60% Ethyl acetate/Petroleum ether gradient @ 35 mL/min). Compound 50.1 (1.3 g, 1.83 mmol, 50.10% yield) was obtained.

LCMS: Retention time: 0.966 min, (M+H)=566.2, 5-95AB_1.5 min_220&254 Shimadzu

Step 2: General Procedure for Preparation of (racemic)-3-cyclopropyl-4-(4-ethynyl-2,6-difluorophenyl)-1-(1-((2-(trimethylsilyl)ethoxy)methyl)-1H-benzo[d]imidazol-5-yl)azetidin-2-one TBAF (1 M, 4.37 mL, 0.95 eq) was added to a mixture of Compound 50.1 (2.6 g, 4.60 mmol, 1 eq) and THF (30 mL) and then the mixture was stirred at 20° C. for 1 hour under $N_2$ atmosphere. The reaction mixture was quenched by addition aqueous NaCl (50 mL) and extracted with ethyl acetate (30 mL*2). The combined organic layers were washed with aqueous NaCl (30 mL), dried over $Na_2SO_4$, filtered and concentrated under reduced pressure. The residue was purified by flash silica gel chromatography (ISCO®; 40 g SepaFlash® Silica Flash Column, Eluent of 0~60% Ethyl acetate/Petroleum ether gradient @ 45 mL/min). Compound 50.2 (900 mg, 837.17 µmol, 18.22% yield) as a brown oil was obtained.

LCMS: Retention time: 2.462 min, (M+H)=494.1, 10-80CD_3 min_220&254 Shimadzu 1.3 General Procedure for Preparation of (racemic)-3-cyclopropyl-4-(2,6-difluoro-4-(1-(trifluoromethyl)-1H-1,2,3-triazol-4-yl)phenyl)-1-(1-((2-(trimethylsilyl)ethoxy)methyl)-1H-benzo[d]imidazol-5-yl)azetidin-2-one To a mixture of $TMSCF_3$ (230.45 mg, 1.62 mmol, 1.6 eq) and N-diazo-4-methyl-benzenesulfonamide (372.89 mg, 1.42 mmol, 1.4 eq) in DMF (2 mL) was added a mixture of CsF (246.19 mg, 1.62 mmol, 59.75 µL, 1.6 eq) DMF (15 mL) at −60° C. and the mixture was stirred at −60--30° C. for 4 hours. A solution of Compound 50.2 (500 mg, 1.01 mmol, 1 eq) in DMF (2 mL) was added. Then $CuSO_4·5H_2O$ (75.87 mg, 303.88 µmol, 0.3 eq) and sodium ascorbate (60.20 mg, 303.88 µmol, 0.3 eq) in $H_2O$ (1 mL) was added and then the mixture was stirred at 25° C. for 16 hour under $N_2$ atmosphere. The reaction mixture was quenched by addition aqueous NaCl (60 mL), and extracted with EA (50 mL*2). The combined organic layers were washed with aqueous NaCl (50 mL), dried over $Na_2SO_4$, filtered and concentrated under reduced pressure. The residue was purified by flash silica gel chromatography (ISCO®; 20 g SepaFlash® Silica Flash Column, Eluent of 0~60% Ethyl acetate/Petroleum ether gradient @ 45 mL/min). Compound 50.3 (300 mg, 264.48 µmol, 26.11% yield) as a brown oil was obtained.

Step 4: General Procedure for Preparation of (Cis and racemic)-1-(1H-benzo[d]imidazol-5-yl)-3-cyclopropyl-4-(2,6-difluoro-4-(1-(trifluoromethyl)-1H-1,2,3-triazol-4-yl)phenyl)azetidin-2-one TFA (1.54 g, 13.51 mmol, 1 mL, 27.22 eq) was added to a mixture of Compound 50.3 (300 mg, 496.16 µmol, 1 eq) in DCM (2 mL) and the mixture was stirred at 25° C. for 16 hours. The reaction mixture was concentrated under reduced pressure. The residue was diluted with $NaHCO_3$ (30 mL) and extracted with EA (30 mL*3). The combined organic layers were dried over $Na_2SO_4$, filtered and concentrated under reduced pressure. The residue was purified by flash silica gel chromatography (ISCO®; 4 g SepaFlash® Silica Flash Column, Eluent of 0~100% Ethyl acetate/Petroleum ether gradient @ 20 mL/min) and by prep-HPLC (column: Phenomenex C18 75*30 mm*3 µm; mobile phase: [water ($NH_3H_2O+NH_4HCO_3$)-ACN]; B %: 40%-70%, 7 min). Compound 50CR (12 mg, 23.64 µmol, 4.76% yield) was obtained.

LCMS: Retention time: 0.857 min, (M+H)=475.1, 5-95AB_220&254_Agilent $^1H$ NMR: (400 MHz, DMSO-$d_6$) δ=12.34 (br s, 1H), 9.60 (s, 1H), 8.16 (s, 1H), 7.93-7.59 (m, 2H), 7.54 (d, J=8.8 Hz, 1H), 7.49-7.42 (m, 2H), 7.23 (br s, 1H), 5.69 (d, J=5.8 Hz, 1H), 3.44 (dd, J=5.8, 9.4 Hz, 1H), 0.78-0.64 (m, 1H), 0.56-0.47 (m, 1H), 0.45-0.37 (m, 1H), 0.24-0.15 (m, 1H), 0.13--0.03 (m, 1H)

Step 5: General Procedure for Preparation of (3S, 4S)-1-(1H-benzo[d]imidazol-5-yl)-3-cyclopropyl-4-(2,6-difluoro-4-(1-(trifluoromethyl)-1H-1,2,3-triazol-4-yl)phenyl)azetidin-2-one (Compound 50A) and (3R,4R)-1-(1H-benzo[d]imidazol-5-yl)-3-cyclopropyl-4-(2,6-difluoro-4-(1-(trifluoromethyl)-1H-1,2,3-triazol-4-yl)phenyl)azetidin-2-one (Compound 50B)

Compound 50CR (12 mg, 25.30 µmol, 1 eq) was purified by SFC (column: Phenomenex-Cellulose-2 (250 mm*30 mm, 10 µm); mobile phase: [0.1% $NH_3·H_2O$ ETOH]; B %: 40%-40%, min). Compound 50A (3.62 mg, 7.56 µmol, 29.90% yield) and Compound 50B (3.12 mg, 6.33 µmol, 25.02% yield) were obtained.

Compound 50A:
SFC: Retention time: 1.19 min.
LCMS: Retention time: 0.854 min, (M+H)=475.1, 5-95AB_220&254_Agilent 8 HPLC: Retention time: 3.959 min, 10-80AB_8 min.lcm $^1H$ NMR: (400 MHz, DMSO-$d_6$) δ=12.49-12.26 (m, 1H), 9.60 (s, 1H), 8.21-8.12 (m, 1H), 7.93-7.10 (m, 5H), 5.69 (d, J=5.8 Hz, 1H), 3.47-3.43 (m, 1H), 0.77-0.65 (m, 1H), 0.56-0.47 (m, 1H), 0.46-0.37 (m, 1H), 0.23-0.14 (m, 1H), 0.13-0.04 (m, 1H).

Compound 50B:
SFC: Retention time: 2.343 min.
LCMS: Retention time: 0.852 min, (M+H)=475.1, 5-95AB_220&254_Agilent HPLC: Retention time: 3.946 min, 10-80AB_8 min.lcm $^1H$ NMR: (400 MHz, DMSO-$d_6$) δ=12.51-12.23 (m, 1H), 9.60 (s, 1H), 8.22-8.11 (m, 1H), 7.91-7.10 (m, 5H), 5.69 (d, J=5.8 Hz, 1H), 3.47-3.41 (m, 1H), 0.77-0.64 (m, 1H), 0.56-0.47 (m, 1H), 0.46-0.38 (m, 1H), 0.23-0.15 (m, 1H), 0.13-0.04 (m, 1H).

Example 22. Synthesis of Compound 52B

Scheme 22.

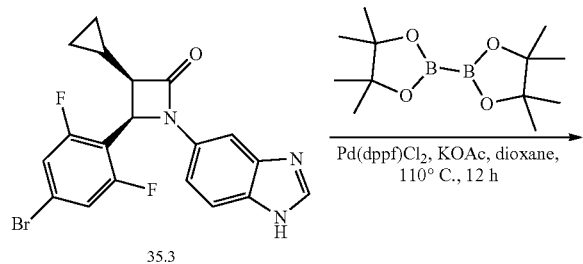

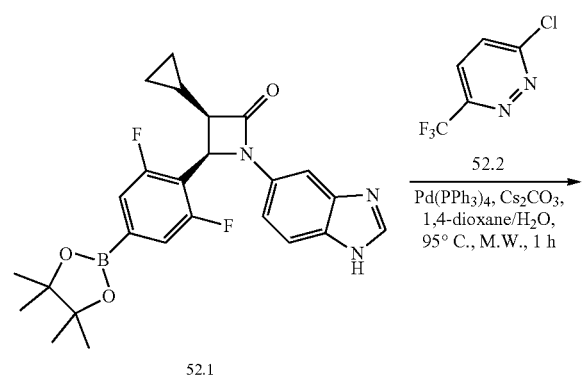

Step 1: General Procedure for Preparation of (3R, 4R)-1-(1H-benzo[d]imidazol-5-yl)-3-cyclopropyl-4-(2,6-difluoro-4-(4,4,5,5-tetramethyl-1,3,2-dioxaborolan-2-yl)phenyl)azetidin-2-one To a solution of Compound 35.3 (1.00 g, 2.39 mmol, 1 eq), 4,4,5,5-tetramethyl-2-(4,4,5,5-tetramethyl-1,3,2-dioxaborolan-2-yl)-1,3,2-dioxaborolane (3.04 g, 11.96 mmol, 5 eq) and KOAc (703.98 mg, 7.17 mmol, 3 eq) in dioxane (40 mL) was degassed and purged with Ar for 3 times and Pd(dppf)Cl$_2$ (174.95 mg, 239.10 μmol, 0.1 eq) was added. The mixture was stirred at 110° C. for 12 hours under Ar atmosphere. The reaction mixture was filtered and the filtrate was concentrated under reduced pressure. The residue was purified by flash silica gel chromatography (ISCO®; 12 g SepaFlash® Silica Flash Column, Eluent of 0~100% Ethyl acetate/Petroleum ether gradient @ 30 mL/min). Compound 52.1 (890 mg, 1.74 mmol, 72.63% yield) was obtained.

LCMS: Retention time: 0.759 min, (M+H–82)=384.1, 10-80AB_2 min_220&25

Step 2: General Procedure for Preparation of (3R, 4R)-1-(1H-benzo[d]imidazol-5-yl)-3-cyclopropyl-4-(2,6-difluoro-4-(6-(trifluoromethyl)pyridazin-3-yl)phenyl)azetidin-2-one (Compound 52B)

Compound 52.1 (70 mg, 0.150 mmol), Compound 52.2 (27.46 mg, 0.150 mmol), Cs$_2$CO$_3$ (147.05 mg, 0.451 mmol) and Pd(PPh$_3$)$_4$ (8.32 mg, 0.023 mmol) in dioxane (1 mL) and H$_2$O (0.25 mL) were degassed and then heated at 95° C. for 1 h under microwave. The reaction mixture was filtered and concentrated under reduced pressure. The residue was purified by flash silica gel chromatography (ISCO®; 4 g SepaFlash® Silica Flash Column, Eluent of 0~100% Ethyl acetate/Petroleum ether gradient @ 25 mL/min) and by prep-HPLC (column: Boston Green ODS 150*30 mm*5 μm; mobile phase: [water (FA)-ACN]; B %: 28%-58%, 7 min). Compound 52B (15.01 mg, 0.030 mmol) was obtained.

SFC: Retention time: 2.215 min.

LCMS: Retention time: 0.984 min, (M+H)=486.1, 10-80AB_2 min_220&25 HPLC: Retention time: 3.714 min, 10-80AB_8 min.met $^1$H NMR: (400 MHz, DMSO-d$_6$) δ=12.55-12.20 (m, 1H), 8.66 (d, J=8.8 Hz, 1H), 8.45 (d, J=9.2 Hz, 1H), 8.30-8.10 (m, 2H), 8.10-7.90 (m, 1H), 7.70-7.10 (m, 3H), 5.75 (d, J=5.6 Hz, 1H), 3.55-3.40 (m, 1H), 0.75-0.65 (m, 1H), 0.60-0.40 (m, 2H), 0.30--0.05 (m, 2H).

Example 23. Synthesis of Compounds 59B and 60B

Scheme 23.

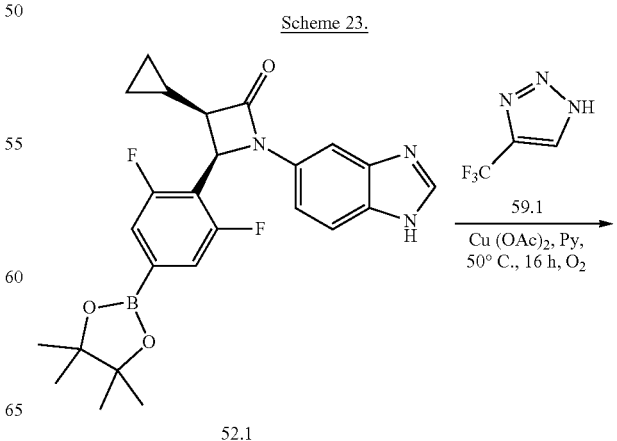

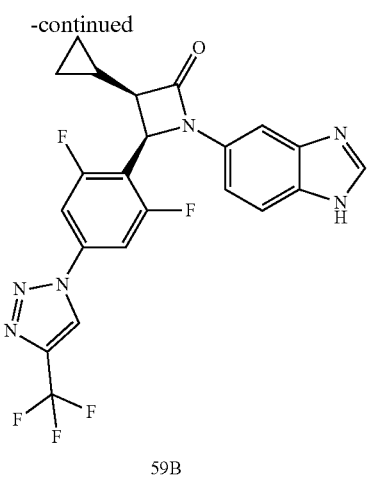

59B

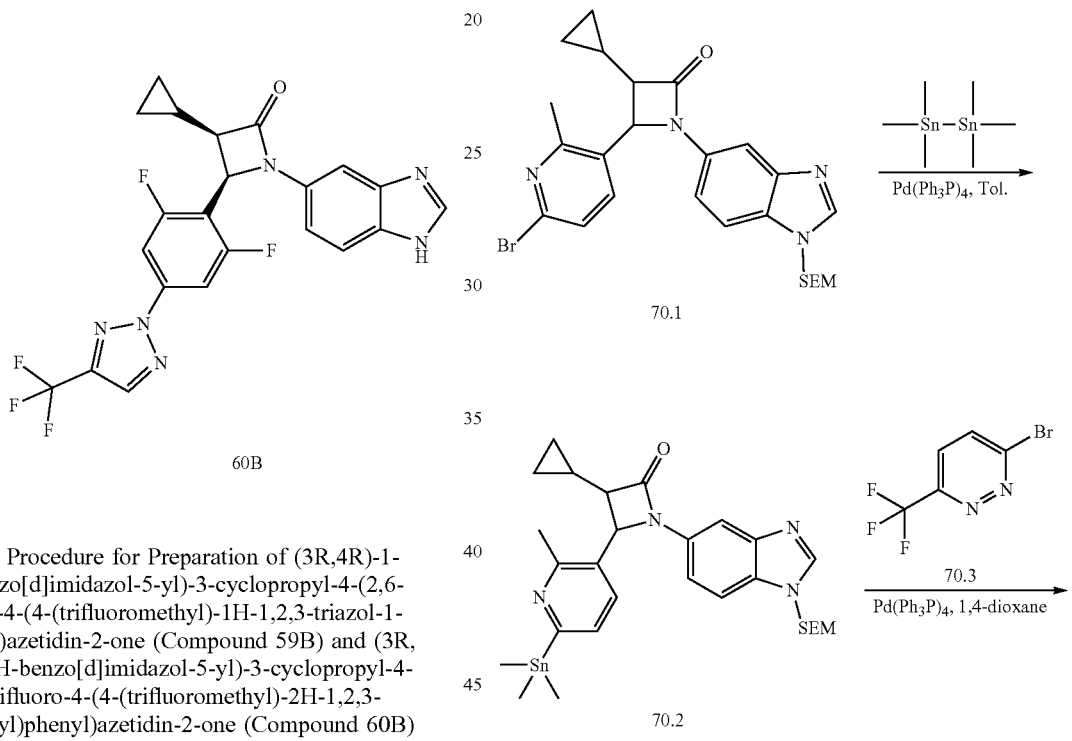

60B

General Procedure for Preparation of (3R,4R)-1-(1H-benzo[d]imidazol-5-yl)-3-cyclopropyl-4-(2,6-difluoro-4-(4-(trifluoromethyl)-1H-1,2,3-triazol-1-yl)phenyl)azetidin-2-one (Compound 59B) and (3R,4R)-1-(1H-benzo[d]imidazol-5-yl)-3-cyclopropyl-4-(2,6-difluoro-4-(4-(trifluoromethyl)-2H-1,2,3-triazol-2-yl)phenyl)azetidin-2-one (Compound 60B)

A solution of Compound 52.1 (150 mg, 322.37 μmol, 1 eq) and Compound 59.1 (106.05 mg, 773.70 μmol, 2.4 eq) in Pyridine (2 mL) was degassed and purged with $O_2$ for 3 times and Cu(OAc)$_2$ (58.55 mg, 322.37 μmol, 1 eq) was added. The mixture was stirred at 80° C. for 16 hours. The mixture was diluted with $H_2O$ (20 mL) and extracted with EA (50 mL*3). The combined organic layers were washed with brine (10 mL*3), dried over anhydrous $Na_2SO_4$, filtered and concentrated under reduced pressure. The crude product was purified by reversed-phase HPLC (column: Xtimate C18 150*40 mm*5 μm; mobile phase: [water (FA)-ACN]; B %: 15%-55%, 8 min) and by SFC. Compound 59B (12.72 mg, 26.25 μmol, 24.91% yield) and Compound 60B (25.76 mg, 49.39 μmol, 46.86% yield) were obtained.

Compound 59B:
LCMS: Retention time: 0.945 min, (M+H)=475.1, 10-80AB_2 min_220&25
HPLC: Retention time: 3.932 min, 10-80AB_8 min.met
$^1$H NMR: (400 MHz, DMSO-d$_6$) δ=12.95-12.25 (m, 1H), 9.65 (s, 1H), 8.77-6.85 (m, 6H), 5.73 (d, J=5.6 Hz, 1H), 3.58-3.44 (m, 1H), 0.76-0.62 (m, 1H), 0.58-0.37 (m, 2H), 0.29-0.03 (m, 2H).

Compound 60B:
LCMS: Retention time: 1.001 min, (M+H)=475.1, 10-80AB_2 min_220&25
HPLC: Retention time: 3.641 min, 10-80AB_8 min.met
$^1$H NMR: (400 MHz, DMSO-d$_6$) δ=13.04-12.10 (m, 1H), 8.85 (s, 1H), 8.61-6.90 (m, 6H), 5.71 (d, J=5.6 Hz, 1H), 3.53-3.43 (m, 1H), 0.76-0.63 (m, 1H), 0.56-0.37 (m, 2H), 0.29-0.02 (m, 2H).

Example 24. Synthesis of Compounds 70A and 70B

Scheme 24.

-continued

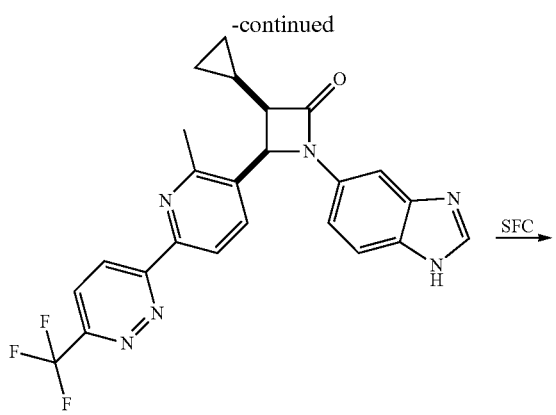

70CR

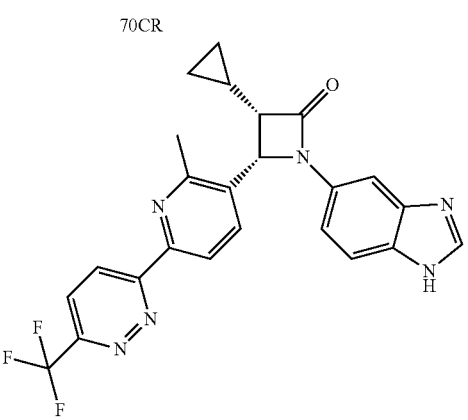

70A

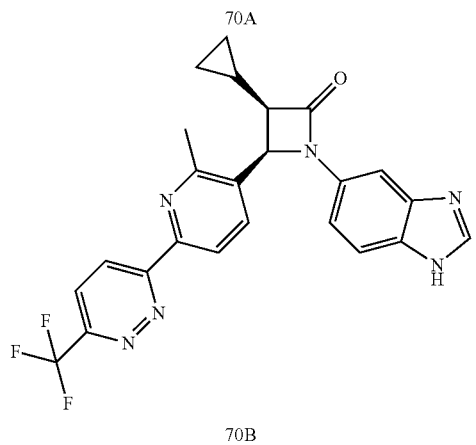

70B

Step 1: General Procedure for Preparation of (racemic)-3-cyclopropyl-4-(2-methyl-6-(trimethylstannyl)pyridin-3-yl)-1-(1-((2-(trimethylsilyl)ethoxy)methyl)-1H-benzo[d]imidazol-5-yl)azetidin-2-one Trimethyl(trimethylstannyl)stannane (530 mg, 1.62 mmol, 335.44 µL, 2.84 eq) was added to a mixture of Compound 70.1 (300 mg, 568.69 µmol, 1 eq), Pd(PPh₃)₄ (131.43 mg, 113.74 µmol, 0.2 eq) in Toluene (15 mL) and the mixture was degassed and purged with N₂ for 3 times. The mixture was stirred at 115° C. for 16 hours under N₂ atmosphere in 100 ml round-bottomed flask. The reaction mixture was quenched by addition aq. KF (30 mL) at 20° C. The mixture was stirred at 20° C. for 2 hours and extracted with ethyl acetate (30 mL*3). The combined organic layers were washed with aqueous NaCl 30 mL, dried over Na₂SO₄, filtered and concentrated under reduced pressure. Compound 70.2 (450 mg, crude) as a brown oil was obtained, which was used for the next step without further purification.

Step 2: General Procedure for Preparation of (racemic)-3-cyclopropyl-4-(2-methyl-6-(6-(trifluoromethyl)pyridazin-3-yl)pyridin-3-yl)-1-(1-((2-(trimethylsilyl)ethoxy)methyl)-1H-benzo[d]imidazol-5-yl)azetidin-2-one To a solution of Compound 70.3 (167.05 mg, 0.736 mmol) and Compound 70.2 (300 mg, 0.491 mmol) in 1,4-Dioxane (5 mL) were added Pd(PPh₃)₄ (113.40 mg, 0.098 mmol) and the reaction was stirred at 110° C. for 16 hours. The reaction was diluted with aqueous NaCl (20 mL) and extracted with Ethyl Acetate (30 mL*3). The organic layer was separated, washed with aqueous NaCl (10 mL) and concentrated under reduced pressure. The residue was purified by silica gel column chromatography eluting with ethyl acetate in petroleum ether (0-80%). Compound 70.4 (150 mg, 0.162 mmol, 32.94%) was obtained.
LCMS: Retention time: 2.437 min, (M+H)=595.3, 10-80CD_3 min_220&254

Step 3: General Procedure for Preparation of (cis and racemic)-1-(1H-benzo[d]imidazol-5-yl)-3-cyclopropyl-4-(2-methyl-6-(6-(trifluoromethyl)pyridazin-3-yl)pyridin-3-yl)azetidin-2-one To a solution of Compound 70.4 (150 mg, 0.252 mmol) in DCM (4 mL) were added TFA (2 mL) and the reaction was stirred at room temperature for 16 hours. The reaction was concentrated under reduced pressure. The residue was diluted with aq. NaHCO₃ (20 mL) and extracted with ethyl acetate (20 mL×3). The combined organic layers were concentrated and purified by preparative HPLC using a Boston Prime C18 150×30 mm×5 µm column (eluent: 45% to 75% (v/v) CH₃CN and H₂O with NH₃H₂O+NH₄HCO₃). Compound 70CR (50 mg, 0.107 mmol, 42.46% yield) was obtained.
LCMS: Retention time: 2.331 min, (M+H)=464.9, 10-80AB_7 min_220&254
¹H NMR: (400 MHz, DMSO-d₆) δ=12.53-12.28 (m, 1H), 8.81 (d, J=8.9 Hz, 1H), 8.45-8.35 (m, 2H), 8.18 (d, J=11.0 Hz, 1H), 7.73-7.66 (m, 1H), 7.63-7.46 (m, 2H), 7.45-7.14 (m, 1H), 5.77-5.67 (m, 1H), 3.60-3.52 (m, 1H), 2.77 (s, 3H), 0.43-0.31 (m, 3H), 0.29-0.11 (m, 2H)

Step 4: General Procedure for Preparation of (3S,4S)-1-(1H-benzo[d]imidazol-5-yl)-3-cyclopropyl-4-(2-methyl-6-(6-(trifluoromethyl)pyridazin-3-yl)pyridin-3-yl)azetidin-2-one (Compound 70A) and (3R,4R)-1-(1H-benzo[d]imidazol-5-yl)-3-cyclopropyl-4-(2-methyl-6-(6-(trifluoromethyl)pyridazin-3-yl)pyridin-3-yl)azetidin-2-one (Compound 70B)

Compound 70CR (50 mg, 0.108 mmol) was purified by SFC (DAICEL CHIRALPAK IC 250 mm×30 mm, 10 µm; isocratic elution: EtOH (containing 0.1% of 25% aq. NH₃): supercritical CO₂, 45%: 55% to 55%: 45% (v/v)). Compound 70A (15.02 mg, 0.032 mmol, 29.51%) and Compound 70B (13.23 mg, 0.028 mmol, 26.39%) were obtained. Compound 70A:
SFC: Retention time: 1.543 min.
LCMS: Retention time: 0.785 min, (M+H)=465.3, 5-95AB_220&254_Agilent.M HPLC: Retention time: 3.565 min, 10-80AB_8 min.met ¹H NMR: (400 MHz, DMSO-d₆) δ=12.40-11.98 (m, 1H), 8.80 (d, J=8.9 Hz, 1H), 8.39 (d, J=8.0 Hz, 1H), 8.33 (d, J=8.9 Hz, 1H), 8.12 (s, 1H), 7.73 (d, J=8.1 Hz, 1H), 7.61-7.49 (m, 2H), 7.45-7.11 (m, 1H), 5.71 (d, J=5.6 Hz, 1H), 3.59 (m, 1H), 2.79 (s, 3H), 0.48-0.32 (m, 3H), 0.31-0.15 (m, 2H).

Compound 70B:

SFC: Retention time: 2.141 min.

LCMS: Retention time: 0.785 min, (M+H)=465.3, 5-95AB_220&254_Agilent.M

HPLC: Retention time: 3.550 min, 10-80AB_8 min.met

¹H NMR: (400 MHz, DMSO-d₆) δ=12.39-12.02 (m, 1H), 8.80 (d, J=8.9 Hz, 1H), 8.39 (d, J=8.0 Hz, 1H), 8.33 (d, J=8.9 Hz, 1H), 8.15-8.08 (m, 1H), 7.73 (d, J=8.0 Hz, 1H), 7.62-7.47 (m, 2H), 7.43-7.13 (m, 1H), 5.71 (d, J=6.0 Hz, 1H), 3.64-3.53 (m, 1H), 2.79 (s, 3H), 0.48-0.32 (m, 3H), 0.31-0.14 (m, 2H).

Example 25. Synthesis of Compounds 72A and 72B

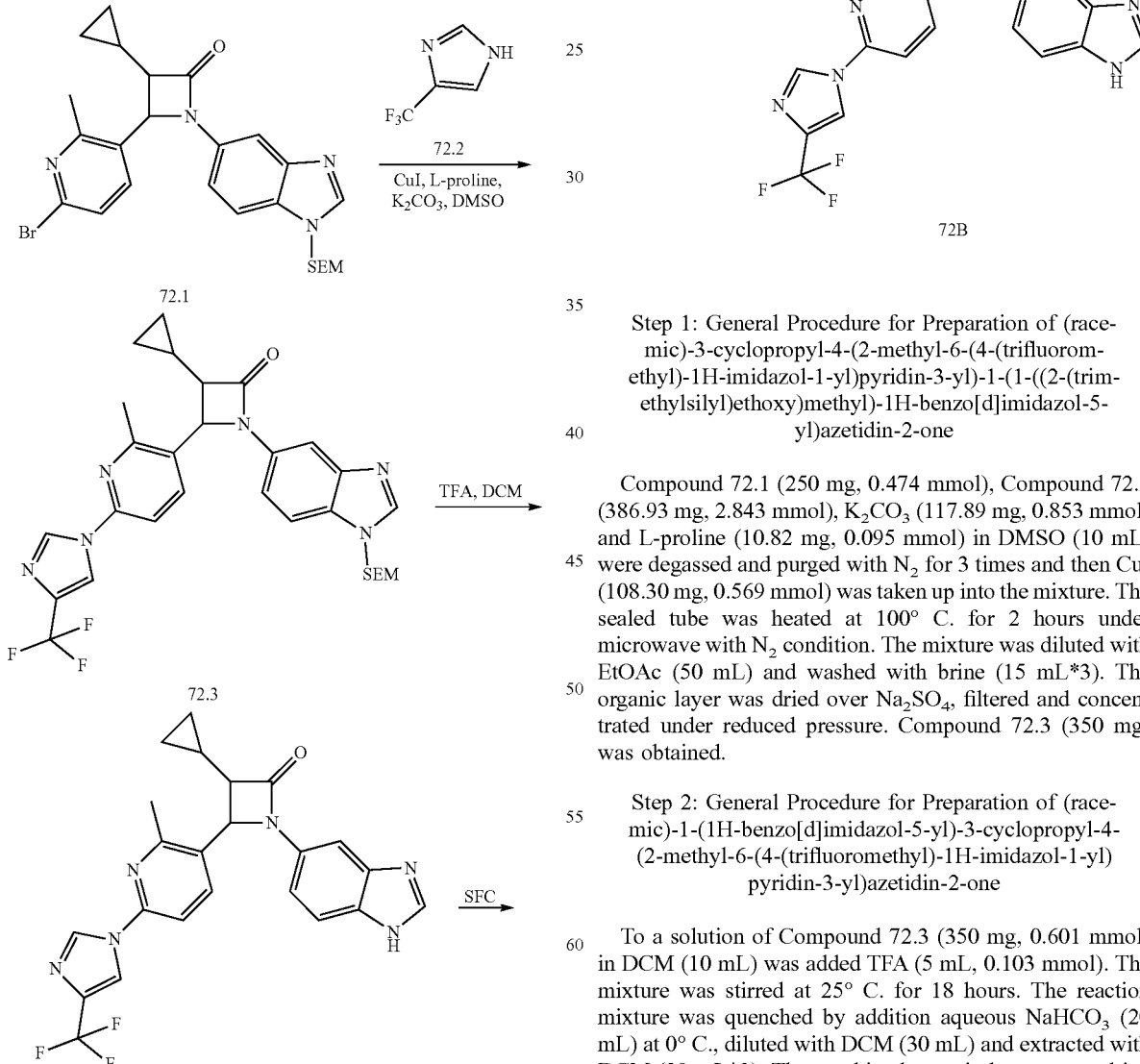

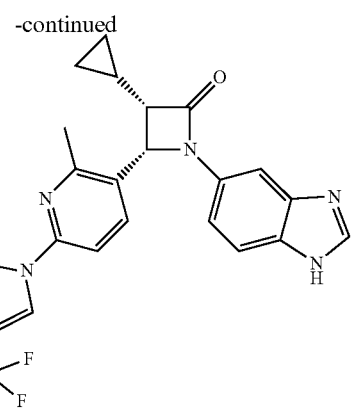

Step 1: General Procedure for Preparation of (racemic)-3-cyclopropyl-4-(2-methyl-6-(4-(trifluoromethyl)-1H-imidazol-1-yl)pyridin-3-yl)-1-(1-((2-(trimethylsilyl)ethoxy)methyl)-1H-benzo[d]imidazol-5-yl)azetidin-2-one Compound 72.1 (250 mg, 0.474 mmol), Compound 72.2 (386.93 mg, 2.843 mmol), K₂CO₃ (117.89 mg, 0.853 mmol) and L-proline (10.82 mg, 0.095 mmol) in DMSO (10 mL) were degassed and purged with N₂ for 3 times and then CuI (108.30 mg, 0.569 mmol) was taken up into the mixture. The sealed tube was heated at 100° C. for 2 hours under microwave with N₂ condition. The mixture was diluted with EtOAc (50 mL) and washed with brine (15 mL*3). The organic layer was dried over Na₂SO₄, filtered and concentrated under reduced pressure. Compound 72.3 (350 mg) was obtained.

Step 2: General Procedure for Preparation of (racemic)-1-(1H-benzo[d]imidazol-5-yl)-3-cyclopropyl-4-(2-methyl-6-(4-(trifluoromethyl)-1H-imidazol-1-yl)pyridin-3-yl)azetidin-2-one To a solution of Compound 72.3 (350 mg, 0.601 mmol) in DCM (10 mL) was added TFA (5 mL, 0.103 mmol). The mixture was stirred at 25° C. for 18 hours. The reaction mixture was quenched by addition aqueous NaHCO₃ (20 mL) at 0° C., diluted with DCM (30 mL) and extracted with DCM (20 mL*3). The combined organic layers were dried over anhydrous Na₂SO₄, filtered and concentrated under reduced pressure.

The residue was purified by pre-HPLC. Compound 72 (40 mg, 0.088 mmol, 14.57%) was obtained.

LCMS: Retention time: 0.813 min, (M+H)=453.1, 5-95AB_220&254 Agilent

Step 3: General Procedure for Preparation of (3S, 4S)-1-(1H-benzo[d]imidazol-5-yl)-3-cyclopropyl-4-(2-methyl-6-(4-(trifluoromethyl)-1H-imidazol-1-yl)pyridin-3-yl)azetidin-2-one (Compound 72A) and (3R,4R)-1-(1H-benzo[d]imidazol-5-yl)-3-cyclopropyl-4-(2-methyl-6-(4-(trifluoromethyl)-1H-imidazol-1-yl)pyridin-3-yl)azetidin-2-one (Compound 72B)

Compound 72 (30 mg, 0.066 mmol) was purified by SFC. Compound 72A (15.27 mg, 0.034 mmol, 50.68% yield) and Compound 72B (13.7 mg, 0.030 mmol, 45.67% yield) were obtained.

Compound 72A:
SFC: Retention time: 1.256 min.
LCMS: Retention time: 0.770 min, (M+H)=453.3, 5-95AB_220&254_Agilent
HPLC: Retention time: 3.431 min, 10-80AB_8 min.met
$^1$H NMR: (400 MHz, DMSO-$d_6$) δ=12.49-12.30 (m, 1H), 8.69 (s, 1H), 8.56 (s, 1H), 8.25-8.14 (m, 1H), 7.66-7.63 (m, 1H), 7.62-7.59 (m, 1H), 7.54-7.49 (m, 1H), 7.47-7.39 (m, 1H), 7.22-7.09 (m, 1H), 5.71-5.62 (m, 1H), 3.58-3.46 (m, 1H), 2.69 (s, 3H), 0.41-0.32 (m, 3H), 0.27-0.12 (m, 2H).
$^1$H NMR: (400 MHz, DMSO-$d_6$) (t=75) δ=12.30-12.10 (m, 1H), 8.62 (s, 1H), 8.46 (s, 1H), 8.18-8.07 (m, 1H), 7.69-7.55 (m, 3H), 7.52-7.48 (m, 1H), 7.41-7.10 (m, 1H), 5.66 (d, J=6.0 Hz, 1H), 3.54 (t, J=6.4 Hz, 1H), 2.70 (s, 3H), 0.43-0.34 (m, 3H), 0.30-0.17 (m, 2H).

Compound 72B:
SFC: Retention time: 2.405 min.
LCMS: Retention time: 0.771 min, (M+H)=453.3, 5-95AB_220&254_Agilent
HPLC: Retention time: 3.435 min, 10-80AB_8 min.met
$^1$H NMR: (400 MHz, DMSO-$d_6$) δ=12.48-12.27 (m, 1H), 8.69 (s, 1H), 8.55 (s, 1H), 8.18 (s, 1H), 7.68-7.20 (m, 5H), 5.67 (d, J=5.6 Hz, 1H), 3.51 (t, J=7.0 Hz, 1H), 2.69 (s, 3H), 0.39-0.31 (m, 3H), 0.26-0.14 (m, 2H).
$^1$H NMR: (400 MHz, DMSO-$d_6$) (t=75) δ=12.35-11.98 (m, 1H), 8.62 (s, 1H), 8.46 (s, 1H), 8.12 (s, 1H), 7.67-7.60 (m, 2H), 7.58-7.52 (m, 1H), 7.52-7.46 (m, 1H), 7.34-7.15 (m, 1H), 5.66 (d, J=6.0 Hz, 1H), 3.56-3.52 (m, 1H), 2.70 (s, 3H), 0.44-0.33 (m, 3H), 0.30-0.17 (m, 2H).

Example 26. Synthesis of Compounds RF-1A and RF-1B

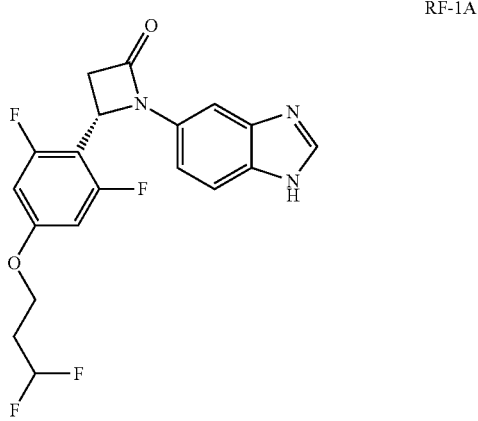

RF-1A

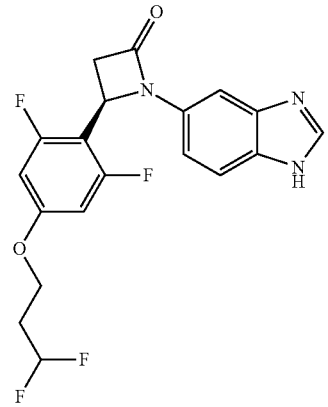

RF-1B (S)-1-(1H-benzo[d]imidazol-5-yl)-4-(4-(3,3-difluoropropoxy)-2,6-difluorophenyl)azetidin-2-one (Compound RF-1A) and (R)-1-(1H-benzo[d]imidazol-5-yl)-4-(4-(3,3-difluoropropoxy)-2,6-difluorophenyl)azetidin-2-one (Compound RF-1B) were synthesized under the same synthetic route as for compound 2, which was determined by HNMR, LCMS and HPLC.

Compound RF-1A:
LCMS: Retention time: 0.789 min, (M+H)=394.1, 5-95AB_1.5 min_220&254 Shimadzu
HPLC: Retention time: 3.26 min, 10-80AB_8 min.met
$^1$H NMR: (400 MHz, DMSO-$d_6$) δ=12.41 (br s, 1H), 8.16 (s, 1H), 7.53 (d, J=8.8 Hz, 1H), 7.33 (s, 1H), 7.14 (d, J=8.0 Hz, 1H), 6.82 (d, J=10.8 Hz, 2H), 6.37-6.01 (m, 1H), 5.45 (d, J=3.6 Hz, 1H), 4.13 (t, J=6.1 Hz, 2H), 3.60 (dd, J=5.8, 14.8 Hz, 1H), 3.22 (dd, J=2.0, 14.8 Hz, 1H), 2.38-2.20 (m, 2H).

Compound RF-1B:
LCMS: Retention time: 0.792 min, (M+H)=394.0, 5-95AB_1.5 min_220&254_Shimadzu
HPLC: Retention time: 3.24 min, 10-80AB_8 min.met
$^1$H NMR: (400 MHz, DMSO-$d_6$) δ=12.52-12.27 (m, 1H), 8.14 (br s, 1H), 7.64-7.43 (m, 1H), 7.41-6.97 (m, 2H), 6.82 (d, J=10.8 Hz, 2H), 6.38-6.01 (m, 1H), 5.45 (br d, J=3.8 Hz, 1H), 4.13 (t, J=6.0 Hz, 2H), 3.60 (dd, J=5.4, 14.8 Hz, 1H), 3.22 (dd, J=1.8, 14.8 Hz, 1H), 2.37-2.18 (m, 2H).

Example 27. Synthesis of Compound 23CR

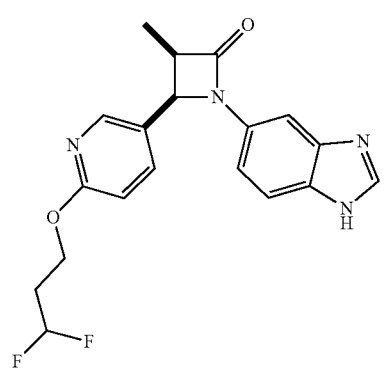 [SMILES: C[C@H]1C(=O)N(c2ccc3[nH]cnc3c2)[C@H]1c1ccc(OCCC(F)F)nc1]

(cis and racemic)-1-(1H-benzo[d]imidazol-5-yl)-4-(6-(3,3-difluoropropoxy) pyridin-3-yl)-3-methylazetidin-2-one (Compound 23CR) was synthesized under the same synthetic route as for Compound 18, which was determined by ¹H NMR, LCMS and HPLC.

LCMS: Retention time: 0.753 min, (M+H)=373.2, 5-95AB_220&254_Agilent

HPLC: Retention time: 3.07 min, 10-80AB_8 min.met

¹H NMR: (400 MHz, DMSO-$d_6$) δ=12.51-12.26 (m, 1H), 8.22-8.09 (m, 2H), 7.63-7.06 (m, 4H), 6.81 (d, J=8.5 Hz, 1H), 6.40-6.03 (m, 1H), 5.46 (d, J=5.8 Hz, 1H), 4.37 (t, J=6.3 Hz, 2H), 3.83-3.72 (m, 1H), 2.38-2.21 (m, 2H), 0.81 (d, J=7.5 Hz, 3H).

Example 28. Synthesis of Compounds 28CR and 28TR

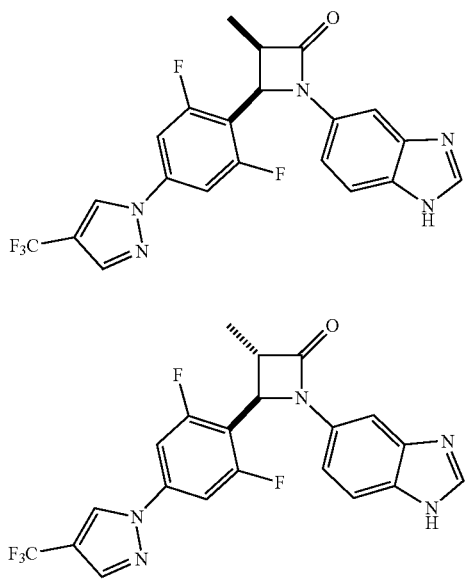

(cis and racemic)-1-(1H-benzo[d]imidazol-5-yl)-4-(2,6-difluoro-4-(4-(trifluoromethyl)-1H-pyrazol-1-yl)phenyl)-3-methylazetidin-2-one (Compound 28CR) and (trans and racemic)-1-(1H-benzo[d]imidazol-5-yl)-4-(2,6-difluoro-4-(4-(trifluoromethyl)-1H-pyrazol-1-yl)phenyl)-3-methylazetidin-2-one (Compound 28TR) were synthesized under the same synthetic route as for Compound 48, which was determined by HNMR, LCMS and HPLC.

Compound 28CR:

LCMS: Retention time: 4.057 min, (M+H)=448.1, 10-80CD_7 min_220&254_Shimadzu

HPLC: Retention time: 3.949 min, 10-80AB_8 min.lcm

¹H NMR: (400 MHz, DMSO-$d_6$) δ=12.54-12.24 (m, 1H), 9.27 (s, 1H), 8.29 (s, 1H), 8.24-8.06 (m, 1H), 7.98-6.98 (m, 5H), 5.71 (d, J=6.0 Hz, 1H), 3.99-3.94 (m, 1H), 1.04 (d, J=7.8 Hz, 3H).

Compound 28TR:

LCMS: Retention time: 0.797 min, (M+H)=448.0, 5-95AB_1.5 min_220&254

HPLC: Retention time: 4.04 min, 10-80AB_8 min.lcm

¹H NMR: (400 MHz, DMSO-$d_6$) δ=12.50-12.31 (m, 1H), 9.25 (s, 1H), 8.28 (s, 1H), 8.19-8.11 (m, 1H), 7.83-7.72 (m, 2H), 7.61-7.45 (m, 1H), 7.43-7.00 (m, 1H), 5.20 (s, 1H), 3.69-3.56 (m, 1H), 1.44 (d, J=7.2 Hz, 3H).

Example 29. Synthesis of Compounds 30A and 30B

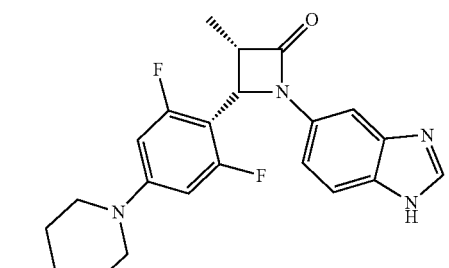

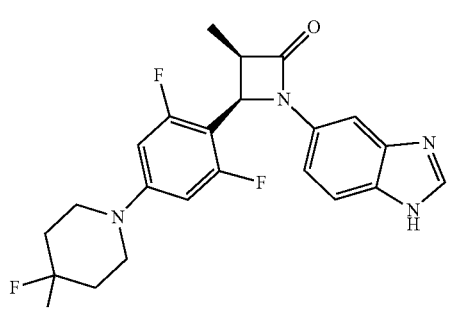

(3S,4S)-1-(1H-benzo[d]imidazol-5-yl)-4-(4-(4,4-difluoropiperidin-1-yl)-2,6-difluorophenyl)-3-methylazetidin-2-one (Compound 30A) and (3R,4R)-1-(1H-benzo[d]imidazol-5-yl)-4-(4-(4,4-difluoropiperidin-1-yl)-2,6-difluorophenyl)-3-methylazetidin-2-one (Compound 30B) were synthesized under the same synthetic route as for Compound 48, which was determined by HNMR, LCMS and HPLC.

Compound 30A:

SFC: Retention time: 1.736 min.

LCMS: Retention time: 0.935 min, (M+H)=433.2, 10-80AB_2 min_Agilent

HPLC: Retention time: 3.709 min, 10-80AB_8 min.lcm

¹H NMR: (400 MHz, DMSO-$d_6$) δ=12.50-12.25 (m, 1H), 8.19-8.11 (m, 1H), 7.59-7.04 (m, 5H), 5.53 (d, J=5.6 Hz, 1H), 3.89-3.78 (m, 1H), 2.55-2.54 (m, 3H), 2.10-1.88 (m, 5H), 1.01 (d, J=7.6 Hz, 3H).

Compound 30B:

SFC: Retention time: 3.764 min.

LCMS: Retention time: 0.935 min, (M+H)=433.2, 10-80AB_2 min_Agilent

HPLC: Retention time: 3.713 min, 10-80AB_8 min.lcm

¹H NMR: (400 MHz, DMSO-$d_6$) δ=12.51-12.24 (m, 1H), 8.24-8.08 (m, 1H), 7.64-6.94 (m, 5H), 5.53 (d, J=5.6 Hz, 1H), 3.90-3.78 (m, 1H), 2.60-2.56 (m, 3H), 2.06-1.90 (m, 5H), 1.01 (d, J=7.6 Hz, 3H).

Example 30. Synthesis of Compounds 32A and 32B

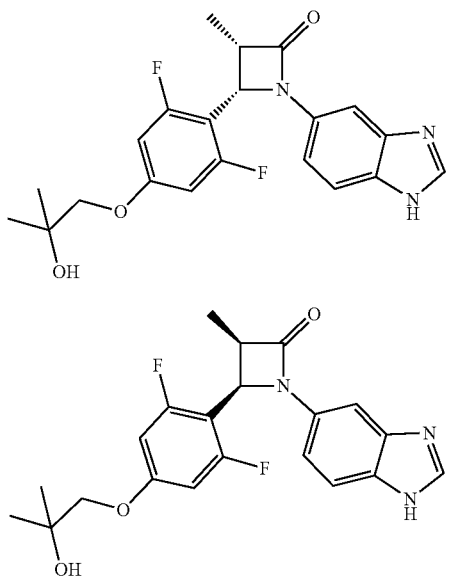

(3S,4S)-1-(1H-benzo[d]imidazol-5-yl)-4-(2,6-difluoro-4-(2-hydroxy-2-methylpropoxy)phenyl)-3-methylazetidin-2-one (Compound 32A) and (3R,4R)-1-(1H-benzo[d]imidazol-5-yl)-4-(2,6-difluoro-4-(2-hydroxy-2-methylpropoxy)phenyl)-3-methylazetidin-2-one (Compound 32B) were synthesized under the same synthetic route as for Compound 18, which was determined by $^1$H NMR, LCMS and HPLC.

Compound 32A:
SFC: Retention time: 3.716 min.
LCMS: Retention time: 0.770 min, (M+H)=402.1, 5-95AB_1.5 min_220&254
HPLC: Retention time: 2.955 min, 10-80AB_8 min.lcm
$^1$H NMR: (400 MHz, DMSO-d$_6$) δ=12.50-12.25 (m, 1H), 8.20-8.10 (m, 1H), 7.59-7.44 (m, 1H), 7.41-7.04 (m, 2H), 6.98-6.60 (m, 2H), 5.58 (d, J=5.7 Hz, 1H), 4.69-4.66 (m, 1H), 3.92-3.82 (m, 1H), 3.75-3.69 (m, 2H), 1.16 (s, 6H), 1.00 (d, J=7.6 Hz, 3H).

Compound 32B:
SFC: Retention time: 4.269 min.
LCMS: Retention time: 0.763 min, (M+H)=402.1, 5-95AB_1.5 min_220&254_Shimadzu
HPLC: Retention time: 2.952 min, 10-80AB 8 min.lcm

Example 31. Synthesis of Compounds 34CR and 34TR

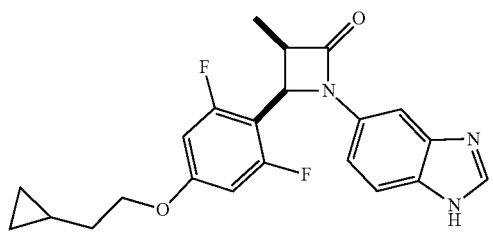

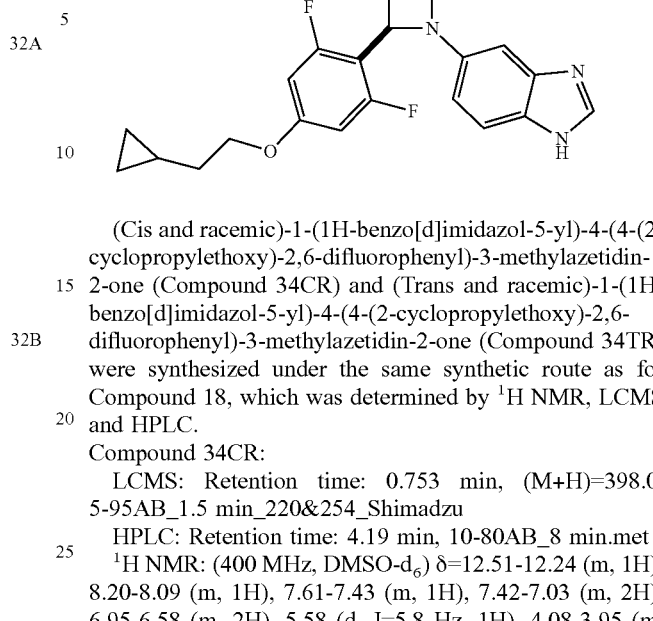

(Cis and racemic)-1-(1H-benzo[d]imidazol-5-yl)-4-(4-(2-cyclopropylethoxy)-2,6-difluorophenyl)-3-methylazetidin-2-one (Compound 34CR) and (Trans and racemic)-1-(1H-benzo[d]imidazol-5-yl)-4-(4-(2-cyclopropylethoxy)-2,6-difluorophenyl)-3-methylazetidin-2-one (Compound 34TR) were synthesized under the same synthetic route as for Compound 18, which was determined by $^1$H NMR, LCMS and HPLC.

Compound 34CR:
LCMS: Retention time: 0.753 min, (M+H)=398.0, 5-95AB_1.5 min_220&254_Shimadzu
HPLC: Retention time: 4.19 min, 10-80AB_8 min.met
$^1$H NMR: (400 MHz, DMSO-d$_6$) δ=12.51-12.24 (m, 1H), 8.20-8.09 (m, 1H), 7.61-7.43 (m, 1H), 7.42-7.03 (m, 2H), 6.95-6.58 (m, 2H), 5.58 (d, J=5.8 Hz, 1H), 4.08-3.95 (m, 2H), 3.92-3.78 (m, 1H), 1.66-1.49 (m, 2H), 1.00 (d, J=7.6 Hz, 3H), 0.87-0.68 (m, 1H), 0.47-0.35 (m, 2H), 0.16-0.02 (m, 2H).

Compound 34TR:
LCMS: Retention time: 0.761 min, (M+H)=398.1, 5-95AB_1.5 min_220&254_Shimadzu
HPLC: Retention time: 4.22 min, 10-80AB_8 min.met
$^1$H NMR: (400 MHz, DMSO-d$_6$) δ=12.61-12.19 (m, 1H), 8.24-8.05 (m, 1H), 7.62-7.44 (m, 1H), 7.41-7.01 (m, 2H), 6.85-6.68 (m, 2H), 5.05 (s, 1H), 4.10-3.91 (m, 2H), 3.57-3.48 (m, 1H), 1.66-1.49 (m, 2H), 1.40 (d, J=7.6 Hz, 3H), 0.85-0.70 (m, 1H), 0.47-0.29 (m, 2H), 0.15--0.05 (m, 2H).

Example 32. Synthesis of Compound 44B

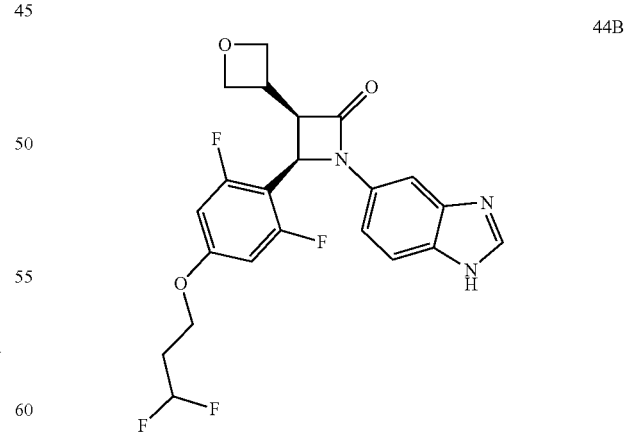

(3R,4R)-1-(1H-benzo[d]imidazol-5-yl)-4-(4-(3,3-difluoropropoxy)-2,6-difluorophenyl)-3-(oxetan-3-yl)azetidin-2-one (Compound 44B) was synthesized under the same synthetic route as for Compound 18, which was determined by $^1$H NMR, LCMS and HPLC.

LCMS: Retention time: 0.838 min, (M+H)=450.2, 10-80AB_2 min_Agilent

HPLC: Retention time: 6.92 min, 0-30AB_8 min.met $^1$H NMR: (400 MHz, DMSO-$d_6$) δ=12.48 (s, 1H), 8.19 (br s, 1H), 7.53 (br s, 1H), 7.38 (br s, 1H), 6.80 (br s, 2H), 6.40-6.03 (m, 1H), 5.64 (d, J=4.0 Hz, 1H), 4.68-4.61 (m, 1H), 4.60-4.54 (m, 1H), 4.40-4.30 (m, 1H), 4.19 (d, J=6.4 Hz, 2H), 4.13 (br s, 2H), 3.62 (br s, 1H), 3.09 (br s, 1H), 2.29-2.20 (m, 2H).

Example 33. Synthesis of Compounds 45A and 45B

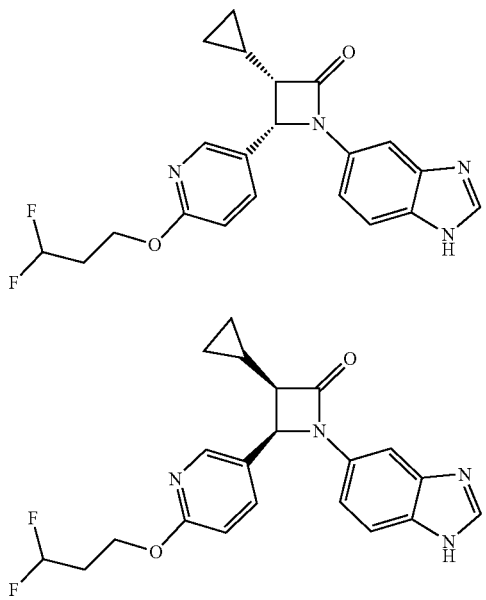

(3S,4S)-1-(1H-benzo[d]imidazol-5-yl)-3-cyclopropyl-4-(6-(3,3-difluoropropoxy)pyridin-3-yl)azetidin-2-one (Compound 45A) and (3R,4R)-1-(1H-benzo[d]imidazol-5-yl)-3-cyclopropyl-4-(6-(3,3-difluoropropoxy)pyridin-3-yl)azetidin-2-one (Compound 45B) were synthesized under the same synthetic route as for compound 18, which was determined by $^1$H NMR, LCMS and HPLC.

Compound 45A:

LCMS: Retention time: 0.790 min, (M+H)=399.2, 5-95AB_220&254_Agilent

HPLC: Retention time: 3.41 min, 10-80AB_8 min.met $^1$H NMR: (400 MHz, DMSO-$d_6$) δ=12.51-12.28 (m, 1H), 8.21-8.11 (m, 2H), 7.65 (dd, J=2.5, 8.6 Hz, 1H), 7.60-7.08 (m, 3H), 6.81 (d, J=8.6 Hz, 1H), 6.39-6.06 (m, 1H), 5.43 (d, J=5.7 Hz, 1H), 4.37 (t, J=6.3 Hz, 2H), 3.32-3.28 (m, 1H), 2.37-2.22 (m, 2H), 0.52-0.32 (m, 3H), 0.16-0.07 (m, 2H).

Compound 45B:

LCMS: Retention time: 0.792 min, (M+H)=399.2, 5-95AB_220&254_Agilent

HPLC: Retention time: 3.41 min, 10-80AB_8 min.met $^1$H NMR: (400 MHz, DMSO-$d_6$) δ=12.54-12.25 (m, 1H), 8.23-8.10 (m, 2H), 7.65 (dd, J=2.4, 8.6 Hz, 1H), 7.60-7.08 (m, 3H), 6.81 (d, J=8.5 Hz, 1H), 6.39-6.05 (m, 1H), 5.43 (d, J=5.7 Hz, 1H), 4.36 (t, J=6.3 Hz, 2H), 3.31-3.27 (m, 1H), 2.37-2.22 (m, 2H), 0.51-0.33 (m, 3H), 0.17-0.08 (m, 2H).

Example 34. Synthesis of Compounds 46A and 46B

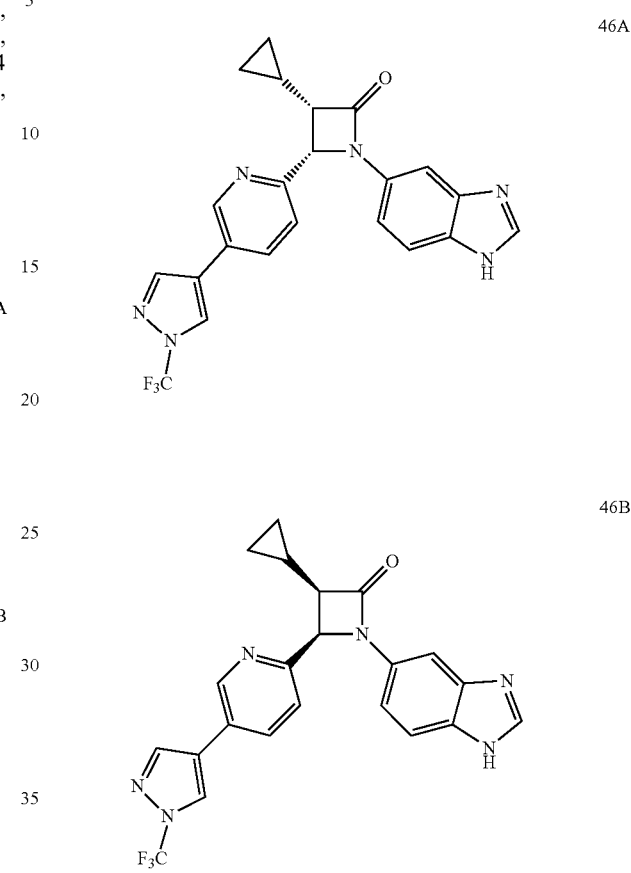

(3S,4S)-1-(1H-benzo[d]imidazol-5-yl)-3-cyclopropyl-4-(5-(1-(trifluoromethyl)-1H-pyrazol-4-yl)pyridin-2-yl)azetidin-2-one (Compound 46A) and (3R,4R)-1-(1H-benzo[d]imidazol-5-yl)-3-cyclopropyl-4-(5-(1-(trifluoromethyl)-1H-pyrazol-4-yl)pyridin-2-yl)azetidin-2-one (Compound 46B) were synthesized under the same synthetic route as for Compound 17, which was determined by $^1$H NMR, LCMS and HPLC.

Compound 46A:

LCMS: Retention time: 0.791 min, (M+H)=439.2, 5-95AB_1.5 min_220&254

HPLC: Retention time: 2.736 min, 10-80AB_4 min.lcm $^1$H NMR: (400 MHz, DMSO-$d_6$) δ=12.62-11.56 (m, 1H), 9.00-8.94 (m, 2H), 8.46 (s, 1H), 8.13-8.09 (m, 1H), 8.08 (s, 1H), 7.54-7.41 (m, 3H), 7.20 (d, J=8.0 Hz, 1H), 5.45 (d, J=6.0 Hz, 1H), 3.44-3.37 (m, 1H), 0.65-0.50 (m, 1H), 0.42-0.31 (m, 2H), 0.18-0.04 (m, 2H).

Compound 46B:

LCMS: Retention time: 0.792 min, (M+H)=439.1, 5-95AB_1.5 min_220&254

HPLC: Retention time: 2.728 min, 10-80AB_4 min.lcm $^1$H NMR: (400 MHz, DMSO-$d_6$) δ=12.42-11.71 (m, 1H), 8.99-8.94 (m, 2H), 8.46 (s, 1H), 8.13-8.09 (m, 1H), 8.08 (s, 1H), 7.53-7.41 (m, 3H), 7.20 (d, J=8.0 Hz, 1H), 5.45 (d, J=6.0 Hz, 1H), 3.43-3.37 (m, 1H), 0.63-0.53 (m, 1H), 0.40-0.33 (m, 2H), 0.17-0.04 (m, 2H).

Example 35. Synthesis of Compound 47B

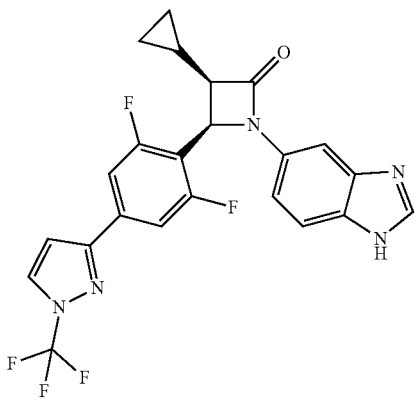 [SMILES: O=C1[C@H](C2CC2)[C@H](c2c(F)cc(-c3ccn(C(F)(F)F)n3)cc2F)N1c1ccc2[nH]cnc2c1]

(3R,4R)-1-(1H-benzo[d]imidazol-5-yl)-3-cyclopropyl-4-(2,6-difluoro-4-(1-(trifluoromethyl)-1H-pyrazol-3-yl)phenyl)azetidin-2-one (Compound 47B) was synthesized under the same synthetic route as for compound 35B, which was determined by $^1$H NMR, LCMS and HPLC.

LCMS: Retention time: 0.817 min, (M+H)=474.2, 5-95AB_1.5 min_220&254

HPLC: Retention time: 4.120 min, 10-80AB_4 min.lcm $^1$H NMR: (400 MHz, DMSO-d$_6$) δ=12.73-12.33 (m, 1H), 8.60 (d, J=2.8 Hz, 1H), 8.19 (s, 1H), 7.88-7.67 (m, 1H), 7.61-7.49 (m, 2H), 7.44-7.43 (m, 1H), 7.28 (d, J=2.8 Hz, 1H), 7.23-7.18 (m, 1H), 5.66 (d, J=6.0 Hz, 1H), 3.44-3.39 (m, 1H), 0.74-0.61 (m, 1H), 0.54-0.36 (m, 2H), 0.25--0.01 (m, 2H).

Example 36. Synthesis of Compound 49B

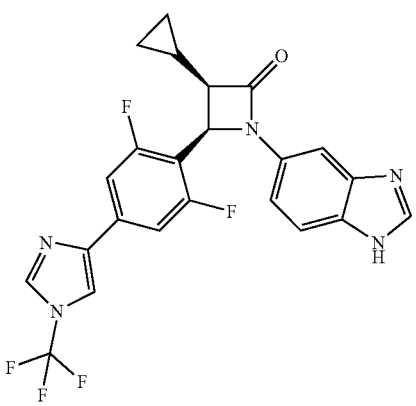 [SMILES: O=C1[C@H](C2CC2)[C@H](c2c(F)cc(-c3cn(C(F)(F)F)cn3)cc2F)N1c1ccc2[nH]cnc2c1]

(3R,4R)-1-(1H-benzo[d]imidazol-5-yl)-3-cyclopropyl-4-(2,6-difluoro-4-(1-(trifluoromethyl)-1H-imidazol-4-yl)phenyl)azetidin-2-one (Compound 49B) was synthesized under the same synthetic route as for Compound 35B, which was determined by $^1$H NMR, LCMS and HPLC.

LCMS: Retention time: 0.749 min, (M+H)=474.1, 5-95AB_1.5 min_220&254

HPLC: Retention time: 3.363 min, 10-80AB_8 min.lcm $^1$HNMR: (400 MHz, DMSO-d$_6$) δ=13.22-12.44 (m, 1H), 8.52 (s, 1H), 8.43 (s, 1H), 7.63-7.59 (m, 1H), 7.52-7.50 (m, 1H), 7.46-7.32 (m, 2H), 7.32-7.17 (m, 2H), 5.72 (d, J=6.0 Hz, 1H), 3.51-3.43 (m, 1H), 3.51-3.43 (m, 1H), 0.74-0.60 (m, 1H), 0.56-0.36 (m, 2H), 0.24-0.01 (m, 2H).

Example 37. Synthesis of Compounds 51A and 51B

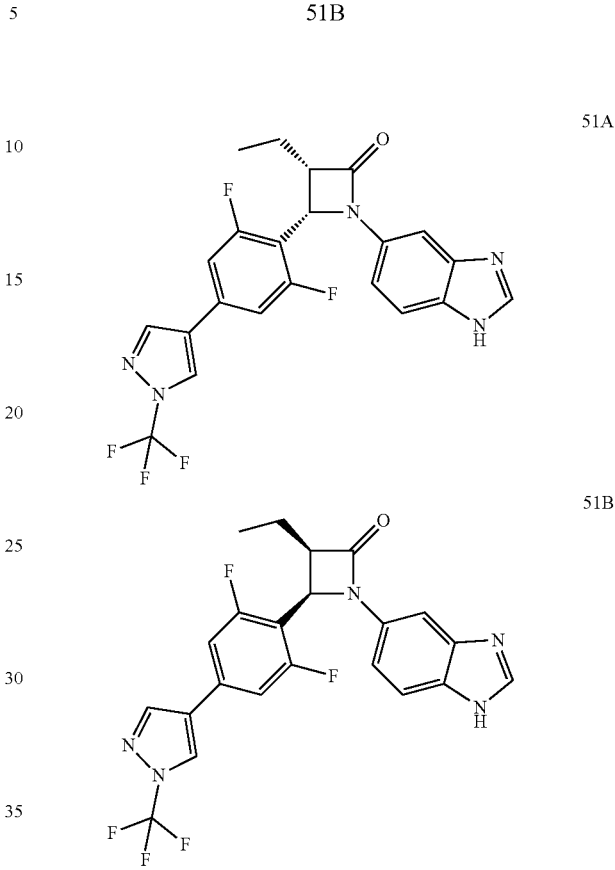

(3S,4S)-1-(1H-benzo[d]imidazol-5-yl)-4-(2,6-difluoro-4-(1-(trifluoromethyl)-1H-pyrazol-4-yl)phenyl)-3-ethylazetidin-2-one (Compound 51A) and (3R,4R)-1-(1H-benzo[d]imidazol-5-yl)-4-(2,6-difluoro-4-(1-(trifluoromethyl)-1H-pyrazol-4-yl)phenyl)-3-ethylazetidin-2-one Compound 51B) were synthesized under the same synthetic route as for Compound 17, which was determined by $^1$H NMR, LCMS and HPLC.

Compound 51A:
SFC: Retention time: 4.532 min.
LCMS: Retention time: 1.967 min, (M+H)=462.1, 10-80CD_3 min_220&254_Agilent
HPLC: Retention time: 3.967 min, 10-80AB_8 min.met
$^1$H NMR: (400 MHz, DMSO-d$_6$) δ=12.86-11.91 (m, 1H), 9.12 (s, 1H), 8.56 (s, 1H), 8.15 (s, 1H), 7.78-7.61 (m, 1H), 7.56-7.48 (m, 2H), 7.40-7.34 (m, 1H), 7.22-7.15 (m, 1H), 5.69 (d, J=6.0 Hz, 1H), 3.80-3.73 (m, 1H), 1.73-1.60 (m, 1H), 1.37-1.28 (m, 1H), 0.84 (t, J=7.6 Hz, 3H).

Compound 51B:
SFC: Retention time: 5.448 min.
LCMS: Retention time: 1.967 min, (M+H)=462.1, 10-80CD_3 min_220&254 Agilent
HPLC: Retention time: 3.970 min, 10-80AB_8 min.met
$^1$HNMR: (400 MHz, DMSO-d$_6$) δ=12.78-11.97 (m, 1H), 9.12 (s, 1H), 8.56 (s, 1H), 8.15 (s, 1H), 7.86-7.66 (m, 1H), 7.63-7.44 (m, 2H), 7.43-7.31 (m, 1H), 7.29-7.00 (m, 1H), 5.69 (d, J=6.0 Hz, 1H), 3.91-3.65 (m, 1H), 1.75-1.60 (m, 1H), 1.41-1.27 (m, 1H), 0.83 (t, J=7.6 Hz, 3H)

Example 38. Synthesis of Compound 54B

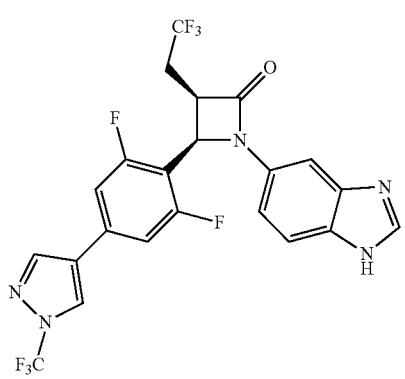 [SMILES: O=C1[C@H](CC(F)(F)F)[C@H](c2c(F)cc(-c3cnn(C(F)(F)F)c3)cc2F)N1c1ccc2[nH]cnc2c1]

54B (3R,4R)-1-(1H-benzo[d]imidazol-5-yl)-4-(2,6-difluoro-4-(1-(trifluoromethyl)-1H-pyrazol-4-yl)phenyl)-3-(2,2,2-trifluoroethyl)azetidin-2-one (Compound 54B) was synthesized under the same synthetic route as for Compound 17, which was determined by $^1$H NMR, LCMS and HPLC.

SFC: Retention time: 2.987 min.

LCMS: Retention time: 0.963 min, (M+H)=516.0, 10-80AB_2 min_Agilent.M

HPLC: Retention time: 4.014 min, 10-80AB 8 min.met $^1$H NMR: (400 MHz, DMSO-d$_6$) δ=12.58-12.26 (m, 1H), 9.14 (s, 1H), 8.56 (s, 1H), 8.23-8.12 (m, 1H), 7.84-7.71 (m, 1H), 7.64-7.47 (m, 2H), 7.45-7.32 (m, 1H), 7.32-7.06 (m, 1H), 5.90-5.79 (m, 1H), 4.31-4.19 (m, 1H), 2.87-2.78 (m, 1H), 2.35-2.30 (m, 1H).

Example 39. Synthesis of Compounds 55A and 55B

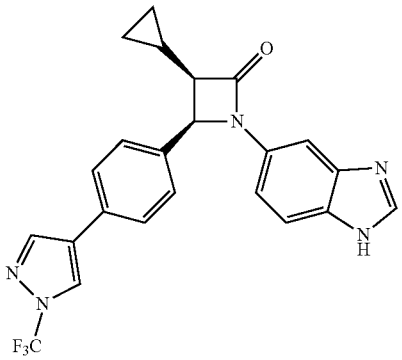

55B (3S,4S)-1-(1H-benzo[d]imidazol-5-yl)-3-cyclopropyl-4-(4-(1-(trifluoromethyl)-1H-pyrazol-4-yl)phenyl)azetidin-2-one (Compound 55A) and (3R,4R)-1-(1H-benzo[d]imidazol-5-yl)-3-cyclopropyl-4-(4-(1-(trifluoromethyl)-1H-pyrazol-4-yl)phenyl)azetidin-2-one (Compound 55B) were synthesized under the same synthetic route as for Compound 17, which was determined by $^1$H NMR, LCMS and HPLC.

Compound 55A:

SFC: Retention time: 3.890 min.

LCMS: Retention time: 1.936 min, (M+H)=438.1, 10-80CD_3 min_220&254_Agilent

HPLC: Retention time: 3.809 min, 10-80AB_8 min.met $^1$H NMR: (400 MHz, DMSO-d$_6$) (t=75) δ=8.84-8.81 (m, 1H), 8.38-8.34 (m, 1H), 8.20-8.16 (m, 1H), 7.75-7.70 (m, 2H), 7.56-7.52 (m, 1H), 7.49-7.47 (m, 1H), 7.43-7.38 (m, 2H), 7.29-7.25 (m, 1H), 5.44 (d, J=5.6 Hz, 1H), 3.34-3.33 (m, 1H), 0.52-0.44 (m, 1H), 0.43-0.36 (m, 2H), 0.20-0.08 (m, 2H).

Compound 55B:

SFC: Retention time: 4.394 min.

LCMS: Retention time: 1.939 min, (M+H)=438.2, 10-80CD_3 min_220&254 Agilent HPLC: Retention time: 3.805 min, 10-80AB_8 min.met $^1$H NMR: (400 MHz, DMSO-d$_6$) (t=75) δ=12.41-11.92 (m, 1H), 8.82 (s, 1H), 8.39-8.33 (m, 1H), 8.09 (s, 1H), 7.76-7.69 (m, 2H), 7.59-7.50 (m, 1H), 7.48-7.44 (m, 1H), 7.43-7.37 (m, 2H), 7.26-7.12 (m, 1H), 5.43 (d, J=5.6 Hz, 1H), 3.36-3.30 (m, 1H), 0.53-0.44 (m, 1H), 0.44-0.35 (m, 2H), 0.21-0.07 (m, 2H).

Example 40. Synthesis of Compounds 56A and 56B

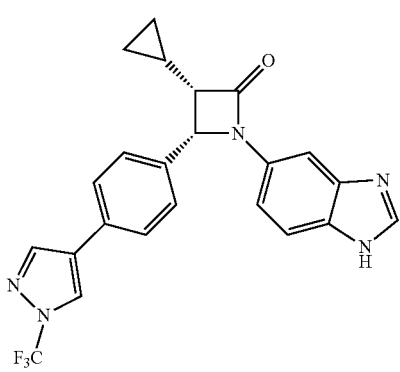

55A

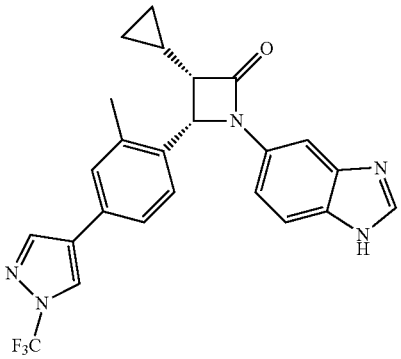

56A

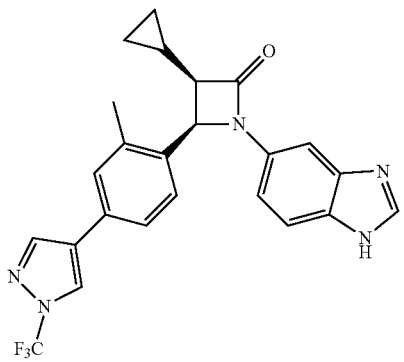

56B

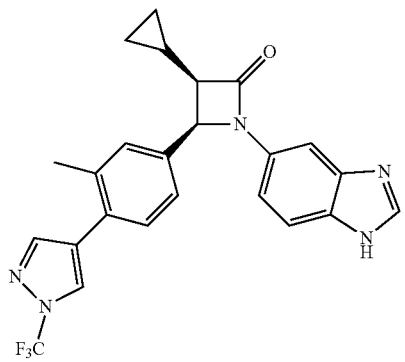

57B (3S,4S)-1-(1H-benzo[d]imidazol-5-yl)-3-cyclopropyl-4-(2-methyl-4-(1-(trifluoromethyl)-1H-pyrazol-4-yl)phenyl)azetidin-2-one (Compound 56A) and (3R,4R)-1-(1H-benzo[d]imidazol-5-yl)-3-cyclopropyl-4-(2-methyl-4-(1-(trifluoromethyl)-1H-pyrazol-4-yl)phenyl)azetidin-2-one (Compound 56B) were synthesized under the same synthetic route as for Compound 17, which was determined by ¹H NMR, LCMS and HPLC.

Compound 56A:
SFC: Retention time: 4.639 min.
LCMS: Retention time: 1.990 min, (M+H)=452.2, 10-80CD_3 min_220&254_Agilent
HPLC: Retention time: 3.981 min, 10-80AB_8 min.met
¹H NMR: (400 MHz, DMSO-$d_6$) δ=12.83-11.89 (m, 1H), 8.92 (s, 1H), 8.42 (s, 1H), 8.17 (s, 1H), 7.72-7.67 (m, 1H), 7.59-7.52 (m, 1H), 7.49-7.41 (m, 2H), 7.30-7.20 (m, 1H), 7.07 (s, 1H), 5.58 (d, J=5.6 Hz, 1H), 3.40-3.37 (m, 1H), 2.47 (s, 3H), 0.38-0.30 (m, 3H), 0.22-0.07 (m, 2H).

Compound 56B:
SFC: Retention time: 4.902 min.
LCMS: Retention time: 1.989 min, (M+H)=452.2, 10-80CD_3 min_220&254_Agilent 8 HPLC: Retention time: 4.004 min, 10-80AB_8 min.met
¹H NMR: (400 MHz, DMSO-$d_6$) δ=12.57-12.22 (m, 1H), 8.92 (s, 1H), 8.42 (s, 1H), 8.19-8.15 (m, 1H), 7.71-7.68 (m, 1H), 7.61-7.50 (m, 1H), 7.48-7.42 (m, 2H), 7.37-7.12 (m, 1H), 7.09-7.04 (m, 1H), 5.58 (d, J=5.6 Hz, 1H), 3.40-3.37 (m, 1H), 2.47 (s, 3H), 0.39-0.29 (m, 3H), 0.22-0.07 (m, 2H).

Example 41. Synthesis of Compounds 57A and 57B

57A (3S,4S)-1-(1H-benzo[d]imidazol-5-yl)-3-cyclopropyl-4-(3-methyl-4-(1-(trifluoromethyl)-1H-pyrazol-4-yl)phenyl)azetidin-2-one (Compound 57A) and (3R,4R)-1-(1H-benzo[d]imidazol-5-yl)-3-cyclopropyl-4-(3-methyl-4-(1-(trifluoromethyl)-1H-pyrazol-4-yl)phenyl)azetidin-2-one (Compound 57B) were synthesized under the same synthetic route as for Compound 17, which was determined by ¹H NMR, LCMS and HPLC.

Compound 57A:
SFC: Retention time: 3.607 min.
LCMS: Retention time: 0.840 min, (M+H)=452.2, 5-95AB_220&254_Agilent
HPLC: Retention time: 3.932 min, 10-80AB_8 min.met
1H NMR: (400 MHz, DMSO-$d_6$) δ=12.49-12.26 (m, 1H), 8.69 (s, 1H), 8.23 (s, 1H), 8.19-8.12 (m, 1H), 7.61-7.12 (m, 6H), 5.41 (d, J=5.8 Hz, 1H), 3.30-3.25 (m, 1H), 2.37 (s, 3H), 0.52-0.34 (m, 3H), 0.16-0.05 (m, 2H).

Compound 57B:
SFC: Retention time: 4.126 min.
LCMS: Retention time: 0.839 min, (M+H)=452.2, 5-95AB_220&254_Agilent
HPLC: Retention time: 3.935 min, 10-80AB_8 min.met
¹H NMR: (400 MHz, DMSO-$d_6$) δ=12.50-12.25 (m, 1H), 8.69 (s, 1H), 8.23 (s, 1H), 8.19-8.12 (m, 1H), 7.61-7.11 (m, 6H), 5.41 (d, J=5.7 Hz, 1H), 3.30-3.25 (m, 1H), 2.37 (s, 3H), 0.52-0.33 (m, 3H), 0.17-0.06 (m, 2H).

Example 42. Synthesis of Compound 53B (3R,4R)-1-(1H-benzo[d]imidazol-5-yl)-3-cyclopropyl-4-(2,6-difluoro-4-(pyrazin-2-yl)phenyl)azetidin-2-one (Compound 53B) was synthesized under the same synthetic route as for Compound 52B, which was determined by ¹H NMR, LCMS and HPLC.

SFC: Retention time: 5.510 min.
LCMS: Retention time: 0.661 min, (M+H)=418.2, 5-95AB_220&254_Agi1
HPLC: Retention time: 3.220 min, 10-80AB_8 min.lcm
$^1$H NMR: (400 MHz, DMSO-d$_6$) δ=12.86-11.83 (m, 1H), 9.36-9.35 (m, 1H), 8.75-8.73 (m, 1H), 8.69-8.67 (m, 1H), 8.18 (s, 1H), 8.09-7.77 (m, 2H), 7.60-7.50 (m, 1H), 7.48-7.40 (m, 1H), 7.30-7.15 (m, 1H), 5.71 (d, J=6.0 Hz, 1H), 3.47-3.41 (m, 1H), 0.71 (s, 1H), 0.54-0.36 (m, 2H), 0.24-0.03 (m, 2H).

Example 43. Synthesis of Compound 58B

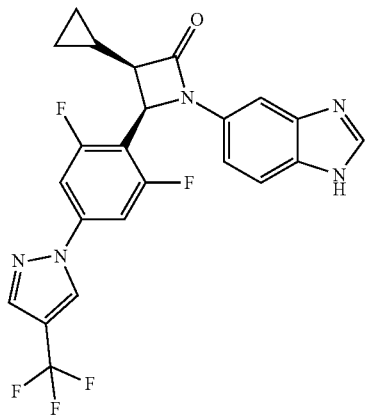 [SMILES: O=C1[C@H](C2CC2)[C@H](c2c(F)cc(-n3cc(C(F)(F)F)cn3)cc2F)N1c1ccc2[nH]cnc2c1]

(3R,4R)-1-(1H-benzo[d]imidazol-5-yl)-3-cyclopropyl-4-(2,6-difluoro-4-(4-(trifluoromethyl)-1H-pyrazol-1-yl)phenyl)azetidin-2-one (Compound 58B) was synthesized under the same synthetic route as for Compound 59, which was determined by $^1$H NMR, LCMS and HPLC.
SFC: Retention time: 1.263 min.
LCMS: Retention time: 2.019 min, (M+H)=474.1, 10-80CD_3 min_220&254_Agilent
HPLC: Retention time: 4.145 min, 10-80AB_8 min.lcm
$^1$H NMR: (400 MHz, DMSO-d$_6$) δ=12.77-12.08 (m, 1H), 9.27 (s, 1H), 8.29 (s, 1H), 8.25-8.04 (m, 1H), 7.96-7.38 (m, 4H), 7.29-7.17 (m, 1H), 5.67 (d, J=5.6 Hz, 1H), 3.45-3.42 (m, 1H), 0.76-0.64 (m, 1H), 0.57-0.37 (m, 2H), 0.26-0.03 (m, 2H).

Example 44. Synthesis of Compound 61B

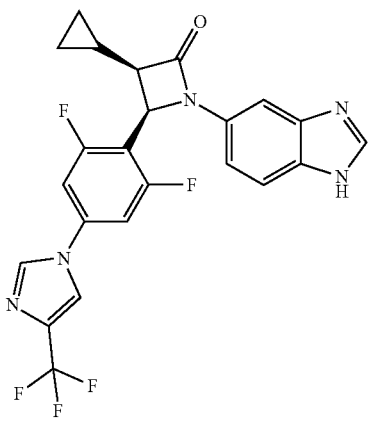 [SMILES: O=C1[C@H](C2CC2)[C@H](c2c(F)cc(-n3cnc(C(F)(F)F)c3)cc2F)N1c1ccc2[nH]cnc2c1]

(3R,4R)-1-(1H-benzo[d]imidazol-5-yl)-3-cyclopropyl-4-(2,6-difluoro-4-(4-(trifluoromethyl)-1H-imidazol-1-yl)phenyl)azetidin-2-one (Compound 61B) was synthesized under the same synthetic route as for Compound 59, which was determined by $^1$H NMR, LCMS and HPLC.
LCMS: Retention time: 0.700 min, (M+H)=474.0, 5-95AB_1.5 min_220&254 Shimadzu
HPLC: Retention time: 2.961 min, 10-80AB_8 min.lcm
$^1$H NMR: (400 MHz, DMSO-d$_6$) δ=12.60-12.19 (m, 1H), 8.59 (s, 1H), 8.56 (s, 1H), 8.17 (s, 1H), 7.96-7.01 (m, 5H), 5.68 (d, J=5.6 Hz, 1H), 3.55-3.44 (m, 1H), 0.76-0.62 (m, 1H), 0.57-0.38 (m, 2H), 0.27--0.04 (m, 2H).

Example 45. Synthesis of Compound 63B

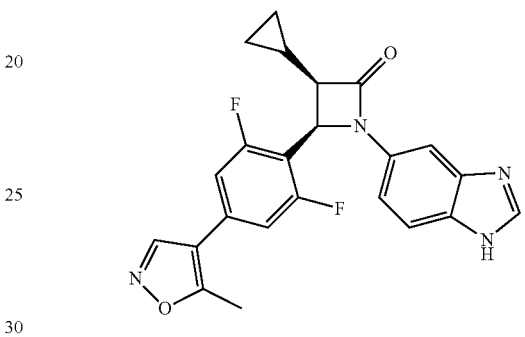

(3R,4R)-1-(1H-benzo[d]imidazol-5-yl)-3-cyclopropyl-4-(2,6-difluoro-4-(5-methylisoxazol-4-yl)phenyl)azetidin-2-one (Compound 63B) was synthesized under the same synthetic route as for Compound 52B, which was determined by $^1$H NMR, LCMS and HPLC.
LCMS: Retention time: 0.796 min, (M+H)=421.2, 5-95AB_220&254_Agilent
HPLC: Retention time: 3.413 min, 10-80AB_8 min.lcm.
$^1$H NMR: (400 MHz, DMSO-d$_6$) δ=12.48-12.11 (m, 1H), 8.89 (s, 1H), 8.12-8.02 (m, 1H), 7.61-6.96 (m, 6H), 5.58 (d, J=5.6 Hz, 1H), 2.53 (s, 3H), 0.66-0.56 (m, 1H), 0.48-0.28 (m, 2H), 0.16--0.05 (m, 2H).

Example 46. Synthesis of Compound 62B

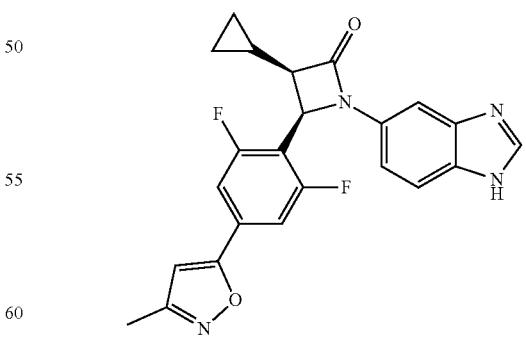

(3R,4R)-1-(1H-benzo[d]imidazol-5-yl)-3-cyclopropyl-4-(2,6-difluoro-4-(3-methylisoxazol-5-yl)phenyl)azetidin-2-one (Compound 62B) was synthesized under the same synthetic route as for Compound 52B, which was determined by $^1$H NMR, LCMS and HPLC.

LCMS: Retention time: 0.800 min, (M+H)=421.2, 5-95AB_220&254_Agilent HPLC: Retention time: 3.495 min, 10-80AB_8 min.lcm $^1$H NMR: (400 MHz, DMSO-d$_6$) δ=12.55-12.10 (m, 1H), 8.21-8.10 (m, 1H), 7.87-7.64 (m, 1H), 7.60-7.53 (m, 1H), 7.51-7.44 (m, 1H), 7.43-7.31 (m, 1H), 7.20-7.07 (m, 1H), 7.05 (s, 1H), 5.68 (d, J=5.6 Hz, 1H), 3.47-3.40 (m, 1H), 2.28 (s, 3H), 0.74-0.60 (m, 1H), 0.56-0.34 (m, 2H), 0.23-0.00 (m, 2H).

Example 47. Synthesis of Compound 64B

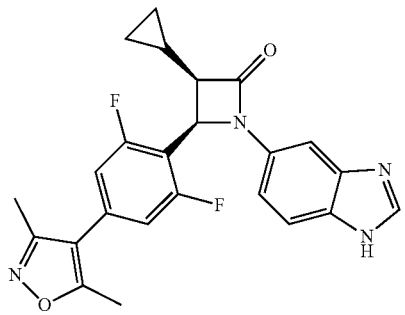

(3R,4R)-1-(1H-benzo[d]imidazol-5-yl)-3-cyclopropyl-4-(4-(3,5-dimethylisoxazol-4-yl)-2,6-difluorophenyl)azetidin-2-one (Compound 64B) was synthesized under the same synthetic route as for Compound 52B, which was determined by $^1$H NMR, LCMS and HPLC.

LCMS: Retention time: 0.894 min, (M+H)=435.1, 10-80AB_2 min_220&25

HPLC: Retention time: 3.478 min, 10-80AB_8 min.lcm $^1$H NMR: (400 MHz, DMSO-d$_6$) δ=12.64-12.14 (m, 1H), 8.17 (s, 1H), 7.57-7.53 (m, 1H), 7.49-7.43 (m, 1H), 7.40-7.06 (m, 3H), 5.68 (d, J=5.6 Hz, 1H), 3.44-3.41 (m, 1H), 2.42 (s, 3H), 2.24 (s, 3H), 0.75-0.63 (m, 1H), 0.56-0.37 (m, 2H), 0.26-0.02 (m, 2H).

Example 48. Synthesis of Compounds 66A and 66B

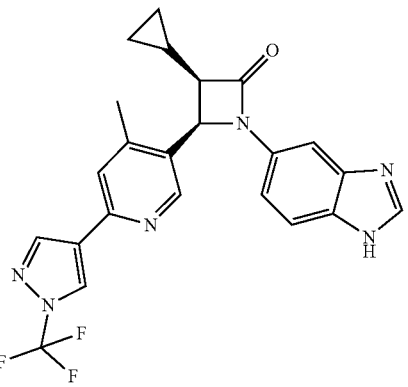

66B (3S,4S)-1-(1H-benzo[d]imidazol-5-yl)-3-cyclopropyl-4-(4-methyl-6-(1-(trifluoromethyl)-1H-pyrazol-4-yl)pyridin-3-yl)azetidin-2-one (Compound 66A) and (3R,4R)-1-(1H-benzo[d]imidazol-5-yl)-3-cyclopropyl-4-(4-methyl-6-(1-(trifluoromethyl)-1H-pyrazol-4-yl)pyridin-3-yl)azetidin-2-one (Compound 66B) were synthesized under the same synthetic route as for Compound 17, which was determined by $^1$H NMR, LCMS and HPLC.

Compound 66A:
SFC: Retention time: 3.979 min.
LCMS: Retention time: 0.921 min, (M+H)=453.1, 10-80AB_2 min_220&25
HPLC: Retention time: 3.008 min, 10-80AB_8 min.lcm
$^1$H NMR: (400 MHz, DMSO-d$_6$) δ=12.36-12.03 (m, 1H), 8.90 (s, 1H), 8.41 (s, 1H), 8.21 (s, 1H), 8.12 (s, 1H), 7.80 (s, 1H), 7.65-7.10 (m, 3H), 5.65 (d, J=5.6 Hz, 1H), 3.60-3.43 (m, 1H), 2.52 (s, 3H), 0.52-0.31 (m, 3H), 0.29-0.14 (m, 2H).

Compound 66B:
SFC: Retention time: 4.688 min.
LCMS: Retention time: 0.923 min, (M+H)=453.1, 10-80AB_2 min_220&25
HPLC: Retention time: 3.017 min, 10-80AB_8 min.lcm
$^1$H NMR: (400 MHz, DMSO-d$_6$) δ=12.58-12.28 (m, 1H), 9.02 (s, 1H), 8.45 (s, 1H), 8.25-8.08 (m, 2H), 7.84 (s, 1H), 7.66-7.11 (m, 3H), 5.66 (d, J=5.6 Hz, 1H), 3.56-3.43 (m, 1H), 2.53-2.51 (m, 3H), 0.46-0.28 (m, 3H), 0.27-0.11 (m, 2H).

Example 49. Synthesis of Compounds 68A and 68B

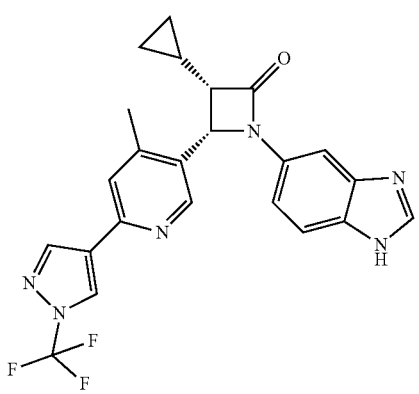

66A

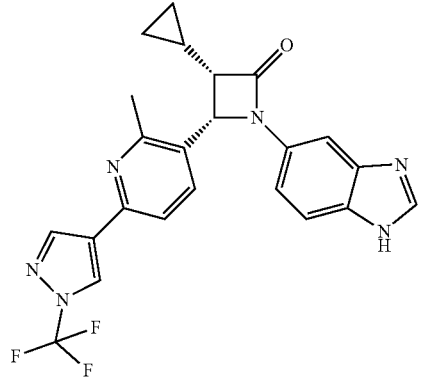

68A

273
-continued

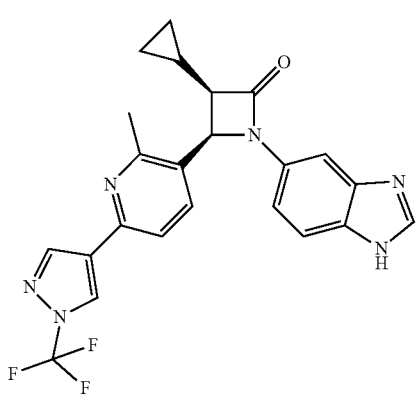

68B

274
-continued

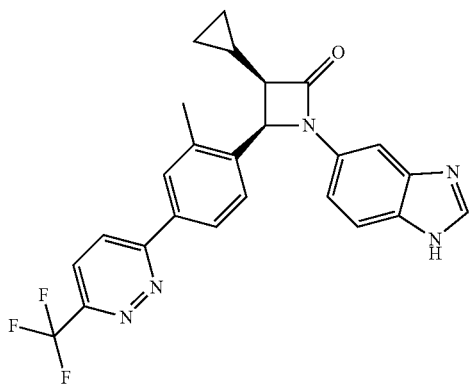

67B (3S,4S)-1-(1H-benzo[d]imidazol-5-yl)-3-cyclopropyl-4-(2-methyl-6-(1-(trifluoromethyl)-1H-pyrazol-4-yl)pyridin-3-yl)azetidin-2-one (Compound 68A) and (3R,4R)-1-(1H-benzo[d]imidazol-5-yl)-3-cyclopropyl-4-(2-methyl-6-(1-(trifluoromethyl)-1H-pyrazol-4-yl)pyridin-3-yl)azetidin-2-one (Compound 68B) were synthesized under the same synthetic route as for Compound 17, which was determined by $^1$H NMR, LCMS and HPLC.

Compound 68A:
SFC: Retention time: 1.930 min.
LCMS: Retention time: 1.816 min, (M+H)=453.1, 10-80CD_3 min_220&254_Agilent
HPLC: Retention time: 3.124 min, 10-80AB_8 min.lcm
$^1$H NMR: (400 MHz, DMSO-d$_6$) δ=12.50-12.28 (m, 1H), 9.01-8.98 (m, 1H), 8.49-8.43 (m, 1H), 8.21-8.14 (m, 1H), 7.61-7.36 (m, 5H), 5.63-5.59 (m, 1H), 3.51-3.45 (m, 1H), 2.66-2.65 (m, 3H), 0.39-0.30 (m, 3H), 0.24-0.10 (m, 2H).

Compound 68B:
SFC: Retention time: 2.381 min.
LCMS: Retention time: 1.813 min, (M+H)=453.2, 10-80CD_3 min_220&254_Agilent
HPLC: Retention time: 3.108 min, 10-80AB_8 min.lcm
$^1$H NMR: (400 MHz, DMSO-d$_6$) δ=12.57-12.22 (m, 1H), 9.00 (s, 1H), 8.47 (s, 1H), 8.22-8.14 (m, 1H), 7.63-7.35 (m, 5H), 5.62 (d, J=5.6 Hz, 1H), 3.50-3.44 (m, 1H), 2.68-2.64 (m, 3H), 0.38-0.30 (m, 3H), 0.25-0.10 (m, 2H).

Example 50. Synthesis of Compounds 67A and 67B

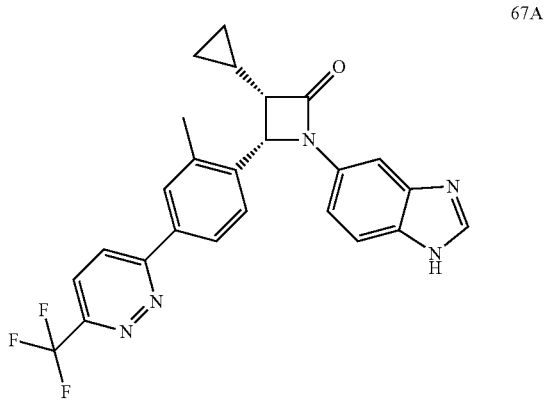

67A (3S,4S)-1-(1H-benzo[d]imidazol-5-yl)-3-cyclopropyl-4-(2-methyl-4-(6-(trifluoromethyl)pyridazin-3-yl)phenyl)azetidin-2-one (Compound 67A) and (3R,4R)-1-(1H-benzo[d]imidazol-5-yl)-3-cyclopropyl-4-(2-methyl-4-(6-(trifluoromethyl)pyridazin-3-yl)phenyl)azetidin-2-one (Compound 67B) were synthesized under the same synthetic route as for Compound 52, which was determined by $^1$H NMR, LCMS and HPLC.

Compound 67A:
SFC: Retention time: 4.785 min.
LCMS: Retention time: 1.004 min, (M+H)=464.1, 10-80AB_2 min_220&25
HPLC: Retention time: 3.761 min, 10-80AB_8 min.lcm
$^1$H NMR: (400 MHz, DMSO-d$_6$) δ=12.50-12.29 (m, 1H), 8.53-8.49 (m, 1H), 8.35-8.31 (m, 1H), 8.23-8.15 (m, 2H), 8.00-7.95 (m, 1H), 7.65-7.46 (m, 2H), 7.32-7.15 (m, 2H), 5.68 (d, J=5.6 Hz, 1H), 3.48-3.42 (m, 1H), 2.58-2.56 (m, 3H), 0.40-0.31 (m, 3H), 0.25-0.09 (m, 2H).

Compound 67B:
SFC: Retention time: 6.358 min.
LCMS: Retention time: 1.004 min, (M+H)=464.1, 10-80AB_2 min_220&25
HPLC: Retention time: 3.748 min, 10-80AB 8 min.lcm
$^1$H NMR: (400 MHz, DMSO-d$_6$) δ=12.51-12.29 (m, 1H), 8.53-8.49 (m, 1H), 8.35-8.30 (m, 1H), 8.24-8.15 (m, 2H), 8.01-7.95 (m, 1H), 7.60-7.24 (m, 4H), 7.23-7.08 (m, 1H), 5.68 (d, J=5.6 Hz, 1H), 2.58-2.56 (m, 3H), 0.38-0.30 (m, 3H), 0.25-0.11 (m, 2H).

Example 51. Synthesis of Compound 65B

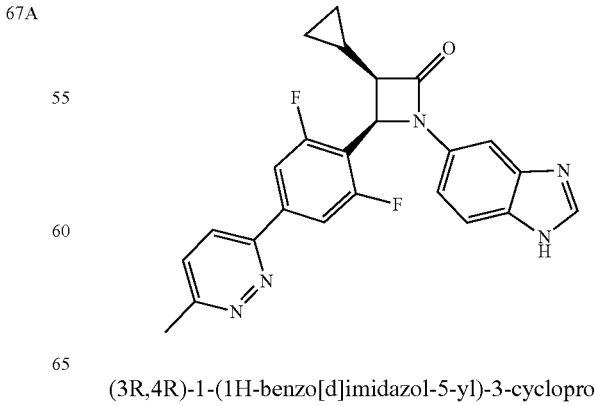

(3R,4R)-1-(1H-benzo[d]imidazol-5-yl)-3-cyclopropyl-4-(2,6-difluoro-4-(6-methylpyridazin-3-yl)phenyl)azetidin-2- one (Compound 65B) was synthesized under the same synthetic route as for Compound 52, which was determined by ¹H NMR, LCMS and HPLC.

LCMS: Retention time: 0.816 min, (M+H)=432.1, 10-80AB_2 min_220&25

HPLC: Retention time: 2.822 min, 0-80AB_8 min.lcm

¹H NMR: (400 MHz, DMSO-d$_6$) δ=12.56-12.17 (m, 1H), 8.26-8.21 (m, 1H), 8.16 (s, 1H), 8.09-7.76 (m, 2H), 7.75-7.67 (m, 1H), 7.61-7.11 (m, 3H), 5.72 (d, J=5.6 Hz, 1H), 3.56-3.41 (m, 1H), 2.67 (s, 3H), 0.78-0.67 (m, 1H), 0.56-0.38 (m, 2H), 0.25-0.05 (m, 2H).

Example 52. Synthesis of Compounds 69A and 69B

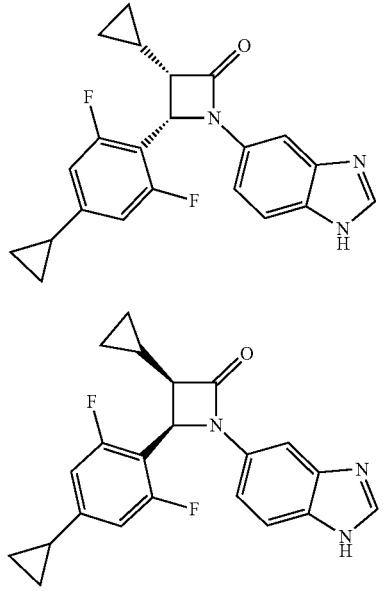

69A

69B (3S,4S)-1-(1H-benzo[d]imidazol-5-yl)-3-cyclopropyl-4-(4-cyclopropyl-2,6-difluorophenyl)azetidin-2-one (Compound 69A) and (3R,4R)-1-(1H-benzo[d]imidazol-5-yl)-3-cyclopropyl-4-(4-cyclopropyl-2,6-difluorophenyl)azetidin-2-one (Compound 69B) were synthesized under the same synthetic route as for Compound 17, which was determined by ¹H NMR, LCMS and HPLC.

Compound 69A:
SFC: Retention time: 1.606 min.
LCMS: Retention time: 0.825 min, (M+H)=380.2, 5-95AB_220&254_Agilent
HPLC: Retention time: 3.660 min, 10-80AB_8 min.lcm
¹H NMR: (400 MHz, DMSO-d$_6$) δ=12.67-12.07 (m, 1H), 8.15 (s, 1H), 7.65-7.29 (m, 2H), 7.26-6.45 (m, 3H), 5.56 (d, J=6.0 Hz, 1H), 3.33-3.28 (m, 1H), 2.00-1.87 (m, 1H), 1.05-0.88 (m, 2H), 0.81-0.71 (m, 2H), 0.70-0.60 (m, 1H), 0.55-0.45 (m, 1H), 0.44-0.32 (m, 1H), 0.23-0.11 (m, 1H), 0.08--0.05 (m, 1H).

Compound 69B:
SFC: Retention time: 2.739 min.
LCMS: Retention time: 0.825 min, (M+H)=380.2, 5-95AB_220&254_Agilent
HPLC: Retention time: 3.664 min, 10-80AB_8 min.lcm
¹H NMR: (400 MHz, DMSO-d$_6$) δ=12.32 (br. s., 1H), 8.12 (s, 1H), 7.49 (br d, J=8.3 Hz, 1H), 7.34 (s, 1H), 7.23-6.62 (m, 3H), 5.53 (d, J=5.8 Hz, 1H), 3.29-3.26 (m, 1H), 1.95-1.85 (m, 1H), 1.00-0.91 (m, 2H), 0.76-0.59 (m, 3H), 0.51-0.42 (m, 1H), 0.45-0.30 (m, 1H), 0.17-0.09 (m, 1H), 0.08--0.05 (m, 1H).

Example 53. Synthesis of Compounds 71A and 71B

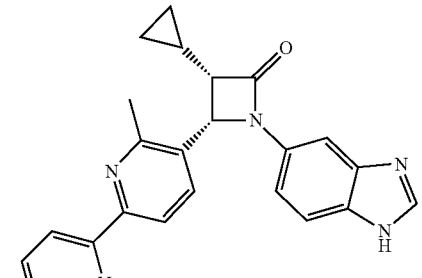

71A

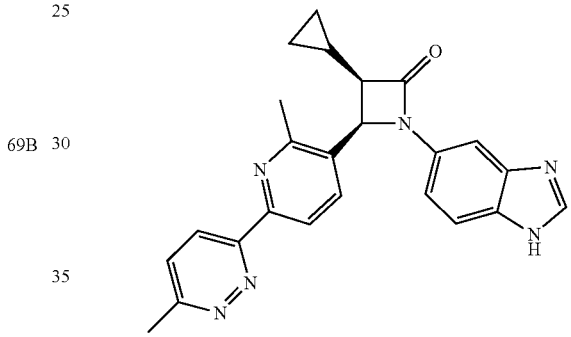

71B (3S,4S)-1-(1H-benzo[d]imidazol-5-yl)-3-cyclopropyl-4-(2-methyl-6-(6-methylpyridazin-3-yl)pyridin-3-yl)azetidin-2-one (Compound 71A) and (3R,4R)-1-(1H-benzo[d]imidazol-5-yl)-3-cyclopropyl-4-(2-methyl-6-(6-methylpyridazin-3-yl)pyridin-3-yl)azetidin-2-one (Compound 71B) were synthesized under the same synthetic route as for Compound 70, which was determined by ¹H NMR, LCMS and HPLC.

Compound 71A:
SFC: Retention time: 1.028 min.
LCMS: Retention time: 0.724 min, (M+H)=411.1, 5-95AB_220&254_Agilent
HPLC: Retention time: 2.379 min, 10-80AB_8 min.lcm
¹H NMR: (400 MHz, DMSO-d$_6$) δ=12.54-12.25 (m, 1H), 8.44 (d, J=8.8 Hz, 1H), 8.32-8.24 (m, 1H), 8.23-8.15 (m, 1H), 7.71 (d, J=8.8 Hz, 1H), 7.65-7.14 (m, 4H), 5.69 (d, J=5.2 Hz, 1H), 3.56-3.49 (m, 1H), 2.74 (s, 3H), 2.68 (s, 3H), 0.43-0.31 (m, 3H), 0.27-0.13 (m, 2H).

Compound 71B:
SFC: Retention time: 1.503 min.
LCMS: Retention time: 0.724 min, (M+H)=411.1, 5-95AB_220&254_Agilent
HPLC: Retention time: 2.378 min, 10-80AB_8 min.lcm
¹H NMR: (400 MHz, DMSO-d$_6$) δ=12.54-12.28 (m, 1H), 8.44 (d, J=8.5 Hz, 1H), 8.31-8.25 (m, 1H), 8.22-8.14 (m, 1H), 7.71 (d, J=9.0 Hz, 1H), 7.66-7.14 (m, 4H), 5.70 (d, J=5.8 Hz, 1H), 3.57-3.49 (m, 1H), 2.74 (s, 3H), 2.68 (s, 3H), 0.43-0.30 (m, 3H), 0.28-0.11 (m, 2H).

Example 54. Synthesis of Compounds 74A and 74B

Example 55. Synthesis of Compounds 73A and 73B

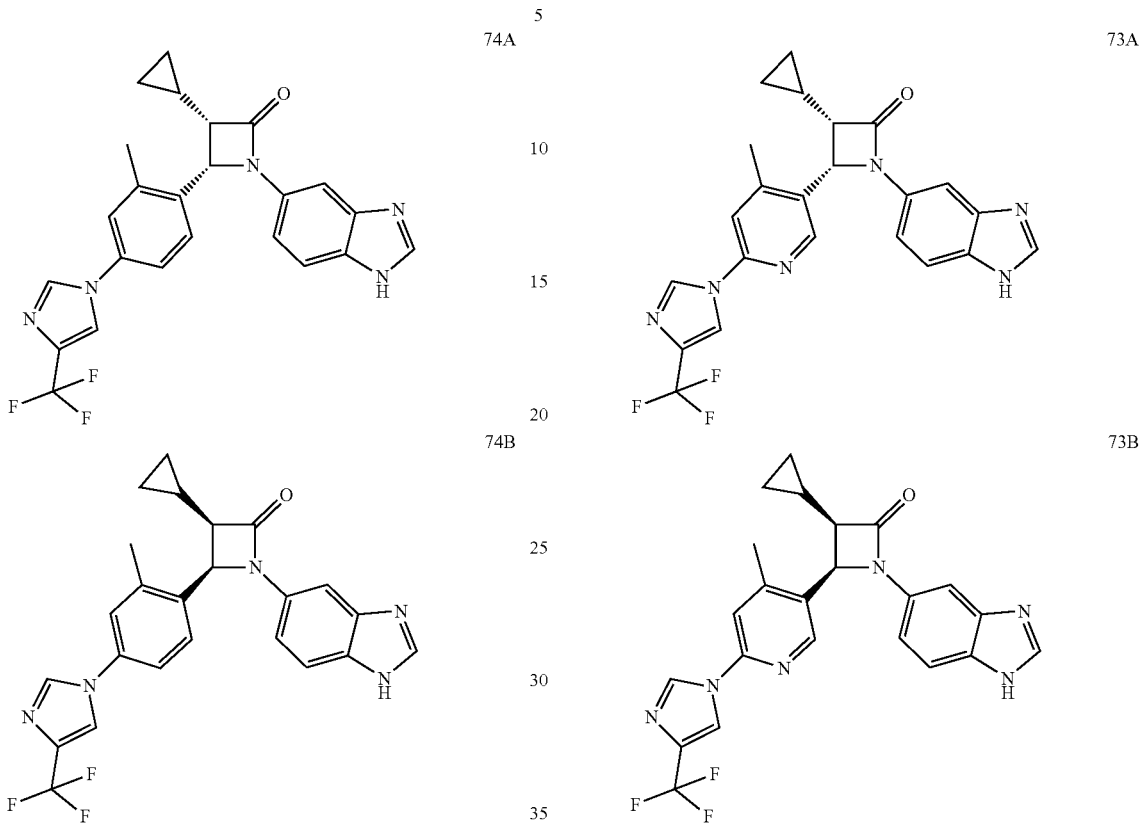

(3S,4S)-1-(1H-benzo[d]imidazol-5-yl)-3-cyclopropyl-4-(2-methyl-4-(4-(trifluoromethyl)-1H-imidazol-1-yl)phenyl)azetidin-2-one (Compound 74A) and (3R,4R)-1-(1H-benzo[d]imidazol-5-yl)-3-cyclopropyl-4-(2-methyl-4-(trifluoromethyl)-1H-imidazol-1-yl)phenyl)azetidin-2-one (Compound 74B) were synthesized under the same synthetic route as for Compound 59, which was determined by $^1$H NMR, LCMS and HPLC.

Compound 74A:

SFC: Retention time: 4.361 min.

LCMS: Retention time: 1.81 min, (M+H)=452.2, 10-80CD_3 min_220&254_Agilent HPLC: Retention time: 3.769 min, 10-80CD_8 min.lcm $^1$H NMR: (400 MHz, DMSO-d$_6$) δ=12.67-11.99 (m, 1H), 8.45-8.39 (m, 2H), 8.16 (s, 1H), 7.73-7.70 (m, 1H), 7.58-7.52 (m, 1H), 7.48-7.41 (m, 2H), 7.35-7.19 (m, 1H), 7.18-7.13 (m, 1H), 5.63 (d, J=5.6 Hz, 1H), 3.42-3.40 (m, 1H), 2.52 (s, 3H), 0.37-0.29 (m, 3H), 0.24-0.09 (m, 2H).

Compound 74B:

SFC: Retention time: 4.970 min.

LCMS: Retention time: 1.81 min, (M+H)=452.2, 10-80CD_3 min_220&254_Agilent

HPLC: Retention time: 3.773 min, 10-80CD_8 min.lcm $^1$H NMR: (400 MHz, DMSO-d$_6$) δ=12.49-12.27 (m, 1H), 8.46 (br s, 2H), 8.20-8.14 (m, 1H), 7.74-7.69 (m, 1H), 7.61-7.38 (m, 3H), 7.27-7.09 (m, 2H), 5.65-5.60 (m, 1H), 3.44-3.39 (m, 1H), 2.54-2.53 (m, 3H), 0.38-0.29 (m, 3H), 0.25-0.08 (m, 2H).

(3S,4S)-1-(1H-benzo[d]imidazol-5-yl)-3-cyclopropyl-4-(4-methyl-6-(4-(trifluoromethyl)-1H-imidazol-1-yl)pyridin-3-yl)azetidin-2-one (Compound 73A) and (3R,4R)-1-(1H-benzo[d]imidazol-5-yl)-3-cyclopropyl-4-(4-methyl-6-(4-(trifluoromethyl)-1H-imidazol-1-yl)pyridin-3-yl)azetidin-2-one (Compound 73B) were synthesized under the same synthetic route as for Compound 72, which was determined by $^1$H NMR, LCMS and HPLC.

Compound 73A:

SFC: Retention time: 1.757 min.

LCMS: Retention time: 1.774 min, (M+H)=453.2, 10-80CD_3 min_220&254_Agilent

HPLC: Retention time: 3.538 min, 10-80CD_8 min.lcm $^1$H NMR: (400 MHz, DMSO-d$_6$) δ=12.55-12.30 (m, 1H), 8.66 (s, 1H), 8.59-8.52 (m, 1H), 8.23-8.16 (m, 1H), 8.11-8.01 (m, 1H), 7.98-7.93 (m, 1H), 7.62-7.13 (m, 3H), 5.73-5.65 (m, 1H), 3.55-3.49 (m, 1H), 2.55 (s, 3H), 0.44-0.31 (m, 3H), 0.28-0.14 (m, 2H).

Compound 73B:

SFC: Retention time: 2.567 min.

LCMS: Retention time: 1.775 min, (M+H)=453.2, 10-80CD_3 min_220&254Agilent

HPLC: Retention time: 3.55 min, 10-80CD_8 min.lcm $^1$H NMR: (400 MHz, DMSO-d$_6$) δ=12.56-12.29 (m, 1H), 8.66 (s, 1H), 8.58-8.53 (m, 1H), 8.23-8.15 (m, 1H), 8.06 (s, 1H), 7.95 (s, 1H), 7.61-7.13 (m, 3H), 5.69 (d, J=5.6 Hz, 1H), 3.54-3.50 (m, 1H), 2.55 (s, 3H), 0.42-0.32 (m, 3H), 0.28-0.16 (m, 2H).

Example 56. Synthesis of Compounds 76A and 76B

Example 57. Synthesis of Compounds 75A and 75B

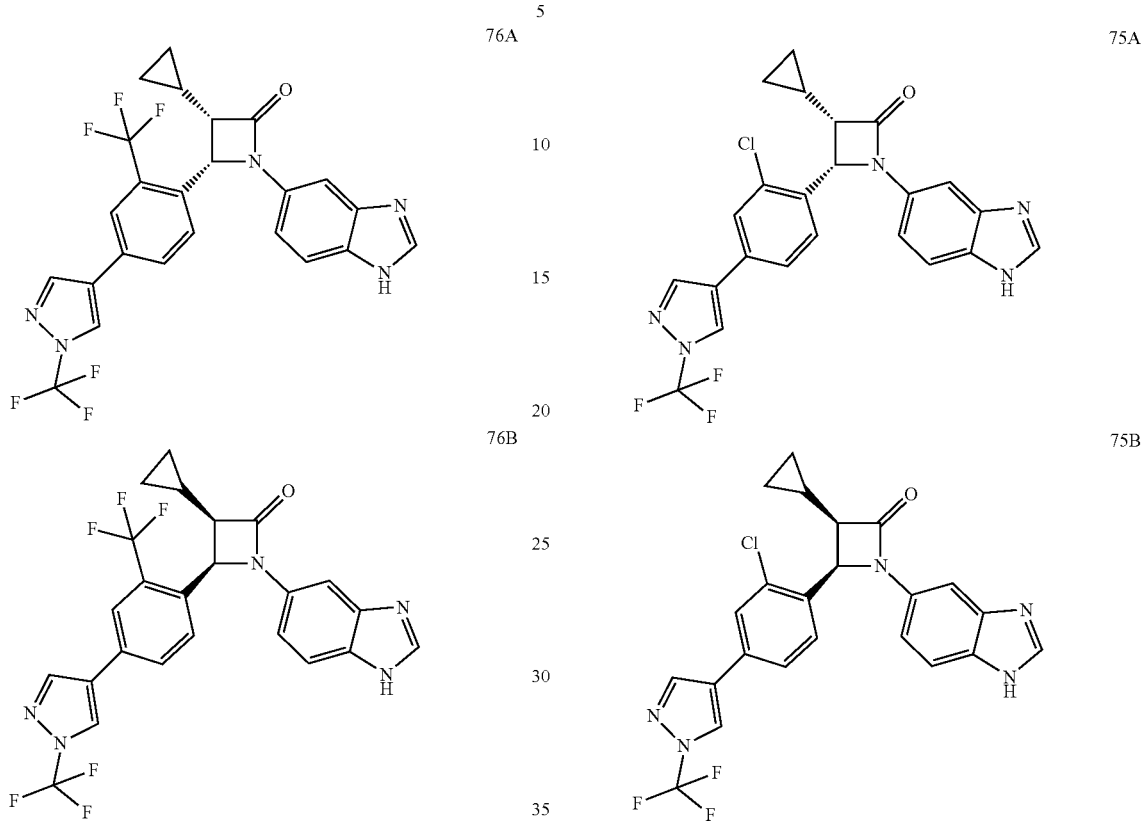

(3S,4S)-1-(1H-benzo[d]imidazol-5-yl)-3-cyclopropyl-4-(2-(trifluoromethyl)-4-(1-(trifluoromethyl)-1H-pyrazol-4-yl)phenyl)azetidin-2-one (Compound 76A) and (3R,4R)-1-(1H-benzo[d]imidazol-5-yl)-3-cyclopropyl-4-(2-(trifluoromethyl)-4-(1-(trifluoromethyl)-1H-pyrazol-4-yl)phenyl)azetidin-2-one (Compound 76B) were synthesized under the same synthetic route as for Compound 17, which was determined by $^1$H NMR, LCMS and HPLC.

Compound 76A:

SFC: Retention time: 2.841 min.

LCMS: Retention time: 3.183 min, (M+H)=506.2, 10-80AB_7 min_220&25

HPLC: Retention time: 3.783 min, 10-80AB_8 min.lcm $^1$H NMR: (400 MHz, DMSO-d$_6$) δ=12.38 (br. s., 1H), 9.17 (s, 1H), 8.65-8.51 (m, 1H), 8.24 (s, 1H), 8.17 (s, 1H), 7.96 (d, J=8.0 Hz, 1H), 7.64-7.46 (m, 2H), 7.45-6.90 (m, 2H), 5.66 (d, J=4.0 Hz, 1H), 3.44-3.42 (m, 1H), 0.55-0.28 (m, 3H), 0.2-0.05 (m, 2H).

Compound 76B:

SFC: Retention time: 3.384 min.

LCMS: Retention time: 3.215 min, (M+H)=506.2, 10-80AB_7 min_220&25

HPLC: Retention time: 3.802 min, 10-80AB_8 min.lcm $^1$H NMR: (400 MHz, DMSO-d$_6$) δ=12.59-12.20 (m, 1H), 9.17 (s, 1H), 8.57 (s, 1H), 8.24 (s, 1H), 8.21-8.12 (m, 1H), 7.96 (d, J=8.0 Hz, 1H), 7.65-7.48 (m, 2H), 7.43-7.01 (m, 2H), 5.66 (d, J=4.4 Hz, 1H), 3.46-3.39 (m, 1H), 0.56-0.27 (m, 3H), 0.19-0.01 (m, 2H).

(3S,4S)-1-(1H-benzo[d]imidazol-5-yl)-4-(2-chloro-4-(1-(trifluoromethyl)-1H-pyrazol-4-yl)phenyl)-3-cyclopropylazetidin-2-one (Compound 75A) and (3R,4R)-1-(1H-benzo[d]imidazol-5-yl)-4-(2-chloro-4-(1-(trifluoromethyl)-1H-pyrazol-4-yl)phenyl)-3-cyclopropylazetidin-2-one (Compound 75B) were synthesized under the same synthetic route as for Compound 17, which was determined by $^1$H NMR, LCMS and HPLC.

Compound 75A:

SFC: Retention time: 5.509 min.

LCMS: Retention time: 2.048 min, (M+H)=472.1, 10-80CD_3 min_220&254Agilent

HPLC: Retention time: 4.429 min, 10-80CD_8 min.lcm $^1$H NMR: (400 MHz, DMSO-d$_6$) δ=12.69-12.11 (m, 1H), 9.07 (s, 1H), 8.51 (s, 1H), 8.18 (s, 1H), 8.03 (s, 1H), 7.70-7.07 (m, 5H), 5.65 (d, J=5.6 Hz, 1H), 3.48-3.42 (m, 1H), 0.52-0.05 (m, 5H).

Compound 75B:

SFC: Retention time: 6.130 min.

LCMS: Retention time: 2.043 min, (M+H)=472.1, 10-80CD_3 min_220&254Agilent

HPLC: Retention time: 4.433 min, 10-80CD_8 min.lcm $^1$H NMR: (400 MHz, DMSO-d$_6$) δ=9.07 (s, 1H), 8.51 (s, 1H), 8.21 (s, 1H), 8.03 (d, J=1.2 Hz, 1H), 7.65 (d, J=8.0 Hz, 1H), 7.58 (d, J=8.4 Hz, 1H), 7.44 (d, J=1.6 Hz, 1H), 7.30-7.11 (m, 2H), 5.66 (d, J=5.6 Hz, 1H), 3.47-3.44 (m, 1H), 0.48-0.08 (m, 5H).

BIOLOGICAL EXAMPLES

Example B-1: In Vitro Assay

Compound $IC_{50}$ were determined against QPCTL using SensoLyte Green Glutaminyl Cyclase Activity Assay K. Materials are listed in Table 2.

TABLE 2

| Assay materials | |
| --- | --- |
|  | Vendor |
| Reagents: | |
| QPCTL | OriGene Technologies |
| Tris | Sigma |
| BSA | Sigma |
| 96-well, Black, flat bottom 96-well plate with non-binding surface | Greiner |
| Pipette tips | Rainin |
| SensoLyte Green Glutaminyl Cyclase Activity Assay Kit | ANASPEC |
| Equipment: | |
| MultiDrop Combi | Thermo |
| Cassette | Thermo |
| Centrifuge | Eppendorf Centrifuge |
| Bravo | Agilent |
| Presicion | Biotek |
| SpectraMax Paradigm Multi-Mode detection platform | Molecular Devices |

Preparation of working solution: 2× Glutaminyl Cyclase substrate was diluted in assay buffer to 5 µM. 2× enzyme solution and QPCTL was diluted in assay buffer to 0.8 nM. Glutaminyl Cyclase Developer was diluted in assay buffer to 1× (containing 10 mM 1-Benzyl-Imidazole). Serial dilution of test compounds was performed in DMSO. The final DMSO concentration in 100 µl reaction was 1%. The assay buffer was 50 mM Tris, pH 8.0, 0.01% BSA.

Procedure: 50 µL of 2× Glutaminyl Cyclase substrate solution was added into the assay plate followed by 50 µL of 2× enzyme solution. The plate was centrifuged for 1 min at 1000 rmp. Next the plate was incubated for 45 minutes at 37° C. This was followed by the additional of 50 µL of the prepared Glutaminyl Cyclase developer and incubated for additional 30 min at 37° C. Results were read on SpectraMax Paradigm detecting with emission at Ex/Em=490 nm/520 nm.

A Z' value was calculated for each assay plate. The Z' value must be >0.5 or the plate was disqualified. If $IC_{50}$ value for the control compound deviates >3 fold from the average, the plate was disqualified. Compound inhibition percentage was calculated by formula: Compound inhibition rate=(ZPE−compound reading)/(ZPE−HPE)*100%. Results were calculated using GraphPad Prism 7 software is used for $IC_{50}$ determination.

Representative biochemical data is presented in Table 3.

TABLE 3

In vitro data.

| Compound ID | QPCTL $IC_{50}$ (nM) |
| --- | --- |
| 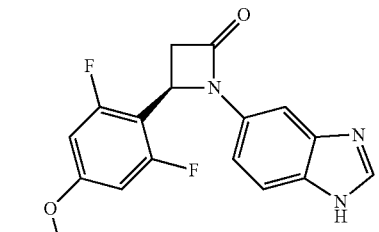 Compound RF-1B | B |
| 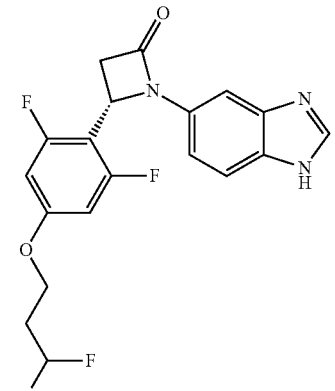 Compound RF-1A | C |
| 2 | D |
| 3 | C |
| 4 | B |
| 7 (cis/trans = 1:1.78, rac.) | B |
| 7A | C |
| 7B | A |
| 8 | B |
| 8A | D |
| 8B | A |
| 8TR | C |
| 9 | C |
| 10CR | B |
| 11CR | B |
| 12CR | B |
| 13A | D |
| 13B | B |
| 14 (cis/trans = 15.9/1, rac.) | B |
| 14A | C |
| 14B | A |
| 15A | D |
| 15B | A |
| 16CR | A |
| 16TR | C |
| 17A | C |
| 17B | A |
| 18A | D |
| 18B | A |
| 22 | A |
| 22A | C |
| 22B | A |
| 23CR | B |

TABLE 3-continued

In vitro data.

| Compound ID | QPCTL IC$_{50}$ (nM) |
|---|---|
| 25CR | A |
| 25TR | B |
| 28CR | B |
| 28TR | B |
| 30A | D |
| 30B | B |
| 32A | C |
| 32B | A |
| 34CR | A |
| 34TR | C |
| 35A | C |
| 35B | A |
| 42B | A |
| 42A | C |
| 43A | C |
| 43B | A |
| 44B | A |
| 45A | C |
| 45B | A |
| 46A | C |
| 46B | A |
| 47B | A |
| 48A | B |
| 48B | A |
| 49B | B |
| 50A | C |
| 50B | A |
| 51A | C |
| 51B | A |
| 52A | C |
| 52B | A |
| 53A | D |
| 53B | A |
| 54B | A |
| 55A | C |
| 55B | A |
| 56A | C |
| 56B | A |
| 57A | C |
| 57B | A |
| 58B | A |
| 59B | A |
| 60B | A |
| 61B | A |
| 62B | A |
| 63B | A |
| 64B | B |
| 65B | A |
| 66A | C |
| 66B | A |
| 67A | C |
| 67B | A |
| 68A | C |
| 68B | A |
| 69A | C |
| 69B | A |
| 70A | C |
| 70B | A |
| 71A | C |
| 71B | A |
| 72A | D |
| 72B | A |
| 73A | C |
| 73B | A |
| 74A | C |
| 74B | A |
| 75A | C |
| 75B | A |
| 76A | A |
| 76B | D |

A: $0 < IC_{50} \leq 2.0$ (nM)
B: $2.0 < IC_{50} \leq 25$ (nM)
C: $25 < IC_{50} \leq 1000$ (nM)
D: $1000 < IC_{50}$ (nM)

Example B-2: SIRPα binding onto MV4-11 and DLD-1

Protocol: MV4-11 or DLD-1 cells were plated in duplicate in the appropriate medium containing DMSO or compounds in the density of 0.5 million/mL. After 48-hour incubation, cells were collected and sequentially stained with LIVE/DEAD Fixable Viability Dye, anti-human CD47-B6H12 and human SIRPα-Fc for 30 min followed by flow cytometry analysis. Mean fluorescence intensity was used to determine the surface binding of antibody or fused protein to the intended cells.

Example B-3: In Vitro Analysis for Phagocytosis by Macrophages in Raji Cells and DLD-1 Cells Protocol: Human monocyte-derived macrophages served as effector cells and Raji B cell lymphoma were used as target cells. Peripheral blood mononuclear cells (PBMCs) were isolated from peripheral blood of healthy individuals. Monocyte isolation was performed by gradient centrifugation on Percoll, followed by negative selection of monocytes by magnetic-activated cell separation. Freshly isolated monocytes were cultured for 7 d at 37° C. and 5% $CO_2$ in RPMI1640 medium supplemented with 10% FBS and 20 ng/ml human macrophage colony-stimulating factor (M-CSF) to allow differentiation into macrophages. Raji cells were pretreated with DMSO and compounds for 48 h and washed twice. Cell count was performed for all the treatments, then Raji cells were stained with CFSE for 8 min, and then diluted to a certain cell density of cell suspension with medium (medium w/o serum+DMSO or Medium w/o serum+compounds), respectively. Then the cell suspension was placed into each well of ultra-low attachment 96-well U bottom plates. Inhibition of SIRPα binding to CD47 on target cells by prior culture in the presence of DMSO or compounds was monitored by detection of SIRPα binding by FACS at the end of each target cell culture. Raji cells were incubated in the presence or absence of the opsonizing anti-CD20 rituximab (1 µg/mL) or anti-CD47 antibody (10 µg/mL as positive control) with differentiated macrophages (1:2 of Raji to macrophage) in 37° C. 5% $CO_2$ for 4 h followed by cell collection, staining with anti-CD11b (4° C. for 60 min) and detect CD11b$^+$ plus CFSE$^+$ population by FACS. The macrophage phagocytosis assay on DLD-1 colorectal cancer cells was similar as that on Raji cells. Exceptionally, DLD-1 cell after treatment with compounds were incubated in the presence or absence of anti-EGFR cetuximab with macrophages (2:1 of DLD-1 to macrophage) for 2 h.

Example B-4: In Vivo MV4-11 Xenograft Tumor Model

Protocol: Six to eight-week-old female BALB/c nude mice were inoculated subcutaneously at the right flank with MV4-11 cells ($10 \times 10^6$ suspended in Matrigel) in 0.2 mL PBS for tumor development. Animals were randomized when the average tumor volume reached average 100-120 mm$^3$. Tumor volume was measured three times weekly in two dimensions using a caliper, and the volume was expressed in mm$^3$ using the formula: $V = 0.5 \, a \times b^2$ where a and b are the long and short diameters of the tumor, respectively. The monitor of the changes in tumor volume and body weight was ended on day 21 after the start of the treatment.

Example B-5: In Vivo Raji Xenograft Mouse Model

Protocol: Six to eight-week-old female CB17 SCID mice were inoculated subcutaneously at the right flank with Raji tumor cells ($5 \times 10^6$ cells suspended in Matrigel) in 0.2 mL PBS for tumor development. Animals were randomized when the average tumor volume reached average 150-200 mm$^3$. Tumor volume was measured three times weekly in two dimensions using a caliper, and the volume was expressed in mm$^3$ using the formula: $V=0.5 \text{ a} \times \text{b}^2$ where a and b are the long and short diameters of the tumor, respectively.

Example B-6: Macrophage Infiltration in the Mouse Acute Peritonitis Model

Protocol: 8-week-old female C$_{57}$BL/6 mice in peritonitis model groups were intraperitoneally injected with 1.5 mL of sterile 3% thioglycollate whereas mice in naïve control group were intraperitoneally injected with DPBS (1.5 mL). In addition, compounds or vehicle were applied by oral administration to non-fasted male mice one hour before thioglycollate was injected intraperitoneally. Mice were dosed orally twice daily thereafter. Three days after stimulation by thioglycollate, mice were anaesthetized by isoflurane and peritoneal lavage was collected with 8 ml pre-warmed PBS. Cells were harvested from 1 ml of lavage fluid and used for inflammatory population plotting by FACS analysis. FC receptor was blocked by incubation with anti-mouse CD16/CD32. The cells were subsequently incubated with anti-mouse F4/80 Clone (BM8), anti-mouse CD11b & anti-Ly6G. Flow cytometric analysis was performed using FACS based on 5000 beads per sample in BD Trucount tubes as reference standard. Monocytes and neutrophils in the peritoneal fluid were analyzed according to the panels of macrophages identified based on CD11b+F4/80+ and neutrophils identified based on CD11b+Ly6G+.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating a disease or condition associated with an aberrant glutaminyl-peptide cyclotransferase-like protein (QPCTL) activity in a subject having the disease or condition associated with the aberrant QPCTL activity, comprising administering to the subject a pharmaceutical composition comprising (i) a compound of Formula (I), or a pharmaceutically acceptable salt or stereoisomer thereof:

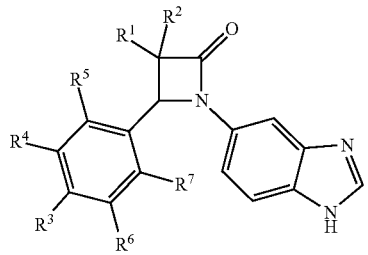

Formula (I)

wherein, $R^1$ is halogen, —OH, $C_1$-$C_6$ alkyl, $C_3$-$C_8$ cycloalkyl, or $C_2$-$C_7$ heterocycloalkyl, wherein the alkyl, cycloalkyl and heterocycloalkyl is optionally, independently substituted with one to three substituents selected from halogen, —OH, oxo, —NO$_2$, CN, NH$_2$, —O($C_1$-$C_6$ alkyl), and —S($C_1$-$C_6$ alkyl);

$R^2$ is H;

each of $R^4$, $R^5$, $R^6$, and $R^7$ is independently selected from H and halogen; and $R^3$ is 5 or 6 membered monocyclic heteroaryl having 1-4 ring heteroatoms independently selected from N, O and S, and wherein $R^3$ is optionally substituted with one or more $R^{31}$, and each $R^{31}$ is independently selected from cyano, oxo, halogen, hydroxy, —SH, NO$_2$, amino, $C_{1-6}$ alkyl, $C_{1-6}$ haloalkyl, $C_{1-6}$ hydroxyalkyl, $C_{1-6}$ aminoalkyl, and $C_{1-6}$ heteroalkyl; and (ii) a pharmaceutically acceptable excipient.

2. The method of claim 1, wherein $R^1$ is $C_1$-$C_6$ alkyl that is optionally substituted with one to three substituents selected from halogen, —OH, oxo, —NO$_2$, CN, NH$_2$, —O($C_1$-$C_6$ alkyl), and —S($C_1$-$C_6$ alkyl).

3. The method of claim 1, wherein $R^1$ is —CH$_3$ or cyclopropyl.

4. The method of claim 1, wherein $R^4$ is F; and $R^7$ is F.

5. The method of claim 1, wherein $R^4$ is H; and $R^6$ is H.

6. The method of claim 1, wherein $R^3$ is

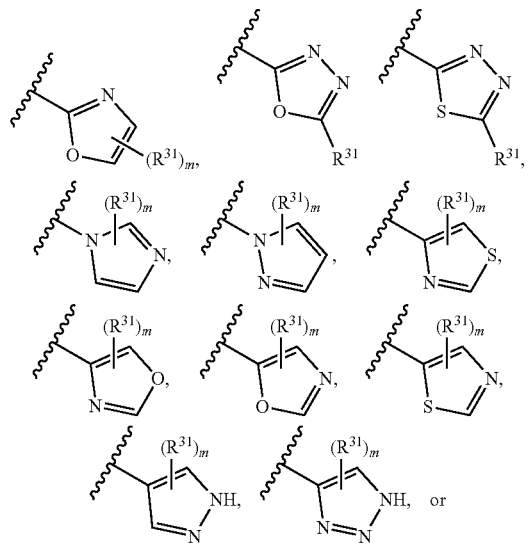

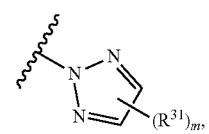

wherein each $R^{31}$ is independently selected from cyano, oxo, halogen, hydroxy, —SH, NO$_2$, amino, $C_{1-6}$ alkyl, $C_{1-6}$ haloalkyl, $C_{1-6}$ hydroxyalkyl, $C_{1-6}$ aminoalkyl, and $C_{1-6}$ heteroalkyl; and m is 0, 1, 2, or 3.

7. The method of claim 6, wherein R³ is

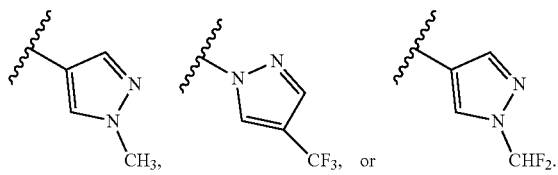 [SMILES: *c1cnn(C)c1 ; *n1cc(C(F)(F)F)cn1 ; *c1cnn(C(F)F)c1]

8. The method of claim 1, wherein:
R¹ is —CH₃ or cyclopropyl;
R⁴ and R⁶ are independently H;
R⁵ and R⁷ are independently halogen; and
R³ is

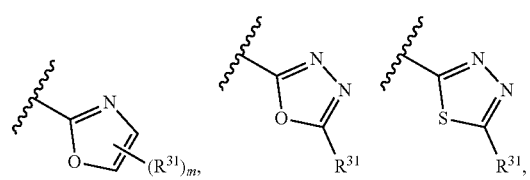

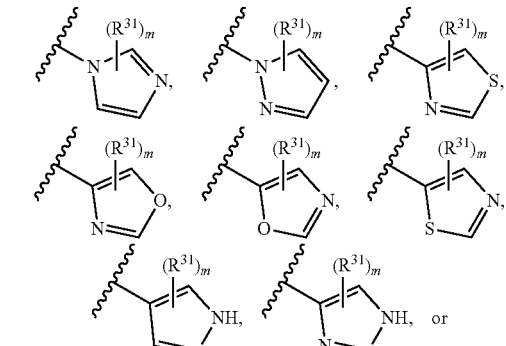

wherein each R³¹ is independently selected from cyano, oxo, halogen, hydroxy, —SH, NO₂, amino, $C_{1-6}$ alkyl, $C_{1-6}$ haloalkyl, $C_{1-6}$ hydroxyalkyl, $C_{1-6}$ aminoalkyl, and $C_{1-6}$ heteroalkyl; and m is 0, 1, 2, or 3.

9. The method of claim 1, wherein the compound is:

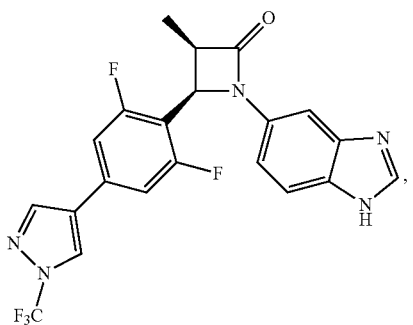

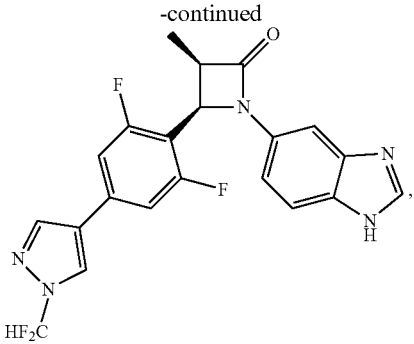

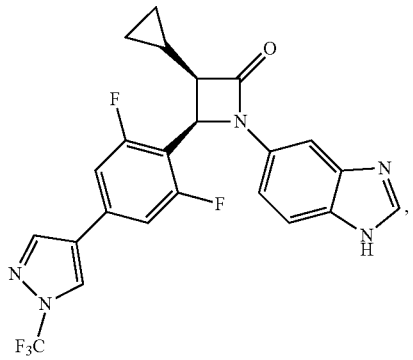

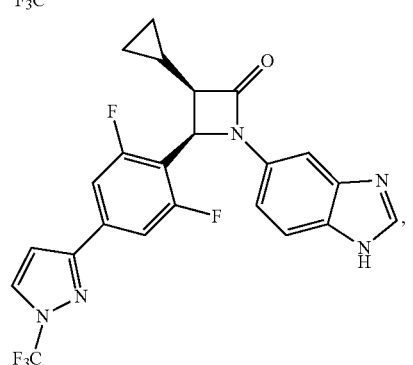

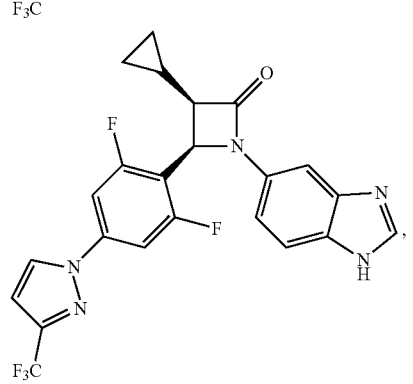

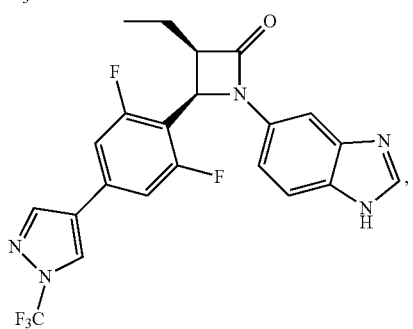

-continued

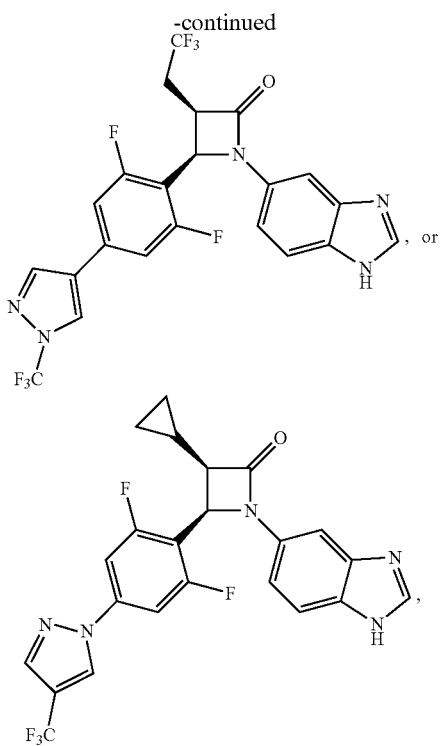

or or a pharmaceutically acceptable salt or stereoisomer thereof.

10. The method of claim 1, wherein the compound is

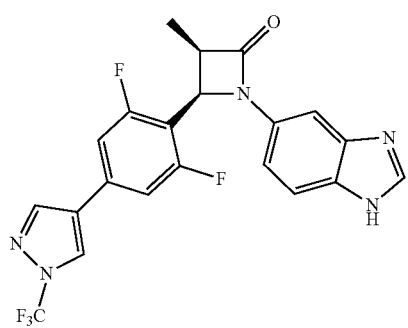 [SMILES: C[C@H]1C(=O)N(c2ccc3[nH]cnc3c2)[C@H]1c1c(F)cc(-c2cnn(C(F)(F)F)c2)cc1F]

or a pharmaceutically acceptable salt or stereoisomer thereof.

11. The method of claim 1, wherein the compound is

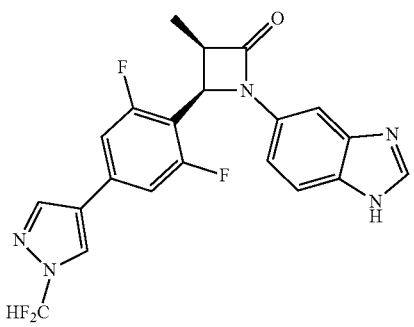

or a pharmaceutically acceptable salt or stereoisomer thereof.

12. The method of claim 1, wherein the compound is

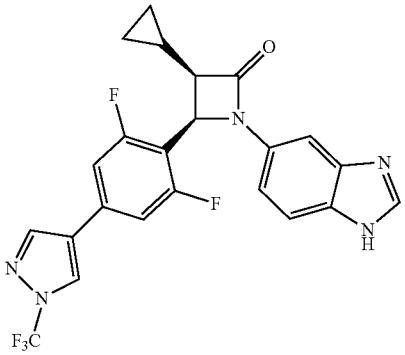 [SMILES: O=C1[C@H](C2CC2)[C@H](c2c(F)cc(-c3cnn(C(F)(F)F)c3)cc2F)N1c1ccc2[nH]cnc2c1]

or a pharmaceutically acceptable salt or stereoisomer thereof.

13. The method of claim 1, wherein the compound is

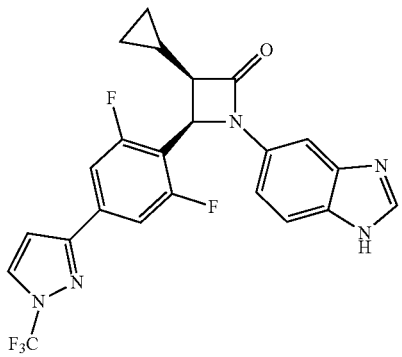 [SMILES: O=C1[C@H](C2CC2)[C@H](c2c(F)cc(-c3ccn(C(F)(F)F)n3)cc2F)N1c1ccc2[nH]cnc2c1]

or a pharmaceutically acceptable salt or stereoisomer thereof.

14. The method of claim 1, wherein the compound is

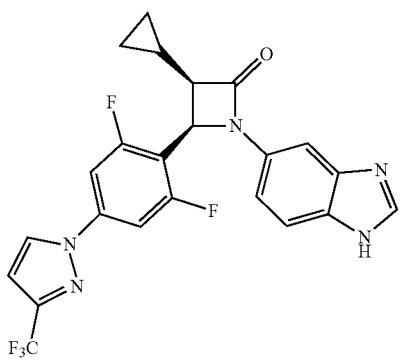 [SMILES: O=C1[C@H](C2CC2)[C@H](c2c(F)cc(-n3ccc(C(F)(F)F)n3)cc2F)N1c1ccc2[nH]cnc2c1]

or a pharmaceutically acceptable salt or stereoisomer thereof.

15. The method of claim 1, wherein the compound is

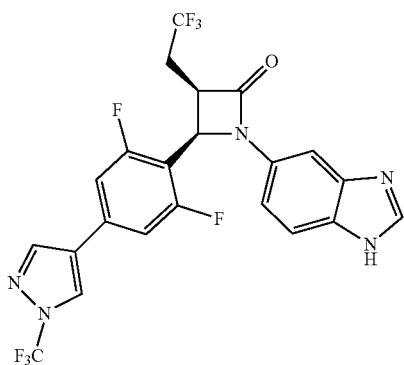 [SMILES: O=C1[C@H](CC(F)(F)F)[C@H](c2c(F)cc(-c3cnn(C(F)(F)F)c3)cc2F)N1c1ccc2[nH]cnc2c1]

or a pharmaceutically acceptable salt or stereoisomer thereof.

16. The method of claim 1, wherein the compound is

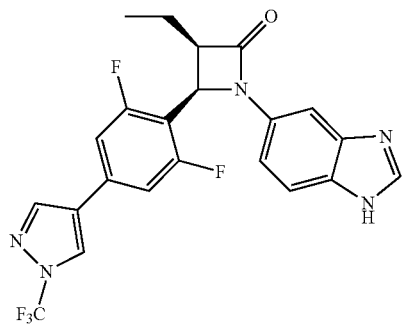 [SMILES: CC[C@H]1C(=O)N(c2ccc3[nH]cnc3c2)[C@H]1c1c(F)cc(-c2cnn(C(F)(F)F)c2)cc1F]

or a pharmaceutically acceptable salt or stereoisomer thereof.

17. The method of claim 1, wherein the compound is

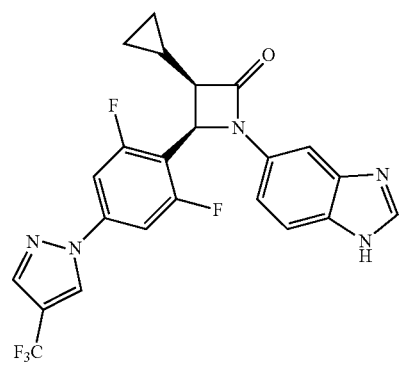

or a pharmaceutically acceptable salt or stereoisomer thereof.

18. The method of claim 1, wherein the disease or condition is cancer.

19. The method of claim 18, wherein the cancer is leukemia, acute myeloid leukemia (AML), chronic myeloid leukemia, acute lymphoblastic leukemia (ALL), non-Hodgkin lymphoma (NHL), Hodgkin lymphoma (HL), multiple myeloma (MM), or myelodysplastic syndrome (MSD).

20. The method of claim 18, wherein the cancer is a skin cancer, ocular cancer, gastrointestinal cancer, thyroid cancer, breast cancer, ovarian cancer, central nervous system cancer, laryngeal cancer, cervical cancer, lymphatic system cancer, genitourinary tract cancer, bone cancer, biliary tract cancer, endometrial cancer, liver cancer, lung cancer, prostate cancer, or colon cancer.

21. The method of claim 1, wherein the disease or condition is atherosclerosis, a fibrotic disease, ischemia-reperfusion injury, or an infectious disease caused by pathogens.

22. The method of claim 21, wherein the disease or condition is a fibrotic disease selected from liver fibrosis, pulmonary fibrosis, renal fibrosis, and scleroderma.

23. The method of claim 1, wherein the disease or condition is a kidney disease.

24. The method of claim 23, wherein the kidney disease is a chronic kidney disease (CKD), diabetic nephropathy, or Focal Segmented Glomerulosclerosis (FSGS).

25. The method of claim 1, wherein the disease or condition is Kennedy's disease, duodenal cancer with or without *Helicobacter pylori* infections, Zolliger-Ellison syndrome, gastric cancer with or without *Helicobacter pylori* infections, pathogenic psychotic conditions, schizophrenia, infertility, neoplasia, inflammatory host responses, cancer, psoriasis, impaired humoral and cell-mediated immune responses, leukocyte adhesion and migration processes in the endothelium, impaired food intake, impaired sleep-wakefulness, impaired homeostatic regulation of energy metabolism, impaired autonomic function, impaired hormonal balance or impaired regulation of body fluids, multiple sclerosis, the Guillain-Barre syndrome, chronic inflammatory demyelinizing polyradiculoneuropathy, mild cognitive impairment, Alzheimer's disease, Familial British Dementia, Familial Danish Dementia, neurodegeneration in Down Syndrome, Huntington's disease, rheumatoid arthritis, atherosclerosis, pancreatitis and restenosis.

* * * * *